US007875728B2

(12) United States Patent
Zhang et al.

(10) Patent No.: US 7,875,728 B2
(45) Date of Patent: Jan. 25, 2011

(54) HYDRAZONOPYRAZOLE DERIVATIVES AND THEIR USE AS THERAPEUTICS

(75) Inventors: Zaihui Zhang, Vancouver (CA); Timothy S Daynard, Vancouver (CA); Mikhail A Chafeev, Vancouver (CA); Shisen Wang, Coquitlam (CA); Gregory B Chopiuk, San Diego, CA (US); Serguei V Sviridov, Burnaby (CA)

(73) Assignee: Valocor Therapeutics, Inc., Vancouver, B.C. (CA)

( * ) Notice: Subject to any disclaimer, the term of this patent is extended or adjusted under 35 U.S.C. 154(b) by 659 days.

(21) Appl. No.: 10/497,046

(22) PCT Filed: Oct. 18, 2002

(86) PCT No.: PCT/CA02/01583

§ 371 (c)(1), (2), (4) Date: Apr. 20, 2005

(87) PCT Pub. No.: WO03/045379

PCT Pub. Date: Jun. 5, 2003

(65) Prior Publication Data

US 2005/0272709 A1 Dec. 8, 2005

Related U.S. Application Data

(60) Provisional application No. 60/335,265, filed on Nov. 30, 2001.

(51) Int. Cl.
*C07D 231/14* (2006.01)
*A61K 31/415* (2006.01)
(52) U.S. Cl. .................... 548/371.4; 514/407
(58) Field of Classification Search ............. 548/371.4; 514/407
See application file for complete search history.

(56) References Cited

U.S. PATENT DOCUMENTS

| 4,006,127 A * | 2/1977 | Raue et al. ................ 534/607 |
| 4,562,248 A | 12/1985 | Weaver et al. |
| 6,214,813 B1 | 4/2001 | Zhang et al. ............... 514/150 |
| 6,436,915 B1 | 8/2002 | Zhang et al. ............... 514/150 |
| 2003/0060453 A1 | 3/2003 | Zhang et al. ............... 514/94 |

FOREIGN PATENT DOCUMENTS

| GB | 955085 | * | 4/1964 |
| GB | 1139361 | | 1/1969 |
| WO | WO 01/56557 A2 | | 8/2001 |
| WO | WO 01/56993 A2 | | 8/2001 |
| WO | WO 01/57022 A2 | | 8/2001 |
| WO | WO 01/77080 A2 | | 10/2001 |
| WO | WO 02/062804 A1 | | 8/2002 |
| WO | WO 03/045379 A1 | | 6/2003 |
| WO | WO 03/055860 A1 | | 7/2003 |

OTHER PUBLICATIONS

CAPLUS abstract Accession # 1989:407356 (Sadek et al. (Liebigs Annalen der Chemie (1989), (5), 501-2).*
"Guidance for Industry, Q3C Impurities: Residual Solvents", FDA, Dec. 1997.*
Gompper et al, Angew. Chem. Int. Ed. Engl. 24 (1985) No. 11, p. 984-985.*
Baig, G., et al., "Triazines and Related Products Part 24. Synthesis of Pyrazol-4-ylidenehydrazinoimidazoles by Hrdrazinolysis of Imidazo [5,1-c] [1,2,4]-triazines t and 2-Arylazoimidazoles by Diazonium Coupling Reactions," *Journal of the Chemical Society, Perkin Transactions 1*(8), 1811-1819, 1982.
Dawood, K., et al., "Heterocyclic Synthesis via Enaminonitriles: A Convenient Route to Some New Pyrazole, Isoxazole, Pyrimidine, Pyrazolo[1,5-a]pyrimidine, Pyrimido [1,2-a]benzimidazole and Pyrido[1,2-a]benzimidazole Derivatives," *J. Chem. Res.* (S):208-209, 1998.
El-Gaby, M., et al., "Preparation of Some Novel 3,5-Diaminopyrazole, pyrazolo-[1,5-a] [1,3,5]Triazine and Pyrazolo [1,5-a]-Pyrimidine Derivatives Containing Sulfonamido Moieties as Antimicrobial Agents," *Acta. Chim. Slov.*, 19:159-171, 2002.
Elgemeie, G., et al., "Novel Synthesis of Mercaptopurine and Pentaaza-as-Indacene Analogues: Reaction of [Bis(methylthio)methylene]malononitrile and Ethyl 2-Cyano-3, 3-bis(methylthio)acrylate with 5-Aminopyrazoles," *Bull. Chem. Soc. Jpn.*, 67(3):738-741, 1994.
Elnagdi, M., et al., "Reactions with Heterocyclic Diazonium Salts: Novel Synthesis of Pyrazolo[4,3-c]pyridazines and of Pyrazolo[4,3-c]pyrazoles," *Journal of the Chemical Society, Perkin Transactions 1*(4):989-991, 1982.
Hanna, M., et al., "Novel Anchored Nitrogen-containing Heterocycles of Potential Biological Activity from 2,3-dioxobutanethioanilide 2-arylhydrazone," *Chem. Papers*, 43(5):651-659, 1989.
Hassan, A., "Chemical Interactions Between Aminopyrazoles and 2,3-Dicyano-1,4-naphthoquinone," *Liebigs Annalen der Chemie*, 6:695-697, 1993.
Kandel, Z., et al., "Activated Nitriles in Heterocyclic Synthesis: Reaction of Cyanogen Bromide with some Functionally Substituted Enamines," *Journal of the Chemical Society, Perkin Transactions 1*, pp. 1499-1502, 1985.
Mourad, A-F., et al., "Pyrimidine Derivatives and Related Compounds: Synthesis of new 3-(2,3-Dimethyl-5-oxo-1-phenyl-pyrazolin-4-yl)-azopyrazolo[1,5-a]pyrimidines," *Archiv Der Pharmazie*, 317(3):241-5, 1984.

(Continued)

Primary Examiner—Robert Havlin
(74) Attorney, Agent, or Firm—Hai Han; Seed IP Law Group PLLC

(57) ABSTRACT

Pharmaceutical compositions and compounds are provided. The compounds of the invention demonstrate anti-proliferative activity, and may promote apoptosis in cells lacking normal regulation of cell cycle and death. In one embodiment of the invention, pharmaceutical compositions of the compounds in combination with a physiologically acceptable carrier are provided. The pharmaceutical compositions are useful in the treatment of hyperproliferative disorders, which disorders include tumor growth, lymphoproliferative diseases, angiogenesis. The compounds of the invention are substituted pyrazoles and pyrazolines.

5 Claims, No Drawings

OTHER PUBLICATIONS

Nawwar, G., et al., "Synthesis of 2-Substituted Benzothiazoles Containing Amino Acid, Imino or Heteroaryl Moieties with Anticipated Fungicidal Activity," *Collect. Czech. Chem. Commun.*, 60:2200-2208, 1995.
Schafer, H., et al., "Substituierte 4-Nitropyrazole aus Nitroketenaminalen," *J. f. Prakt. Chemie.*, 323(2):332-336, 1981.
Chemical Abstracts, vol. 68, No. 11, Abstract No. 49503j, 1968.
World Patent Index (Thomson Derwent), Database Accession No. 1977-75291Y, 1977.
CHEMCATS Database (Chemical Abstracting Service), Database Accession Nos. 2002:1111382, 2002:1110659, 2002:935464, 2002:933931, 2001:2659752, Jan. 21, 2002.
CHEMCATS Database (Chemical Abstracting Service), Database Accession Nos. 2002:1409323 and 2001:1349750, Jul. 1, 2001.
CHEMCATS Database (Chemical Abstracting Service), Database Accession No. 2002:144647, Feb. 11, 2002.
CHEMCATS Database (Chemical Abstracting Service), Database Accession Nos. 2002:2994140 and 2002:638291, Jan. 17, 2002.
CHEMCATS Database (Chemical Abstracting Service), Database Accession Nos. 2002:820781 and 2002:3111028, Oct. 4, 2002.
CHEMCATS Database (Chemical Abstracting Service), Database Accession No. 2002:3207695, Mar. 22, 2001.
CHEMCATS Database (Chemical Abstracting Service), Database Accession Nos. 2002:2774951, 2002:2774930, 2002:2021345, 2002:2021344, 2002:1828293, 2002:1975388, 2002:1828294, Jul. 9, 2002.
Chemical Abstracts Database, Accession No. 2000:41863, 2000.
Chemical Abstracts Database, Accession No. 1995:954284, 1995.
Chemical Abstracts Database, Accession No. 1970:414400, 1970.
Chemical Abstracts Database, Accession No. 1996:12389, 1996.
Chemical Abstracts Database, Accession No. 1994:54519, 1994.
Chemical Abstracts Database, Accession No. 1978:443341, 1978.
Chemical Abstracts Database, Accession No. 1975:72860, 1975.
Chemical Abstracts Database, Accession No. 1974:82349, 1974.
Chemical Abstracts Database, Accession No. 1994:409222, 1994.
Chemical Abstracts Database, Accession No. 1974:108415, 1974.
Chemical Abstracts Database, Accession No. 2000:530709, 2000.
Chemical Abstracts Database, Accession No. 1969:422058, 1969.
Chemical Abstracts Database, Accession No. 1986:5847, 1986.
Chemical Abstracts Database, Accession No. 1984:551788, 1984.
Chemical Abstracts Database, Accession No. 1994:164052, 1994.
Chemical Abstracts Database, Accession No. 1978:509222, 1978.
Chemical Abstracts Database, Accession No. 1965:463025, 1965.
Chemical Abstracts Database, Accession No. 1986:50853, 1986.
Chemical Abstracts Database, Accession No. 1990:139004, 1990.
Chemical Abstracts Database, Accession No. 1986:148149, 1986.
Chemical Abstracts Database, Accession No. 1999:87103, 1999.
Chemical Abstracts Database, Accession No. 1987:477760, 1987.
Chemical Abstracts Database, Accession No. 1985:541920, 1985.
Behr, L., et al., *Pyrazoles, Pyrazolines, Pyrazolidines, Indazoles and Condensed Rings*, (Wiley, R. ed.), Interscience Publishers, New York, 1967, Ch. 2, "Tautomerism and Isomerism," pp. 4-9.
Delcommenne, M., et al., "Phosphoinositide-3-OH Kinase-dependent Regulation of Glycogen Synthase kinase 3 and Protein Kinase B/AKT by the Integrin-linked Kinase," *Proc Natl Acad Sci U S A.*, 95(19):11211-6, Sep. 15, 1998.
Golub, T., et al; "Molecular Classification of Cancer: Class Discovery and Class Prediction by Gene Expression Monitoring," *Science*, 286(5439):531-7, Oct. 15, 1999.
Chemical Abstracts, vol. 64, Abstract No. 5068f, 1966.
Chemical Abstracts, vol. 82, Abstract No. 66061v, 1975.
Chemical Abstracts, vol. 105, Abstract No. 191071, 1986.
Chemical Abstracts Database, Accession No. 1994:323476, 1994.
Chemical Abstracts Database, Accession No. 1968:418743, 1968.
Chemical Abstracts Database, Accession No. 1988:131679, 1988.
Chemical Abstracts Database, Accession No. 1979:439437, 1979.
Chemical Abstracts Database, Accession No. 1973:478677, 1973.
Chemical Abstracts Database, Accession No. 1984:530079, 1984.
Chemical Abstracts Database, Accession No. 1994:8545, 1994.
Chemical Abstracts Database, Accession No. 1982:562888, 1982.
Cea et al., "Compuestos Interlaminares Coordinados de Cianuro de Niguel con Aminas Alifaticas," Anales de Quimica 81(1): 11-17, 1985.
El-Haty et al., "Solvent and pH effects on the electronic spectra of some 4-arylazo-3,5-diaminopyrazoles," Bull Soc Chim Fr 128: 869-872, 1991.
Elagamey et al., "Nitriles in heterocyclic synthesis: synthesis of pyrazolo[1,5-a] pyrimidine, pyrazolo[1,5-c] [1,2,4] triazine and pyrazolo[4,3-e] [1,2,4]triazine derivatives," Journal fuer Praktische Chemie (Leipzig) 333(2): 333-338, 1991; CAPLUS Accession No. 1991:607960.
Elnagdi et al., "Reactions of alpha-Arylhydrazono-beta-oxo-beta-phenyl-propionitriles," Journal f. pract. Chemie. Band 816(6): S. 975-980, 1974.
Farag et al., "Synthesis and Reactivity of 3-(Benzothiazol-2-yl)-3-oxopropanenitrile," Tetrahedron 52(23): 7893-7900, 1996.
Gompper et al., "Dimethylamino-pyrazole und -pyrazolyliumsalze," Angew. Chem. 97(11): 998-999, 1985.
Hassanien et al., "Utility of (p-Sulfonamidophenyl)azomalononitrile, and Ethyl Acetoacetate in Synthesis of Fused Azole and Azines Derivatives II," Journal of the Chinese Chemical Society 47(6): 1273-1278, 2000.
Kandeel, "Nitriles in Heterocyclic Synthesis: A Single-step Synthesis of Azolo[1,5-a]pyrimidine and Benzimidazolo [1,5-a]pyridine Derivatives," Journal of Chemical Research (S) 7: 290-291, 1995.
Khalik, Mervat Mohammed Abdel, "Studies with 3-Oxoalkanenitriles: Synthesis of New Pyrazolo[1,5-a] pyrimidines and Pyrazolo[5,1-c]-1,2,4-triazines and Reactivity of 4-Phenyl-3-oxobutanenitrile Derivatives," Journal of Chemical Research (S) 6: 198-199, 1997.
Shvekhgeimer et al., "Synthesis of Novel 3,5-Diamino-4-(2-Cyano-Arylazo)Pyrazoles," Chemistry of Heterocyclic Compounds 37(3): 370-371, 2001.

\* cited by examiner

HYDRAZONOPYRAZOLE DERIVATIVES AND THEIR USE AS THERAPEUTICS

CROSS REFERENCE TO RELATED APPLICATIONS

This application is a national stage application filed under 35 U.S.C. 371 of International Application No. PCT/CA02/01583, accorded an International Filing Date of Oct. 18, 2002; which claims priority to U.S. Provisional Patent Application No. 60/335,265 filed Nov. 30, 2001.

FIELD OF INVENTION

It has become increasingly clear in recent years that cell death is as important to the health of a multicellular organism as cell division: where proliferation exists, so must a means of regulating its cellular progeny. By repeated cell division and differentiation throughout development or tissue repair, surplus or even harmful cells are generated, and they must be removed or killed. In adults, senescent cells are removed and replaced by newly generated cells to maintain homeostasis.

The delicate interplay between growth and cell death in an organism is mirrored in the complex molecular balance that determines whether an individual cell undergoes division; arrests in the cell cycle; or commits to programmed cell death. Signal transduction is the term describing the process of conversion of extracellular signals, such as hormones, growth factors, neurotransmitters, cytokines, and others, to a specific intracellular response such as gene expression, cell division, or apoptosis. This process begins at the cell membrane where an external stimulus initiates a cascade of enzymatic reactions inside the cell that typically include phosphorylation of proteins as mediators of downstream processes which most often end in an event in the cell nucleus. The checks and balances of these signal transduction pathways can be thought of as overlapping networks of interacting molecules that control "go-no go" control points. Since almost all known diseases exhibit dysfunctional aspects in these networks, there has been a great deal of enthusiasm for research that provides targets and therapeutic agents based on signal transduction components linked to disease.

Dysregulation of cell proliferation, or a lack of appropriate cell death, has wide ranging clinical implications. A number of diseases associated with such dysregulation involve hyperproliferation, inflammation, tissue remodelling and repair. Familiar indications in this category include cancers, restenosis, neointimal hyperplasia, angiogenesis, endometriosis, lymphoproliferative disorders, graft-rejection, polyposis, loss of neural function in the case of tissue remodelling, and the like. Such cells may lose the normal regulatory control of cell division, and may also fail to undergo appropriate cell death.

In one example, epithelial cells, endothelial cells, muscle cells, and others undergo apoptosis when they lose contact with extracellular matrix, or bind through an inappropriate integrin. This phenomenon, which has been termed "anoikis" (the Greek word for "homelessness"), prevents shed epithelial cells from colonizing elsewhere, thus protecting against neoplasia, endometriosis, and the like. It is also an important mechanism in the initial cavitation step of embryonic development, in mammary gland involution, and has been exploited to prevent tumor angiogenesis. Epithelial cells may become resistant to anoikis through overactivation of integrin signaling. Anoikis resistance can also arise from the loss of apoptotic signaling, for example, by overexpression of Bcl-2 or inhibition of caspase activity.

An aspect of hyperproliferation that is often linked to tumor growth is angiogenesis. The growth of new blood vessels is essential for the later stages of solid tumor growth. Angiogenesis is caused by the migration and proliferation of the endothelial cells that form blood vessels.

In another example, a major group of systemic autoimmune diseases is associated with abnormal lymphoproliferation, as a result of defects in the termination of lymphocyte activation and growth. Often such diseases are associated with inflammation, for example with rheumatoid arthritis, insulin dependent diabetes mellitus, multiple sclerosis, systemic lupus erythematosus, and the like. Recent progress has been made in understanding the causes and consequences of these abnormalities. At the molecular level, multiple defects may occur, which result in a failure to set up a functional apoptotic machinery.

The development of compounds that inhibit hyperproliferative diseases, particularly where undesirable cells are selectively targeted, is of great medical and commercial interest.

Related Literature

The regulation of integrin linked kinase by phosphatidylinositol (3,4,5) trisphosphate is described by Delcommenne et al. (1998) *Proc. Natl. Acad. Sci.* 95:11211-6. Activated nitriles in heterocyclic synthesis are discussed in Kandeel et al. (1985) *J. Chem. Soc. Perkin. Trans.* 1499.

SUMMARY OF THE INVENTION

Pharmaceutical compositions and compounds are provided. The compounds of the invention are substituted pyrazoles and pyrazolines. In one embodiment of the invention, formulations of the compounds in combination with a physiologically acceptable carrier are provided. The pharmaceutical compositions are useful in the treatment of disorders associated with hyperproliferation and tissue remodelling or repair. The compounds are also active in the inhibition of specific protein kinases.

Accordingly, in one aspect, the invention provides pharmaceutical compositions which comprise a pharmaceutically acceptable carrier, diluent or excipient and a compound of formula (I):

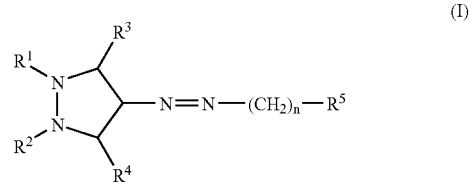

wherein:

n is 0 to 5;

$R^1$ and $R^2$ are each independently hydrogen, alkyl, aryl, aralkyl or —C(O)$R^6$;

or $R^1$ and $R^2$ can each independently be a part of a double bond within the pyrazole ring;

$R^3$ and $R^4$ are each independently —N($R^7$)$_2$ or —N($R^7$)C(O)$R^6$;

$R^5$ is aryl optionally substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, —$R^8$—[O—$R^8$]$_m$—O$R^6$ (where m is 1 to 4), —S(O)$_2$OH, —S(O)$_t$$R^7$ (where t is 0 to 2), —S(O)$_t$—R$^8$—OR$^6$, —S(O)$_t$—N(R$^6$)$_2$, —R$^8$—P(O)(OR$^9$)$_2$, —C(O)OR$^6$, —R$^8$—C(O)OR$^6$, —C(O)N(R$^6$)$_2$, —N(R$^7$)$_2$, —R$^8$—N(R$^7$)$_2$, and —N(R$^9$)C(O)R$^6$;

or R$^5$ is heterocyclyl optionally substituted with one or more substituents selected from the group consisting of alkyl, halo, nitro, cyano, haloalkyl, haloalkoxy, aryl, heterocyclyl, heterocyclylalkyl, —OR$^6$, —R$^8$—OR$^6$, —R$^8$—[O—R$^8$]$_m$—OR$^6$ (where m is 1 to 4), —S(O)$_2$OH, —S(O)R$^7$ (where t is 0 to 2), —S(O)$_t$—R$^8$—OR$^6$, —S(O)$_t$—N(R$^6$)$_2$, —R$^8$—P(O)(OR$^9$)$_2$, —C(O)OR$^6$, —R$^8$—C(O)OR$^6$, —C(O)N(R$^6$)$_2$, —N(R$^7$)$_2$, —R$^8$—N(R$^7$)$_2$, and —N(R$^9$)C(O)R$^6$;

each R$^6$ is independently hydrogen, alkyl, aryl, aralkyl, hetereocyclyl or heterocyclylalkyl;

each R$^7$ is independently hydrogen, alkyl, haloalkyl, aryl, aralkyl, heterocyclyl, heterocyclylalkyl, or —R$^8$—OR$^9$;

each R$^8$ is a straight or branched alkylene chain; and each R$^9$ is hydrogen or alkyl;

as a single stereoisomer, a mixture of stereoisomers, a solvate or a polymorph; or a pharmaceutically acceptable salt thereof.

In another aspect, the invention provides pharmaceutical compositions comprising a pharmaceutically acceptable carrier, diluent or excipient and a compound of formula (Ia):

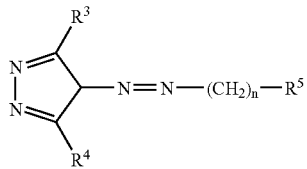

(Ia)

wherein:

n is 0;

R$^3$ and R$^4$ are each —NH$_2$; and

R$^5$ is phenyl substituted at the 4-position by fluoro and at the 3-position by trifluoromethyl, namely, 4-[(4-fluoro-3-trifluoromethylphenyl)hydrazono]-4H-pyrazole-3,5-diamine.

In another aspect, the invention provides methods of treating a hyperproliferative disorder in a mammal, wherein the method comprises administering to a mammal in need thereof a therapeutically effective amount of a pharmaceutical composition comprising a pharmaceutically acceptable carrier, diluent or excipient and a compound of formula (I) as described above.

In another aspect, the invention provides compounds of formula (I):

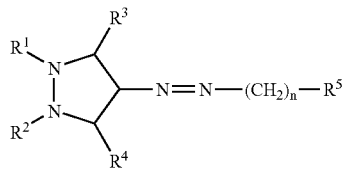

(I)

wherein:

n is 0 to 5;

R$^1$ and R$^2$ are each independently hydrogen, alkyl, aryl, aralkyl or —C(O)R$^6$;

or R$^1$ and R$^2$ can each independently be a part of a double bond within the pyrazole ring;

R$^3$ and R$^4$ are each independently —N(R$^7$)$_2$ or —N(R$^7$)C(O)R$^6$;

R$^5$ is aryl optionally substituted with one or more substituents selected from the group consisting of alkyl, halo, nitro, cyano, haloalkyl, haloalkoxy, aryl, heterocyclyl, heterocyclylalkyl, —OR$^6$, —R$^8$—OR$^6$, —R$^8$—[O—R$^8$]$_m$—OR$^6$ (where m is 1 to 4), —S(O)$_2$OH, —S(O)R$^7$ (where t is 0 to 2), —S(O)$_t$—R$^8$—OR$^6$, —S(O)$_t$—N(R$^6$)$_2$, —R$^8$—P(O)(OR$^9$)$_2$, —C(O)OR$^6$, —R$^8$—C(O)OR$^6$, —C(O)N(R$^6$)$_2$, —N(R$^7$)$_2$, —R$^8$—N(R$^7$)$_2$, and —N(R$^9$)C(O)R$^6$;

or R$^5$ is heterocyclyl optionally substituted with one or more substituents selected from the group consisting of alkyl, halo, nitro, cyano, haloalkyl, haloalkoxy, aryl, heterocyclyl, heterocyclylalkyl, —OR$^6$, —R$^8$—OR$^6$, —R$^8$—[O—R$^8$]$_m$—OR$^6$ (where m is 1 to 4), —S(O)$_2$OH, —S(O)R$^7$ (where t is 0 to 2), —S(O)$_t$—R$^8$—OR$^6$, —S(O)$_t$—N(R$^6$)$_2$, —R$^8$—P(O)(OR$^9$)$_2$, —C(O)OR$^6$, —R$^8$—C(O)OR$^6$, —C(O)N(R$^6$)$_2$, —N(R$^7$)$_2$, —R$^8$—N(R$^7$)$_2$, and —N(R$^9$)C(O)R$^6$;

each R$^6$ is independently hydrogen, alkyl, aryl, aralkyl, hetereocyclyl or heterocyclylalkyl;

each R$^7$ is independently hydrogen, alkyl, haloalkyl, aryl, aralkyl, heterocyclyl, heterocyclylalkyl, or —R$^8$—OR$^9$;

each R$^8$ is a straight or branched alkylene chain; and each R$^9$ is hydrogen or alkyl;

provided that when n is 0, R$^1$ is phenyl, R$^2$ is hydrogen, R$^3$ and R$^4$ are both —NH$_2$, R$^5$ can not be unsubstituted phenyl; and provided that when n is 0, R$^1$ and R$^2$ are both hydrogen, and R$^3$ and R$^4$ are both —NH$_2$, R$^5$ can not be phenyl, napht-2-yl, pyridin-3-yl, 3-methoxyphenyl, 3-chlorophenyl, 4-bromophenyl, 2-methylphenyl, 2-chlorophenyl, 3-nitrophenyl, 4-aminosulfonylphenyl, or 4-(pyrimidin-2-yl)aminosulfonylphenyl;

as a single stereoisomer, a mixture of stereoisomers, a solvate or a polymorph; or a pharmaceutically acceptable salt thereof.

In another aspect, this invention provides pharmaceutical compositions comprising a pharmaceutically excipient and a compound of formula (Ic):

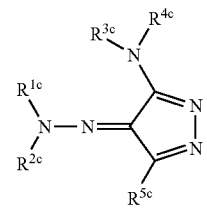

(Ic)

as a single tautomer, a mixture of tautomers, a single stereoisomer, a mixture of stereoisomers, or a racemic mixture; or a pharmaceutically acceptable salt or solvate thereof; wherein:

R$^{1c}$ is hydrogen, alkyl, aryl or aralkyl;

R$^{2c}$ is aryl (optionally substituted with one or more substituents selected from the group consisting of halo, alkoxy, nitro, haloalkyl, —R$^{6c}$—N(R$^{8c}$)$_2$, —S(O)$_2$—R$^{6c}$—OH, —S(O)$_2$—N(R$^{7c}$)R$^{8c}$ and heterocyclylalkyl);

or R$^{2c}$ is N-heterocyclyl (optionally substituted one or more substituents selected from the group consisting of alkyl, halo, and —C(O)OR$^{7c}$);

R$^{4c}$ is hydrogen or alkyl;

$R^{3c}$ is hydrogen, alkyl, heterocyclylalkyl, or heterocyclylcarbonyl;

$R^{5c}$ is hydrogen, alkyl, alkenyl, —$R^{6c}$—O—$R^{12c}$, —$R^{6c}$—S—$R^{12c}$, —$R^{6c}$—N($R^{9c}$)$_2$, cycloalkyl (optionally substituted by one or more substituents selected from the group consisting of alkyl and aryl), aryl (optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups), nitro, —C(O)O$R^{7c}$, and —N($R^{7c}$)—C(O)—$R^{7c}$), aralkyl (wherein the aryl group is optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups), nitro, —C(O)O$R^{7c}$, and —N($R^{7c}$)—C(O)—$R^{7c}$), aralkenyl (wherein the aryl group is optionally substituted by one or more halo groups), heterocyclyl (optionally substituted by one or more substituents selected from the group consisting of alkyl, halo, haloalkyl, alkyl thio, and aryl (optionally substituted with one or more halo groups)), or heterocyclylalkyl;

each $R^{6c}$ is independently a straight or branched alkylene chain;

each $R^{7c}$ is independently hydrogen, alkyl, aryl, aralkyl or heterocyclylakyl;

$R^{8c}$ is hydrogen, alkyl, aryl aralkyl or hydroxyalkyl;

each $R^{9c}$ is independently hydrogen, heterocyclylalkyl, —C(O)—$R^{11c}$, —C(O)—$R^{10c}$—C(O)O$R^{7c}$, —$R^{10c}$—C(O)O$R^{7c}$, or —S(O)$_2$—$R^{7c}$;

each $R^{10c}$ is independently a direct bond, straight or branched alkylene chain or straight or branched alkenylene chain;

$R^{11c}$ is aryl (optionally substituted by one or more substituents selected from the group consisting of alkyl and halo), heterocyclyl (optionally substituted by one or more substituents selected from the group consisting of —C(O)O$R^{7c}$ and —C(O)N($R^{7c}$)$_2$) or heterocyclylalkyl (optionally substituted by one or more substituents selected from the group consisting of —C(O)O$R^{7c}$ and —C(O)N($R^{7c}$)$_2$); and each $R^{12c}$ is independently aryl or aralkyl (optionally substituted by one or more substituents selected from group consisting of halo and nitro).

In another aspect, this invention is directed to certain compounds of formula (Ic) as described above.

In another aspect, this invention is directed to methods of using the compounds of formula (Ic) as described above in the treatment of disorders associated with hyperproliferation and tissue remodelling or repair. The compounds are also useful in the inhibition of specific protein kinases.

DETAILED DESCRIPTION OF THE INVENTION

A. Definitions

In general, all technical and scientific terms used herein have the same meaning as commonly understood to one of ordinary skill in the art to which this invention belongs, unless clearly indicated otherwise. For clarification, listed below are definitions for certain terms used herein to describe the present invention. These definitions apply to the terms as they are used throughout this specification, unless otherwise clearly indicated.

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

"Alkyl" refers to a straight or branched monovalent hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, it is understood that for radicals, as defined below, that contain a substituted alkyl or alkenyl group that the substitution can occur on any carbon of the alkyl group.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like.

"Alkenyl" refers to a straight or branched monovalent hydrocarbon chain radical consisting solely of carbon and hydrogen atoms, containing at least one double bond, having from two to eight carbon atoms, and which is attached to the rest of the molecule by a single bond, e.g., ethenyl, prop-1-enyl, but-1-enyl, pent-1-enyl, penta-1,4-dienyl, and the like.

"Alkoxy" refers to a radical of the formula —O$R_a$ where $R_a$ is an alkyl radical as defined above, e.g., methoxy, ethoxy, n-propoxy, 1-methylethoxy(iso-propoxy), n-butoxy, n-pentoxy, 1,1-dimethylethoxy(t-butoxy), and the like.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, —$R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$—N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$ wherein $R^6$, $R^7$ and R are as defined herein.

"Aralkyl" refers to a radical of the formula —$R_a$$R_b$ where $R_a$ is an alkyl radical as defined above and $R_b$ is one or more aryl radicals as defined above, e.g., benzyl, diphenylmethyl, and the like. The aryl radical may be optionally substituted as described above.

"Aralkenyl" refers to a radical of the formula —$R_e$—$R_b$ where $R_b$ is an aryl radical as defined above and $R_e$ is an alkenyl radical as defined above, e.g., 2-phenylethenyl, and the like.

"Carboxy" refers to the —C(O)OH radical.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkoxy, halo, haloalkyl, haloalkoxy, hydroxy, amino, and carboxy.

"Halo" refers to bromo, chloro, iodo or fluoro.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —OR$_c$ where R$_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

"Heterocyclyl" refers to a stable 3- to 15-membered ring radical which consists of carbon atoms and from one to five heteroatoms selected from the group consisting of nitrogen, oxygen and sulfur. For purposes of this invention, the heterocyclyl radical may be a monocyclic, bicyclic or tricyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be aromatic or partially or fully saturated. The heterocyclyl radical may not be attached to the rest of the molecule at any heteroatom atom. Examples of such heterocyclyl radicals include, but are not limited to, azepinyl, acridinyl, benzimidazolyl, benzthiazolyl, benzothiadiazolyl, benzoxazolyl, benzodioxolyl, benzodioxinyl, benzopyranyl, benzopyranonyl, benzofuranyl, benzofuranonyl, benzothienyl (benzothiophenyl), benzotriazolyl, carbazolyl, cinnolinyl, decahydroisoquinolyl, dioxolanyl, furanyl, furanonyl, isothiazolyl, imidazolyl, imidazolinyl, imidazolidinyl, isothiazolidinyl, indolyl, indazolyl, isoindolyl, indolinyl, isoindolinyl, indolizinyl, isoxazolyl, isoxazolidinyl, morpholinyl, naphthyridinyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, oxiranyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydrofuryl, triazinyl, tetrahydropyranyl, thienyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, halo, nitro, cyano, haloalkyl, haloalkoxy, aryl, heterocyclyl, heterocyclylalkyl, —OR$^6$, —R$^8$—OR$^6$, —R$^8$—[O—R$^8$]$_m$—OR$^6$ (where m is 1 to 4), —S(O)$_2$OH, —S(O)$_t$R$^7$ (where t is 0 to 2), —S(O)$_t$—R$^8$—OR$^6$, —S(O)$_t$—N(R$^6$)$_2$, —R$^8$—P(O)(OR$^9$)$_2$, —C(O)OR$^6$, —R$^8$—C(O)OR$^6$, —C(O)N(R$^6$)$_2$, —N(R$^7$)$_2$, —R$^8$—N(R$^7$)$_2$, and —N(R$^9$)C(O)R$^6$ wherein R$^6$, R$^7$ and R$^8$ and R$^9$ are as defined herein. Heterocyclyls that are preferred for R$^5$ include benzodioxolyl, benzodioxinyl, benzothiazolyl, triazolyl, pyrazolyl, pyridinyl, carbazolyl, indazolyl, quinolinyl, isoquinolinyl, benzotriazolyl, benzothiadiazolyl, quinazolinyl, benzothiophenyl (benzothienyl), phthalazinyl, piperidinyl, morpholinyl, and piperazinyl. Heterocyclyls that are preferred for substitutents on the aryl choice for R$^5$ include morpholinyl, piperidinyl, pyrrolidinyl, piperidinyl and piperazinyl.

"N-heterocyclyl" refers to a heterocyclyl radical as defined above wherein the one to five heteroatoms contained therein are selected only from nitrogen. Preferred N-heterocyclyl radicals for R$^2$ are those radicals selected from the group consisting of pyridinyl, thiazolyl, tetrazolyl, pyrazolyl, isoquinolinyl, quinolinyl, and phthalazinyl;

"Heterocyclylalkyl" refers to a radical of the formula —R$_a$R$_d$ where R$_a$ is an alkyl radical as defined above and R$_d$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above. Preferred hetereocyclyl radicals are defined above.

"Heterocyclylcarbonyl" refers to a radical of the formula —C(O)—R$_d$ where R$_d$ is a heterocyclyl radical as defined above, and if the heterocyclyl is a nitrogen-containing heterocyclyl, the heterocyclyl may be attached to the carbonyl at the nitrogen atom. A preferred hetereocyclylcarbonyl radical for R$^3$ is pyridinylcarbonyl.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland, Oreg.), Trans World Chemicals, Inc. (Rockville, Md.), and Wako Chemicals USA, Inc. (Richmond, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," *A. C. S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domesticated animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" and "salts thereof" in the compounds of the present invention refers to pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable excipient" as used herein is intended to include without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or stabilizer which has been approved by the United States Food and Drug Administration as being acceptable for use in humans or domestic animals.

"Treating" or "treatment" as used herein covers the treatment of a hyperproliferative disorder in a mammal, preferably a human, which disorder is characterized by integrin linked kinase (ILK) activity, and includes:
  (i) preventing the disorder from occurring in a mammal, in particular a human, when such mammal is predisposed to the disorder but has not yet been diagnosed as having it;
  (ii) inhibiting the disorder, i.e., arresting its development; or
  (iii) relieving the disorder, i.e., causing regression of the condition.

The nomenclature used herein is a modified form of the I.U.P.A.C. nomenclature system wherein the compounds of the invention are named herein as derivatives of the pyrazole-3,5-diamine moiety if no other functional group of higher nomenclature priority is present. Thus, a compound of formula (Ia) wherein n is 0, $R^1$ and $R^2$ are each hydrogen, $R^3$ and $R^4$ are each —$NH_2$, and $R^5$ is phenyl is named herein as 4-(phenylhydrazono)-4H-pyrazole-3,5-diamine.

In compounds of formula (I), formula (Ia) and formula (Ib) the following structural moiety:

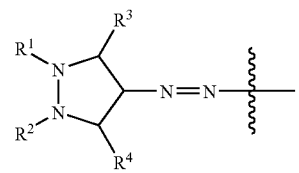

is used to represent a family of tautomeric structures. In part, the particular tautomeric structure(s) encompassed by the compounds of formula (1), formula (Ia) and formula (Ib) depend on the selection of $R^3$ and $R^4$. For example, when $R^3$ and $R^4$ are each —$NH_2$, and $R^1$ and $R^2$ are each hydrogen or independently a part of a double bond, the following tautomeric structures are possible for compounds of formula (I), formula (Ia) and formula (Ib):

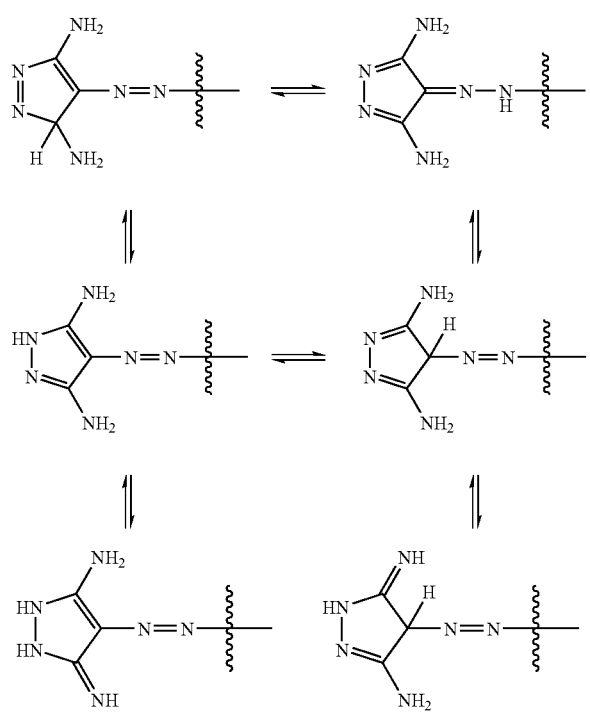

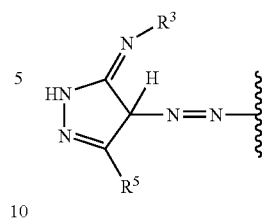

-continued

Unless otherwise indicated by the nomenclature, compound names are intended to include any single tautomer, single stereoisomer, enantiomer, racemate or mixtures thereof.

B. Pharmaceutical Compositions and Administration

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

Depending on the substitutions at $R^1$, $R^2$, $R^3$ and $R^4$ of formula (I), one of ordinary skill in the art could easily ascertain which tautomeric structure would be available. All such tautomers are considered to be within the scope of the invention. Similar tautomeric structures are also available for compounds of formula (Ia) and formula (Ib), as set forth above in the Summary of the Invention and herein, and are also considered to be within the scope of the invention.

Likewise, the following tautomeric structures are encompassed by the structure depicted as formula (Ic):

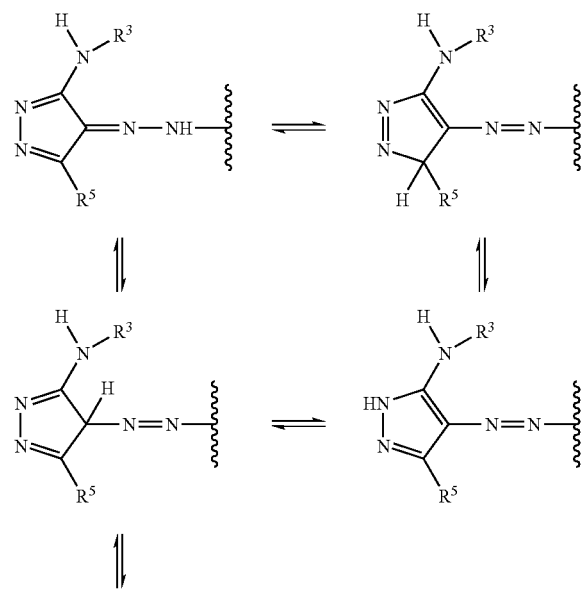

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The compounds can be utilized in aerosol formulation to be administered via inhalation. The compounds of the present invention can be formulated into pressurized acceptable propellants such as dichlorodifluoromethane, propane, nitrogen and the like.

Furthermore, the compounds can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at ambient temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more compounds of the present invention. Similarly, unit dosage forms for injection or intravenous administration may comprise the compound of the present invention in a composition as a solution in sterile water, normal saline or another pharmaceutically acceptable carrier.

Implants for sustained release formulations are well known in the art. Implants are formulated as microspheres, slabs, etc. with biodegradable or non-biodegradable polymers. For example, polymers of lactic acid and/or glycolic acid form an erodible polymer that is well tolerated by the host. The implant containing the inhibitory compounds is placed in proximity to the site of the tumor, so that the local concentration of active agent is increased relative to the rest of the body.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

The combined use of the provided inhibitory compounds and other cytotoxic agents has the advantages that the required dosages for the individual drugs is lower, and the effect of the different drugs complementary. Depending on the patient and condition being treated and on the administration route, the subject inhibitory compounds may be administered in dosages of 0.1 µg to 10 mg/kg body weight per day. The range is broad, since in general the efficacy of a therapeutic effect for different mammals varies widely with doses typically being 20, 30 or even 40 times smaller (per unit body weight) in man than in the rat. Similarly the mode of administration can have a large effect on dosage. Thus for example oral dosages in the rat may be ten times the injection dose. Higher doses may be used for localized routes of delivery.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

For use in the subject methods, the subject compounds may be formulated with other pharmaceutically active agents, particularly other anti-metastatic, anti-tumor or anti-angiogenic agents. Angiostatic compounds of interest include angiostatin, endostatin, carboxy terminal peptides of collagen alpha (XV), etc. Cytotoxic and cytostatic agents of interest include adriamycin, alkeran, Ara-C, BICNU, busulfan, CNNU, cis-platinum, cytoxan, daunorubicin, DTIC, 5-FU, hydrea, ifosfamide, methotrexate, mithramycin, mitomycin, mitoxantrone, nitrogen mustard, velban, vincristine, vinblastine, VP-16, carboplatinum, fludarabine, gemcitabine, idarubicin, irinotecan, leustatin, navelbine, taxol, taxotere, topotecan, etc.

C. Methods of Use

The compounds and pharmaceutical compositions of the invention are administered to a subject having a hyperproliferative disorders, e.g. to inhibit tumor growth, to inhibit angiogenesis, to decrease inflammation associated with a lymphoproliferative disorder, to inhibit graft rejection, or neurological damage due to tissue repair, etc. The present compounds are useful for prophylactic or therapeutic purposes. The prevention of proliferation is accomplished by administration of the subject compounds prior to development of overt disease, e.g. to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one h and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by protein kinases. Protein kinases are involved in signaling pathways for such important cellular activities as responses to extracellular signals and cell cycle checkpoints. Inhibition of specific protein kinases provides a means of intervening in these signaling pathways, for example to block the effect of an extracellular signal, to release a cell from cell cycle checkpoint, etc. Defects in the activity of protein kinases are associated with a variety of pathological or clinical conditions, where there is a defect in signaling mediated by protein kinases. Such conditions include those associated with defects in cell cycle regulation or in response to extracellular signals, e.g. hyperglycemia and diabetes Type I and Type II, immunological disorders, e.g. autoimmune and immunodeficiency diseases; hyperproliferative disorders, which may include psoriasis, arthritis, inflammation, angiogenesis, endometriosis, scarring, cancer, etc.

The compounds of the present invention are active in inhibiting purified kinase proteins, i.e. there is a decrease in the phosphorylation of a specific substrate in the presence of the compound. A protein kinase of particular interest in integrin linked kinase (ILK). ILK is a serine threonine kinase. The DNA and predicted amino acid sequence may be accessed at Genbank, no. U40282, or as published in Hannigan et al. (1996) *Nature* 379:91-96. ILK regulates integrin extracellular activity (ECM interactions) from inside the cell via its direct interaction with the integrin subunit. Interfering with ILK activity allows the specific targeting of integrin function, while leaving other essential signaling pathways intact. Increased levels of cellular ILK activity short circuits the normal requirement for adhesion to extracellular membrane in regulating cell growth. Thus, inhibiting ILK activity may inhibit anchorage-independent cell growth.

It is also known that many cell types undergo apoptosis if the appropriate contacts with extracellular matrix proteins are not maintained (anoikis). The induction of apoptosis by the subject compounds in such cells predicts an association with the ILK signaling pathway.

The compounds of the present invention bind to protein kinases at a high affinity, and find use as affinity reagents for the isolation and/or purification of such kinases. Affinity chromatography is used as a method of separating and purifying protein kinases and phosphatases using the biochemical affinity of the enzyme for inhibitors that act on it. The compounds are coupled to a matrix or gel. Preferably a microsphere or matrix is used as the support. Such supports are known in the art and commercially available. The inhibitor coupled support is used to separate an enzyme that binds to the inhibitor from a complex mixture, e.g. a cell lysate, that may optionally be partially purified. The sample mixture is contacted with the inhibitor coupled support under conditions that minimize non-specific binding. Methods known in the art include columns, gels, capillaries, etc. The unbound compounds are washed free of the resin, and the bound proteins are then eluted in a suitable buffer.

The compounds of the invention may also be useful as reagents for studying signal transduction or any of the clinical disorders listed throughout this application.

Hyper-Proliferative Disorders of Interest

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature. Angiogenesis may be inhibited by affecting the cellular ability to interact with the extracellular environment and to migrate, which is an integrin-specific function, or by regulating apoptosis of the endothelial cells. Integrins function in cell-to-cell and cell-to-extracellular matrix (ECM) adhesive interactions and transduce signals from the ECM to the cell interior and vice versa. Since these properties implicate integrin involvement in cell migration, invasion, intra- and extravasation, and platelet interaction, a role for integrins in tumor growth and metastasis is obvious.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Some cancers of particular interest include breast cancers, which are primarily adenocarcinoma subtypes. Ductal carcinoma in situ is the most common type of noninvasive breast cancer. In DCIS, the malignant cells have not metastasized through the walls of the ducts into the fatty tissue of the breast. Infiltrating (or invasive) ductal carcinoma (IDC) has metastasized through the wall of the duct and invaded the fatty tissue of the breast. Infiltrating (or invasive) lobular carcinoma (ILC) is similar to IDC, in that it has the potential metastasize elsewhere in the body. About 10% to 15% of invasive breast cancers are invasive lobular carcinomas.

Also of interest is non-small cell lung carcinoma. Non-small cell lung cancer (NSCLC) is made up of three general subtypes of lung cancer. Epidermoid carcinoma (also called squamous cell carcinoma) usually starts in one of the larger bronchial tubes and grows relatively slowly. The size of these tumors can range from very small to quite large. Adenocarcinoma starts growing near the outside surface of the lung and may vary in both size and growth rate. Some slowly growing adenocarcinomas are described as alveolar cell cancer. Large cell carcinoma starts near the surface of the lung, grows rapidly, and the growth is usually fairly large when diagnosed. Other less common forms of lung cancer are carcinoid, cylindroma, mucoepidermoid, and malignant mesothelioma.

Melanoma is a malignant tumor of melanocytes. Although most melanomas arise in the skin, they also may arise from mucosal surfaces or at other sites to which neural crest cells migrate. Melanoma occurs predominantly in adults, and more than half of the cases arise in apparently normal areas of the skin. Prognosis is affected by clinical and histological factors and by anatomic location of the lesion. Thickness and/or level of invasion of the melanoma, mitotic index, tumor infiltrating lymphocytes, and ulceration or bleeding at the primary site affect the prognosis. Clinical staging is based on whether the tumor has spread to regional lymph nodes or distant sites. For disease clinically confined to the primary site, the greater the thickness and depth of local invasion of the melanoma, the higher the chance of lymph node metastases and the worse the prognosis. Melanoma can spread by local extension (through lymphatics) and/or by hematogenous routes to distant sites. Any organ may be involved by metastases, but lungs and liver are common sites.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

Thus, in one aspect the present invention relates to therapeutic compositions and methods for the treatment of inflammatory disorders including autoimmune diseases using compounds that inhibit ILK activity. Such disorders and diseases include, but are not limited to, psoriasis, rheumatoid arthritis, multiple sclerosis, scleroderma, systemic lupus erythematosus, Sjögren's syndrome, atopic dermatitis, asthma, and allergy. Target cells susceptible to the treatment include cells involved in instigating autoimmune reactions as well as those suffering or responding from the effects of autoimmune attack or inflammatory events.

Although psoriasis is not life threatening, the social stigma and reduction in quality of life associated with disease are profound issues for these patients and their families. Established anti-psoriasis therapies have been grouped into suppressive and remittive types. Suppressive therapies (e.g. cyclosporine, topical calcitriol, methotrexate, retinoids), produce plaque clearance although these medications are not associated with a complete normalization of skin pharmacodynamic markers or large reductions in plaque T cell numbers. Phototherapy with ultraviolet (UV) B (280-320 nm) light alone or in combination with coal tar derivatives and photochemotherapy with 8-methoxypsoralen combined with UVA (320-400 nm) light (PUVA) are classified as remittive-type anti-psoriasis therapies. UVB light and PUVA are typically delivered in multiple treatment sessions, often several times weekly, until plaque clearance is achieved. The present invention provides compounds that may be administered in combination with established anti-psoriasis therapies.

Renal Disorders of Interest

In one aspect of the invention, the compounds disclosed herein may be used to modulate integrin-linked kinase (ILK) for the treatment of renal diseases. Thus, the present invention provides therapeutic compositions and methods for treating renal disease, and specifically provides therapeutic compositions and methods directed to modulating, and especially inhibiting, the activity of ILK so as to ameliorate glomerular renal disease states which may result in proteinuria, or states characterized by tubular or tubulo-interstitial damage. Preferred compounds of the invention may be identified by screening for biological activity in an ILK-based functional assay, e.g. in vitro or in vivo ILK kinase activity.

According to current therapies, chronic progression of renal disease can be slowed for 6-12 months using angiotensin-converting enzyme (ACE) inhibitors, but there is no other satisfactory treatment at this time besides dialysis and ultimately transplantation of the organ. According to the present invention, compounds of the invention serving as ILK inhibiting agents may be administered at an appropriate time, before, concurrent or after, in relation to a second therapy for treating renal disorder, where that second therapy includes, but is not limited to, administration of an ACE inhibitor, or a pharmaceutically acceptable salt thereof, and a pharmaceutically acceptable carrier to a mammal in need thereof. ACE inhibitors include, but are not limited to, captopril, benazepril, enalapril, fosinopril, lisinopril, quinapril, ramipril, imidapril, perindopril, erbumine, and trandolapril. ACE Receptor Blockers may also be used in place of, or as well as, ACE inhibitors, and these include losartan, irbesartan, candesartan, cilexetil, and valsartan.

Thus, in one aspect, the present invention provides a method for treating a patient with renal dysfunction comprising administering to the patient an effective amount of a compound or pharmaceutical composition of the invention. In various embodiments, the compound or composition is administered orally, or the compound is administered intravenously, or the compound is administered intraperitneally. The compound may be administered intralumenally in or around the kidney. The patient may also be treated with an ACE inhibitor.

In one aspect, the present invention provides a method for lowering the protein levels in urine, comprising administering to that patient an effective amount of an compound or pharmaceutical composition of the invention. In various embodiments, the compound or composition is administered orally, or intravenously, or intraperitneally. The compound may be administered intralumenally in or around the kidney. The patient may also be treated with an ACE inhibitor.

Eye Disorders

In one aspect, the present invention relates to the use of the compounds and pharmaceutical compositions of the invention as disclosed herein as inhibitors of integrin-linked kinase (ILK) in the treatment of various eye diseases with underlining pathology of neovascularization of cornea, iris, retina or choroids. The subject methods are used for prophylactic or therapeutic purposes to treat ocular diseases to prevent, reduce or reverse the loss of visual acuity as well as loss of vision secondary to neovascularization of cornea, iris, retina or choroid. While treatment during early stages is desirable, the adverse symptoms of the disease may be at least partially alleviated by treatment during later stages.

In one aspect, compounds of the invention that modulate the activity of integrin linked kinase (ILK) are administered systemically or locally to treat ophthalmic diseases with an underlining pathology that is characteristic of ocular neovascularization. Such a treatment is used alone as single therapy or in combination with a second therapy as an adjunct to prevent, to reduce or to reverse the loss of visual acuity as well as loss of vision secondary to neovascularization of cornea, iris, retina or choroids.

For example, in one aspect the invention is directed to a method to prevent, to reduce or to reverse ocular neovascularization in an eye of an animal having a neovascular lesion, comprising the steps of identifying said lesion in the eye of the animal, administering to the animal an amount of a compound of the invention as disclosed herein sufficient to allow said compound to localize in said lesion. Methods utilizing local administration that provides for a prolonged localized concentration, which may utilize sustained release implants, viscous solutions, or other topical formulation, are of particular interest. A compound of the invention may be administered alone as single therapy, or in combination with a second therapy, for example at an appropriate time, before, concurrent or after, in relation to a second therapy including but not limited to Visudyne™ therapy, photocoagulation or transpupillary thermotherapy as an adjunct treatment for ocular neovascularization.

Some examples of ocular disorders that may be treated by various embodiments of the present invention include, without limitation: retinal diseases (diabetic retinopathy, chronic glaucoma, retinal detachment, sickle cell retinopathy, age related macular degeneration (AMD) due to subretinal neovascularization); rubeosis iritis; inflammatory diseases; chronic uveitis; neoplasms (retinoblastoma, pseudoglioma); Fuchs' heterochromic iridocyclitis; neovascular glaucoma; corneal neovascularization (inflammatory, transplantation, developmental hypoplasia of the iris); neovascularization resulting following a combined vitrectomy and lensectomy; vascular diseases (retinal ischemia, choroidal vascular insufficiency, choroidal thrombosis, carotid artery ischemia); neovascularization of the optic nerve; and neovascularization due to penetration of the eye or contusive ocular injury.

In practicing the method of treatment or use of a compound of the invention in an ophthalmic diseases with an underlining pathology that is characteristic of ocular neovascularization, a therapeutically effective amount of a compound of the invention is administered to a subject afflicted with a disease or disorder related to neovascularization, or to a tissue that has been neovascularized. The compound may be administered in accordance with the method of the invention either alone or in combination with other known therapies for neovascularization. When co-administered with one or more other therapies, the compound may be administered either simultaneously with the other treatment(s), or sequentially. If administered sequentially, the attending physician will decide on the appropriate sequence of administration, which may be before or after a second therapy.

Secondary therapies of interest include verteporfin (VISUDYNE™) therapy, see, for example Madreperla (2001) *Arch Ophthalmol.* 119(11):1606-1610; Harding (2001) *Eye* 15(Pt 3):407-12; Sharma (2001) *Can Fam Physician* 47:955, 963; and photocoagulation or transpupillary thermotherapy, see, e.g., Rogers et al. (2001) *Curr Opin Ophthalmol* 12(3):212-5; Ardjomand et al. (2001) *Ophthalmologica* 215(3):241-4; Mainster et al. (2000) *Ophthalmic Surg Lasers* 31(5):359-73. Other therapies include, without limitation, those set forth in U.S. Pat. No. 6,297,228, "Use of angiostatic steroids in photodynamic therapy", U.S. Pat. No. 6,271,233 "Method for treating ocular neovascular diseases"; U.S. Pat. No. 6,248,734 "Use of photodynamic therapy for prevention of secondary cataracts"; U.S. Pat. RE37,180 "Photochemotherapeutical obstruction of newly-formed blood vessels"; U.S. Pat. No. 6,225,303 "Use of green porphyrins to treat neovasculature in the eye"; U.S. Pat. No. 6,217,895 "Method for treating and/or preventing retinal diseases with sustained release corticosteroids"; U.S. Pat. No. 6,214,819 "Method for treating ocular neovascular diseases", and the like.

Some eye diseases lend themselves to acute treatment while others require longer term therapy. Proliferative retinopathy can reach a threshold in a matter of days as seen in ROP, some cases of diabetic retinopathy, and neovascular glaucoma. Premature infants are at risk for neovascularization around what would be 35 weeks gestation, a few weeks after birth, and will remain at risk for a short period of time until the retina becomes vascularized. Diabetic retinopathy can be acute but may also smolder in the proliferative phase for considerably longer. Suitable animal models exist for determination of appropriate dosage, although the efficacy of a therapeutic effect for different mammals varies widely, for example doses typically are 20, 30 or even 40 times smaller (per unit body weight) in man than in the rat. Similarly the mode of administration can have a large effect on dosage. A murine model of oxygen-induced retinal neovascularization has been established which occurs in 100% of treated animals and is quantifiable (Smith et al. (1994) *Invest. Ophthalmol. Vis. Sci* 35:101-111). Bioactivity can be determined by methods including the Miles vessel permeability assay (Miles and Miles (1952) *J. Physiol.* (Lond.) 118:228), which measures vessel permeability, and endothelial cell mitogenicity, which measures cell growth.

For local application, a range of about 0.05 to 0.2 or about 0.5 mg/ml of a compound of the invention in an appropriate formulation is administered either intra-ocularly (intra-vitreous, subretinal, intra-anterior chamber, intra-scleral), peri-ocularly, or topically onto the cornea. For systemic application, a range of 0.05 to 100 mg/kg body weight, preferably less than about 10 mg/kg is administered to treat eye disease. For intra- or peri-ocular administration, a compound of the invention in an injectable formulation is administered by either an intra-ocular injection at above-described concentrations and at a frequency of once every 2-6 months or by an intra-ocular implantation of a device or a specific formulation of a compound of the invention allowing sustained release of the ILK inhibitor over a period of time. For corneal application, a compound of the invention in an appropriate formulation is applied topically onto the cornea at a frequency of once very 4-6 hours. For systemic application, a compound of the invention in appropriate formulation is administered orally 1-3 times a day.

Thus, in one aspect, the present invention provides a method for treating ocular neovascularization, the method comprising administering a compound or pharmaceutical composition of the invention to treat ocular neovascularization. Optionally, the treatment reduces or reverses the loss of visual acuity secondary to neovascularization of cornea, iris, retina or choroid. The method may further comprise administering a second therapy for ocular neovascularization, where a suitable second therapy is selected from the group consisting of Visudyne™ therapy, photocoagulation and transpupillary thermotherapy. In the present method, the ocular neovascularization may be selected from the group consisting of diabetic retinopathy, chronic glaucoma, retinal detachment, sickle cell retinopathy, age related macular degeneration (AMD) due to subretinal neovascularization; rubeosis iritis; inflammatory diseases; chronic uveitis; neoplasms; Fuchs' heterochromic iridocyclitis; neovascular glaucoma; corneal neovascularization; neovascularization resulting following a combined vitrectomy and lensectomy; retinal ischemia, choroidal vascular insufficiency, choroidal thrombosis, carotid artery ischemia; neovascularization of the optic nerve; and neovascularization due to penetration of the eye or contusive ocular injury. In various embodiments, the compound of the invention is administered systemically, or intra-ocularly, or peri-ocularly, or is administered topically onto the cornea, or is administered by intra-ocular injection, or is administered by intra-ocular implantation.

D. Preferred Embodiments

Of the pharmaceutical compositions described above in the Summary of the Invention, a preferred group is that group of pharmaceutical compositions comprising a pharmaceutically acceptable carrier, diluent or excipient and a compound of formula (I) wherein $R^1$ and $R^2$ are each part of a double bond of the pyrazole ring, i.e., a compound of formula (Ia):

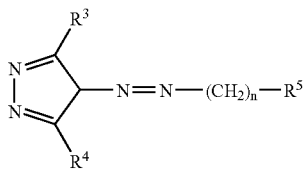

(Ia)

Of this preferred group of pharmaceutical compositions, a preferred subgroup is that subgroup of pharmaceutical compostions comprising a pharmaceutically acceptable carrier, diluent or excipient and a compound of formula (Ia) wherein:
n is 0 to 5;
$R^3$ and $R^4$ are each independently —$N(R^7)_2$ or —$N(R^7)C(O)R^6$;
$R^5$ is aryl optionally substituted with one or more substituents selected from the group consisting of alkyl, halo, nitro, cyano, haloalkyl, haloalkoxy, aryl, heterocyclyl, heterocyclylalkyl, —$OR^6$, —$R^8$—$OR^6$, —$R^8$—$[O$—$R^8]_m$—$OR^6$ (where m is 1 to 4), —$S(O)_2OH$, —$S(O)_tR^7$ (where t is 0 to 2), —$S(O)_t$—$R^8$—$OR^6$, —$S(O)_t$—$N(R^6)_2$, —$R^8$—$P(O)(OR^9)_2$, —$C(O)OR^6$, —$R^8$—$C(O)OR^6$, —$C(O)N(R^6)_2$, —$N(R^7)_2$, —$R^8$—$N(R^7)_2$, and —$N(R^9)C(O)R^6$;
each $R^6$ is independently hydrogen, alkyl, aryl, aralkyl, hetereocyclyl or heterocyclylalkyl;
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred subgroup of pharmaceutical compositions, a preferred class is that class of pharmaceutical compositions comprising a pharmaceutically acceptable carrier, diluent or excipient and a compound of formula (Ia) wherein:
n is 0;
$R^3$ and $R^4$ are each —$N(R^7)_2$;
$R^5$ is aryl optionally substituted with one or more substituents selected from the group consisting of alkyl, halo, nitro, cyano, haloalkyl, haloalkoxy, aryl, heterocyclyl, heterocyclylalkyl, —$OR^6$, —$R^8$—$OR^6$, —$R^8$—$[O$—$R^8]_m$—$OR^6$ (where m is 1 to 4), —$S(O)_2OH$, —$S(O)_tR^7$ (where t is 0 to 2), —$S(O)_t$—$R^8$—$OR^6$, —$S(O)_t$—$N(R^6)_2$, —$R^8$—$P(O)(OR^9)_2$, —$C(O)OR^6$, —$R^8$—$C(O)OR^6$, —$C(O)N(R^6)_2$, —$N(R^7)_2$, —$R^8$—$N(R^7)_2$, and —$N(R^9)C(O)R^6$;
each $R^6$ is independently hydrogen, alkyl, aryl, aralkyl, hetereocyclyl or heterocyclylalkyl;
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred class of pharmaceutical compositions, a preferred subclass is that subclass of pharmaceutical compositions comprising a pharmaceutically acceptable carrier, diluent or excipient and a compound of formula (Ia) wherein:
n is 0;
$R^3$ and $R^4$ are each —$N(R^7)_2$;
$R^5$ is aryl optionally substituted with one or more substituents selected from the group consisting of alkyl, halo, haloalkyl, haloalkoxy, aryl, and aralkyl.
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred subclass of pharmaceutical compositions, a preferred set of pharmaceutical compositions is that set comprising a pharmaceutically acceptable carrier, diluent or excipient and a compound of formula (Ia) wherein:
n is 0;
$R^3$ and $R^4$ are each —$N(R^7)_2$;
$R^5$ is aryl optionally substituted with one or more substituents selected from the group consisting of alkyl, halo, haloalkyl, haloalkoxy, aryl and aralkyl; and
each $R^7$ is independently hydrogen or alkyl.

Of this preferred set of pharmaceutical compositions, a preferred subset is that subset of pharmaceutical compositions comprising a pharmaceutically acceptable carrier, diluent or excipient and a compound of formula (Ia) wherein:
n is 0:
$R^3$ and $R^4$ are each —$N(R^7)_2$;
$R^5$ is phenyl optionally substituted with one or more substituents selected from the group consisting of alkyl, halo, haloalkyl, haloalkoxy, aryl, and aralkyl optionally substituted by —$N(R^7)_2$; and
each $R^7$ is hydrogen or alkyl.

Of this preferred subset of pharmaceutical compositions, preferred pharmaceutical compositions are those comprising a pharmaceutically acceptable carrier, diluent or excipient and a compound selected from the group consisting of the following:
4-[(4-fluorophenyl)hydrazono]-4H-pyrazole-3,5-diamine;
4-[(3-ethylphenyl)hydrazono]-4H-pyrazole-3,5-diamine;
4-[(3-chlorophenyl)hydrazono]-4H-pyrazole-3,5-diamine;
4-[(3-fluorophenyl)hydrazono]-4H-pyrazole-3,5-diamine;
4-[(4-trifluoromethylphenyl)hydrazono]-4H-pyrazole-3,5-diamine;
4-(3-phenylphenylhydrazono)-4H-pyrazole-3,5-diamine;
4-[(2-bromophenyl)hydrazono]-4H-pyrazole-3,5-diamine;
4-[(3-bromophenyl)hydrazono]-4H-pyrazole-3,5-diamine;
4-[(4-bromophenyl)hydrazono]-4H-pyrazole-3,5-diamine;
4-[(4-iodophenyl)hydrazono]-4H-pyrazole-3,5-diamine;
4-(o-tolylhydrazono)-4H-pyrazole-3,5-diamine;
4-[(2,6-difluorophenyl)hydrazono]-4H-pyrazole-3,5-diamine;
4-[(3,4-difluorophenyl)hydrazono]-4H-pyrazole-3,5-diamine;
4-[(3,4-dichlorophenyl)hydrazono]-4H-pyrazole-3,5-diamine;
4-[(3,5-dichlorophenyl)hydrazono]-4H-pyrazole-3,5-diamine;
4-[(2-isopropylphenyl)hydrazono]-4H-pyrazole-3,5-diamine;
4-[(3-trifluoromethylphenyl)hydrazono]-4H-pyrazole-3,5-diamine;
4-[(2-chlorophenyl)hydrazono]-4H-pyrazole-3,5-diamine;
4-[(3-iodophenyl)hydrazono]-4H-pyrazole-3,5-diamine;
4-(2,3,4,5,6-pentafluorophenylhydrazono)-4H-pyrazole-3,5-diamine;
4-[(3,5-difluorophenyl)hydrazono]-4H-pyrazole-3,5-diamine;
4-[(2,3,4-trifluorophenyl)hydrazono]4H-pyrazole-3,5-diamine;
4-[(3-trifluoromethoxyphenyl)hydrazono]-4H-pyrazole-3,5-diamine;
4-[(4-chloro-3-trifluoromethylphenyl)hydrazono]-4H-pyrazole-3,5-diamine;
4-[(4-benzylphenyl)hydrazono]-4H-pyrazole-3,5-diamine;
4-(4-(phenyl)phenylhydrazono)-4H-pyrazole-3,5-diamine;
4-{[4-(4-methylaminobenzyl)phenyl]hydrazono}-4H-pyrazole-3,5-diamine;
4-[(2,3-difluoro-4-trifluoromethylphenyl)hydrazono]-4H-pyrazole-3,5-diamine;

4-[(3-fluoro-5-trifluoromethylphenyl)hydrazono]-4H-pyrazole-3,5-diamine; and

N-ethyl-4-(phenylhydrazono)-4H-pyrazole-3,5-diamine.

Of the preferred subclass of pharmaceutical compositions set forth above, another preferred set of pharmaceutical compositions is that set comprising a pharmaceutically acceptable carrier, diluent or excipient and a compound of formula (Ia) wherein:

n is 0:

$R^3$ and $R^4$ are each —$NH_2$; and $R^5$ is naphthyl optionally substituted with one or more substituents selected from the group consisting of alkyl, halo, haloalkyl, and haloalkoxy.

Of this preferred set of pharmaceutical compositions, preferred pharmaceutical compositions are those comprising a pharmaceutically acceptable carrier, diluent or excipient and a compound selected from the group consisting of the following:

4-(naphthalen-2-ylhydrazono)-4H-pyrazole-3,5-diamine; and

4-[(4-bromonaphthalen-1-yl)hydrazono]-4H-pyrazole-3,5-diamine.

Of the preferred class of pharmaceutical compositions set forth above, another preferred subclass is that subclass of pharmaceutical compositions comprising a pharmaceutically acceptable carrier, diluent or excipient and a compound of formula (Ia) wherein:

n is 0;

$R^3$ and $R^4$ are each —$N(R^7)_2$;

$R^5$ is aryl optionally substituted with one or more substituents selected from the group consisting of halo, haloalkyl, haloalkoxy, —$OR^6$, —$R^8$—$OR^6$, and —$R^8$—[O—$R^8$]$_m$—$OR^6$ (where m is 1 to 4);

each $R^6$ is independently hydrogen, alkyl, aryl, or aralkyl;

each $R^7$ is independently hydrogen, alkyl, aryl, or aralkyl; and each $R^8$ is a straight or branched alkylene chain.

Of this preferred subclass of pharmaceutical compositions, a preferred set is that set of pharmaceutical compositions comprising a pharmaceutically acceptable carrier, diluent or excipient and a compound of formula (Ia) wherein:

n is 0;

$R^3$ and $R^4$ are each —$NH_2$; and $R^5$ is phenyl optionally substituted with one or more substituents selected from the group consisting of halo, haloalkyl, haloalkoxy, —$OR^6$, —$R^8$—$OR^6$, and —$R^8$—[O—$R^8$]$_m$—$OR^6$ (where m is 1 to 4);

each $R^6$ is independently hydrogen, alkyl, aryl, or aralkyl; and each $R^8$ is a straight or branched alkylene chain.

Of this preferred set of pharmaceutical compositions, preferred pharmaceutical compositions are those comprising a pharmaceutically acceptable carrier, diluent or excipient and a compound selected from the group consisting of the following:

3-[N'-(3,5-diaminopyrazol-4-ylidene)hydrazino]phenol;

4-[(3-methoxyphenyl)hydrazono]4H-pyrazole-3,5-diamine;

4-[(3-fluoro-4-methoxyphenyl)hydrazono]-4H-pyrazole-3,5-diamine;

4-[(3-phenoxy-phenyl)hydrazono]-4H-pyrazole-3,5-diamine;

4-[(4-phenoxyphenyl)hydrazono]-4H-pyrazole-3,5-diamine;

4-[(3-chloro-4-methoxyphenyl)hydrazono]-4H-pyrazole-3,5-diamine;

4-[(3,4-dimethoxyphenyl)hydrazono]-4H-pyrazole-3,5-diamine;

4-[(3-methoxy-5-trifluoromethylphenyl)hydrazono]-4H-pyrazole-3,5-diamine;

{2-[N'-(3,5-diaminopyrazol-4-ylidene)hydrazino]phenyl}methanol;

{2-[N'-(3,5-diaminopyrazol-4-ylidene)hydrazino]phenyl}methanol; and 4-({3-[2-(2-methoxyethoxy)ethoxymethyl]phenyl}hydrazono)-4H-pyrazole-3,5-diamine.

Of the preferred class of pharmaceutical compositions set forth above, another preferred subclass is that subclass of pharmaceutical compositions comprising a pharmaceutically acceptable carrier, diluent or excipient and a compound of formula (Ia) wherein:

n is 0;

$R^3$ and $R^4$ are each —$N(R^7)_2$;

$R^5$ is aryl optionally substituted with one or more substituents selected from the group consisting of alkyl, nitro, —$OR^6$, —$R^8$—$OR^6$, —$C(O)OR^6$, —$C(O)N(R^6)_2$, —$N(R^7)_2$, —$R^8$—$N(R^7)_2$, and —$N(R^9)C(O)R^6$;

each $R^6$ is independently hydrogen, alkyl, aryl, aralkyl, hetereocyclyl or heterocyclylalkyl;

each $R^7$ is independently hydrogen, alkyl, haloalkyl, aryl, aralkyl, heterocyclyl, heterocyclylalkyl, or —$R^8$—$OR^9$;

each $R^8$ is a straight or branched alkylene chain; and each $R^9$ is hydrogen or alkyl.

Of this preferred subclass of pharmaceutical compositions, a preferred set is that set of pharmaceutical compositions comprising a pharmaceutically acceptable carrier, diluent or excipient and a compound of formula (Ia) wherein:

n is 0;

$R^3$ and $R^4$ are each —$NH_2$;

$R^5$ is phenyl optionally substituted with one or more substituents selected from the group consisting of alkyl, nitro, —$OR^6$, —$R^8$—$OR^6$, —$C(O)OR^6$, —$C(O)N(R^6)_2$, —$N(R^7)_2$, —$R^8$—$N(R^7)_2$, and —$N(R^9)C(O)R^6$;

each $R^6$ is independently hydrogen, alkyl, aryl, or aralkyl;

each $R^7$ is independently hydrogen, alkyl, haloalkyl, aryl, aralkyl, —$R^8$—$OR^9$, or heterocyclyl optionally substituted by —$C(O)N(R^9)_2$;

each $R^8$ is a straight or branched alkylene chain; and each $R^9$ is hydrogen or alkyl.

Of this preferred set of pharmaceutical compositions, preferred pharmaceutical compositions are those comprising a pharmaceutically acceptable carrier, diluent or excipient and a compound selected from the group consisting of the following:

5-{4-[N'-(3,5-diaminopyrazol-4-ylidene)hydrazino]benzylamino}-[2,1,3]-thiadiazole-4-carboxylic acid amide;

4-[N'-(3,5-diaminopyrazol-4-ylidene)hydrazino]benzoic acid ethyl ester;

3-[N'-(3,5-diaminopyrazol-4-ylidene)hydrazino]benzoic acid ethyl ester;

4-[(3-nitrophenyl)hydrazono]-4H-pyrazole-3,5-diamine;

4-[(4-methoxy-3-nitrophenyl)hydrazono]-4H-pyrazole-3,5-diamine;

4-[(4-nitro-3-trifluoromethylphenyl)hydrazono]-4H-pyrazole-3,5-diamine;

4-[(4-phenylaminophenyl)hydrazono]-4H-pyrazole-3,5-diamine;

4-[N'-(3,5-diaminopyrazol-4-ylidene)hydrazino]-2-diethylaminomethylphenol;

4-[(2-methyl-5-nitrophenyl)hydrazono]-4H-pyrazole-3,5-diamine;

{3-[N'-(3,5-diaminopyrazol-4-ylidene)hydrazino]-5-nitrophenyl}methanol;

4-[(3-diethylaminomethylphenyl)hydrazono]-4H-pyrazole-3,5-diamine; and

4-[(3-dimethylaminomethylphenyl)hydrazono]-4H-pyrazole-3,5-diamine.

Of the preferred class of pharmaceutical compositions set forth above, another preferred subclass is that subclass of pharmaceutical compositions comprising a pharmaceutically acceptable carrier, diluent or excipient and a compound of formula (Ia) wherein:

n is 0;

$R^3$ and $R^4$ are each —$N(R^7)_2$;

$R^5$ is phenyl optionally substituted with one or more substituents selected from the group consisting of —$S(O)_2OH$, —$S(O)_tR^7$ (where t is 0 to 2), —$S(O)_t$—$R^8$—$OR^6$, —$S(O)_t$—$N(R^6)_2$, and —$R^8$—$P(O)(OR^9)_2$, each $R^6$ is independently hydrogen, alkyl, aryl, aralkyl, hetereocyclyl or heterocyclylalkyl;

each $R^7$ is independently hydrogen, alkyl, haloalkyl, aryl, aralkyl, heterocyclyl, heterocyclylalkyl, or —$R^8$—$OR^9$;

each $R^8$ is a straight or branched alkylene chain; and each $R^9$ is hydrogen or alkyl.

Of this preferred subclass of pharmaceutical compositions, preferred pharmaceutical compositions are those comprising a pharmaceutically acceptable carrier, diluent or excipient and a compound selected from the group consisting of the following:

4-[(4-methylsulfanylphenyl)hydrazono]-4H-pyrazole-3,5-diamine;

4-[(2-benzenesulfonylphenyl)hydrazono]-4H-pyrazole-3,5-diamine;

4-[N'-(3,5-diaminopyrazol-4-ylidene)hydrazino]-N-(2,6-dimethylpyrimidin-4-yl)benzenesulfonamide;

4-[N'-(3,5-diaminopyrazol-4-ylidene)hydrazino]benzenesulfonamide;

4-[(3-methylsulfanylphenyl)hydrazono]-4H-pyrazole-3,5-diamine;

4-[N'-(3,5-diaminopyrazol-4-ylidene)hydrazino]-N-(pyrimidin-2-yl)benzenesulfonamide;

1-{3-[N'-(3,5-diaminopyrazol-4-ylidene)hydrazino]phenyl}ethanethione;

{4-[N'-(3,5-diaminopyrazol-4-ylidene)hydrazino]benzyl}phosphonic acid diethyl ester;

3-[N'-(3,5-diaminopyrazol-4-ylidene)hydrazino]benzenesulfonamide;

4-[(4-trifluoromethanesulfonylphenyl)hydrazono]-4H-pyrazole-3,5-diamine;

4-[(4-methanesulfonylphenyl)hydrazono]-4H-pyrazole-3,5-diamine;

N-butyl-3-[N'-(3,5-diaminopyrazol-4-ylidene)hydrazino]benzenesulfonamide;

4-[(3-methanesulfonylphenyl)hydrazono]-4H-pyrazole-3,5-diamine;

4-{[4-(morpholine-4-sulfonyl)phenyl]hydrazono}-4H-pyrazole-3,5-diamine;

4-{[4-(pyrrolidine-1-sulfonyl)phenyl]hydrazono}-4H-pyrazole-3,5-diamine;

4-[(3-trifluoromethanesulfonylphenyl)hydrazono]-4H-pyrazole-3,5-diamine;

2-{3-[N'-(3,5-diaminopyrazol-4-ylidene)hydrazino]benzenesulfonyl}ethanol;

4-[N'-(3,5-diaminopyrazol-4-ylidene)hydrazino]-N-methyl-benzenesulfonamide;

3-[N'-(3,5-diaminopyrazol-4-ylidene)hydrazino]-N-methyl-benzenesulfonamide;

4-[N'-(3,5-diaminopyrazol-4-ylidene)hydrazino]-N-ethyl-benzenesulfonamide;

3-[N'-(3,5-diaminopyrazol-4-ylidene)hydrazino]-N-ethyl-benzenesulfonamide;

3-[N'-(3,5-diaminopyrazol-4-ylidene)hydrazino]-N-(2-hydroxyethyl)benzenesulfonamide;

3-[N'-(3-amino-5-dimethylaminopyrazol-4-ylidene)-hydrazino]-N-methyl-benzenesulfonamide; and 3-[N'-(3-amino-5-morpholin-4-yl-pyrazol-4-ylidene)-hydrazino]-benzenesulfonamide.

Of the preferred class of pharmaceutical compositions set forth above, another preferred subclass is that subclass of pharmaceutical compositions comprising a pharmaceutically acceptable carrier, diluent or excipient and a compound of formula (Ia) wherein:

n is 0;

$R^3$ and $R^4$ are each —$N(R^7)_2$;

$R^5$ is phenyl optionally substituted with one or more substituents selected from the group consisting of alkyl, nitro, halo, haloalkyl, haloalkoxy, heterocyclyl, heterocyclylalkyl (optionally substituted by alkyl), and —$OR^6$;

$R^6$ is hydrogen or alkyl;

each $R^7$ is independently hydrogen, alkyl, haloalkyl, aryl, aralkyl, heterocyclyl, heterocyclylalkyl, or —$R^8$—$OR^9$;

each $R^8$ is a straight or branched alkylene chain; and each $R^9$ is hydrogen or alkyl.

Of this preferred subclass, a preferred set is that set of pharmaceutical compositions comprising a pharmaceutically acceptable carrier, diluent or excipient and a compound of formula (Ia) wherein:

n is 0;

$R^3$ and $R^4$ are each —$N(R^7)_2$;

$R^5$ is phenyl optionally substituted with one or more substituents selected from the group consisting of alkyl, nitro, halo, haloalkyl, haloalkoxy, morpholinyl, piperidinyl, morpholinylmethyl, morpholinylethyl, pyrrolidinylmethyl, piperidinylmethyl, and piperazinylmethyl (optionally substituted by alkyl), and —$OR^6$; and $R^6$ is hydrogen or alkyl; and each $R^7$ is independently hydrogen or alkyl.

Of this preferred set of pharmaceutical compositions, preferred pharmaceutical compositions are those comprising a pharmaceutically acceptable carrier, diluent or excipient and a compound selected from the group consisting of the following:

4-[(4-morpholin-4-ylphenyl)hydrazono]4H-pyrazole-3,5-diamine;

4-[(3-chloro-4-(morpholin-4-yl)phenyl)hydrazono]-4H-pyrazole-3,5-diamine;

4-[(4-(piperidin-1yl)phenyl)hydrazono]-4H-pyrazole-3,5-diamine;

4-[(3-(morpholin-4-ylmethyl)phenyl)hydrazono]-4H-pyrazole-3,5-diamine;

4-[(3-(piperidin-1-ylmethyl)phenyl)hydrazono]-4H-pyrazole-3,5-diamine;

4-[(4-methyl-3-(morpholin-4-yl)phenyl)hydrazono]-4H-pyrazole-3,5-diamine;

4-[(4-methoxy-3-(morpholin-4-yl)methylphenyl)hydrazono]-4H-pyrazole-3,5-diamine;

4-[N'-(3,5-diaminopyrazol-4-ylidene)hydrazino]-2-(morpholin-4-yl)methylphenol;

4-[(2-methyl-4-(morpholin-4-yl)phenyl)hydrazono]-4H-pyrazole-3,5-diamine;

4-[(4-fluoro-2-(morpholin-4-ylmethyl)phenyl)hydrazono]-4H-pyrazole-3,5-diamine;

4-[(3-(morpholin-4-ylmethyl)-5-trifluoromethylphenyl)hydrazono]-4H-pyrazole-3,5-diamine;

4-[(3-fluoro-4-(morpholin-4-ylmethyl)phenyl)hydrazono]-4H-pyrazole-3,5-diamine;

4-[(4-(morpholin-4-ylmethyl)phenyl)hydrazono]-4H-pyrazole-3,5-diamine;

4-{[4-((4-methylpiperazin-1-yl)methyl)phenyl]hydrazono}-4H-pyrazole-3,5-diamine;

4-{[3-((4-methylpiperazin-1-yl)methyl)phenyl]hydrazono}-4H-pyrazole-3,5-diamine;
4-[(3-(morpholin-4-ylmethyl)-5-nitrophenyl)hydrazono]-4H-pyrazole-3,5-diamine;
4-{[4-(2-(morpholin-4-yl)ethyl)phenyl]hydrazono}-4H-pyrazole-3,5-diamine;
4-[(3-(pyrrolidin-1-ylmethyl)phenyl)hydrazono]-4H-pyrazole-3,5-diamine;
4-[(4-(piperidin-1-ylmethyl)phenyl)hydrazono]-4H-pyrazole-3,5-diamine;
4-[(3-fluoro-phenyl)-hydrazono]-N,N-dimethyl-4H-pyrazole-3,5-diamine;
{3-[N'-(3-amino-5-dimethylaminopyrazol-4-ylidene)-hydrazino]-5-trifluoromethylphenyl}-methano; and
N,N-dimethyl-4-[(3-morpholin-4-ylmethylphenyl)-hydrazono]-4H-pyrazole-3,5-diamine.

Of the preferred subgroup of pharmaceutical compositions set forth above, another preferred class is that class of pharmaceutical compositions comprising a pharmaceutically acceptable carrier, diluent or excipient and a compound of formula (Ia) wherein:
n is 0 to 5;
$R^3$ and $R^4$ are each independently —$N(R^7)_2$ or —$N(R^7)C(O)R^6$;
$R^5$ is heterocyclyl optionally substituted with one or more substituents selected from the group consisting of alkyl, halo, nitro, cyano, haloalkyl, haloalkoxy, aryl, heterocyclyl, heterocyclylalkyl, —$OR^6$, —$R^8$—$OR^6$, —$R^8$—[O—$R^8]_m$—$OR^6$ (where m is 1 to 4), —$S(O)_2OH$, —$S(O)_tR^7$ (where t is 0 to 2), —$S(O)_t$—$R^8$—$OR^6$, —$S(O)_t$—$N(R^6)_2$, —$R^8$—$P(O)(OR^9)_2$, —$C(O)OR^6$, —$R^8$—$C(O)OR^6$, —$C(O)N(R^6)_2$, —$N(R^7)_2$, —$R^8$—$N(R^7)_2$, and —$N(R^9)C(O)R^6$;
each $R^6$ is independently hydrogen, alkyl, aryl, aralkyl, hetereocyclyl or heterocyclylalkyl;
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred class of pharmaceutical compositions, a preferred subclass is that subclass of pharmaceutical compositions comprising a pharmaceutically acceptable carrier, diluent or excipient and a compound of formula (Ia) wherein:
n is 0;
$R^3$ and $R^4$ are each independently —$N(R^7)_2$;
$R^5$ is heterocyclyl optionally substituted with one or more substituents selected from the group consisting of alkyl, halo, haloalkyl, heterocyclyl, heterocyclylalkyl, —$OR^6$, —$R^8$—$OR^6$, and —$N(R^7)_2$
$R^6$ is alkyl, aryl, aralkyl, hetereocyclyl or heterocyclylalkyl;
each $R^7$ is independently hydrogen, alkyl, haloalkyl, aryl, aralkyl, or —$R^8$—$OR^9$;
each $R^8$ is a straight or branched alkylene chain; and
each $R^9$ is hydrogen or alkyl.

Of this preferred subclass of pharmaceutical compositions, a preferred set is that set of pharmaceutical compositions comprising a pharmaceutically acceptable carrier, diluent or excipient and a compound of formula (Ia) wherein:
n is 0;
$R^3$ and $R^4$ are each independently —$N(R^7)_2$;
$R^5$ is heterocyclyl optionally substituted with one or more substituents selected from the group consisting of alkyl, halo, haloalkyl, —$OR^6$, —$R^8$—$OR^6$, and —$N(R^7)_2$, morpholinyl, piperidinyl, piperazinyl (optionally substituted by alkyl);
$R^6$ is hydrogen, alkyl, aryl, or aralkyl;
each $R^7$ is independently hydrogen, alkyl, haloalkyl, aryl, aralkyl, or —$R^8$—$OR^9$;
each $R^8$ is a straight or branched alkylene chain; and
each $R^9$ is hydrogen or alkyl.

Of this preferred set of pharmaceutical compositions, preferred pharmaceutical compositions are those comprising a pharmaceutically acceptable carrier, diluent or excipient and a compound of formula (Ia) selected from the group consisting of the following:
4-(benzo[1,3]dioxol-5-ylhydrazono)-4H-pyrazole-3,5-diamine;
4-[(2,3-dihydrobenzo[1,4]dioxin-6-yl)hydrazono]-4H-pyrazole-3,5-diamine;
4-[(5-methoxybenzothiazol-2-yl)hydrazono]-4H-pyrazole-3,5-diamine;
4-(benzothiazol-2-ylhydrazono)-4H-pyrazole-3,5-diamine;
4-[(4H-[1,2,4]-triazol-3-yl)hydrazono]-4H-pyrazole-3,5-diamine;
4-[(1H-pyrazol-3-yl)hydrazono]-4H-pyrazole-3,5-diamine;
4-(pyridin-4-ylhydrazono)-4H-pyrazole-3,5-diamine;
4-(pyridin-3-ylhydrazono)-4H-pyrazole-3,5-diamine;
4-[(9-ethyl-9H-carbazol-3-yl)hydrazono]-4H-pyrazole-3,5-diamine;
4-[(6-methoxypyridin-3-yl)hydrazono]-4H-pyrazole-3,5-diamine;
4-[(1H-indazol-5-yl)hydrazono]-4H-pyrazole-3,5-diamine;
4-(quinolin-6-ylhydrazono)-4H-pyrazole-3,5-diamine;
4-[(6-chloropyridin-3-yl)hydrazono]-4H-pyrazole-3,5-diamine;
4-(isoquinolin-5-ylhydrazono)-4H-pyrazole-3,5-diamine;
4-(quinolin-3-ylhydrazono)-4H-pyrazole-3,5-diamine;
4-(benzo[1,2,5]thiadiazol-4-ylhydrazono)-4H-pyrazole-3,5-diamine;
4-(quinolin-8-ylhydrazono)-4H-pyrazole-3,5-diamine;
4-(quinolin-5-ylhydrazono)-4H-pyrazole-3,5-diamine;
4-[(2H-benzotriazol-5-yl)hydrazono]-4H-pyrazole-3,5-diamine;
4-[(2-methyl-2H-benzotriazol-5-yl)hydrazono]-4H-pyrazole-3,5-diamine;
4-(benzo[2,1,3]thiadiazol-5-ylhydrazono)-4H-pyrazole-3,5-diamine;
7-[N'-(3,5-diaminopyrazol-4-ylidene)hydrazino]-4-trifluoromethylchroman-2-one;
4-(quinazolin-6-ylhydrazono)-4H-pyrazole-3,5-diamine;
4-[(1-methyl-1H-benzotriazol-5-yl)hydrazono]-4H-pyrazole-3,5-diamine;
4-[(3-methyl-3H-benzotriazol-5-yl)hydrazono]-4H-pyrazole-3,5-diamine;
4-[(2,2-difluorobenzo[1,3]dioxol-5-yl)hydrazono]-4H-pyrazole-3,5-diamine;
4-[(2,2,3,3-tetrafluoro-2,3-dihydrobenzo[1,4]dioxin-6-yl)hydrazono]-4H-pyrazole-3,5-diamine;
4-[(1,1-dioxo-1H-benzo[b]thiophen-6-yl)hydrazono]-4H-pyrazole-3,5-diamine;
4-(phthalazin-5-ylhydrazono)-4H-pyrazole-3,5-diamine;
4-[(6-(piperidin-1-yl)pyridin-3-yl)hydrazono]-4H-pyrazole-3,5-diamine;
4-[(6-(morpholin-4-yl)pyridin-3-yl)hydrazono]-4H-pyrazole-3,5-diamine;
4-{[6-(4-methylpiperazin-1-yl)pyridin-3-yl]hydrazono}-4H-pyrazole-3,5-diamine;
2-[{5-[N'-(3,5-diaminopyrazol-4-ylidene)hydrazino]pyridin-2-yl}(2-hydroxyethyl)amino]ethanol;
4-[(2,6-dimethoxypyridin-3-yl)hydrazono]-4H-pyrazole-3,5-diamine;
4-[(2,6-dichloropyridin-3-yl)hydrazono]-4H-pyrazole-3,5-diamine;

4-[(6-fluoropyridin-3-yl)hydrazono]-4H-pyrazole-3,5-diamine;
4-[(4-methylpyridin-3-yl)hydrazono]-4H-pyrazole-3,5-diamine;
N,N-dimethyl-4-(quinolin-6-yl-hydrazono)-4H-pyrazole-3,5-diamine;
4-[(6-chloro-pyridin-3-yl)-hydrazono]-N,N-dimethyl-4H-pyrazole-3,5-diamine;
4-[(6-fluoro-pyridin-3-yl)hydrazono]-N,N-dimethyl-4H-pyrazole-3,5-diamine;
N,N-dimethyl-4-(phthalazin-5-yl-hydrazono)-4H-pyrazole-3,5-diamine; and
N,N-dimethyl-4-(pyridin-3-yl-hydrazono)-4H-pyrazole-3,5-diamine.

Of the pharmaceutical compositions described above in the Summary of the Invention, another preferred group is that group of pharmaceutical compositions comprising a pharmaceutically acceptable carrier, diluent or excipient and a compound of formula (I) having the following formula (Ib):

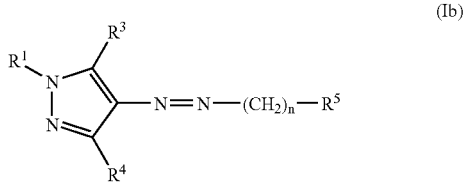

(Ib)

wherein:
n is 0 to 5;
$R^1$ is hydrogen, alkyl, aryl, aralkyl or —C(O)$R^6$;
$R^3$ and $R^4$ are each independently —N($R^7$)$_2$ or —N($R^7$)C(O)$R^6$;
$R^5$ is aryl optionally substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, —$R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$—N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$;
or $R^5$ is heterocyclyl optionally substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, —$R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$—N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$;
each $R^6$ is independently hydrogen, alkyl, aryl, aralkyl, heterocyclyl or heterocyclylalkyl;
each $R^7$ is independently hydrogen, alkyl, haloalkyl, aryl, aralkyl, heterocyclyl, heterocyclylalkyl, or —$R^8$—O$R^9$;
each $R^8$ is a straight or branched alkylene chain; and
each $R^9$ is hydrogen or alkyl.

Of this preferred group of pharmaceutical compositions, a preferred subgroup is that subgroup of pharmaceutical compositions comprising a pharmaceutically acceptable carrier, diluent or excipient and a compound of formula (Ib) wherein:
n is 0;
$R^1$ is hydrogen, alkyl, aryl, aralkyl or —C(O)$R^6$;
$R^3$ and $R^4$ are each independently —N($R^7$)$_2$;
$R^5$ is phenyl optionally substituted with one or more substituents selected from the group consisting of alkyl, halo, haloalkyl, haloalkoxy, or aryl;
or $R^5$ is pyridinyl;
$R^6$ is alkyl, aryl, or aralkyl; and
each $R^7$ is independently hydrogen or alkyl.

Of this preferred subgroup of pharmaceutical compositions, preferred pharmaceutical compositions are those comprising a pharmaceutically acceptable carrier, diluent or excipient and a compound of formula (Ib) selected from group consisting of the following:
1-phenyl-4-phenylazo-1H-pyrazole-3,5-diamine;
(3,5-diamino-4-phenylazopyrazol-1-yl)phenylmethanone;
1-(4-bromophenyl)-4-phenylazo-1H-pyrazole-3,5-diamine;
4-(3,5-diamino-4-phenylazopyrazol-1-yl)benzoic acid;
1-(4-fluorophenyl)-4-phenylazo-1H-pyrazole-3,5-diamine;
1-methyl-4-phenylazo-1H-pyrazole-3,5-diamine;
1-benzyl-4-phenylazo-1H-pyrazole-3,5-diamine;
1-{2-[3,5-diamino-4-(pyridin-3-ylazo)pyrazol-1-yl]-2-oxoethyl}pyrrolidine-2-carboxylic acid methyl ester; and
4-(isoquinolin-5-ylazo)-1-methyl-1H-pyrazole-3,5-diamine.

Of the pharmaceutical compositions set forth above in the Summary of the Invention, a preferred pharmaceutical composition comprises a pharmaceutically acceptable carrier, diluent or excipient and a compound of formula (Ia):

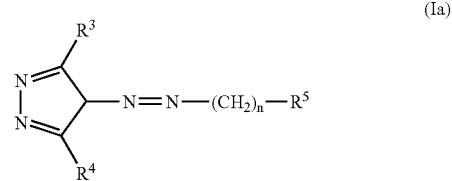

(Ia)

wherein:
n is 0;
$R^3$ and $R^4$ are each —NH$_2$; and
$R^5$ is phenyl substituted at the 4-position by fluoro and at the 3-position by trifluoromethyl, namely, 4-[(4-fluoro-3-trifluoromethylphenyl)hydrazono]-4H-pyrazole-3,5-diamine.

Of the methods of treating a hyperproliferative disorder in a mammal as set forth above in the Summary of the Invention, a preferred method is that method wherein the mammal is a human. Of this preferred method, preferred hyperproliferative disorders include the growth of solid tumor carcinoma cells, angiogenesis, neointimal hyperplasia, lymphoproliferative disorder, cellular migration. Preferably the preferred method comprises administering to a human in need thereof a therapeutically effective amount of a pharmaceutical composition comprising a pharmaceutically acceptable carrier, diluent or excipien and the compound, 4-[(4-fluoro-3-trifluoromethylphenyl)hydrazono]-4H-pyrazole-3,5-diamine.

Of the compounds of formula (I) as set forth above in the Summary of the Invention, a preferred group is that group of compounds of formula (Ia):

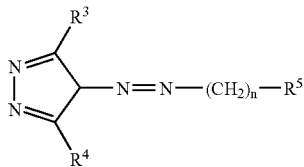

(Ia)

Of this preferred group of compounds, a preferred subgroup is that subgroup of compounds wherein:
n is 0 to 5;
$R^3$ and $R^4$ are each independently —$N(R^7)_2$ or —$N(R^7)C(O)R^6$;
$R^5$ is aryl optionally substituted with one or more substituents selected from the group consisting of alkyl, halo, nitro, cyano, haloalkyl, haloalkoxy, aryl, heterocyclyl, heterocyclylalkyl, —$OR^6$, —$R^8$—$OR^6$, —$R^8$—$[O$—$R^8]_m$—$OR^6$ (where m is 1 to 4), —$S(O)_2OH$, —$S(O)_tR^7$ (where t is 0 to 2), —$S(O)_t$—$R^8$—$OR^6$, —$S(O)_t$—$N(R^6)_2$, —$R^8$—$P(O)(OR^9)_2$, —$C(O)OR^6$, —$R^8$—$C(O)OR^6$, —$C(O)N(R^6)_2$, —$N(R^7)_2$, —$R^8$—$N(R^7)_2$, and —$N(R^9)C(O)R^6$;
each $R^6$ is independently hydrogen, alkyl, aryl, aralkyl, hetereocyclyl or heterocyclylalkyl;
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred subgroup, a preferred class is that class of compounds wherein:
n is 0;
$R^3$ and $R^4$ are each —$N(R^7)_2$;
$R^5$ is aryl optionally substituted with one or more substituents selected from the group consisting of alkyl, halo, nitro, cyano, haloalkyl, haloalkoxy, aryl, heterocyclyl, heterocyclylalkyl, —$OR^6$, —$R^8$—$OR^6$, —$R^8$—$[O$—$R^8]_m$—$OR^6$ (where m is 1 to 4), —$S(O)_2OH$, —$S(O)_tR^7$ (where t is 0 to 2), —$S(O)_t$—$R^8$—$OR^6$, —$S(O)_t$—$N(R^6)_2$, —$R^8$—$P(O)(OR^9)_2$, —$C(O)OR^6$, —$R^8$—$C(O)OR^6$, —$C(O)N(R^6)_2$, —$N(R^7)_2$, —$R^8$—$N(R^7)_2$, and —$N(R^9)C(O)R^6$;
each $R^6$ is independently hydrogen, alkyl, aryl, aralkyl, hetereocyclyl or heterocyclylalkyl;
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred class of compounds, a preferred subclass is that subclass of compounds wherein:
n is 0;
$R^3$ and $R^4$ are each —$N(R^7)_2$;
$R^5$ is aryl optionally substituted with one or more substituents selected from the group consisting of alkyl, halo, haloalkyl, haloalkoxy, aryl, and aralkyl.
each $R^7$ is independently hydrogen, alkyl, haloalkyl, aryl, aralkyl, heterocyclyl, heterocyclylalkyl, or —$R^8$—$OR^9$;
each $R^8$ is a straight or branched alkylene chain; and
each $R^9$ is hydrogen or alkyl.

Of this preferred subclass of compound, a preferred set is that set of compounds wherein:
n is 0;
$R^3$ and $R^4$ are each —$N(R^7)_2$;
$R^5$ is aryl optionally substituted with one or more substituents selected from the group consisting of alkyl, halo, haloalkyl, haloalkoxy, aryl and aralkyl; and
each $R^7$ is independently hydrogen or alkyl.

Of this preferred set of compounds, a preferred subset is that subset of compounds wherein:
n is 0:
$R^3$ and $R^4$ are each —$N(R^7)_2$;
$R^5$ is phenyl optionally substituted with one or more substituents selected from the group consisting of alkyl, halo, haloalkyl, haloalkoxy, aryl, and aralkyl optionally substituted by —$N(R^7)_2$; and
each $R^7$ is hydrogen or alkyl.

Of this preferred subset of compounds, preferred compounds are selected from the group consisting of the following:
4-[(4-fluorophenyl)hydrazono]-4H-pyrazole-3,5-diamine;
4-[(3-ethylphenyl)hydrazono]-4H-pyrazole-3,5-diamine;
4-[(3-fluorophenyl)hydrazono]-4H-pyrazole-3,5-diamine;
4-[(4-trifluoromethylphenyl)hydrazono]-4H-pyrazole-3,5-diamine;
4-(3-phenylphenylhydrazono)-4H-pyrazole-3,5-diamine;
4-[(2-bromophenyl)hydrazono]-4H-pyrazole-3,5-diamine;
4-[(3-bromophenyl)hydrazono]-4H-pyrazole-3,5-diamine;
4-[(4-iodophenyl)hydrazono]-4H-pyrazole-3,5-diamine;
4-[(2,6-difluorophenyl)hydrazono]-4H-pyrazole-3,5-diamine;
4-[(3,4-difluorophenyl)hydrazono]-4H-pyrazole-3,5-diamine;
4-[(3,4-dichlorophenyl)hydrazono]-4H-pyrazole-3,5-diamine;
4-[(3,5-dichlorophenyl)hydrazono]-4H-pyrazole-3,5-diamine;
4-[(2-isopropylphenyl)hydrazono]-4H-pyrazole-3,5-diamine;
4-[(3-trifluoromethylphenyl)hydrazono]-4H-pyrazole-3,5-diamine;
4-[(3-iodophenyl)hydrazono]-4H-pyrazole-3,5-diamine;
4-(2,3,4,5,6-pentafluorophenylhydrazono)-4H-pyrazole-3,5-diamine;
4-[(3,5-difluorophenyl)hydrazono]-4H-pyrazole-3,5-diamine;
4-[(2,3,4-trifluorophenyl)hydrazono]-4H-pyrazole-3,5-diamine;
4-[(3-trifluoromethoxyphenyl)hydrazono]-4H-pyrazole-3,5-diamine;
4-[(4-chloro-3-trifluoromethylphenyl)hydrazono]-4H-pyrazole-3,5-diamine;
4-[(4-benzylphenyl)hydrazono]-4H-pyrazole-3,5-diamine;
4-(4-(phenyl)phenylhydrazono)-4H-pyrazole-3,5-diamine;
4-{[4-(4-methylaminobenzyl)phenyl]hydrazono}-4H-pyrazole-3,5-diamine;
4-[(2,3-difluoro-4-trifluoromethylphenyl)hydrazono]-4H-pyrazole-3,5-diamine;
4-[(3-fluoro-5-trifluoromethylphenyl)hydrazono]-4H-pyrazole-3,5-diamine; and
N-ethyl-4-(phenylhydrazono)-4H-pyrazole-3,5-diamine.

Of the preferred subclass of compounds set forth above, another preferred set of compounds is that set of compounds wherein:
n is 0:
$R^3$ and $R^4$ are each —$NH_2$; and
$R^5$ is naphthyl optionally substituted with one or more substituents selected from the group consisting of alkyl, halo, haloalkyl, and haloalkoxy.

Of this preferred set of compounds, a preferred compound is 4-[(4-bromonaphthalen-1-yl)hydrazono]-4H-pyrazole-3,5-diamine.

Of the preferred class of compounds set forth above, another preferred subclass is that subclass of compounds wherein:

n is 0;

$R^3$ and $R^4$ are each —$N(R^7)_2$;

$R^5$ is aryl optionally substituted with one or more substituents selected from the group consisting of halo, haloalkyl, haloalkoxy, —$OR^6$, —$R^8$—$OR^6$, and —$R^8$—$[O$—$R^8]_m$—$OR^6$ (where m is 1 to 4);

each $R^6$ is independently hydrogen, alkyl, aryl, or aralkyl;

each $R^7$ is independently hydrogen, alkyl, aryl, or aralkyl; and each $R^8$ is a straight or branched alkylene chain.

Of this preferred subclass of compounds, a preferred set is that set of compounds wherein:

n is 0;

$R^3$ and $R^4$ are each —$NH_2$; and $R^5$ is phenyl optionally substituted with one or more substituents selected from the group consisting of halo, haloalkyl, haloalkoxy, —$OR^6$, —$R^8$—$OR^6$, and —$R^8$—$[O$—$R^8]_m$—$OR^6$ (where m is 1 to 4);

each $R^6$ is independently hydrogen, alkyl, aryl, or aralkyl; and each $R^8$ is a straight or branched alkylene chain.

Of this preferred set of compounds, preferred compounds are selected from the group consisting of the following:

3-[N'-(3,5-diaminopyrazol-4-ylidene)hydrazino]phenol;

4-[(3-fluoro-4-methoxyphenyl)hydrazono]-4H-pyrazole-3,5-diamine;

4-[(3-phenoxy-phenyl)hydrazono]-4H-pyrazole-3,5-diamine;

4-[(4-phenoxyphenyl)hydrazono]-4H-pyrazole-3,5-diamine;

4-[(3-chloro-4-methoxyphenyl)hydrazono]-4H-pyrazole-3,5-diamine;

4-[(3,4-dimethoxyphenyl)hydrazono]-4H-pyrazole-3,5-diamine;

4-[(3-methoxy-5-trifuoromethylphenyl)hydrazono]-4H-pyrazole-3,5-diamine;

{2-[N'-(3,5-diaminopyrazol-4-ylidene)hydrazino]phenyl}methanol;

{2-[N'-(3,5-diaminopyrazol-4-ylidene)hydrazino]phenyl}methanol; and 4-({3-[2-(2-methoxyethoxy)ethoxymethyl]phenyl}hydrazono)-4H-pyrazole-3,5-diamine.

Of the preferred class of compounds set forth above, another preferred subclass is that subclass of compounds wherein:

n is 0;

$R^3$ and $R^4$ are each —$N(R^7)_2$;

$R^5$ is aryl optionally substituted with one or more substituents selected from the group consisting of alkyl, nitro, —$OR^6$, —$R^8$—$OR^6$, —$C(O)OR^6$, —$C(O)N(R^6)_2$, —$N(R^7)_2$, —$R^8$—$N(R^7)_2$, and —$N(R^9)C(O)R^6$;

each $R^6$ is independently hydrogen, alkyl, aryl, aralkyl, hetereocyclyl or heterocyclylalkyl;

each $R^7$ is independently hydrogen, alkyl, haloalkyl, aryl, aralkyl, heterocyclyl, heterocyclylalkyl, or —$R^8$—$OR^9$;

each $R^8$ is a straight or branched alkylene chain; and each $R^9$ is hydrogen or alkyl.

Of this preferred subclass of compounds, a preferred set is that set of compounds wherein:

n is 0;

$R^3$ and $R^4$ are each —$NH_2$;

$R^5$ is phenyl optionally substituted with one or more substituents selected from the group consisting of alkyl, nitro, —$OR^6$, —$R^8$—$OR^6$, —$C(O)OR^6$, —$C(O)N(R^6)_2$, —$N(R^7)_2$, —$R^8$—$N(R^7)_2$, and —$N(R^9)C(O)R^6$;

each $R^6$ is independently hydrogen, alkyl, aryl, or aralkyl;

each $R^7$ is independently hydrogen, alkyl, haloalkyl, aryl, aralkyl, —$R^8$—$OR^9$, or heterocyclyl optionally substituted by —$C(O)N(R^9)_2$;

each $R^8$ is a straight or branched alkylene chain; and each $R^9$ is hydrogen or alkyl.

Of this preferred set of compounds, preferred compounds are selected from the group consisting of the following:

5-{4-[N'-(3,5-diaminopyrazol-4-ylidene)hydrazino]benzylamino}-[2,1,3]-thiadiazole-4-carboxylic acid amide;

4-[N'-(3,5-diaminopyrazol-4-ylidene)hydrazino]benzoic acid ethyl ester;

3-[N'-(3,5-diaminopyrazol-4-ylidene)hydrazino]benzoic acid ethyl ester;

4-[(4-methoxy-3-nitrophenyl)hydrazono]-4H-pyrazole-3,5-diamine;

4-[(4-nitro-3-trifluoromethylphenyl)hydrazono]-4H-pyrazole-3,5-diamine;

4-[(4-phenylaminophenyl)hydrazono]-4H-pyrazole-3,5-diamine;

4-[N'-(3,5-diaminopyrazol-4-ylidene)hydrazino]-2-diethylaminomethylphenol;

4-[(2-methyl-5-nitrophenyl)hydrazono]-4H-pyrazole-3,5-diamine;

{3-[N'-(3,5-diaminopyrazol-4-ylidene)hydrazino]-5-nitrophenyl}methanol;

4-[(3-diethylaminomethylphenyl)hydrazono]-4H-pyrazole-3,5-diamine; and

4-[(3-dimethylaminomethylphenyl)hydrazono]-4H-pyrazole-3,5-diamine.

Of the preferred class of compounds set forth above, another preferred subclass is that subclass of compounds wherein:

n is 0;

$R^3$ and $R^4$ are each —$N(R^7)_2$;

$R^5$ is phenyl optionally substituted with one or more substituents selected from the group consisting of —$S(O)_2OH$, —$S(O)_tR^7$ (where t is 0 to 2), —$S(O)_t$—$R^8$—$OR^6$, —$S(O)_t$—$N(R^6)_2$, and —$R^8$—$P(O)(OR^9)_2$;

each $R^6$ is independently hydrogen, alkyl, aryl, aralkyl, hetereocyclyl or heterocyclylalkyl;

each $R^7$ is independently hydrogen, alkyl, haloalkyl, aryl, aralkyl, heterocyclyl, heterocyclylalkyl, or —$R^8$—$OR^9$;

each $R^8$ is a straight or branched alkylene chain; and each $R^9$ is hydrogen or alkyl.

Of this preferred subclass of compounds, preferred compounds are selected from the group consisting of the following:

4-[(4-methylsulfanylphenyl)hydrazono]-4H-pyrazole-3,5-diamine;

4-[(2-benzenesulfonylphenyl)hydrazono]-4H-pyrazole-3,5-diamine;

4-[N'-(3,5-diaminopyrazol-4-ylidene)hydrazino]-N-(2,6-dimethylpyrimidin-4-yl)benzenesulfonamide;

4-[(3-methylsulfanylphenyl)hydrazono]-4H-pyrazole-3,5-diamine;

1-{3-[N'-(3,5-diaminopyrazol-4-ylidene)hydrazino]phenyl}ethanethione;

{4-[N'-(3,5-diaminopyrazol-4-ylidene)hydrazino]benzyl}phosphonic acid diethyl ester;

3-[N'-(3,5-diaminopyrazol-4-ylidene)hydrazino]benzenesulfonamide;

4-[(4-trifluoromethanesulfonylphenyl)hydrazono]-4H-pyrazole-3,5-diamine;

4-[(4-methanesulfonylphenyl)hydrazono]-4H-pyrazole-3,5-diamine;

N-butyl-3-[N'-(3,5-diaminopyrazol-4-ylidene)hydrazino]benzenesulfonamide;

4-[(3-methanesulfonylphenyl)hydrazono]-4H-pyrazole-3,5-diamine;

4-{[4-(morpholine-4-sulfonyl)phenyl]hydrazono}-4H-pyrazole-3,5-diamine;
4-{[4-(pyrrolidine-1-sulfonyl)phenyl]hydrazono}-4H-pyrazole-3,5-diamine;
4-[(3-trifluoromethanesulfonylphenyl)hydrazono]-4H-pyrazole-3,5-diamine;
2-{3-[N'-(3,5-diaminopyrazol-4-ylidene)hydrazino]benzenesulfonyl}ethanol;
4-[N'-(3,5-diaminopyrazol-4-ylidene)hydrazino]-N-methylbenzenesulfonamide;
3-[N'-(3,5-diaminopyrazol-4-ylidene)hydrazino]-N-methylbenzenesulfonamide;
4-[N'-(3,5-diaminopyrazol-4-ylidene)hydrazino]-N-ethylbenzenesulfonamide;
3-[N'-(3,5-diaminopyrazol-4-ylidene)hydrazino]-N-ethylbenzenesulfonamide;
3-[N'-(3,5-diaminopyrazol-4-ylidene)hydrazino]-N-(2-hydroxyethyl)benzenesulfonamide;
3-[N'-(3-amino-5-dimethylaminopyrazol-4-ylidene)-hydrazino]-N-methyl-benzenesulfonamide; and
3-[N'-(3-amino-5-morpholin-4-yl-pyrazol-4-ylidene)-hydrazino]-benzenesulfonamide.

Of the preferred class of compounds set forth above, another preferred subclass is that subclass of compounds wherein:
n is 0;
$R^3$ and $R^4$ are each $—N(R^7)_2$;
$R^5$ is phenyl optionally substituted with one or more substituents selected from the group consisting of alkyl, nitro, halo, haloalkyl, haloalkoxy, heterocyclyl, heterocyclylalkyl (optionally substituted by alkyl), and $—OR^6$;
$R^6$ is hydrogen or alkyl;
each $R^7$ is independently hydrogen, alkyl, haloalkyl, aryl, aralkyl, heterocyclyl, heterocyclylalkyl, or $—R^8—OR^9$;
each $R^8$ is a straight or branched alkylene chain; and
each $R^9$ is hydrogen or alkyl.

Of this preferred subclass of compounds, a preferred set is that set of compounds wherein:
n is 0;
$R^3$ and $R^4$ are each $—N(R^7)_2$;
$R^5$ is phenyl optionally substituted with one or more substituents selected from the group consisting of alkyl, nitro, halo, haloalkyl, haloalkoxy, morpholinyl, piperidinyl, morpholinylmethyl, morpholinylethyl, pyrrolidinylmethyl, piperidinylmethyl, and piperazinylmethyl (optionally substituted by alkyl), and $—OR^6$; and
$R^6$ is hydrogen or alkyl; and
each $R^7$ is independently hydrogen or alkyl.

Of this preferred set of compounds, preferred compounds are selected from the group consisting of the following:
4-[(4-morpholin-4-ylphenyl)hydrazono]4H-pyrazole-3,5-diamine;
4-[(3-chloro-4-(morpholin-4-yl)phenyl)hydrazono]-4H-pyrazole-3,5-diamine;
4-[(4-(piperidin-1yl)phenyl)hydrazono]-4H-pyrazole-3,5-diamine;
4-[(3-(morpholin-4-ylmethyl)phenyl)hydrazono]-4H-pyrazole-3,5-diamine;
4-[(3-(piperidin-1-ylmethyl)phenyl)hydrazono]-4H-pyrazole-3,5-diamine;
4-[(4-methyl-3-(morpholin-4-yl)phenyl)hydrazono]-4H-pyrazole-3,5-diamine;
4-[(4-methoxy-3-(morpholin-4-yl)methylphenyl)hydrazono]4H-pyrazole-3,5-diamine;
4-[N'-(3,5-diaminopyrazol-4-ylidene)hydrazino]-2-(morpholin-4-yl)methylphenol;
4-[(2-methyl-4-(morpholin-4-yl)phenyl)hydrazono]-4H-pyrazole-3,5-diamine;
4-[(4-fluoro-2-(morpholin-4-ylmethyl)phenyl)hydrazono]-4H-pyrazole-3,5-diamine;
4-[(3-(morpholin-4-ylmethyl)-5-trifluoromethylphenyl)hydrazono]-4H-pyrazole-3,5-diamine;
4-[(3-fluoro-4-(morpholin-4-ylmethyl)phenyl)hydrazono]-4H-pyrazole-3,5-diamine;
4-[(4-(morpholin-4-ylmethyl)phenyl)hydrazono]-4H-pyrazole-3,5-diamine;
4-{[4-((4-methylpiperazin-1-yl)methyl)phenyl]hydrazono}-4H-pyrazole-3,5-diamine;
4-{[3-((4-methylpiperazin-1-yl)methyl)phenyl]hydrazono}-4H-pyrazole-3,5-diamine;
4-[(3-(morpholin-4-ylmethyl 5-nitrophenyl)hydrazono]-4H-pyrazole-3,5-diamine;
4-{[4-(2-(morpholin-4-yl)ethyl)phenyl]hydrazono}-4H-pyrazole-3,5-diamine;
4-[(3-(pyrrolidin-1-ylmethyl)phenyl)hydrazono]-4H-pyrazole-3,5-diamine;
4-[(4-(piperidin-1-ylmethyl)phenyl)hydrazono]-4H-pyrazole-3,5-diamine;
4-[(3-fluoro-phenyl)-hydrazono]-N,N-dimethyl-4H-pyrazole-3,5-diamine;
{3-[1'-(3-amino-5-dimethylaminopyrazol-4-ylidene)-hydrazino]-5-trifluoromethylphenyl}methano; and
N,N-dimethyl-4-[(3-morpholin-4-ylmethylphenyl)-hydrazono]-4H-pyrazole-3,5-diamine.

Of the preferred subgroup of compounds set forth above, another preferred class is that class of compounds wherein:
n is 0 to 5;
$R^3$ and $R^4$ are each independently $—N(R^7)_2$ or $—N(R^7)C(O)R^6$;
$R^5$ is heterocyclyl optionally substituted with one or more substituents selected from the group consisting of alkyl, halo, nitro, cyano, haloalkyl, haloalkoxy, aryl, heterocyclyl, heterocyclylalkyl, $—OR^6$, $—R^8—OR^6$, $R^8—[O—R^8]_m—OR^6$ (where m is 1 to 4), $—S(O)_2OH$, $—S(O)_tR^7$ (where t is 0 to 2), $—S(O)_t—R^8—OR^6$, $—S(O)_t—N(R^6)_2$, $—R^8—P(O)(OR^9)_2$, $—C(O)OR^6$, $—R^8—C(O)OR^6$, $—C(O)N(R^6)_2$, $—N(R^7)_2$, $—R^8—N(R^7)_2$, and $—N(R^9)C(O)R^6$;
each $R^6$ is independently hydrogen, alkyl, aryl, aralkyl, hetereocyclyl or heterocyclylalkyl;
each $R^7$ is independently hydrogen, alkyl, haloalkyl, aryl, aralkyl, heterocyclyl, heterocyclylalkyl, or $—R^8—OR^9$;
each $R^8$ is a straight or branched alkylene chain; and
each $R^9$ is hydrogen or alkyl.

Of this preferred class of compounds, a preferred subclass is that subclass of compounds wherein:
n is 0;
$R^3$ and $R^4$ are each independently $—N(R^7)_2$;
$R^5$ is heterocyclyl optionally substituted with one or more substituents selected from the group consisting of alkyl, halo, haloalkyl, heterocyclyl, heterocyclylalkyl, $—OR^6$, $—R^8—OR^6$, and $—N(R^7)_2$
$R^6$ is alkyl, aryl, aralkyl, hetereocyclyl or heterocyclylalkyl;
each $R^7$ is independently hydrogen, alkyl, haloalkyl, aryl, aralkyl, or $—R^8—OR^9$;
each $R^8$ is a straight or branched alkylene chain; and
each $R^9$ is hydrogen or alkyl.

Of this preferred subclass of compounds, a preferred set is that set of compounds wherein:
n is 0;
$R^3$ and $R^4$ are each independently $—N(R^7)_2$;
$R^5$ is heterocyclyl optionally substituted with one or more substituents selected from the group consisting of alkyl, halo, haloalkyl, —OR⁶, —R⁸—OR⁶, and —N(R⁷)₂, morpholinyl, piperidinyl, piperazinyl (optionally substituted by alkyl);
R⁶ is hydrogen, alkyl, aryl, or aralkyl;
each R⁷ is independently hydrogen, alkyl, haloalkyl, aryl, aralkyl, or —R⁸—OR⁹;
each R⁸ is a straight or branched alkylene chain; and
each R⁹ is hydrogen or alkyl.

Of this preferred set of compounds, preferred compounds are selected from the group consisting of the following:
4-(benzo[1,3]dioxol-5-ylhydrazono)-4H-pyrazole-3,5-diamine;
4-[(2,3-dihydrobenzo[1,4]dioxin-6-yl)hydrazono]-4H-pyrazole-3,5-diamine;
4-[(5-methoxybenzothiazol-2-yl)hydrazono]-4H-pyrazole-3,5-diamine;
4-(benzothiazol-2-ylhydrazono)-4H-pyrazole-3,5-diamine;
4-[(4H-[1,2,4]-triazol-3-yl)hydrazono]-4H-pyrazole-3,5-diamine;
4-[(1H-pyrazol-3-yl)hydrazono]-4H-pyrazole-3,5-diamine;
4-(pyridin-4-ylhydrazono)-4H-pyrazole-3,5-diamine;
4-[(9-ethyl-9H-carbazol-3-yl)hydrazono]-4H-pyrazole-3,5-diamine;
4-[(6-methoxypyridin-3-yl)hydrazono]-4H-pyrazole-3,5-diamine;
4-[(1H-indazol-5-yl)hydrazono]-4H-pyrazole-3,5-diamine;
4-(quinolin-6-ylhydrazono)-4H-pyrazole-3,5-diamine;
4-[(6-chloropyridin-3-yl)hydrazono]-4H-pyrazole-3,5-diamine;
4-(isoquinolin-5-ylhydrazono)-4H-pyrazole-3,5-diamine;
4-(quinolin-3-ylhydrazono)-4H-pyrazole-3,5-diamine;
4-(benzo[1,2,5]thiadiazol-4-ylhydrazono)-4H-pyrazole-3,5-diamine;
4-(quinolin-8-ylhydrazono)-4H-pyrazole-3,5-diamine;
4-(quinolin-5-ylhydrazono)-4H-pyrazole-3,5-diamine;
4-[(2H-benzotriazol-5-yl)hydrazono]4H-pyrazole-3,5-diamine;
4-[(2-methyl-2H-benzotriazol-5-yl)hydrazono]-4H-pyrazole-3,5-diamine;
4-(benzo[2,1,3]thiadiazol-5-ylhydrazono)-4H-pyrazole-3,5-diamine;
7-[N'-(3,5-diaminopyrazol-4-ylidene)hydrazino]-4-trifuoromethylchroman-2-one;
4-(quinazolin-6-ylhydrazono)-4H-pyrazole-3,5-diamine;
4-[(1-methyl-1H-benzotriazol-5-yl)hydrazono]-4H-pyrazole-3,5-diamine;
4-[(3-methyl-3H-benzotriazol-5-yl)hydrazono]-4H-pyrazole-3,5-diamine;
4-[(2,2-difluorobenzo[1,3]dioxol-5-yl)hydrazono]-4H-pyrazole-3,5-diamine;
4-[(2,2,3,3-tetrafluoro-2,3-dihydrobenzo[1,4]dioxin-6-yl)hydrazono]-4H-pyrazole-3,5-diamine;
4-[(1,1-dioxo-1H-benzo[b]thiophen-6-yl)hydrazono]-4H-pyrazole-3,5-diamine;
4-(phthalazin-5-ylhydrazono)-4H-pyrazole-3,5-diamine;
4-[(6-(piperidin-1-yl)pyridin-3-yl)hydrazono]-4H-pyrazole-3,5-diamine;
4-[(6-(morpholin-4-yl)pyridin-3-yl)hydrazono]-4H-pyrazole-3,5-diamine;
4-{[6-(4-methylpiperazin-1-yl)pyridin-3-yl]hydrazono}-4H-pyrazole-3,5-diamine;
2-[{5-[N'-(3,5-diaminopyrazol-4-ylidene)hydrazino]pyridin-2-yl}(2-hydroxyethyl)amino]ethanol;
4-[(2,6-dimethoxypyridin-3-yl)hydrazono]-4H-pyrazole-3,5-diamine;
4-[(2,6-dichloropyridin-3-yl)hydrazono]-4H-pyrazole-3,5-diamine;
4-[(6-fluoropyridin-3-yl)hydrazono]-4H-pyrazole-3,5-diamine;
4-[(4-methylpyridin-3-yl)hydrazono]-4H-pyrazole-3,5-diamine;
N,N-dimethyl-4-(quinolin-6-yl-hydrazono)-4H-pyrazole-3,5-diamine;
4-[(6-chloro-pyridin-3-yl)-hydrazono]-N,N-dimethyl-4H-pyrazole-3,5-diamine;
4-[(6-fluoro-pyridin-3-yl)-hydrazono]-N,N-dimethyl-4H-pyrazole-3,5-diamine;
N,N-dimethyl-4-(phthalazin-5-yl-hydrazono)-4H-pyrazole-3,5-diamine; and
N,N-dimethyl-4-(pyridin-3-yl-hydrazono)-4H-pyrazole-3,5-diamine.

Of the compounds of formula (I) set forth above in the Summary of the Invention, another preferred group is that group of compounds having the following formula (Ib):

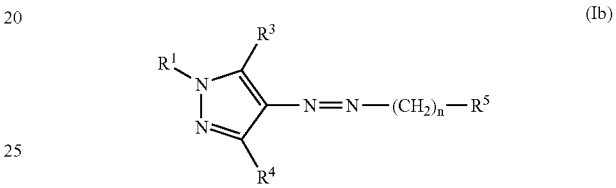

wherein:
n is 0 to 5;
R¹ is hydrogen, alkyl, aryl, aralkyl or —C(O)R⁶;
R³ and R⁴ are each independently —N(R⁷)₂ or —N(R⁷)C(O)R⁶;
R⁵ is aryl optionally substituted with one or more substituents selected from the group consisting of alkyl, halo, nitro, cyano, haloalkyl, haloalkoxy, aryl, heterocyclyl, heterocyclylalkyl, —OR⁶, —R⁸—OR⁶, —R⁸—[O—R⁸]ₘ—OR⁶ (where m is 1 to 4), —S(O)₂OH, —S(O)ₜR⁷ (where t is 0 to 2), —S(O)ₜ—R⁸—OR⁶, —S(O)ₜ—N(R⁶)₂, —R⁸—P(O)(OR⁹)₂, —C(O)OR⁶, —R⁸—C(O)OR⁶, —C(O)N(R⁶)₂, —N(R⁷)₂, —R⁸—N(R⁷)₂, and —N(R⁹)C(O)R⁶;
or R⁵ is heterocyclyl optionally substituted with one or more substituents selected from the group consisting of alkyl, halo, nitro, cyano, haloalkyl, haloalkoxy, aryl, heterocyclyl, heterocyclylalkyl, —OR⁶, —R⁸—OR⁶, —R⁸—[O—R⁸]ₘ—OR⁶ (where m is 1 to 4), —S(O)₂OH, —S(O)ₜR⁷ (where t is 0 to 2), —S(O)ₜ—R⁸—OR⁶, —S(O)ₜ—N(R⁶)₂, —R⁸—P(O)(OR⁹)₂, —C(O)OR⁶, —R⁸—C(O)OR⁶, —C(O)N(R⁶)₂, —N(R⁷)₂, —R⁸—N(R⁷)₂, and —N(R⁹)C(O)R⁶;
each R⁶ is independently hydrogen, alkyl, aryl, aralkyl, hetereocyclyl or heterocyclylalkyl;
each R⁷ is independently hydrogen, alkyl, haloalkyl, aryl, aralkyl, heterocyclyl, heterocyclylalkyl, or —R⁸—OR⁹;
each R⁸ is a straight or branched alkylene chain; and
each R⁹ is hydrogen or alkyl.

Of this preferred group of compounds, a preferred subgroup is that subgroup of compounds wherein:
n is 0;
R¹ is hydrogen, alkyl, aryl, aralkyl or —C(O)R⁶;
R³ and R⁴ are each independently —N(R⁷)₂;
R⁵ is phenyl optionally substituted with one or more substituents selected from the group consisting of alkyl, halo, haloalkyl, haloalkoxy, or aryl;
or R⁵ is pyridinyl;
R⁶ is alkyl, aryl, or aralkyl; and
each R⁷ is independently hydrogen or alkyl.

Of this preferred subgroup, preferred compounds are selected from group consisting of the following:
(3,5-diamino-4-phenylazopyrazol-1-yl)phenylmethanone;
1-(4-bromophenyl)-4-phenylazo-1H-pyrazole-3,5-diamine;
4-(3,5-diamino-4-phenylazopyrazol-1-yl)benzoic acid;
1-(4-fluorophenyl)-4-phenylazo-1H-pyrazole-3,5-diamine;
1-methyl-4-phenylazo-1H-pyrazole-3,5-diamine;
1-benzyl-4-phenylazo-1H-pyrazole-3,5-diamine;
1-{2-[3,5-diamino-4-(pyridin-3-ylazo)pyrazol-1-yl]-2-oxoethyl}pyrrolidine-2-carboxylic acid methyl ester; and
4-(isoquinolin-5-ylazo)-1-methyl-1H-pyrazole-3,5-diamine.

Of the compounds of formula (I) set forth above in the Summary of the Invention, a preferred compound is a compound of formula (Ia):

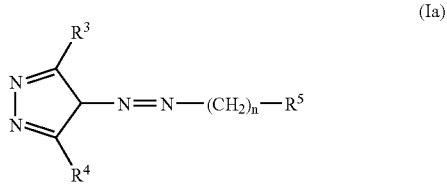

(Ia)

wherein:
n is 0;
$R^3$ and $R^4$ are each —$NH_2$; and
$R^5$ is phenyl substituted at the 4-position by fluoro and at the 3-position by trifluoromethyl, namely, 4-[(4-fluoro-3-trifluoromethylphenyl)hydrazono]-4H-pyrazole-3,5-diamine.

Of the compounds of formula (I) as set forth above in the Summary of the Invention, another group is that group of compounds of formula (I):

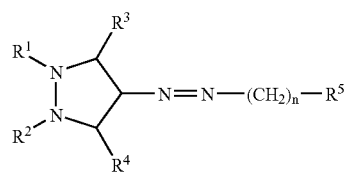

(I)

wherein:
n is 0 to 5;
$R^1$ and $R^2$ are each independently hydrogen, alkyl, aryl, aralkyl or —C(O)$R^6$;
or $R^1$ and $R^2$ can each independently be a part of a double bond within the pyrazole ring;
$R^3$ and $R^4$ are each independently —N($R^7$)$_2$ or —N($R^7$)C(O)$R^6$;
$R^5$ is phenyl substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, —$R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$—N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$;
or $R^5$ is heterocyclyl optionally substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, $R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$;
each $R^6$ is independently hydrogen, alkyl, aryl, aralkyl, heterocyclyl or heterocyclylalkyl;
each $R^7$ is independently hydrogen, alkyl, haloalkyl, aryl, aralkyl, heterocyclyl, heterocyclylalkyl, or —$R^8$—O$R^9$;
each $R^8$ is a straight or branched alkylene chain; and
each $R^9$ is hydrogen or alkyl;
provided that when n is 0, $R^1$ is phenyl, $R^2$ is hydrogen, $R^3$ and $R^4$ are both —$NH_2$, $R^5$ can not be unsubstituted phenyl; and
provided that when n is 0, $R^1$ and $R^2$ are both hydrogen, and $R^3$ and $R^4$ are both —$NH_2$, $R^5$ can not be phenyl, naphth-2-yl, pyridin-3-yl, 3-methoxyphenyl, 3-chlorophenyl, 4-bromophenyl, 2-methylphenyl, 2-chlorophenyl, 3-nitrophenyl, 4-aminosulfonylphenyl, or 4-(pyrimidin-2-yl)aminosulfonylphenyl;
as a single stereoisomer, a mixture of stereoisomers, a solvate or a polymorph; or a pharmaceutically acceptable salt thereof.

Of this preferred group of compounds, a preferred subgroup is that subgroup of compounds wherein $R^1$ and $R^2$ are each part of a double bond of the pyrazole ring, i.e., compounds of formula (Ia):

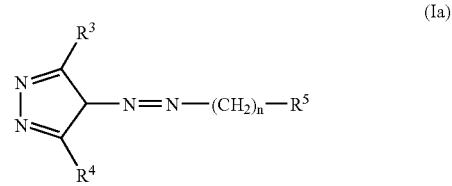

(Ia)

wherein:
n is 0 to 5;
$R^3$ and $R^4$ are each independently —$NH_2$;
$R^5$ is phenyl substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, —$R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$—N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$;
or $R^5$ is heterocyclyl optionally substituted with one or more substituents selected from the group consisting of alkyl, halo, nitro, cyano, haloalkyl, haloalkoxy, aryl, heterocyclyl, heterocyclylalkyl, —O$R^6$, —$R^8$—O$R^6$, $R^8$—[O—$R^8$]$_m$—O$R^6$ (where m is 1 to 4), —S(O)$_2$OH, —S(O)$_t$$R^7$ (where t is 0 to 2), —S(O)$_t$—$R^8$—O$R^6$, —S(O)$_t$—N($R^6$)$_2$, —$R^8$—P(O)(O$R^9$)$_2$, —C(O)O$R^6$, —$R^8$—C(O)O$R^6$, —C(O)N($R^6$)$_2$, —N($R^7$)$_2$, —$R^8$—N($R^7$)$_2$, and —N($R^9$)C(O)$R^6$, wherein the heterocyclyl is selected from the group consisting of pyridinyl, indazolyl, quinolinyl, isoquinolyl, benzothiadiazolyl, benzotriazolyl, pyrazolyl, quinazolinyl, benzodioxolyl, benzodioxinyl, benzothiophenyl, phthalazinyl, piperidinyl, morpholinyl, and piperazinyl;
each $R^6$ is independently hydrogen, alkyl, aryl, aralkyl, heterocyclyl or heterocyclylalkyl;
each $R^7$ is independently hydrogen, alkyl, haloalkyl, aryl, aralkyl, heterocyclyl, heterocyclylalkyl, or —$R^8$—O$R^9$;
each $R^8$ is a straight or branched alkylene chain; and
each $R^9$ is hydrogen or alkyl.

Of this preferred subgroup of compounds, preferred compounds are selected from the group consisting of the following:

4-[(3-trifluoromethoxyphenyl)hydrazono]-4H-pyrazole-3,5-diamine;
4-[(4-chloro-3-trifluoromethylphenyl)hydrazono]-4H-pyrazole-3,5-diamine;
4-[(4-benzylphenyl)hydrazono]-4H-pyrazole-3,5-diamine;
4-(4-(phenyl)phenylhydrazono)-4H-pyrazole-3,5-diamine;
4-{[4-(4-methylaminobenzyl)phenyl]hydrazono}-4H-pyrazole-3,5-diamine;
4-[(2,3-difluoro-4-trifluoromethylphenyl)hydrazono]-4H-pyrazole-3,5-diamine;
4-[(3-fluoro-5-trifluoromethylphenyl)hydrazono]-4H-pyrazole-3,5-diamine;
N-ethyl-4-(phenylhydrazono)-4H-pyrazole-3,5-diamine;
{2-[N'-(3,5-diaminopyrazol-4-ylidene)hydrazino]phenyl}methanol;
{2-[N'-(3,5-diaminopyrazol-4-ylidene)hydrazino]phenyl}methanol;
4-({3-[2-(2-methoxyethoxy)ethoxymethyl]phenyl}hydrazono)-4H-pyrazole-3,5-diamine;
4-[(4-methoxy-3-nitrophenyl)hydrazono]-4H-pyrazole-3,5-diamine;
4-[(4-nitro-3-trifluoromethylphenyl)hydrazono]-4H-pyrazole-3,5-diamine;
4-[(4-phenylaminophenyl)hydrazono]-4H-pyrazole-3,5-diamine;
4-[N'-(3,5-diaminopyrazol-4-ylidene)hydrazino]-2-diethylaminomethylphenol;
4-[(2-methyl-5-nitrophenyl)hydrazono]-4H-pyrazole-3,5-diamine;
{3-[N'-(3,5-diaminopyrazol-4-ylidene)hydrazino]-5-nitrophenyl}methanol;
4-[(3-diethylaminomethylphenyl)hydrazono]-4H-pyrazole-3,5-diamine;
4-[(3-dimethylaminomethylphenyl)hydrazono]-4H-pyrazole-3,5-diamine;
4-[N'-(3,5-diaminopyrazol-4-ylidene)hydrazino]-N-(2,6-dimethylpyrimidin-4-yl)benzenesulfonamide;
4-[(3-methylsulfanylphenyl)hydrazono]-4H-pyrazole-3,5-diamine;
1-{3-[N'-(3,5-diaminopyrazol-4-ylidene)hydrazino]phenyl}ethanethione;
{4-[N'-(3,5-diaminopyrazol-4-ylidene)hydrazino]benzyl}phosphonic acid diethyl ester;
3-[N'-(3,5-diaminopyrazol-4-ylidene)hydrazino]benzenesulfonamide;
4-[(4-trifluoromethanesulfonylphenyl)hydrazono]-4H-pyrazole-3,5-diamine;
4-[(4-methanesulfonylphenyl)hydrazono]-4H-pyrazole-3,5-diamine;
N-butyl-3-[N'-(3,5-diaminopyrazol-4-ylidene)hydrazino]benzenesulfonamide;
4-[(3-methanesulfonylphenyl)hydrazono]-4H-pyrazole-3,5-diamine;
4-{[4-(morpholine-4-sulfonyl)phenyl]hydrazono}-4H-pyrazole-3,5-diamine;
4-{[4-(pyrrolidine-1-sulfonyl)phenyl]hydrazono}-4H-pyrazole-3,5-diamine;
4-[(3-trifluoromethanesulfonylphenyl)hydrazono]-4H-pyrazole-3,5-diamine;
2-{3-[N'-(3,5-diaminopyrazol-4-ylidene)hydrazino]benzenesulfonyl}ethanol;
4-[N'-(3,5-diaminopyrazol-4-ylidene)hydrazino]-N-methylbenzenesulfonamide;
3-[N'-(3,5-diaminopyrazol-4-ylidene)hydrazino]-N-methylbenzenesulfonamide;
4-[N'-(3,5-diaminopyrazol-4-ylidene)hydrazino]-N-ethylbenzenesulfonamide;
3-[N'-(3,5-diaminopyrazol-4-ylidene)hydrazino]-N-ethylbenzenesulfonamide;
3-[N'-(3,5-diaminopyrazol-4-ylidene)hydrazino]-N-(2-hydroxyethyl)benzenesulfonamide;
4-[(4-morpholin-4-ylphenyl)hydrazono]4H-pyrazole-3,5-diamine;
4-[(3-chloro-4-(morpholin-4-yl)phenyl)hydrazono]-4H-pyrazole-3,5-diamine;
4-[(4-(piperidin-1-yl)phenyl)hydrazono]-4H-pyrazole-3,5-diamine;
4-[(3-(morpholin-4-ylmethyl)phenyl)hydrazono]-4H-pyrazole-3,5-diamine;
4-[(3-(piperidin-1-ylmethyl)phenyl)hydrazono]-4H-pyrazole-3,5-diamine;
4-[(4-methyl-3-(morpholin-4-yl)phenyl)hydrazono]-4H-pyrazole-3,5-diamine;
4-[(4-methoxy-3-(morpholin-4-yl)methylphenyl)hydrazono]-4H-pyrazole-3,5-diamine;
4-[N'-(3,5-diaminopyrazol-4-ylidene)hydrazino]-2-(morpholin-4-yl)methylphenol;
4-[(2-methyl-4-(morpholin-4-yl)phenyl)hydrazono]-4H-pyrazole-3,5-diamine;
4-[(4-fluoro-2-(morpholin-4-ylmethyl)phenyl)hydrazono]-4H-pyrazole-3,5-diamine
4-[(3-(morpholin-4-ylmethyl)-5-trifluoromethylphenyl)hydrazono]-4H-pyrazole-3,5-diamine
4-[(3-fluoro-4-(morpholin-4-ylmethyl)phenyl)hydrazono]-4H-pyrazole-3,5-diamine
4-[(4-(morpholin-4-ylmethyl)phenyl)hydrazono]-4H-pyrazole-3,5-diamine
4-{[4-((4-methylpiperazin-1-yl)methyl)phenyl]hydrazono}-4H-pyrazole-3,5-diamine
4-{[3-((4-methylpiperazin-1-yl)methyl)phenyl]hydrazono}-4H-pyrazole-3,5-diamine
4-[(3-(morpholin-4-ylmethyl)-5-nitrophenyl)hydrazono]-4H-pyrazole-3,5-diamine;
4-{[4-(2-(morpholin-4-yl)ethyl)phenyl]hydrazono}-4H-pyrazole-3,5-diamine;
4-[(3-(pyrrolidin-1-ylmethyl)phenyl)hydrazono]-4H-pyrazole-3,5-diamine;
4-[(4-(piperidin-1-ylmethyl)phenyl)hydrazono]-4H-pyrazole-3,5-diamine;
4-[(6-methoxypyridin-3-yl)hydrazono]-4H-pyrazole-3,5-diamine;
4-[(1H-indazol-5-yl)hydrazono]-4H-pyrazole-3,5-diamine;
4-(quinolin-6-ylhydrazono)-4H-pyrazole-3,5-diamine;
4-[(6-chloropyridin-3-yl)hydrazono]-4H-pyrazole-3,5-diamine;
4-(isoquinolin-5-ylhydrazono)-4H-pyrazole-3,5-diamine;
4-(quinolin-3-ylhydrazono)-4H-pyrazole-3,5-diamine;
4-(benzo[1,2,5]thiadiazol-4-ylhydrazono)-4H-pyrazole-3,5-diamine;
4-(quinolin-8-ylhydrazono)-4H-pyrazole-3,5-diamine;
4-(quinolin-5-ylhydrazono)-4H-pyrazole-3,5-diamine;
4-[(2H-benzotriazol-5-yl)hydrazono]-4H-pyrazole-3,5-diamine;
4-[(2-methyl-2H-benzotriazol-5-yl)hydrazono]-4H-pyrazole-3,5-diamine;
4-(benzo[2,1,3]thiadiazol-5-ylhydrazono)-4H-pyrazole-3,5-diamine;
7-[N'-(3,5-diaminopyrazol-4-ylidene)hydrazino]-4-trifluoromethylchroman-2-one;
4-(quinazolin-6-ylhydrazono)-4H-pyrazole-3,5-diamine;

4-[(1-methyl-1H-benzotriazol-5-yl)hydrazono]-4H-pyrazole-3,5-diamine;
4-[(3-methyl-3H-benzotriazol-5-yl)hydrazono]-4H-pyrazole-3,5-diamine;
4-[(2,2-difluorobenzo[1,3]dioxol-5-yl)hydrazono]-4H-pyrazole-3,5-diamine;
4-[(2,2,3,3-tetrafluoro-2,3-dihydrobenzo[1,4]dioxin-6-yl)hydrazono]-4H-pyrazole-3,5-diamine;
4-[(1,1-dioxo-1H-benzo[b]thiophen-6-yl)hydrazono]-4H-pyrazole-3,5-diamine;
4-(phthalazin-5-ylhydrazono)-4H-pyrazole-3,5-diamine;
4-[(6-(piperidin-1-yl)pyridin-3-yl)hydrazono]-4H-pyrazole-3,5-diamine;
4-[(6-(morpholin-4-yl)pyridin-3-yl)hydrazono]-4H-pyrazole-3,5-diamine;
4-{[6-(4-methylpiperazin-1-yl)pyridin-3-yl]hydrazono}-4H-pyrazole-3,5-diamine;
2-[{5-[N'-(3,5-diaminopyrazol-4-ylidene)hydrazino]pyridin-2-yl}(2-hydroxyethyl)amino]ethanol;
4-[(2,6-dimethoxypyridin-3-yl)hydrazono]4H-pyrazole-3,5-diamine;
4-[(2,6-dichloropyridin-3-yl)hydrazono]-4H-pyrazole-3,5-diamine;
4-[(6-fluoropyridin-3-yl)hydrazono]-4H-pyrazole-3,5-diamine; and
4-[(4-methylpyridin-3-yl)hydrazono]-4H-pyrazole-3,5-diamine.

Of the preferred group of compounds as set forth above, another preferred subgroup is that subgroup of compounds having the following formula (Ib):

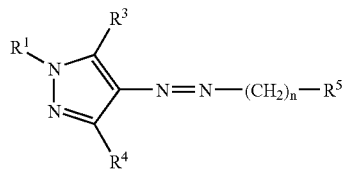

(Ib)

wherein:
n is 0;
$R^1$ is hydrogen, alkyl, aryl, aralkyl or —C(O)$R^6$;
$R^3$ and $R^4$ are each independently —N($R^7$)$_2$;
$R^5$ is phenyl substituted with one or more substituents selected from the group consisting of alkyl, halo, haloalkyl, haloalkoxy, or aryl;
or $R^5$ is pyridinyl;
$R^6$ is alkyl, aryl, or aralkyl; and
each $R^7$ is independently hydrogen or alkyl.

Of this preferred subgroup of compounds, preferred compounds are selected from group consisting of the following:
1-benzyl-4-phenylazo-1H-pyrazole-3,5-diamine;
1-{2-[3,5-diamino-4-(pyridin-3-ylazo)pyrazol-1-yl]-2-oxoethyl}pyrrolidine-2-carboxylic acid methyl ester; and
4-(isoquinolin-5-ylazo)-1-methyl-1H-pyrazole-3,5-diamine.

Of the compounds of formula (Ic) as set forth above in the Summary of the Invention, a preferred group of compounds is that subgroup of compounds wherein:
$R^{1c}$ and $R^{4c}$ are each hydrogen; and
$R^{2c}$ is aryl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl).

Of this group of compounds, a preferred subgroup of compounds is that subgroup of compounds of formula (Ic) wherein:
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl); and
$R^{5c}$ is aryl (optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups), nitro, —C(O)O$R^{7c}$, and —N($R^{7c}$)—C(O)—$R^{7c}$).

Of this subgroup of compounds, a preferred class of compounds is that class of compounds wherein:
$R^{5c}$ is phenyl (optionally substituted by one or more substituents selected from the group consisting of alkyl, alkoxy, halo, haloalkyl, haloalkoxy, haloalkylthio, phenylthioalkyl (wherein the phenyl group is optionally substituted with one or more halo groups), nitro, —C(O)O$R^{7c}$, and —N($R^{7c}$)—C(O)—$R^{7c}$).

Of this class of compounds, preferred compounds are selected from the group consisting of the following:
5-phenyl-4-(phenylhydrazono)-4H-pyrazol-3-ylamine;
4-[(3-fluorophenyl)hydrazono]-5-m-tolyl-4H-pyrazol-3-ylamine;
4-[(3-fluorophenyl)hydrazono]-5-p-tolyl-4H-pyrazol-3-ylamine;
5-(3-chlorophenyl)-4-[(3-fluorophenyl)hydrazono]-4H-pyrazol-3-ylamine;
5-(4-chlorophenyl)-4-[(3-fluorophenyl)hydrazono]-4H-pyrazol-3-ylamine;
4-[(3-fluorophenyl)hydrazono]-5-(3-trifluoromethylphenyl)-4H-pyrazol-3-ylamine;
4-[(3-fluorophenyl)hydrazono]-5-(4-trifluoromethoxyphenyl)-4H-pyrazol-3-ylamine;
4-[(3-fluorophenyl)hydrazono]-5-(4-methoxyphenyl)-4H-pyrazol-3-ylamine;
4-[(3-fluorophenyl)hydrazono]-5-m-tolyl-4H-pyrazol-3-ylamine;
4-[(3-fluorophenyl)hydrazono]-5-p-tolyl-4H-pyrazol-3-ylamine;
5-(3-chlorophenyl)-4-[(3-fluorophenyl)hydrazono]-4H-pyrazol-3-ylamine;
5-(4-chlorophenyl)-4-[(3-fluorophenyl)hydrazono]-4H-pyrazol-3-ylamine;
4-[(3-fluorophenyl)hydrazono]-5-(3-trifluoromethylphenyl)-4H-pyrazol-3-ylamine;
4-[(3-fluorophenyl)hydrazono]-5-(4-trifluoromethoxyphenyl)-4H-pyrazol-3-ylamine;
4-[(3-fluorophenyl)hydrazono]-5-(4-methoxyphenyl)-4H-pyrazol-3-ylamine;
(2-morpholin-4-ylethyl)[5-phenyl-4-(phenylhydrazono)-4H-pyrazol-3-yl]amine;
N-[5-phenyl-4-(phenylhydrazono)-4H-pyrazol-3-yl]nicotinamide;
5-(2-fluorophenyl)-4-(phenylhydrazono)-4H-pyrazol-3-ylamine;
5-(3,4-dimethoxyphenyl)-4-(phenylhydrazono)-4H-pyrazol-3-ylamine;
4-{5-amino-4-[(3-fluorophenyl)hydrazono]-4H-pyrazol-3-yl}benzoic acid;
5-(2-nitrophenyl)-4-(phenylhydrazono)-4H-pyrazol-3-ylamine;
5-(4-chloro-3-nitrophenyl)-4-(phenylhydrazono)-4H-pyrazol-3-ylamine;

5-(3-fluorophenyl)-4-(phenylhydrazono)-4H-pyrazol-3-ylamine;
5-(4-nitrophenyl)-4-(phenylhydrazono)-4H-pyrazol-3-ylamine;
5-(3-nitrophenyl)-4-(phenylhydrazono)-4H-pyrazol-3-ylamine;
5-(3-bromophenyl)-4-(phenylhydrazono)-4H-pyrazol-3-ylamine;
5-(4-fluoro-3-methylphenyl)-4-(phenylhydrazono)-4H-pyrazol-3-ylamine;
5-(4-fluorophenyl)-4-(phenylhydrazono)-4H-pyrazol-3-ylamine;
5-(3-nitrophenyl)-4-(phenylhydrazono)-4H-pyrazol-3-ylamine;
5-(3,4-difluorophenyl)-4-(phenylhydrazono)-4H-pyrazol-3-ylamine;
5-(3-fluoro-4-methylphenyl)-4-(phenylhydrazono)-4H-pyrazol-3-ylamine;
5-(3,4-dimethylphenyl)-4-(phenylhydrazono)-4H-pyrazol-3-ylamine;
4-(phenylhydrazono)-5-(2-trifluoromethoxyphenyl)-4H-pyrazol-3-ylamine;
4-(phenylhydrazono)-5-(4-trifluoromethylsulfanylphenyl)-4H-pyrazol-3-ylamine;
5-(3,5-difluorophenyl)-4-(phenylhydrazono)-4H-pyrazol-3-ylamine;
4-(phenylhydrazono)-5-(4-trifluoromethylphenyl)-4H-pyrazol-3-ylamine;
4-(phenylhydrazono)-5-(3,4,5-trimethoxyphenyl)-4H-pyrazol-3-ylamine;
5-[3-(4-chlorophenylsulfanylmethyl)phenyl]-4-(phenylhydrazono)-4H-pyrazol-3-ylamine; and
N-{4-[5-amino-4-(phenylhydrazono)-4H-pyrazol-3-yl]phenyl}acetamide.

Particularly preferred is
5-(4-nitrophenyl)-4-(phenylhydrazono)-4H-pyrazol-3-ylamine.

Another preferred subgroup of the preferred group of compounds is that subgroup of compounds wherein:
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl); and
$R^{5c}$ is aralkyl (wherein the aryl group is optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups) or aralkenyl (wherein the aryl group is optionally substituted by one or more halo groups).

Of this subgroup of compounds, a preferred class of compound is that class of compounds wherein:
$R^{5c}$ is phenylalkyl (wherein the phenyl group is optionally substituted by one or more substituents selected from the group consisting of alkyl, alkoxy, halo, haloalkyl, haloalkoxy, haloalkylthio, phenylthioalkyl (wherein the phenyl group is optionally substituted with one or more halo groups) or phenylalkenyl (wherein the phenyl group is optionally substituted by one or more halo groups).

Of this class of compounds, preferred compounds are selected from the group consisting of the following:
5-(4-methoxybenzyl)-4-(phenylhydrazono)-4H-pyrazol-3-ylamine;
4-[(3-fluorophenyl)hydrazono]-5-phenethyl-4H-pyrazol-3-ylamine;
4-[(3-chlorophenyl)hydrazono]-5-phenethyl-4H-pyrazol-3-ylamine;
4-[(3,5-difluorophenyl)hydrazono]-5-phenethyl-4H-pyrazol-3-ylamine;
5-(4-chlorobenzyl)-4-(phenylhydrazono)-4H-pyrazol-3-ylamine;
5-benzhydryl-4-(phenylhydrazono)-4H-pyrazol-3-ylamine;
5-(2,5-dimethoxy-benzyl)-4-(phenyl-hydrazono)-4H-pyrazol-3-ylamine;
5-(3,4-dimethoxybenzyl)-4-(phenylhydrazono)-4H-pyrazol-3-ylamine;
5-phenethyl-4-(phenylhydrazono)-4H-pyrazol-3-ylamine; and
5-(3-ethyl-benzyl)-4-(phenyl-hydrazono)-4H-pyrazol-3-ylamine.

Another preferred subgroup of compounds is that subgroup wherein
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl); and
$R^{5c}$ is heterocyclyl (optionally substituted by one or more substituents selected from the group consisting of alkyl, halo, haloalkyl, alkylthio, and aryl (optionally substituted with one or more halo groups)).

Of this subgroup of compounds, a preferred class is that class of compounds wherein $R^{5c}$ is a heterocyclyl selected from the group consisting of piperidinyl, morpholinyl, pyrrolidinyl, furanyl, isooxazolyl, pyridinyl, thienyl, pyrrolyl, quinolinyl, benzothienyl, benzodioxolyl, benzooxadiazolyl, pyrazolyl, thiadiazolyl, and quinoxalinyl.

Of this class of compounds, preferred compounds are selected from the group consisting of the following:
4-[(3-fluorophenyl)hydrazono]-5-furan-2-yl-4H-pyrazol-3-ylamine;
4-[(3-fluorophenyl)hydrazono]-5-(2-methylfuran-3-yl)-4H-pyrazol-3-ylamine;
5-(2,5-dimethyl-furan-3-yl)-4-(phenylhydrazono)-4H-pyrazol-3-ylamine;
4-(phenylhydrazono)-5-pyridin-4-yl-4H-pyrazol-3-ylamine;
5-(2-chloro-6-methylpyridin-4-yl)-4-(phenylhydrazono)-4H-pyrazol-3-ylamine;
5-(3,5-dimethylisoxazol-4-yl)-4-(phenylhydrazono)-4H-pyrazol-3-ylamine;
5-(1-methyl-1H-pyrrol-2-yl)-4-(phenylhydrazono)-4H-pyrazol-3-ylamine;
4-(phenylhydrazono)-5-thiophen-3-yl-4H-pyrazol-3-ylamine;
5-(5-methyl-2-trifluoromethylfuran-3-yl)-4-(phenylhydrazono)-4H-pyrazol-3-ylamine;
5-(2-tert-butyl-5-methylfuran-3-yl)-4-(phenylhydrazono)-4H-pyrazol-3-ylamine;
5-(2-methylfuran-3-yl)-4-(phenylhydrazono)-4H-pyrazol-3-ylamine;
5-furan-2-yl-4-(phenylhydrazono)-4H-pyrazol-3-ylamine;
4-(phenylhydrazono)-5-quinolin-6-yl-4H-pyrazol-3-ylamine;
5-[5-(4-chlorophenyl)-2-methylfuran-3-yl]-4-(phenylhydrazono)-4H-pyrazol-3-ylamine;
5-benzo[b]thiophen-3-yl-4-(phenylhydrazono)-4H-pyrazol-3-ylamine;
2-{3-[N'-(3-amino-5-pyridin-4-yl-pyrazol-4-ylidene)hydrazino]benzenesulfonyl}ethanol;
4-[(3-fluorophenyl)hydrazono]-5-pyridin-4-yl-4H-pyrazol-3-ylamine;

4-[1'-(3-amino-5-pyridin-4-ylpyrazol-4-ylidene)hydrazino]
 benzenesulfonamide;
5-(2-chloropyridin-4-yl)-4-(phenylhydrazono)-4H-pyrazol-
 3-ylamine;
5-benzo[1,3]dioxol-5-yl-4-(phenylhydrazono)-4H-pyrazol-
 3-ylamine;
5-benzo[1,2,5]oxadiazol-5-yl-4-(phenylhydrazono)-4H-
 pyrazol-3-ylamine;
5-(5-bromopyridin-3-yl)-4-(phenylhydrazono)-4H-pyrazol-
 3-ylamine;
4-[(3-morpholin-4-ylmethylphenyl)hydrazono]-5-pyridin-
 4-yl-4H-pyrazol-3-ylamine;
4-[(3-fluoro-4-methoxyphenyl)hydrazono]-5-pyridin-4-yl-
 4H-pyrazol-3-ylamine;
5-(2-methylsulfanylpyridin-3-yl)-4-(phenylhydrazono)-4H-
 pyrazol-3-ylamine;
5-(6-chloropyridin-3-yl)-4-(phenylhydrazono)-4H-pyrazol-
 3-ylamine;
5-benzo[b]thiophen-2-yl-4-(phenylhydrazono)-4H-pyrazol-
 3-ylamine;
1'-phenyl-4-(phenylhydrazono)-5'-propyl-4H,1H-[3,4']bi-
 pyrazolyl-5-ylamine;
5-(4-methyl-[1,2,3]thiadiazol-5-yl)-4-(phenylhydrazono)-
 4H-pyrazol-3-ylamine;
4-(phenylhydrazono)-5-quinoxalin-2-yl-4H-pyrazol-3-
 ylamine;
2',5'-dimethyl-4-(phenylhydrazono)-4H,2'H-[3,3']bipyra-
 zolyl-5-ylamine;
5-(5-methyl-3-phenylisoxazol-4-yl)-4-(phenylhydrazono)-
 4H-pyrazol-3-ylamine;
4-[(3,4-difluorophenyl)hydrazono]-5-pyridin-4-yl-4H-pyra-
 zol-3-ylamine;
4-[(3,4-difluoro-phenyl)-hydrazono]-5-pyridin-3-yl-4H-
 pyrazol-3-ylamine;
4-(phenylhydrazono)-5-pyridin-3-yl-4H-pyrazol-3-ylamine;
5-(3-chlorothiophen-2-yl)-4-(phenylhydrazono)-4H-pyra-
 zol-3-ylamine;
{4-[(3-fluorophenyl)hydrazono]-5-pyridin-4-yl-4H-pyra-
 zol-3-yl}methylamine;
{4-[(3,4-difluorophenyl)hydrazono]-5-pyridin-4-yl-4H-
 pyrazol-3-yl}methylamine;
4-(phenylhydrazono)-5-thiophen-2-yl-4H-pyrazol-3-
 ylamine;
4-(phenylhydrazono)-5-pyridin-2-yl-4H-pyrazol-3-ylamine;
5-(3-methoxythiophen-2-yl)-4-(phenylhydrazono)-4H-
 pyrazol-3-ylamine;
5-morpholin-4-yl-4-(phenyl-hydrazono)-4H-pyrazol-3-
 ylamine;
4-[(3-fluorophenyl)hydrazono]-5-morpholin-4-yl-4H-pyra-
 zol-3-ylamine;
4-{N'-[3-amino-5-(4-methylpiperazin-1-yl)-pyrazol-4-
 ylidene]-hydrazino}-benzenesulfonamide;
4-[N'-(3-amino-5-pyrrolidin-1-yl-pyrazol-4-ylidene)-hy-
 drazino]-benzenesulfonamide;
5-(4-methylpiperazin-1-yl)-4-(phenylhydrazono)-4H-pyra-
 zol-3-ylamine dihydrochloride;
5-pyrrolidin-1-yl-4-[(3-trifluoromethyl-phenyl)-hydra-
 zono]-4H-pyrazol-3-ylamine;
3-[N'-(3-amino-5-pyrrolidin-1-yl-pyrazol-4-ylidene)-hy-
 drazino]-N-methyl-benzenesulfonamide;
3-[N'-(3-amino-5-pyrrolidin-1-yl-pyrazol-4-ylidene)-hy-
 drazino]-benzenesulfonamide;
4-[(3-fluoro-phenyl)-hydrazono]-5-pyrrolidin-1-yl-4H-
 pyrazol-3-ylamine;
5-pyrrolidin-1-yl-4-[(3-pyrrolidin-1-ylmethyl-phenyl)-hy-
 drazono]-4H-pyrazol-3-ylamine;
4-[(3-dimethylaminomethylphenyl)-hydrazono]-5-morpho-
 lin-4-yl-4H-pyrazol-3-ylamine;
4-[(3-morpholin-4-ylmethyl-phenyl)-hydrazono]-5-pyrroli-
 din-1-yl-4H-pyrazol-3-ylamine;
4-[(3-fluoro-4-methoxyphenyl)-hydrazono]-5-morpholin-4-
 yl-4H-pyrazol-3-ylamine;
3-[N'-(3-amino-5-morpholin-4-yl-pyrazol-4-ylidene)-hy-
 drazino]-benzenesulfonamide;
3-[N'-(3-amino-5-morpholin-4-yl-pyrazol-4-ylidene)-hy-
 drazino]-N-methyl-benzenesulfonamide; and
3-[N'-(3-amino-5-morpholin-4-yl-pyrazol-4-ylidene)-hy-
 drazino]-N-(2-hydroxyethyl)-benzenesulfonamide.

Particularly preferred are those compounds selected from the group consisting of the following:

4-[(3-fluorophenyl)hydrazono]-5-furan-2-yl-4H-pyrazol-3-
 ylamine;
4-(phenylhydrazono)-5-pyridin-4-yl-4H-pyrazol-3-ylamine;
4-(phenylhydrazono)-5-thiophen-3-yl-4H-pyrazol-3-
 ylamine;
5-furan-2-yl-4-(phenylhydrazono)-4H-pyrazol-3-ylamine;
2-{3-[N'-(3-amino-5-pyridin-4-yl-pyrazol-4-ylidene)hy-
 drazino]benzenesulfonyl}ethanol;
4-[(3-fluorophenyl)hydrazono]-5-pyridin-4-yl-4H-pyrazol-
 3-ylamine;
4-[N'-(3-amino-5-pyridin-4-yl-pyrazol-4-ylidene)hy-
 drazino]benzenesulfonamide;
4-[(3-morpholin-4-ylmethylphenyl)hydrazono]-5-pyridin-
 4-yl-4H-pyrazol-3-ylamine;
4-[(3-fluoro-4-methoxyphenyl)hydrazono]-5-pyridin-4-yl-
 4H-pyrazol-3-ylamine;
4-[(3,4-difluoro-phenyl)-hydrazono]-5-pyridin-3-yl-4H-
 pyrazol-3-ylamine; and
4-(phenylhydrazono)-5-pyridin-3-yl-4H-pyrazol-3-ylamine.

Another preferred subgroup of compounds is that subgroup of compounds wherein $R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl); and $R^{5c}$ is heterocyclylalkyl selected from the group consisting of the following: isoindoledionylalkyl, morpholinylalkyl, and triazolylalkyl.

Of this subgroup of compounds, preferred compounds are selected from the group consisting of the following:

2-{5-amino-4-[(3,4-difluorophenyl)hydrazono]-4H-pyra-
 zol-3-ylmethyl}isoindole-1,3-dione;
2-{5-amino-4-[(3-fluorophenyl)hydrazono]-4H-pyrazol-3-
 ylmethyl}isoindole-1,3-dione;
4-[(3-fluorophenyl)hydrazono]-5-morpholin-4-ylmethyl-
 4H-pyrazol-3-ylamine;
4-[(3,4-difluorophenyl)hydrazono]-5-morpholin-4-ylm-
 ethyl-4H-pyrazol-3-ylamine;
5-(1-methyl-1-[1,2,4]triazol-1-ylethyl)-4-(phenylhydra-
 zono)-4H-pyrazol-3-ylamine;
5-(2-morpholin-4-ylethyl)-4-(phenylhydrazono)-4H-pyra-
 zol-3-ylamine;
4-[((3-fluorophenyl)hydrazono]-5-(3-morpholin-4-yl-pro-
 pyl)-4H-pyrazol-3-ylamine; and
5-(4-morpholin-4-ylbutyl)-4-(phenylhydrazono)-4H-pyra-
 zol-3-ylamine.

Particularly preferred is 4-[(3-fluorophenyl)hydrazono]-5-morpholin-4-yl-methyl-4H-pyrazol-3-ylamine.

Another preferred subgroup is that subgroup of compounds of formula (Ic) wherein:

$R^{2c}$ is phenyl (optionally substituted with one or more substituents selected from the group consisting of halo, alkoxy, nitro, haloalkyl, —$R^{6c}$—$N(R^{8c})_2$, —$S(O)_2$—$R^{6c}$—OH, —$S(O)_2$—$N(R^{7c})R^{8c}$ and heterocyclylalkyl); and $R^{5c}$ is hydrogen, alkyl, alkenyl, or cycloalkyl (optionally substituted by one or more substituents selected from the group consisting of alkyl and phenyl);

$R^{6c}$ is a straight or branched alkylene chain.

Of this subgroup of compounds, a preferred class of compounds are those compounds wherein the compound is selected from the group consisting of the following:
tert-butyl-[5-methyl-4-(phenylhydrazono)-4H-pyrazol-3-yl]amine;
4-[(3-fluorophenyl)hydrazono]-4H-pyrazol-3-ylamine;
5-methyl-4-(phenyl-hydrazono)-4H-pyrazol-3-ylamine;
4-(3-fluorophenylhydrazono)-5-methyl-2H-pyrazol-3-ylamine
4-[(3-chlorophenyl)hydrazono]-5-methyl-4H-pyrazol-3-ylamine;
4-[(3,4-difluorophenyl)hydrazono]-4H-pyrazol-3-ylamine;
5-tert-butyl-4-[(3-fluorophenyl)hydrazono]-4H-pyrazol-3-ylamine;
4-(phenylhydrazono)-4H-pyrazol-3-ylamine;
5-but-3-enyl-4-[(3,4-difluorophenyl)hydrazono]-4H-pyrazol-3-ylamine;
4-[(3,4-difluorophenyl)hydrazono]-5-methyl-4H-pyrazol-3-ylamine;
5-methyl-4-[(4-trifluoromethylphenyl)hydrazono]-4H-pyrazol-3-ylamine;
5-methyl-4-[(3-nitrophenyl)hydrazono]-4H-pyrazol-3-ylamine;
5-but-3-enyl-4-[(3-nitrophenyl)hydrazono]-4H-pyrazol-3-ylamine;
{4-[(3,4-difluorophenyl)hydrazono]-5-methyl-4H-pyrazol-3-yl}ethylamine;
5-ethyl-4-(phenylhydrazono)-4H-pyrazol-3-ylamine;
ethyl-{4-[(3-fluoro-phenyl)hydrazono]-5-methyl-4H-pyrazol-3-yl}amine;
{4-[(3,4-difluorophenyl)hydrazono]-5-methyl-4H-pyrazol-3-yl}methylamine;
4-[N'-(3-aminopyrazol-4-ylidene)hydrazino]benzenesulfonamide;
5-cyclopropyl-4-(phenylhydrazono)-4H-pyrazol-3-ylamine;
4-[(3-fluoro-4-methoxyphenyl)hydrazono]-4H-pyrazol-3-ylamine;
5-isopropyl-4-(phenylhydrazono)-4H-pyrazol-3-ylamine;
5-(2,2-dimethylpropyl)-4-(phenylhydrazono)-4H-pyrazol-3-ylamine;
5-(2-phenylcyclopropyl)-4-(phenylhydrazono)-4H-pyrazol-3-ylamine;
5-(1-ethylpropyl)-4-(phenylhydrazono)-4H-pyrazol-3-ylamine;
5-isobutyl-4-(phenylhydrazono)-4H-pyrazol-3-ylamine;
{4-[(3-fluorophenyl)-hydrazono]-5-methyl-4H-pyrazol-3-yl}methylamine;
4-[(4-methoxyphenyl)hydrazono]-5-methyl-4H-pyrazol-3-ylamine;
N-{5-amino-4-[(3-fluorophenyl)hydrazono]-4H-pyrazol-3-ylmethyl}-2-chloro-6-methyl-nicotinamide;
3-[N'-(3-amino-5-cyclopropylpyrazol-4-ylidene)hydrazino]-n-(2-hydroxyethyl)-benzenesulfonamide; and
3-[N-(3-amino-5-cyclopropylpyrazol-4-ylidene)hydrazino]benzenesulfonamide.

Particularly preferred are those compounds selected from the group consisting of the following:
4-[(3-fluorophenyl)hydrazono]-4H-pyrazol-3-ylamine;
5-methyl-4-[(3-nitrophenyl)hydrazono]-4H-pyrazol-3-ylamine; and
4-[(3-fluoro-4-methoxyphenyl)hydrazono]-4H-pyrazol-3-ylamine.

Another preferred subgroup of the compounds of formula (Ic is that subgroup wherein:
$R^{2c}$ is phenyl (optionally substituted with one or more substituents selected from the group consisting of halo, alkoxy, nitro, haloalkyl, —$R^{6c}$—$N(R^{8c})_2$, —$S(O)_2$—$R^{6c}$—OH, —$S(O)_2$—$N(R^{7c})R^{8c}$ and heterocyclylalkyl);
$R^{5c}$ is —$R^{6c}$—O—$R^{12c}$, —$R^{6}$—S—$R^{12c}$, —$R^{6c}$—$N(R^{9c})_2$;
each $R^{9c}$ is independently hydrogen, alkyl, aryl, aralkyl, heterocyclylalkyl, —C(O)—$R^{11c}$, —C(O)—$R^{10c}$—C(O)OR$^{7c}$, —$R^{10c}$—C(O)OR$^{7c}$, or —$S(O)_2$—$R^{7c}$;
each $R^{10c}$ is independently a direct bond, straight or branched alkylene chain or straight or branched alkenylene chain;
$R^{11c}$ is aryl (optionally substituted by one or more substituents selected from the group consisting of alkyl and halo), heterocyclyl (optionally substituted by one or more substituents selected from the group consisting of —C(O)OR$^{7c}$ and —C(O)N(R$^{7c}$)$_2$) or heterocyclylalkyl (optionally substituted by one or more substituents selected from the group consisting of —C(O)OR$^{7c}$ and —C(O)N(R$^{7c}$)$_2$); and
each $R^{12c}$ is independently aryl or aralkyl (optionally substituted by one or more substituents selected from group consisting of halo and nitro).

A preferred class of compounds of this subgroup of compounds is that class of compounds wherein the compound is a compound of formula (Ic) wherein $R^{5c}$ is —$R^{6c}$—O—$R^{12c}$ or —$R^{6c}$—S—$R^{12c}$.

Of this class of compounds, preferred compounds are selected from the group consisting of the following:
5-(4-chlorophenoxymethyl)-4-(phenylhydrazono)-4H-pyrazol-3-ylamine;
5-(3-phenoxypropyl)-4-(phenylhydrazono)-4H-pyrazol-3-ylamine;
5-(2-methylsulfanylethyl)-4-(phenylhydrazono)-4H-pyrazol-3-ylamine; and
5-(2-nitrophenoxymethyl)-4-(phenylhydrazono)-4H-pyrazol-3-ylamine.

Another preferred class of compounds is that class of compounds of formula (Ic) wherein:
$R^{5c}$ is —$R^{6c}$—$N(R^{9c})_2$; and
one $R^{9c}$ is hydrogen and the other $R^{9c}$ is hydrogen, alkyl, aryl, aralkyl, heterocyclylalkyl, —C(O)—$R^{11c}$, —C(O)—$R^{10c}$—C(O)OR$^{7c}$, —$R^{10c}$—C(O)OR$^{7c}$, or —$S(O)_2$—$R^{7c}$.

Of this class of compounds, preferred compounds are selected from the group consisting of the following:
5-aminomethyl-4-[(3-fluorophenyl)hydrazono]-4H-pyrazol-3-ylamine;
3-({5-amino-4-[(3-fluorophenyl)hydrazono]-4H-pyrazol-3-ylmethyl}carbamoyl)acrylic acid;
N-{5-amino-4-[(3-fluorophenyl)hydrazono]-4H-pyrazol-3-ylmethyl}isonicotinamide;
N-{5-amino-4-[(3-fluorophenyl)hydrazono]-4H-pyrazol-3-ylmethyl}nicotinamide;
1-[({5-amino-4-[(3-fluorophenyl)hydrazono]-4H-pyrazol-3-ylmethyl}carbamoyl)methyl]pyrrolidine-2-carboxylic acid methyl ester;
1-[3-({5-amino-4-[(3-fluorophenyl)hydrazono]-4H-pyrazol-3-ylmethyl}carbamoyl)acryloyl]-pyrrolidine-2-carboxylic acid methyl ester;
N-{5-amino-4-[(3-fluorophenyl)hydrazono]-4H-pyrazol-3-ylmethyl}methanesulfonamide;
N-{5-amino-4-[(3-fluorophenyl)hydrazono]-4H-pyrazol-3-ylmethyl}succinamic acid;
1-[({5-amino-4-[(3-fluorophenyl)hydrazono]-4H-pyrazol-3-ylmethyl}carbamoyl)methyl]pyrrolidine-2-carboxylic acid;

N-{5-amino-4-[(3,4-difluorophenyl)hydrazono]-4H-pyrazol-3-ylmethyl}nicotinamide;
4-[(3,4-difluorophenyl)-hydrazono]-5-[(2-morpholin-4-yl-ethylamino)methyl]-4H-pyrazol-3-yl-amine;
N-{5-amino-4-[(3-fluorophenyl)hydrazono]-4H-pyrazol-3-ylmethyl}-4-fluorobenzenesulfonamide;
N-{5-amino-4-[(3-fluorophenyl)hydrazono]-4H-pyrazol-3-ylmethyl}malonamic acid benzyl ester;
butane-1-sulfonic acid {5-amino-4-[(3-fluorophenyl)hydrazono]-4H-pyrazol-3-ylmethyl}amide;
N-{5-amino-4-[(3,4-difluorophenyl)hydrazono]-4H-pyrazol-3-ylmethyl}-2-chloro-6-methyl-nicotinamide;
N-{5-amino-4-[(3-fluorophenyl)hydrazono]-4H-pyrazol-3-ylmethyl}-2-chloro-6-methyl-nicotinamide; and
5-(3-aminopropyl)-4-(phenylhydrazono)-4H-pyrazol-3-ylamine.

Another preferred class of compounds is that class of compounds of formula (Ic) wherein:
$R^{5c}$ is $—R^{6c}—N(R^{9c})_2$; and
each $R^{9c}$ is the same and selected from the group consisting of heterocyclylalkyl and $—R^{10c}—C(O)OR^{7c}$.

Of this class of compounds, preferred compounds are selected from the group consisting of the following:
5-{[bis-(2-morpholin-4-ylethyl)amino]methyl}-4-[(3,4-difluorophenyl)hydrazono]-4H-pyrazol-3-ylamine;
5-[(bis-pyridin-3-ylmethylamino)methyl]-4-[(3,4-difluorophenyl)hydrazono]-4H-pyrazol-3-ylamine;
5-[(bis-pyridin-2-ylmethylamino)methyl]-4-[(3,4-difluorophenyl)hydrazono]-4H-pyrazol-3-ylamine; and
({5-amino-4-[(3,4-difluorophenyl)hydrazono]-4H-pyrazol-3-ylmethyl}ethoxycarbonylmethylamino)-acetic acid ethyl ester.

Another preferred subgroup of compounds of formula (Ic) is that subgroup of compounds wherein:
$R^{1c}$ and $R^{4c}$ are each hydrogen; and
$R^{2c}$ is N-heterocyclyl (optionally substituted one or more substituents selected from the group consisting of alkyl, halo, and $—C(O)OR^{7c}$).

Of this preferred subgroup, a preferred class of compounds of formula (Ic) is that subgroup of compounds wherein:
$R^{2c}$ is N-heterocyclyl selected from the group consisting of pyridinyl, thiazolyl, tetrazolyl, pyrazolyl, isoquinolinyl, quinolinyl, and phthalazinyl;
$R^{3c}$ is hydrogen or alkyl; and
$R^{5c}$ is hydrogen, alkyl, alkenyl, $—R^{6c}—NH_2$, cycloalkyl, phenylalkyl (wherein the phenyl group is optionally substituted by one or more substituents selected from the group consisting of alkoxy and halo), or heterocyclyl selected from the group consisting of morpholin-4-yl, piperidin-4-yl, pyridin-4-yl, thien-2-yl, pyrrolyl, and pyrrolidin-2-yl.

Of this class of compounds, preferred compounds are selected from the group consisting of the following:
5-methyl-4-[(4H-[1,2,4]triazol-3-yl)hydrazono]-4H-pyrazol-3-ylamine;
5-methyl-4-[(2H-tetrazol-5-yl)hydrazono]-4H-pyrazol-3-ylamine;
3-[N'-(3-amino-5-methylpyrazol-4-ylidene)hydrazino]-1H-pyrazole-4-carboxylic acid ethyl ester;
3-[N'-(3-amino-5-methylpyrazol-4-ylidene)hydrazino]-1H-pyrazole-4-carboxylic acid;
5-[N'-(3-amino-5-methylpyrazol-4-ylidene)hydrazino]-2H-[1,2,3]triazole-4-carboxylic acid;
4-(phenylhydrazono)-4H-pyrazol-3-ylamine;
5-(4-methoxybenzyl)-4-(pyridin-3-ylhydrazono)-4H-pyrazol-3-ylamine;
5-tert-butyl-4-[(1H-tetrazol-5-yl)hydrazono]-4H-pyrazol-3-ylamine;
4-(isoquinolin-5-ylhydrazono)-5-phenethyl-4H-pyrazol-3-ylamine;
5-but-3-enyl-4-(isoquinolin-5-ylhydrazono)-4H-pyrazol-3-ylamine;
5-aminomethyl-4-(isoquinolin-5-ylhydrazono)-4H-pyrazol-3-ylamine;
4-(isoquinolin-5-ylhydrazono)-5-methyl-4H-pyrazol-3-ylamine;
5-methyl-4-(pyridin-3-ylhydrazono)-4H-pyrazol-3-ylamine;
5-but-3-enyl-4-(quinolin-6-ylhydrazono)-4H-pyrazol-3-ylamine;
5-but-3-enyl-4-(pyridin-3-ylhydrazono)-4H-pyrazol-3-ylamine;
ethyl-[5-methyl-4-(pyridin-3-ylhydrazono)-4H-pyrazol-3-yl]amine;
4-(isoquinolin-5-ylhydrazono)-5-pyridin-4-yl-4H-pyrazol-3-ylamine;
5-pyridin-4-yl-4-(pyridin-3-ylhydrazono)-4H-pyrazol-3-ylamine;
5-methyl-4-(phthalazin-5-ylhydrazono)-4H-pyrazol-3-ylamine;
methyl-[4-(phthalazin-5-ylhydrazono)-5-pyridin-4-yl-4H-pyrazol-3-yl]amine;
4-(pyridin-3-yl-hydrazono)-5-thiophen-2-yl-4H-pyrazol-3-ylamine;
5-(1-methyl-1H-pyrrol-2-yl)-4-(pyridin-3-ylhydrazono)-4H-pyrazol-3-ylamine;
5-(1-methyl-1H-pyrrol-2-yl)-4-(quinolin-6-ylhydrazono)-4H-pyrazol-3-ylamine;
5-cyclopropyl-4-(pyridin-3-ylhydrazono)-4H-pyrazol-3-ylamine;
5-morpholin-4-yl-4-(pyridin-3-yl-hydrazono)-4H-pyrazol-3-ylamine;
4-[(6-chloropyridin-3-yl)-hydrazono]-5-morpholin-4-yl-4H-pyrazol-3-ylamine;
5-pyrrolidin-1-yl-4-(quinolin-6-yl-hydrazono)-4H-pyrazol-3-ylamine;
4-[(6-chloro-pyridin-3-yl)-hydrazono]-5-pyrrolidin-1-yl-4H-pyrazol-3-ylamine;
4-[(6-fluoro-pyridin-3-yl)-hydrazono]-5-pyrrolidin-1-yl-4H-pyrazol-3-ylamine;
5-morpholin-4-yl-4-(phthalazin-5-ylhydrazono)-4H-pyrazol-3-ylamine; and
4-[(6-methyl-pyridin-3-yl)-hydrazono]-5-morpholin-4-yl-4H-pyrazol-3-ylamine.

Particularly preferred are those compounds selected from the group consisting of the following:
5-(4-methoxybenzyl)-4-(pyridin-3-ylhydrazono)-4H-pyrazol-3-ylamine;
4-(isoquinolin-5-ylhydrazono)-5-methyl-4H-pyrazol-3-ylamine;
5-but-3-enyl-4-(pyridin-3-ylhydrazono)-4H-pyrazol-3-ylamine;
4-(isoquinolin-5-ylhydrazono)-5-pyridin-4-yl-4H-pyrazol-3-ylamine;
5-pyridin-4-yl-4-(pyridin-3-ylhydrazono)-4H-pyrazol-3-ylamine;
5-methyl-4-(phthalazin-5-ylhydrazono)-4H-pyrazol-3-ylamine;
5-(1-methyl-1H-pyrrol-2-yl)-4-(pyridin-3-ylhydrazono)-4H-pyrazol-3-ylamine; and
5-(1-methyl-1H-pyrrol-2-yl)-4-(quinolin-6-ylhydrazono)-4H-pyrazol-3-ylamine.

Another preferred class of compounds is that class of compounds of formula (Ic) wherein:

$R^{2c}$ is N-heterocyclyl selected from the group consisting of pyridinyl, thiazolyl, tetrazolyl, pyrazolyl, isoquinolinyl, quinolinyl, and phthalazinyl;

$R^{3c}$ is hydrogen or alkyl; and $R^{5c}$ is phenyl (optionally substituted by one or more substituents selected from the group consisting of alkoxy and halo).

A preferred compound of this class is
5-(2-fluorophenyl)-4-(phthalazin-5-ylhydrazono)-4H-pyrazol-3-ylamine.

Another preferred group of compounds of formula (I) is that group of compounds having formula (Ic)

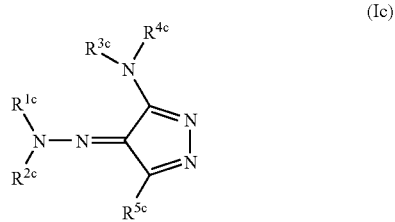

(Ic)

as a single tautomer, a mixture of tautomers, a single stereoisomer, a mixture of stereoisomers, or a racemic mixture; or a pharmaceutically acceptable salt or solvate thereof; wherein:

$R^{1c}$ is hydrogen, alkyl, aryl or aralkyl;

$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl);

$R^{3c}$ is hydrogen, alkyl, heterocyclylalkyl, or heterocyclylcarbonyl;

$R^{4c}$ is hydrogen or alkyl;

$R^{5c}$ is aryl (optionally substituted by one or more substituents selected from the group consisting of alkoxy, halo, haloalkyl, haloalkoxy, haloalkylthio, arylthioalkyl (wherein the aryl group is optionally substituted with one or more halo groups), nitro, —C(O)O$R^{7c}$, and —N($R^{7c}$)—C(O)—$R^{7c}$);

$R^{6c}$ is a straight or branched alkylene chain:

each $R^{7c}$ is independently hydrogen, alkyl, aryl, aralkyl or heterocyclylakyl; and $R^{8c}$ is hydrogen, alkyl, aryl, aralkyl or hydroxyalkyl.

Of this group of compounds, a preferred subgroup is that subgroup of compounds wherein:

$R^{1c}$ and $R^{4c}$ are each hydrogen;

$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl); and $R^{5c}$ is phenyl (optionally substituted by one or more substituents selected from the group consisting of alkoxy, halo, haloalkyl, haloalkoxy, haloalkylthio, phenylthioalkyl (wherein the phenyl group is optionally substituted with one or more halo groups), nitro, —C(O)O$R^{7c}$, and —N($R^{7c}$)—C(O)—$R^{7c}$).

Of this preferred subgroup, preferred compounds are selected from the group consisting of the following:

5-phenyl-4-(phenylhydrazono)-4H-pyrazol-3-ylamine;
4-[(3-fluorophenyl)hydrazono]-5-m-tolyl-4H-pyrazol-3-ylamine;
4-[(3-fluorophenyl)hydrazono]-5-p-tolyl-4H-pyrazol-3-ylamine;
5-(3-chlorophenyl)-4-[(3-fluorophenyl)hydrazono]-4H-pyrazol-3-ylamine;
5-(4-chlorophenyl)-4-[(3-fluorophenyl)hydrazono]-4H-pyrazol-3-ylamine;
4-[(3-fluorophenyl)hydrazono]-5-(3-trifluoromethylphenyl)-4H-pyrazol-3-ylamine;
4-[(3-fluorophenyl)hydrazono]-5-(4-trifluoromethoxyphenyl)-4H-pyrazol-3-ylamine;
4-[(3-fluorophenyl)hydrazono]-5-(4-methoxyphenyl)-4H-pyrazol-3-ylamine;
4-[(3-fluorophenyl)hydrazono]-5-m-tolyl-4H-pyrazol-3-ylamine;
4-[(3-fluorophenyl)hydrazono]-5-p-tolyl-4H-pyrazol-3-ylamine;
5-(3-chlorophenyl)-4-[(3-fluorophenyl)hydrazono]-4H-pyrazol-3-ylamine;
5-(4-chlorophenyl)-4-[(3-fluorophenyl)hydrazono]-4H-pyrazol-3-ylamine;
4-[(3-fluorophenyl)hydrazono]-5-(3-trifluoromethylphenyl)-4H-pyrazol-3-ylamine;
4-[(3-fluorophenyl)hydrazono]-5-(4-trifluoromethoxyphenyl)-4H-pyrazol-3-ylamine;
4-[(3-fluorophenyl)hydrazono]-5-(4-methoxyphenyl)-4H-pyrazol-3-ylamine;
(2-morpholin-4-ylethyl)[5-phenyl-4-(phenylhydrazono)-4H-pyrazol-3-yl]amine;
N-[5-phenyl-4-(phenylhydrazono)-4H-pyrazol-3-yl]nicotinamide;
5-(2-fluorophenyl)-4-(phenylhydrazono)-4H-pyrazol-3-ylamine;
5-(3,4-dimethoxyphenyl)-4-(phenylhydrazono)-4H-pyrazol-3-ylamine;
4-{5-amino-4-[(3-fluorophenyl)hydrazono]-4H-pyrazol-3-yl}benzoic acid;
5-(2-nitrophenyl)-4-(phenylhydrazono)-4H-pyrazol-3-ylamine;
5-(4-chloro-3-nitrophenyl)-4-(phenylhydrazono)-4H-pyrazol-3-ylamine;
5-(3-fluorophenyl)-4-(phenylhydrazono)-4H-pyrazol-3-ylamine;
5-(4-nitrophenyl)-4-(phenylhydrazono)-4H-pyrazol-3-ylamine;
5-(3-nitrophenyl)-4-(phenylhydrazono)-4H-pyrazol-3-ylamine;
5-(3-bromophenyl)-4-(phenylhydrazono)-4H-pyrazol-3-ylamine;
5-(4-fluoro-3-methylphenyl)-4-(phenylhydrazono)4H-pyrazol-3-ylamine;
5-(4-fluorophenyl)-4-(phenylhydrazono)-4H-pyrazol-3-ylamine;
5-(3-nitrophenyl)-4-(phenylhydrazono)-4H-pyrazol-3-ylamine;
5-(3,4-difluorophenyl)-4-(phenylhydrazono)-4H-pyrazol-3-ylamine;
5-(3-fluoro-4-methylphenyl)-4-(phenylhydrazono)-4H-pyrazol-3-ylamine;
5-(3,4-dimethylphenyl)-4-(phenylhydrazono)-4H-pyrazol-3-ylamine;
4-(phenylhydrazono)-5-(2-trifluoromethoxyphenyl)-4H-pyrazol-3-ylamine;
4-(phenylhydrazono)-5-(4-trifluoromethylsulfanylphenyl)-4H-pyrazol-3-ylamine;
5-(3,5-difluorophenyl)-4-(phenylhydrazono)-4H-pyrazol-3-ylamine;

4-(phenylhydrazono)-5-(4-trifluoromethylphenyl)-4H-pyrazol-3-ylamine;
4-(phenylhydrazono)-5-(3,4,5-trimethoxyphenyl)-4H-pyrazol-3-ylamine;
5-[3-(4-chlorophenylsulfanylmethyl)phenyl]-4-(phenylhydrazono)-4H-pyrazol-3-ylamine; and
N-{4-[5-amino-4-(phenylhydrazono)-4H-pyrazol-3-yl]phenyl}acetamide.

Particularly preferred is 5-(4-nitrophenyl)-4-(phenylhydrazono)-4H-pyrazol-3-ylamine.

Another preferred group of compounds of formula (Ic) is that group of compounds having the following formula (Ic):

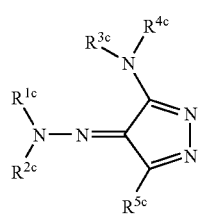

as a single tautomer, a mixture of tautomers, a single stereoisomer, a mixture of stereoisomers, or a racemic mixture; or a pharmaceutically acceptable salt or solvate thereof; wherein:
$R^{1c}$ is hydrogen, alkyl, aryl or aralkyl;
$R^{2c}$ is aryl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl);
$R^{3c}$ is hydrogen, alkyl, heterocyclylalkyl, or heterocyclylcarbonyl;
$R^{4c}$ is hydrogen or alkyl;
$R^{5c}$ is aralkyl (wherein the aryl group is optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups) or aralkenyl (wherein the aryl group is optionally substituted by one or more halo groups);
$R^{6c}$ is a straight or branched alkylene chain;
$R^{7c}$ is hydrogen, alkyl, aryl, aralkyl or heterocyclylakyl; and
$R^{8c}$ is hydrogen, alkyl, aryl, aralkyl or hydroxyalkyl, provided that when $R^{1c}$, $R^{3c}$ and $R^{4c}$ are all hydrogen and $R^{2c}$ is unsubstituted phenyl, $R^{5c}$ can not be unsubstituted benzyl.

Of this group of compounds, a preferred subgroup is that subgroup wherein:
$R^{1c}$ and $R^{4c}$ are each hydrogen;
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—COH, —S(O)$_2$—N($R^{7c}$)$R^{8c}$ and heterocyclylalkyl); and
$R^{5c}$ is phenylalkyl (wherein the phenyl group is optionally substituted by one or more substituents selected from the group consisting of alkyl, alkoxy, halo, haloalkyl, haloalkoxy, haloalkylthio, phenylthioalkyl (wherein the phenyl group is optionally substituted with one or more halo groups) or phenylalkenyl (wherein the phenyl group is optionally substituted by one or more halo groups).

Of this subgroup of compounds, preferred compounds are selected from the group consisting of the following:
5-(4-methoxybenzyl)-4-(phenylhydrazono)-4H-pyrazol-3-ylamine;
4-[(3-fluorophenyl)hydrazono]-5-phenethyl-4H-pyrazol-3-ylamine;
4-[(3-chlorophenyl)hydrazono]-5-phenethyl-4H-pyrazol-3-ylamine;
4-[(3,5-difluorophenyl)hydrazono]-5-phenethyl-4H-pyrazol-3-ylamine;
5-(4-chlorobenzyl)-4-(phenylhydrazono)-4H-pyrazol-3-ylamine;
5-benzhydryl-4-(phenylhydrazono)-4H-pyrazol-3-ylamine;
5-(2,5-dimethoxy-benzyl)-4-(phenyl-hydrazono)-4H-pyrazol-3-ylamine;
5-(3,4-dimethoxybenzyl)-(phenylhydrazono)-4H-pyrazol-3-ylamine;
5-phenethyl-4-(phenylhydrazono)-4H-pyrazol-3-ylamine; and
5-(3-ethyl-benzyl)-4-(phenyl-hydrazono)-4H-pyrazol-3-ylamine.

Another preferred group of compounds of formula (Ic) is that group of compounds having the formula (Ic):

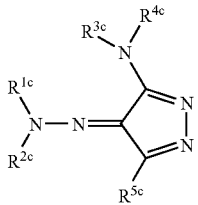

as a single tautomer, a mixture of tautomers, a single stereoisomer, a mixture of stereoisomers, or a racemic mixture; or a pharmaceutically acceptable salt or solvate thereof; wherein:
$R^{1c}$ is hydrogen, alkyl, aryl or aralkyl;
$R^{2c}$ is aryl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl);
$R^{3c}$ is hydrogen, alkyl, heterocyclylalkyl, or heterocyclylcarbonyl;
$R^{4c}$ is hydrogen or alkyl;
$R^{5c}$ is heterocyclyl (optionally substituted by one or more substituents selected from the group consisting of alkyl, halo, haloalkyl, alkylthio, and aryl (optionally substituted with one or more halo groups));
$R^{6c}$ is a straight or branched alkylene chain;
$R^{7c}$ is hydrogen, alkyl, aryl, aralkyl or heterocyclylakyl; and
$R^{8c}$ is hydrogen, alkyl, aryl, aralkyl or hydroxyalkyl;
provided that when $R^{1c}$, $R^{3c}$, and $R^{4c}$ is hydrogen, and $R^{2c}$ is unsubstituted phenyl, $R^{5c}$ can not be pyrazolonyl, benzothiazolyl or thioxotriazinyl.

Of this group of compounds, a preferred subgroup is that subgroup wherein $R^{5c}$ is a heterocyclyl selected from the group consisting of piperidinyl, morpholinyl, pyrrolidinyl, furanyl, isooxazolyl, pyridinyl, thienyl, pyrrolyl, quinolinyl, benzothienyl, benzodioxolyl, benzooxadiazolyl, pyrazolyl, thiadiazolyl, and quinoxalinyl.

Of this subgroup of compounds, preferred compounds are selected from the group consisting of the following:
4-[(3-fluorophenyl)hydrazono]-5-furan-2-yl-4H-pyrazol-3-ylamine;
4-[(3-fluorophenyl)hydrazono]-5-(2-methylfuran-3-yl)-4H-pyrazol-3-ylamine;
5-(2,5-dimethyl-furan-3-yl)-4-(phenylhydrazono)-4H-pyrazol-3-ylamine;

4-(phenylhydrazono)-5-pyridin-4-yl-4H-pyrazol-3-ylamine;
5-(2-chloro-6-methylpyridin-4-yl)-4-(phenylhydrazono)-4H-pyrazol-3-ylamine;
5-(3,5-dimethylisoxazol-4-yl)-4-(phenylhydrazono)-4H-pyrazol-3-ylamine;
5-(1-methyl-1H-pyrrol-2-yl)-4-(phenylhydrazono)4H-pyrazol-3-ylamine;
4-(phenylhydrazono)-5-thiophen-3-yl-4H-pyrazol-3-ylamine;
5-(5-methyl-2-trifluoromethylfuran-3-yl)-4-(phenylhydrazono)-4H-pyrazol-3-ylamine;
5-(2-tert-butyl-5-methylfuran-3-yl)-4-(phenylhydrazono)-4H-pyrazol-3-ylamine;
5-(2-methylfuran-3-yl)-4-(phenylhydrazono)-4H-pyrazol-3-ylamine;
5-furan-2-yl-4-(phenylhydrazono)-4H-pyrazol-3-ylamine;
4-(phenylhydrazono)-5-quinolin-6-yl-4H-pyrazol-3-ylamine;
5-[5-(4-chlorophenyl)-2-methylfuran-3-yl]-4-(phenylhydrazono)-4H-pyrazol-3-ylamine;
5-benzo[b]thiophen-3-yl-4-(phenylhydrazono)-4H-pyrazol-3-ylamine;
2-{3-[N'-(3-amino-5-pyridin-4-yl-pyrazol-4-ylidene)hydrazino]benzenesulfonyl}ethanol;
4-[(3-fluorophenyl)hydrazono]-5-pyridin-4-yl-4H-pyrazol-3-ylamine;
4-[N'-(3-amino-5-pyridin-4-yl-pyrazol-4-ylidene)hydrazino]benzenesulfonamide;
5-(2-chloropyridin-4-yl)-4-(phenylhydrazono)-4H-pyrazol-3-ylamine;
5-benzo[1,3]dioxol-5-yl-4-(phenylhydrazono)-4H-pyrazol-3-ylamine;
5-benzo[1,2,5]oxadiazol-5-yl-4-(phenylhydrazono)-4H-pyrazol-3-ylamine;
5-(5-bromopyridin-3-yl)-4-(phenylhydrazono)-4H-pyrazol-3-ylamine;
4-[(3-morpholin-4-ylmethylphenyl)hydrazono]-5-pyridin-4-yl-4H-pyrazol-3-ylamine;
4-[(3-fluoro-4-methoxyphenyl)hydrazono]-5-pyridin-4-yl-4H-pyrazol-3-ylamine;
5-(2-methylsulfanylpyridin-3-yl)-4-(phenylhydrazono)-4H-pyrazol-3-ylamine;
5-(6-chloropyridin-3-yl)-4-(phenylhydrazono)-4H-pyrazol-3-ylamine;
5-benzo[b]thiophen-2-yl-4-(phenylhydrazono)-4H-pyrazol-3-ylamine;
1'-phenyl-4-(phenylhydrazono)-5'-propyl-4H, 1'H-[3,4']bipyrazolyl-5-ylamine;
5-(4-methyl-[1,2,3]thiadiazol-5-yl)-4-(phenylhydrazono)-4H-pyrazol-3-ylamine;
4-(phenylhydrazono)-5-quinoxalin-2-yl-4H-pyrazol-3-ylamine;
2',5'-dimethyl-4-(phenylhydrazono)-4H,2'H-[3,3']bipyrazolyl-5-ylamine;
5-(5-methyl-3-phenylisoxazol-4-yl)-4-(phenylhydrazono)-4H-pyrazol-3-ylamine;
4-[(3,4-difluorophenyl)hydrazono]-5-pyridin-4-yl-4H-pyrazol-3-ylamine;
4-[(3,4-difluoro-phenyl)-hydrazono]-5-pyridin-3-yl-4H-pyrazol-3-ylamine;
4-(phenylhydrazono)-5-pyridin-3-yl-4H-pyrazol-3-ylamine;
5-(3-chlorothiophen-2-yl)-4-(phenylhydrazono)-4H-pyrazol-3-ylamine;
{4-[(3-fluorophenyl)hydrazono]-5-pyridin-4-yl-4H-pyrazol-3-yl}methylamine;
{4-[(3,4-difluorophenyl)hydrazono]-5-pyridin-4-yl-4H-pyrazol-3-yl}methylamine;
4-(phenylhydrazono)-5-thiophen-2-yl-4H-pyrazol-3-ylamine;
4-(phenylhydrazono)-5-pyridin-2-yl-4H-pyrazol-3-ylamine;
5-(3-methoxythiophen-2-yl)-4-(phenylhydrazono)-4H-pyrazol-3-ylamine;
5-morpholin-4-yl-4-(phenyl-hydrazono)-4H-pyrazol-3-ylamine;
4-[(3-fluorophenyl)hydrazono]-5-morpholin-4-yl-4H-pyrazol-3-ylamine;
4-{N'-[3-amino-5-(4-methylpiperazin-1-yl)-pyrazol-4-ylidene]-hydrazino}-benzenesulfonamide;
4-[N'-(3-amino-5-pyrrolidin-1-yl-pyrazol-4-ylidene)-hydrazino]-benzenesulfonamide;
5-(4-methylpiperazin-1-yl)-4-(phenylhydrazono)-4H-pyrazol-3-ylamine dihydrochloride;
5-pyrrolidin-1-yl-4-[(3-trifluoromethyl-phenyl)-hydrazono]-4H-pyrazol-3-ylamine;
3-[N'-(3-amino-5-pyrrolidin-1-yl-pyrazol-4-ylidene)-hydrazino]-N-methyl-benzenesulfonamide;
3-[N'-(3-amino-5-pyrrolidin-1-yl-pyrazol-4-ylidene)-hydrazino]-benzenesulfonamide;
4-[(3-fluoro-phenyl)-hydrazono]-5-pyrrolidin-1-yl-4H-pyrazol-3-ylamine;
5-pyrrolidin-1-yl-4-[(3-pyrrolidin-1-ylmethyl-phenyl)-hydrazono]-4H-pyrazol-3-ylamine;
4-[(3-dimethylaminomethylphenyl)-hydrazono]-5-morpholin-4-yl-4H-pyrazol-3-ylamine;
4-[(3-morpholin-4-ylmethyl-phenyl)-hydrazono]-5-pyrrolidin-1-yl-4H-pyrazol-3-ylamine;
4-[(3-fluoro-4-methoxyphenyl)-hydrazono]-5-morpholin-4-yl-4H-pyrazol-3-ylamine;
3-[N'-(3-amino-5-morpholin-4-yl-pyrazol-4-ylidene)-hydrazino]-benzenesulfonamide;
3-[N'-(3-amino-5-morpholin-4-yl-pyrazol-4-ylidene)-hydrazino]-N-methyl-benzenesulfonamide; and
3-[N'-(3-amino-5-morpholin-4-yl-pyrazol-4-ylidene)-hydrazino]-N-(2-hydroxyethyl)-benzenesulfonamide.

Particularly preferred compounds are selected from the group consisting of the following:

4-[(3-fluorophenyl)hydrazono]-5-furan-2-yl-4H-pyrazol-3-ylamine;
4-(phenylhydrazono)-5-pyridin-4-yl-4H-pyrazol-3-ylamine;
4-(phenylhydrazono)-5-thiophen-3-yl-4H-pyrazol-3-ylamine;
5-furan-2-yl-4-(phenylhydrazono)-4H-pyrazol-3-ylamine;
2-{3-[N'-(3-amino-5-pyridin-4-yl-pyrazol-4-ylidene)hydrazino]benzenesulfonyl}ethanol;
4-[(3-fluorophenyl)hydrazono]-5-pyridin-4-yl-4H-pyrazol-3-ylamine;
4-[N'-(3-amino-5-pyridin-4-ylpyrazol-4-ylidene)hydrazino]benzenesulfonamide;
4-[(3-morpholin-4-ylmethylphenyl)hydrazono]-5-pyridin-4-yl-4H-pyrazol-3-ylamine;
4-[(3-fluoro-4-methoxyphenyl)hydrazono]-5-pyridin-4-yl-4H-pyrazol-3-ylamine;
4-[(3,4-difluoro-phenyl)-hydrazono]-5-pyridin-3-yl-4H-pyrazol-3-ylamine; and
4-(phenylhydrazono)-5-pyridin-3-yl-4H-pyrazol-3-ylamine.

Another preferred group of compounds of formula (Ic) is that group of compounds having the formula (Ic):

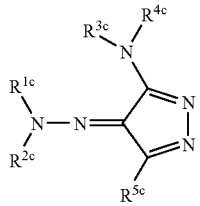

(Ic)

as a single tautomer, a mixture of tautomers, a single stereoisomer, a mixture of stereoisomers, or a racemic mixture; or a pharmaceutically acceptable salt or solvate thereof; wherein:
$R^{1c}$ is hydrogen, alkyl, aryl or aralkyl;
$R^{2c}$ is aryl (optionally substituted with one or more substituents selected from the group consisting of halo, alkoxy, nitro, haloalkyl, $—R^{6c}—N(R^{8c})_2$, $—S(O)_2—R^{6c}—OH$, $—S(O)_2—N(R^{7c})R^{8c}$ and heterocyclylalkyl);
$R^{3c}$ is hydrogen, alkyl, heterocyclylalkyl, or heterocyclylcarbonyl;
$R^{4c}$ is hydrogen or alkyl;
$R^{5c}$ is heterocyclylalkyl selected from the group consisting of the following: isoindoledionylalkyl, morpholinylalkyl, and triazolylalkyl;
$R^{6c}$ is a straight or branched alkylene chain;
$R^{7c}$ is hydrogen, alkyl, aryl, aralkyl or heterocyclylakyl; and
$R^{8c}$ is hydrogen, alkyl, aryl, aralkyl or hydroxyalkyl.

Of this group of compounds, preferred compounds are selected from the group consisting of the following:
2-{5-amino-4-[(3,4-difluorophenyl)hydrazono]-4H-pyrazol-3-ylmethyl}isoindole-1,3-dione;
2-{5-amino-4-[(3-fluorophenyl)hydrazono]-4H-pyrazol-3-ylmethyl}isoindole-1,3-dione;
4-[(3-fluorophenyl)hydrazono]-5-morpholin-4-ylmethyl-4H-pyrazol-3-ylamine;
4-[(3,4-difluorophenyl)hydrazono]-5-morpholin-4-ylmethyl-4H-pyrazol-3-ylamine;
5-(1-methyl-1-[1,2,4]triazol-1-ylethyl)-4-(phenylhydrazono)-4H-pyrazol-3-ylamine;
5-(2-morpholin-4-ylethyl)-4-(phenylhydrazono)-4H-pyrazol-3-ylamine;
4-[(3-fluorophenyl)hydrazono]-5-(3-morpholin-4-yl-propyl)-4H-pyrazol-3-ylamine; and
5-(4-morpholin-4-ylbutyl)-4-(phenylhydrazono)-4H-pyrazol-3-ylamine.

Particularly preferred is 4-[(3-fluorophenyl)hydrazono]-5-morpholin-4-yl-methyl-4H-pyrazol-3-ylamine.

Another preferred group of compounds of formula (Ic) is that group having the formula (Ic):

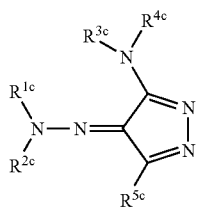

(Ic)

as a single tautomer, a mixture of tautomers, a single stereoisomer, a mixture of stereoisomers, or a racemic mixture; or a pharmaceutically acceptable salt or solvate thereof; wherein:
$R^{1c}$ is hydrogen, alkyl, aryl or aralkyl;
$R^{2c}$ is aryl (optionally substituted with one or more substituents selected from the group consisting of halo, alkoxy, nitro, haloalkyl, $—R^{6c}—N(R^{8c})_2$, $—S(O)_2—R^{6c}—OH$, $—S(O)_2—N(R^{7c})R^{8c}$ and heterocyclylalkyl);
$R^{3c}$ is hydrogen, alkyl, heterocyclylalkyl, or heterocyclylcarbonyl;
$R^{4c}$ is hydrogen or alkyl;
$R^{5c}$ is hydrogen, alkyl, alkenyl, or cycloalkyl (optionally substituted by one or more substituents selected from the group consisting of alkyl and phenyl);
$R^{6c}$ is a straight or branched alkylene chain;
$R^{7c}$ is hydrogen, alkyl, aryl, aralkyl or heterocyclylakyl; and
$R^{8c}$ is hydrogen, alkyl, aryl, aralkyl or hydroxyalkyl,
provided that when $R^{1c}$, $R^{3c}$, $R^{4c}$ and $R^{5c}$ are all hydrogen, $R^{2c}$ can not be unsubstituted phenyl and when $R^{1c}$, $R^{3c}$ and $R^{4c}$ are all hydrogen and $R^{5c}$ is methyl, $R^{2c}$ can not be phenyl optionally substituted with one or more substituents selected from the group consisting of chloro, bromo or alkyl.

Preferred compounds of this group of compounds are selected from the group consisting of the following:
tert-butyl-[5-methyl-4-(phenylhydrazono)-4H-pyrazol-3-yl]amine;
4-[(3-fluorophenyl)hydrazono]-4H-pyrazol-3-ylamine;
4-(3-fluorophenylazo)-5-methyl-2H-pyrazol-3-ylamine;
4-[(3,4-difluorophenyl)hydrazono]-4H-pyrazol-3-ylamine;
5-tert-butyl-4-[(3-fluorophenyl)hydrazono]-4H-pyrazol-3-ylamine;
5-but-3-enyl-4-[(3,4-difluorophenyl)hydrazono]-4H-pyrazol-3-ylamine;
4-[(3,4-difluorophenyl)hydrazono]-5-methyl-4H-pyrazol-3-ylamine;
5-methyl-4-[(4-trifluoromethylphenyl)hydrazono]-4H-pyrazol-3-ylamine;
5-methyl-4-[(3-nitrophenyl)hydrazono]-4H-pyrazol-3-ylamine;
5-but-3-enyl-4-[(3-nitrophenyl)hydrazono]-4H-pyrazol-3-ylamine;
{4-[(3,4-difluorophenyl)hydrazono]-5-methyl-4H-pyrazol-3-yl}ethylamine;
5-ethyl-4-(phenylhydrazono)-4H-pyrazol-3-ylamine;
ethyl-{4-[(3-fluoro-phenyl)hydrazono]-5-methyl-4H-pyrazol-3-yl}amine;
{4-[(3,4-difluorophenyl)hydrazono]-5-methyl-4H-pyrazol-3-yl}methylamine;
4-[N'-(3-aminopyrazol-4-ylidene)hydrazino]benzenesulfonamide;
5-cyclopropyl-4-(phenylhydrazono)-4H-pyrazol-3-ylamine;
4-[(3-fluoro-4-methoxyphenyl)hydrazono]-4H-pyrazol-3-ylamine;
5-isopropyl-4-(phenylhydrazono)-4H-pyrazol-3-ylamine;
5-(2,2-dimethylpropyl)-4-(phenylhydrazono)-4H-pyrazol-3-ylamine;
5-(2-phenylcyclopropyl)-4-(phenylhydrazono)-4H-pyrazol-3-ylamine;
5-(1-ethylpropyl)-4-(phenylhydrazono)-4H-pyrazol-3-ylamine;
5-isobutyl-4-(phenylhydrazono)-4H-pyrazol-3-ylamine;
{4-[(3-fluorophenyl)-hydrazono]-5-methyl-4H-pyrazol-3-yl}methylamine;
4-[(4-methoxyphenyl)hydrazono]-5-methyl-4H-pyrazol-3-ylamine;
N-{5-amino-4-[(3-fluorophenyl)hydrazono]-4H-pyrazol-3-ylmethyl}-2-chloro-6-methyl-nicotinamide;
3-[N'-(3-amino-5-cyclopropylpyrazol-4-ylidene)hydrazino]-N-(2-hydroxyethyl)benzene-sulfonamide; and 3-[N-(3-amino-5-cyclopropylpyrazol-4-ylidene)hydrazino]benzenesulfonamide.

Particularly preferred are those compounds selected from the group consisting of the following:
4-[(3-fluorophenyl)hydrazono]-4H-pyrazol-3-ylamine;
5-methyl-4-[(3-nitrophenyl)hydrazono]-4H-pyrazol-3-ylamine; and
4-[(3-fluoro-4-methoxyphenyl)hydrazono]-4H-pyrazol-3-ylamine.

Another preferred group of compounds of formula (Ic) is that group of compounds having the formula (Ic):

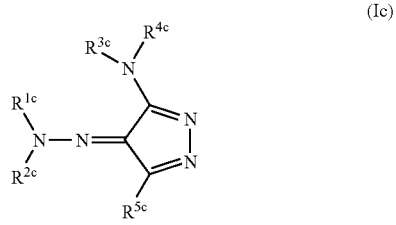

as a single tautomer, a mixture of tautomers, a single stereoisomer, a mixture of stereoisomers, or a racemic mixture; or a pharmaceutically acceptable salt or solvate thereof; wherein:
$R^{1c}$ is hydrogen, alkyl, aryl or aralkyl;
$R^{2c}$ is aryl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl);
$R^{4c}$ is hydrogen or alkyl;
$R^{3c}$ is hydrogen, alkyl, heterocyclylalkyl, or heterocyclylcarbonyl;
$R^{5c}$ is $R^{6c}$—OR$^{12c}$, $R^{6c}$—S—R$^{12c}$, —$R^{6c}$—N($R^{9c}$)$_2$;
each $R^{6c}$ is independently a straight or branched alkylene chain;
each $R^{7c}$ is independently hydrogen, alkyl, aryl, aralkyl or heterocyclylakyl;
$R^{8c}$ is hydrogen, alkyl, aryl, aralkyl or hydroxyalkyl;
each $R^{9c}$ is independently hydrogen, alkyl, aryl, aralkyl, heterocyclylalkyl, —C(O)—R$^{11c}$, —C(O)—R$^{10c}$—C(O)OR$^{7c}$, —R$^{10c}$—C(O)OR$^{7c}$, or —S(O)$_2$—R$^{7c}$;
each $R^{10c}$ is independently a direct bond, straight or branched alkylene chain or straight or branched alkenylene chain;
$R^{11c}$ is aryl (optionally substituted by one or more substituents selected from the group consisting of alkyl and halo), heterocyclyl (optionally substituted by one or more substituents selected from the group consisting of —C(O)OR$^{7c}$ and —C(O)N(R$^{7c}$)$_2$) or heterocyclylalkyl (optionally substituted by one or more substituents selected from the group consisting of —C(O)OR$^{7c}$ and —C(O)N(R$^{7c}$)$_2$); and
each $R^{12}$ is independently aryl or aralkyl (optionally substituted by one or more substituents selected from group consisting of halo and nitro).

Of this group of compounds, a preferred subgroup of compounds is tht subgroup wherein:
$R^{1c}$ and $R^{4c}$ are each hydrogen;
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl); and
$R^{5c}$ is —$R^{6c}$—O—$R^{12c}$ or $R^{6c}$—S—$R^{12c}$.

Of this subgroup of compounds, preferred compounds are selected from the group consisting of the following:
5-(4-chlorophenoxymethyl)-4-(phenylhydrazono)-4H-pyrazol-3-ylamine;
5-(3-phenoxypropyl)-4-(phenylhydrazono)-4H-pyrazol-3-ylamine;
5-(2-methylsulfanylethyl)-4-(phenylhydrazono)-4H-pyrazol-3-ylamine; and
5-(2-nitrophenoxymethyl)-4-(phenylhydrazono)-4H-pyrazol-3-ylamine.

Another preferred group of compounds is that group wherein:
$R^{1c}$ and $R^{4c}$ are each hydrogen;
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl);
$R^{5c}$ is —$R^{6c}$—N($R^{9c}$)$_2$; and
one $R^{9c}$ is hydrogen and the other $R^{9c}$ is hydrogen, alkyl, aryl, aralkyl, heterocyclylalkyl, —C(O)—R$^{11c}$, —C(O)—R$^{10c}$—C(O)OR$^{7c}$, —R$^{10c}$—C(O)OR$^{7c}$, or —S(O)$_2$—R$^{7c}$.

Of this group of compounds, preferred compounds are selected from the group consisting of the following:
5-aminomethyl-4-[(3-fluorophenyl)hydrazono]-4H-pyrazol-3-ylamine;
3-({5-amino-4-[(3-fluorophenyl)hydrazono]-4H-pyrazol-3-ylmethyl}carbamoyl)acrylic acid;
N-{5-amino-4-[(3-fluorophenyl)hydrazono]-4H-pyrazol-3-ylmethyl}isonicotinamide;
N-{5-amino-4-[(3-fluorophenyl)hydrazono]-4H-pyrazol-3-ylmethyl}nicotinamide;
1-[({5-amino-4-[(3-fluorophenyl)hydrazono]-4H-pyrazol-3-ylmethyl}carbamoyl)methyl]-pyrrolidine-2-carboxylic acid methyl ester;
1-[3-({5-amino-4-[(3-fluorophenyl)hydrazono]-4H-pyrazol-3-ylmethyl}carbamoyl)acryloyl]-pyrrolidine-2-carboxylic acid methyl ester;
N-{5-amino-4-[(3-fluorophenyl)hydrazono]-4H-pyrazol-3-ylmethyl}methanesulfonamide;
N-{5-amino-4-[(3-fluorophenyl)hydrazono]-4H-pyrazol-3-ylmethyl}succinamic acid;
1-[({5-amino-4-[(3-fluorophenyl)hydrazono]-4H-pyrazol-3-ylmethyl}carbamoyl)methyl]pyrrolidine-2-carboxylic acid;
N-{5-amino-4-[(3,4-difluorophenyl)hydrazono]-4H-pyrazol-3-ylmethyl}nicotinamide;
4-[(3,4-difluorophenyl)-hydrazono]-5-[(2-morpholin-4-yl-ethylamino)methyl]-4H-pyrazol-3-yl-amine;
N-{5-amino-4-[(3-fluorophenyl)hydrazono]-4H-pyrazol-3-ylmethyl}-4-fluorobenzenesulfonamide;
N-{5-amino-4-[(3-fluorophenyl)hydrazono]-4H-pyrazol-3-ylmethyl}malonamic acid benzyl ester;
butane-1-sulfonic acid {5-amino-4-[(3-fluorophenyl)hydrazono]-4H-pyrazol-3-ylmethyl}amide;
N-{5-amino-4-[(3,4-difluorophenyl)hydrazono]-4H-pyrazol-3-ylmethyl}-2-chloro-6-methyl-nicotinamide;
N-{5-amino-4-[(3-fluorophenyl)hydrazono]-4H-pyrazol-3-ylmethyl}-2-chloro-6-methyl-nicotinamide; and
5-(3-aminopropyl)-4-(phenylhydrazono)-4H-pyrazol-3-ylamine.

Another preferred group of compounds of formula (Ic) is that group wherein:
$R^{1c}$ and $R^{4c}$ are each hydrogen;
$R^{2c}$ is phenyl (optionally substituted with one or more substituents selected from the group consisting of halo, alkoxy, nitro, haloalkyl, —$R^{6c}$—N($R^{8c}$)$_2$, —S(O)$_2$—$R^{6c}$—OH, —S(O)$_2$—N($R^{7c}$)$R^{8c}$ and heterocyclylalkyl);
$R^{5c}$ is —$R^{5c}$—N($R^{9c}$)$_2$; and each $R^{9c}$ is the same and selected from the group consisting of heterocyclylalkyl and —$R^{10c}$—C(O)O$R^{7c}$.

Of this group of compounds, preferred compounds are selected from the group consisting of the following:

5-{[bis-(2-morpholin-4-ylethyl)amino]methyl}-4-[(3,4-difluorophenyl)hydrazono]-4H-pyrazol-3-yl-amine;

5-[(bis-pyridin-3-ylmethylamino)methyl]-4-[(3,4-difluorophenyl)hydrazono]-4H-pyrazol-3-yl amine;

5-[(bis-pyridin-2-ylmethylamino)methyl]-4-[(3,4-difluorophenyl)hydrazono]-4H-pyrazol-3-yl amine; and (5-amino-4-[(3,4-difluorophenyl)hydrazono]-4H-pyrazol-3-ylmethylethoxycarbonylmethyl-amino)acetic acid ethyl ester.

Another preferred group of compounds of formula (Ic) is that group of compounds having the formula (Ic):

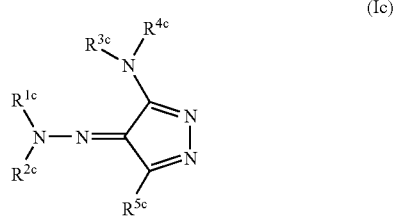

(Ic)

as a single tautomer, a mixture of tautomers, a single stereoisomer, a mixture of stereoisomers, or a racemic mixture; or a pharmaceutically acceptable salt or solvate thereof; wherein:

$R^{1c}$ is hydrogen, alkyl, aryl or aralkyl;

$R^{2c}$ is N-heterocyclyl (optionally substituted one or more substituents selected from the group consisting of alkyl, halo and —C(O)O$R^{7c}$);

$R^{3c}$ is hydrogen, alkyl, aryl, aralkyl, heterocyclylalkyl, or heterocyclylcarbonyl;

$R^{4c}$ is hydrogen or alkyl;

$R^{5c}$ is hydrogen, alkyl, alkenyl, —$R^{6c}$—O—$R^{12c}$, —$R^{6c}$—S—$R^{12c}$, —$R^{6c}$—N($R^{9c}$)$_2$, cycloalkyl (optionally substituted by one or more substituents selected from the group consisting of alkyl and aryl), aryl (optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups), nitro, —C(O)O$R^{7c}$, and —N($R^{7c}$)—C(O)—$R^{7c}$), aralkyl (wherein the aryl group is optionally substituted by one or more substituents selected from the group consisting of alkyl, alkoxy, halo, haloalkyl, haloalkoxy, haloalkylthio, arylthioalkyl (wherein the aryl group is optionally substituted with one or more halo groups), nitro, —C(O)O$R^{7c}$, and —N($R^{7c}$)—C(O)—$R^{7c}$), aralkenyl (wherein the aryl group is optionally substituted by one or more halo groups), heterocyclyl (optionally substituted by one or more substituents selected from the group consisting of alkyl, halo, haloalkyl, alkylthio, and aryl (optionally substituted with one or more halo groups)), or heterocyclylalkyl;

each $R^{6c}$ is independently a straight or branched alkylene chain;

each $R^{7c}$ is independently hydrogen, alkyl, aryl, aralkyl or heterocyclylakyl;

each $R^{9c}$ is independently hydrogen, alkyl, aryl, aralkyl, heterocyclylalkyl, —C(O)—$R^{11c}$, —C(O)—$R^{10c}$—C(O)O$R^{7c}$, —$R^{10c}$—C(O)O$R^{7c}$, or —S(O)$_2$—$R^{7c}$;

each $R^{10c}$ is independently a direct bond, straight or branched alkylene chain or straight or branched alkenylene chain;

$R^{11c}$ is aryl (optionally substituted by one or more substituents selected from the group consisting of alkyl and halo), heterocyclyl (optionally substituted by one or more substituents selected from the group consisting of —C(O)O$R^{7c}$ and —C(O)N($R^{7c}$)$_2$) or heterocyclylalkyl (optionally substituted by one or more substituents selected from the group consisting of —C(O)O$R^{7c}$ and —C(O)N($R^{7c}$)$_2$); and each $R^{12c}$ is independently aryl or aralkyl (optionally substituted by one or more substituents selected from group consisting of halo and nitro);

provided that when $R^{1c}$, $R^{3c}$, $R^{4c}$ and $R^{5c}$ are all hydrogen, $R^{2c}$ can not be thiadiazolyl; and when $R^{1c}$, $R^{3c}$ and $R^{4c}$ are all hydrogen, $R^{2c}$ and $R^{5c}$ can not be both pyrazolonyl; and when $R^{1c}$, $R^{3c}$ and $R^{4c}$ are all hydrogen, and $R^{5c}$ is methyl, $R^{2c}$ can not be optionally substituted pyrazolyl; and when $R^{1c}$, $R^{3c}$ and $R^{4c}$ are all hydrogen, and $R^{5c}$ is t-butyl, $R^{2c}$ can not be pyridin-3-yl optionally substituted with chloro.

Of this preferred group of compounds, a preferred subgroup is that subgroup wherein wherein:

$R^{1c}$ and $R^{4c}$ are each hydrogen;

$R^{2c}$ is N-heterocyclyl selected from the group consisting of pyridinyl, thiazolyl, tetrazolyl, pyrazolyl, isoquinolinyl, quinolinyl, and phthalazinyl;

$R^{3c}$ is hydrogen or alkyl; and $R^{5c}$ is hydrogen, alkyl, alkenyl, —$R^{6c}$—NH$_2$, cycloalkyl, phenylalkyl (wherein the phenyl group is optionally substituted by one or more substituents selected from the group consisting of alkoxy and halo), or heterocyclyl selected from the group consisting of pyridin-4-yl, thien-2-yl, or pyrrol-2-yl.

Of this group of compounds, preferred compounds are selected from the group consisting of the following:

5-methyl-4-[(4H-[1,2,4]triazol-3-yl)hydrazono]-4H-pyrazol-3-ylamine;

5-methyl-4-[(2H-tetrazol-5-yl)hydrazono]-4H-pyrazol-3-ylamine;

3-[N'-(3-amino-5-methylpyrazol-4-ylidene)hydrazino]-1H-pyrazole-4-carboxylic acid ethyl ester;

3-[N'-(3-amino-5-methylpyrazol-4-ylidene)hydrazino]-1H-pyrazole-4-carboxylic acid;

5-[N'-(3-amino-5-methylpyrazol-4-ylidene)hydrazino]-2H-[1,2,3]triazole-4-carboxylic acid;

5-(4-methoxybenzyl)-4-(pyridin-3-ylhydrazono)-4H-pyrazol-3-ylamine;

5-tert-butyl-4-[(1H-tetrazol-5-yl)hydrazono]-4H-pyrazol-3-ylamine;

4-(isoquinolin-5-ylhydrazono)-5-phenethyl-4H-pyrazol-3-ylamine;

5-but-3-enyl-4-(isoquinolin-5-ylhydrazono)-4H-pyrazol-3-ylamine;

5-aminomethyl-4-(isoquinolin-5-ylhydrazono)-4H-pyrazol-3-ylamine;

4-(isoquinolin-5-ylhydrazono)-5-methyl-4H-pyrazol-3-ylamine;

5-methyl-4-(pyridin-3-ylhydrazono)-4H-pyrazol-3-ylamine;

5-but-3-enyl-4-(quinolin-6-ylhydrazono)-4H-pyrazol-3-ylamine;

5-but-3-enyl-4-(pyridin-3-ylhydrazono)-4H-pyrazol-3-ylamine;

ethyl-[5-methyl-4-(pyridin-3-ylhydrazono)-4H-pyrazol-3-yl]amine;

4-(isoquinolin-5-ylhydrazono)-5-pyridin-4-yl-4H-pyrazol-3-ylamine;

5-pyridin-4-yl-4-(pyridin-3-ylhydrazono)-4H-pyrazol-3-ylamine;

5-methyl-4-(phthalazin-5-ylhydrazono)-4H-pyrazol-3-ylamine;
methyl-[4-(phthalazin-5-ylhydrazono)-5-pyridin-4-yl-4H-pyrazol-3-yl]amine;
4-(pyridin-3-yl-hydrazono)-5-thiophen-2-yl-4H-pyrazol-3-ylamine;
5-(1-methyl-1H-pyrrol-2-yl)-4-(pyridin-3-ylhydrazono)-4H-pyrazol-3-ylamine;
5-(1-methyl-1H-pyrrol-2-yl)-4-(quinolin-6-ylhydrazono)-4H-pyrazol-3-ylamine;
5-cyclopropyl-4-(pyridin-3-ylhydrazono)4H-pyrazol-3-ylamine;
5-morpholin-4-yl-4-(pyridin-3-yl-hydrazono)-4H-pyrazol-3-ylamine;
4-[(6-chloropyridin-3-yl)-hydrazono]-5-morpholin-4-yl-4H-pyrazol-3-ylamine;
5-pyrrolidin-1-yl-4-(quinolin-6-yl-hydrazono)-4H-pyrazol-3-ylamine;
4-[(6-chloro-pyridin-3-yl)-hydrazono]-5-pyrrolidin-1-yl-4H-pyrazol-3-ylamine;
4-[(6-fluoro-pyridin-3-yl)-hydrazono]-5-pyrrolidin-1-yl-4H-pyrazol-3-ylamine;
5-morpholin-4-yl-4-(phthalazin-5-yl-hydrazono)-4H-pyrazol-3-ylamine; and
4-[(6-methyl-pyridin-3-yl)-hydrazono]-5-morpholin-4-yl-4H-pyrazol-3-ylamine.

Particularly preferred are thos compounds selected from the group consisting of the following:
5-(4-methoxybenzyl)-4-(pyridin-3-ylhydrazono)-4H-pyrazol-3-ylamine;
4-(isoquinolin-5-ylhydrazono)-5-methyl-4H-pyrazol-3-ylamine;
5-but-3-enyl-4-(pyridin-3-ylhydrazono)-4H-pyrazol-3-ylamine;
4-(isoquinolin-5-ylhydrazono)-5-pyridin-4-yl-4H-pyrazol-3-ylamine;
5-pyridin-4-yl-4-(pyridin-3-ylhydrazono)-4H-pyrazol-3-ylamine;
5-methyl-4-(phthalazin-5-ylhydrazono)-4H-pyrazol-3-ylamine;
5-(1-methyl-1H-pyrrol-2-yl)-4-(pyridin-3-ylhydrazono)-4H-pyrazol-3-ylamine; and
5-(1-methyl-1H-pyrrol-2-yl)-4-(quinolin-6-ylhydrazono)-4H-pyrazol-3-ylamine.

Another preferred group of compounds of formula (Ic) is that group wherein:
$R^{1c}$ and $R^{4c}$ are each hydrogen;
$R^{2c}$ is N-heterocyclyl selected from the group consisting of pyridinyl, thiazolyl, tetrazolyl, pyrazolyl, isoquinolinyl, quinolinyl, and phthalazinyl;
$R^{3c}$ is hydrogen or alkyl;
$R^{5c}$ is phenyl (optionally substituted by one or more substituents selected from the group consisting of alkoxy and halo).

Of this group, a preferred compound is 5-(2-fluorophenyl)-4-(phthalazin-5-yl-hydrazono)-4H-pyrazol-3-ylamine.

E. Preparation of the Compounds of the Invention

It is understood that in the following description, combinations of substituents and/or variables of the depicted formulae are permissible only if such contributions result in stable compounds.

It will also be appreciated by those skilled in the art that in the process described below and in the following Preparations and Examples the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—$R^8$ (where $R^8$ is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of the invention, as described above in the Summary of the Invention, may not possess pharmacological activity as such, they may be administered to a mammal having a disease-state characterized by thrombotic activity and thereafter metabolized in the body to form compounds of the invention which are pharmacologically active. Such derivatives may therefore be described as "prodrugs". All prodrugs of compounds of the invention are included within the scope of the invention.

Accordingly, compounds of the invention as set forth in the Summary of the Invention may be prepared by methods disclosed in the literature, herein and/or as summarized in the following Reaction Schemes. The following Preparations (intermediates, made) and Examples (compounds of the invention, pharmaceutical compositions comprising the compounds and assays demonstrating their utility) are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

Compounds of formula (I), formula (Ia) and formula (Ib) are prepared as illustrated below in Reaction Scheme 1 wherein n is 0 to 5, and $R^1$, $R^2$, and $R^5$ are as described above in the Summary of the Invention, preferably where $R^1$ and $R^2$ are hydrogen or alkyl; and $R^3$ and $R^4$ are each —$NH_2$:

REACTION SCHEME 1

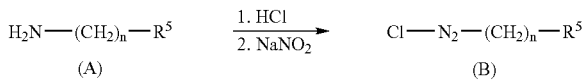

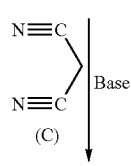

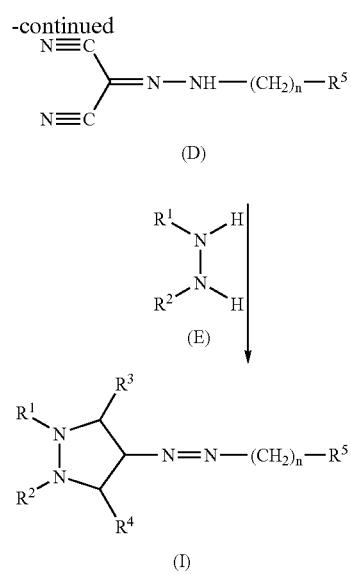

Compounds of formula (A), formula (C) and formula (E) are commercially available, for example, from Aldrich Chemical Co., or may be prepared according to methods known to one of ordinary skill in the art, or by the methods disclosed herein in the Preparations.

In general, compounds of the invention are prepared by first diazotizing a primary amine of formula (A) by treatment with hydrochloric acid and sodium nitrite. The intermediate diazo compound of formula (B) is then treated, in the presence of a base, for example, sodium acetate, with a compound of formula (C), i.e., a compound including a methylene group flanked by the electron withdrawing cyano groups, to provide a compound of formula (D). The compound of formula (D) is then reacted with a hydrazine compound of formula (E) to provide compounds of the invention.

The following Preparation and Examples exemplify the above Reaction Scheme 1 in more detail.

Preparation 1

Preparation of Pyridinyl-3-amines

A. A solution of 2-chloro-5-nitropyridine (1.58 g, 10 mmol) and appropriate amine (20 mmol) in THF (60 mL) was heated for several hours at 60° C. The solvent was evaporated and water was then added to the reaction mixture. The product was isolated by filtration (piperidine, morpholine), or extracted from the water solution with ethyl acetate (1-methylpiperazine, 2-(2-hydroxyethylamino)ethanol)).

B. To a solution of substituted nitropyridine (1 mmol) in THF:ethanol mixture (1:1) (50 mL) was added a catalytical amount of Raney-Nickel and hydrazine hydrate (4 mmol) and the mixture was stirred for 15 minutes at ambient temperature, filtered through a Celite pad and the filtrate was evaporated to provide the crude amine in very high yield. All amines were used in further reactions without purification.

C. The following pyrdin-3-ylamines were prepared by the method described above:
6-(piperidin-1-yl)pyridin-3-ylamine;
6-(morpholin-4-yl)pyridin-3-ylamine;
6-(4-methylpiperazin-1-yl)pyridin-3-ylamine; and
6-[di-(2-hydroxyethyl)amino]pyridin-3-ylamine.

Preparation 2

Preparation of 3-(Morpholin-4-yl)methylphenylamine

A. A solution of 1-bromomethyl-3-nitrobenzene (2.16 g, 10 mmol), morpholine (1.76 g, 20.2 mmol) and triethylamine (1.0 mL) in THF (60 mL) was heated for two hours at 60° C. The solvent was evaporated and water was then added to the reaction mixture. The product was isolated by extraction with ether. The ether layer was dried over anhydrous Mg$_2$SO$_4$ and the solvent was evaporated. The crystalline residue was used in further reactions without further purification. The yield of 4-(3-nitrobenzyl)morpholine was 94% (2.09 g).

B. To a solution of 4-(3-nitrobenzyl)morpholine (2.0 g; 9.0 mmol) in THF/ethanol mixture (1:1) (50 mL) was added a catalytical amount of Raney-Nickel and hydrazine hydrate (36.0 mmol) and the mixture was stirred at ambient temperature for 15 minutes, then filtered through a Celite-pad and the filtrate was evaporated to provide pure 3-(morpholin-4-yl) methylphenylamine (2.03 g, 98%), which was used in further reactions without purification.

Preparation 3

Preparation of 3-(Piperidin-1-yl)methylphenylamine

A. A solution of 1-bromomethyl-3-nitrobenzene (2.16 g, 10 mmol), piperidine (1.70 g, 20.2 mmol) and triethylamine (1.0 mL) in THF (60 mL) was heated for two hours at 60° C. The solvent was evaporated and water was then added to the reaction mixture. The product was isolated by extraction with ether. The ether extract was dried over anhydrous Mg$_2$SO$_4$ and the solvent was evaporated. The crystalline residue obtained was used in the next step without further purification. The yield of 1-(3-nitrobenzyl)piperidine was 91% (2.01 g).

B. To a solution of 1-(3-nitrobenzyl)piperidine (263 mg; 1.19 mmol) in THF:ethanol mixture (1:1) (15 mL) was added a catalytical amount of Raney-Nickel and hydrazine hydrate (6.0 mmol) and the mixture was stirred for 15 minutes at ambient temperature, filtered through a Celite-pad and the filtrate was evaporated to provide the title compound (180 mg, 95%), which was used in futher reactions without purification.

Preparation 4

Preparation of 3-fluoro-4-(morpholin-4-yl)methylphenylamine

A. 2-Fluoro-4-nitrotoluene (1.55 g, 10 mmol), N-bromosuccinimide (1.82 g, 10 mmol), and benzoyl peroxide (0.1 g, 0.4 mmol) were dissolved in CCl$_4$ (50 mL). The mixture was heated at reflux, and irradiated with light (100 W bulb) for 4 hours. The reaction mixture was then filtered and concentrated. The residue was dissolved in THF (50 mL). Morpholine (1.91 g, 22 mmol) was added to it. The mixture was stirred at ambient temperature for 1 hour and then filtered. The filtrate was evaporated. The bright orange residue was purified by column chromatography eluted with hexane:ethyl acetate, 10:1 to provide 4-(2-fluoro-4-nitrobenzyl)morpholine (1.32 g, 5.5 mmol, yield 55%).

B. To a solution of 4-(2-fluoro-4-nitrobenzyl)morpholine (240 mg, 1.0 mmol) in THF/ethanol mixture (1:1) (25 mL) was added a catalytical amount of Raney-Ni and hydrazine hydrate (9.0 mmol) and the mixture was stirred at ambient temperature for 15 minutes, filtered through a Celite pad. The filtrate was evaporated to provide the title compound, (197 mg, 94%), which was used in further reactions without purification.

Preparation 5

Preparation of N-Methyl-3-nitrobenzenesulfonamide and N-Methyl-4-nitrobenzenesulfonamide To a solution of 1.326 g (6.0 mmol) of 3-nitrobenzenesulfonyl chloride or 4-nitrobenzenesulfonyl chloride in 30 mL of dry THF was added 1.37 g (13.5 mmol) of triethylamine and then 4.0 mL (8.0 mmol) of methylamine as a solution in THF at 0° C. with stirring. The resulting cloudy solution was stirred overnight at ambient temperature. After this time period, the reaction mixture was diluted with 100 mL of saturated sodium chloride solution and 50 mL of ethyl acetate, then transferred to a 500 mL separatory funnel, mixed thoroughly, and the organic phase was separated. The aqueous phase was extracted twice with 50 mL of ethyl acetate. The combined organic layers were dried over anhydrous $Na_2SO_4$, filtered, and concentrated under reduced pressure, and the resulting residue purified by recrystallization from EtOH. The yield of N-methyl-3-nitrobenzenesulfonamide was 83% (1.074 g) and 90% for N-methyl-4-nitrobenzenesulfonamide (1.17 g).

Preparation 6

Preparation of N-Ethyl-3-nitrobenzenesulfonamide and N-Ethyl-4-nitrobenzenesulfonamide To a suspension of 0.7 g (3.16 mmol) of 3-nitrobenzenesulfonyl chloride or 4-nitrobenzenesulfonyl chloride in 10 mL of water was added ethylamine (5.0 ml, 70% in water) with stirring. The resulting solution was stirred overnight at ambient temperature. After this time period, the reaction mixture was diluted with 20 mL of saturated sodium chloride solution and 50 mL of ether, then transferred to a separatory funnel, mixed thoroughly, and the organic phase was separated. The aqueous phase was extracted twice with 50 mL of ether. The combined organic layers were washed with 10% hydrochloric acid, dried over $Na_2SO_4$, concentrated under reduced pressure, and the resulting residue was purified by recrystallization from EtOH. The yield of N-ethyl-3-nitrobenzenesulfonamide was 85% (0.618 g, 2.69 mmol) and 84% for N-ethyl-4-nitrobenzenesulfonamide (0.648 g, 2.82 mmol).

Preparation 7

Preparation of 3-Amino-5-nitrobenzoic acid ethyl ester

3-Amino-5-nitrobenzoic acid (910 mg, 5.0 mmol) was dissolved in EtOH (25 mL). DCC (1.51 g, 7.3 mmol) was added, and the mixture was stirred under reflux overnight. The solid precipitation was filtered off and the filtrate was evaporated. The residue was triturated in the solvent mixture ether:hexane:ethyl acetate, 5:5:1. The title compound was isolated as a fine light yellow powder (0.9 g, 85.7%).

Preparation 8

Preparation of Morpholin-4-yl-(3-nitro-5-(trifluoromethyl)phenyl)methanone

To a solution of 3-nitro-5-(trifluoromethyl)benzoic acid (470 mg, 2 mmol) in methylene chloride (10 mL) was added thionyl chloride (2.0 mL) and one drop of DMF under stirring and ice-cooling. The solution was stirred at ambient temperature for 2 hours. All solvents were evaporated and the residue was dissolved in THF (15 mL). The mixture was cooled to 0° C. and morpholine (180 mg) was added. The cloudy solution was stirred at ambient temperature overnight, filtered off and evaporated. The residue was mixed with 5% HCl solution and extracted with ether. The ether layer was washed with NaOH solution, dried over anhydrous $Na_2SO_4$ and evaporated to dryness to afford morpholin-4-yl-(3-nitro-5-(trifluoromethyl)phenyl)methanone (545 mg, 1.79 mmol, 89%).

Preparation 9

Preparation of 4-(5-Fluoro-2-nitrobenzyl)morpholine

5-Fluoro-2-nitrotoluene (1.55 g, 10 mmol), N-bromosuccinimide (1.82 g, 10 mmol), and benzoyl peroxide (0.1 g, 0.4 mmol) were dissolved in $CCl_4$ (50 mL), heated at reflux, and irradiated with light (100 W bulb) for 4 hours. The reaction mixture was filtered and concentrated. The residue was dissolved in THF (50 mL). Morpholine (1.9 g, 22 mmol) was added to the THF solution. The mixture was stirred at ambient temperature for 1 hour and then filtered. The solvent of the filtrate was evaporated. The bright orange residue obtained was then mixed with 5% HCl solution (30 mL) and extracted with ethyl acetate (2×25 mL). The aqueous layer was basified with NaOH solution to pH 8 and then extracted with methylene chloride. Both ethyl acetate solution and methylene chloride solution were dried over anhydrous $Na_2SO_4$ separately. Evaporation of ethyl acetate solution afforded an orange oil which was recrystallized from hexane:ether solution to yield 450 mg of a yellow solid, 4-(3-methyl-4-nitrophenyl)morpholine (18%), the by-product. Evaporation of methylene chloride solution afforded 660 mg of the desired compound, 4-(5-fluoro-2-nitrobenzyl)morpholine (27.5%).

Preparation 10

Preparation of 4-(3-Nitro-5-trifluoromethylbenzyl)morpholine

To a solution of morpholin-4-yl-(3-nitro-5-(trifluoromethyl)phenyl)methanone (304 mg, 1.0 mmol) in 15 mL of THF was added lithium aluminum hydride (152 mg, 4 mmol) in THF (7 mL) under nitrogen. The dark colored solution was refluxed for 2 hours and then cooled. NaOH solution was added (0.5 N, 15 mL) dropwise. The basic solution was washed with methylene chloride (3×40 mL) and the pooled organic layers were washed with HCl solution (5%). The aqueous layer was separated, basified with NaOH to pH 8, and extracted with ethyl acetate. The ethyl acetate solution was dried over anhydrous $Na_2SO_4$. The solution was used in further reactions without further work-up.

Preparation 11

Preparation of 4-Fluoro-2-morpholin-4-ylmethylphenylamine

To a solution of 4-(5-fluoro-2-nitrobenzyl)morpholine (240 mg; 1.0 mmol) in THF:ethanol mixture (1:1) (40 mL) was added a catalytical amount of Raney-Nickel and hydrazine hydrate (6.0 mmol). The mixture was stirred for 30 minutes at ambient temperature, then filtered through a Celite pad and the filtrate was evaporated to provide the title compound (208 mg, 99%), which was used in further reactions without purification.

Preparation 12

Preparation of 3-Fluoro-4-morpholin-4-ylmethylphenylamine

2-Fluoro-4-nitrotoluene (1.55 g, 10 mmol), N-bromosuccinimide (1.82 g, 10 mmol), and benzoyl peroxide (0.1 g, 0.4 mmol) were dissolved in CCl$_4$ (50 mL). The mixture was heated at reflux, and irradiated with light (100 W bulb) for 4 hours. The reaction mixture was filtered and concentrated. The residue was dissolved in THF (50 mL) and morpholine (1.9 g, 22 mmol) was added to this solution. The mixture was stirred at ambient temperature for 1 hour, and then filtered. The filtrate was evaporated. The title compound was isolated by column chromatography in an amount of 710 mg (30% yield).

Preparation 13

Preparation of 3-fluoro-4-(morpholin-4-yl)methylphenylamine

To a solution of 4-(2-fluoro-4-nitrobenzyl)morpholine (245 mg; 1.02 mmol) in THF:ethanol mixture (1:1) (40 mL) was added a catalytical amount of Raney-Nickel and hydrazine hydrate (6.0 mmol) and the mixture was stirred for 20 minutes at ambient temperature, then filtered through a Celite/silica gel pad. The filtrate was evaporated to provide the title compound (210 mg, 99%), which was used in further reactions without purification.

Preparation 14

Preparation of 3-(Morpholin-4-yl)methyl-5-trifluoromethylphenylamine

A. To a solution of morpholin-4-yl-(3-nitro-5-(trifluoromethyl)phenyl)methanone (457 mg, 1.5 mmol) in THF (5 mL) was added dropwise a solution of borane tetrahydrofuran complex solution (3.1 mL, 3.1 mmol) at ambient temperature and the mixture was heated under reflux for 30 minutes, then cooled. The solvent was evaporated. Aqueous HCl (5 mL) was added and the resulting mixture was heated at 100° C. for 1 hour, then cooled and extracted with ether. The acidic aqueous layer was separated, basified to pH 8 with NaOH and extracted with ether. The ether solution was dried over anhydrous Na$_2$SO$_4$. Evaporation of ether provided 168 mg (0.57 mmol) of 4-(3-Nitro-5-trifluoromethylbenzyl)morpholine (38%).

B. To a solution of 4-(3-nitro-5-trifluoromethylbenzyl) morpholine (168 mg; 0.57 mmol) in THF:ethanol mixture (1:1) (30 mL) was added a catalytical amount of Raney-Nickel and hydrazine hydrate (4.0 mmol) and the mixture was stirred for 2 hours at ambient temperature, then filtered through a Celite/silical gel pad. The filtrate was evaporated to provide the title compound (152 mg, 98%), which was used in further reactions without purification.

Preparation 15

Preparation of (3-Amino-5-nitrophenyl)methanol

To a solution of 3-amino-5-nitrobenzoic acid (1.12 g, 6.16 mmol) in THF (5 mL) was added dropwise a solution of borane tetrahydrofuran complex solution (13.6 mL, 13.6 mmol) at ambient temperature and the mixture was stirred for 90 minutes. The solvent was then evaporated. Aqueous NaOH (15 mL) was added and the resulting mixture was extracted with ether. The ether solution was dried over anhydrous Na$_2$SO$_4$. Evaporation of ether afforded 921 mg of the title compound (89%).

Preparation 16

Preparation of p- and m-methylphenylamines

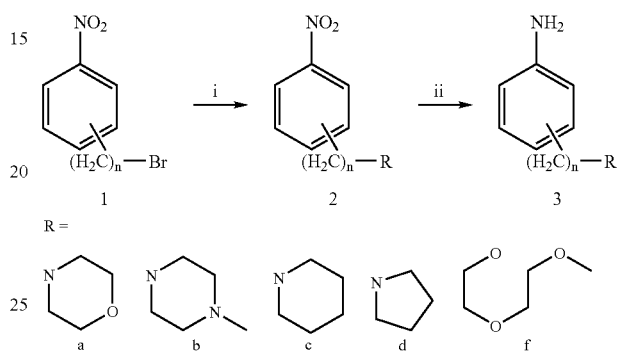

A. A solution of 1-bromomethyl-3(or 4)-nitrobenzene (1 above) (n=1) (432 mg; 2.0 mmol), an appropriate amine (a-d above) (4.1 mmol) and triethylamine (0.3 mL) in THF (15 mL) was heated for 2 hour at 60° C. The solvent was evaporated. Water was added to the residue and the product was isolated by extraction with ether (3×20 mL). The ether extract was dried over anhydrous MgSO$_4$ and the solvent was removed. The residue was used in the next step without further purification. The yield of compounds (2a-d above) ranged from 81-99%.

B. To a solution of compounds 2a-d above (1.0 mmol) in THF:ethanol mixture (1:1) (15 mL) was added a catalytical amount of Raney-Nickel and hydrazine hydrate (4.0 mmol) and the mixture was stirred for 30-60 minutes at ambient temperature, then filtered through a Celite/silica gel pad. The filtrate was evaporated to provide pure compounds 3a-d above in almost quantitative yield, which were used in further reactions without purification.

Preparation 17

Preparation of 4-[2-(4-Nitrophenyl)ethyl]morpholine

To a solution of 1-(2-bromoethyl)-4-nitrobenzene (460 mg, 2.0 mmol) in acetone (15 mL) was added morpholine (610 mg, 7.0 mmol) and 680 mg of K$_2$CO$_3$. The mixture was stirred for 80 hours at ambient temperature, and then poured into water. The aqueous mixture was extracted with ether. The organic layer was washed with brine, dried over MgSO$_4$, and evaporated in vacuo to give 456 mg (1.93 mmol; 97%) of the title compound, which was converted to the appropriate amine by the method disclosed in Preparation 16.

Preparation 18

Preparation of 1-[2-(2-Methoxyethoxy)ethoxymethyl]-3-nitrobenzene

To a solution of 1-bromomethyl-3-nitrobenzene (2 mmol; 432 mg) in di(ethylene glycol)methyl ether (15 mL) was added KOH powder (0.5 g) and the solution was stirred at ambient temperature overnight. Water (70 mL) was added and the product extracted with ether. The organic layer was dried over anhydrous $Na_2SO_4$ and concentrated in vacuum to provide the title compound (342 mg, 1.52 mmol, 67% yield), which was converted to the appropriate amine by method disclosed in Preparation 16.

Preparation 19

Preparation of N-methyl-3-nitrobenzenesulfonamide

To a solution of 4.42 g (20.0 mmol) of 3-nitrobenzenesulfonyl chloride in 150 mL of dry THF was added 25.0 mL (50.0 mmol) of methylamine as a 2 M solution in THF under ice cooling and stirring. The resulting cloudy solution was stirred overnight at ambient temperature. After this time period, the reaction mixture was diluted with 150 mL of saturated sodium chloride solution and 50 mL of ethyl acetate, then transferred to a 500 mL separatory funnel, mixed thoroughly, and the organic phase was separated. The aqueous phase was extracted twice with 50 mL of ethyl acetate. The combined organic layers were dried over $Na_2SO_4$, filtered, and concentrated under reduced pressure. The resulting residue was purified by recrytallization from EtOH. The yield of the title compound was 97% (4.20 g, 19.48 mmol).

Preparation 20

Preparation of
3-(Morpholin-4-yl)methyl-5-nitrophenylamine

A. A solution of (3-amino-5-nitrophenyl)methanol (872.5 mg; 5.14 mmol) in 7 mL of anhydrous hydrogen bromide in glacial acetic acid was refluxed for 8 hours. The solution was cooled to about 20° C. and then mixed with 5% NaOH (30 mL) solution and extracted with ether. Organic layer was separated, dried over $MgSO_4$ and concentrated in vacuo to yield a yellow solid (889 mg), which was purified by column chromatography. The light yellow crystals, 3-bromomethyl-5-nitrophenylamine, were isolated in an amount of 490 mg (2.12 mmol, 41%); MS (m/z, ES+): 231 (M+1 ($^{79}$Br)), 233 (M+1 ($^{81}$Br), 100%).

B. A solution of 3-bromomethyl-5-nitrophenylamine (398 mg, 1.72 mmol), triethylamine (0.3 mL) and morpholine (0.2 mL) in 15 mL of THF was heated at 60° C. for 30 minutes. The solvent was evaporated in vacuo. The residue was mixed with water (20 mL) and extracted with ether. Organic layer was separated, dried over $MgSO_4$ and concentrated in vacuo to afford a yellow solid (411 mg), which was purified by column chromatography. The title compound was isolated as yellow crystals in an amount of 302 mg (1.274 mmol, 74%); MS (m/z, ES+): 238 (M+1, 100%).

Example 1

Preparation of 4-[(4-methoxyphenyl)hydrazono]-4H-pyrazole-3,5-diamine

A. To a flask containing p-anisidine (5.46 g, 44.3 mmol) and concentrated HCl solution (11 mL) in 75 mL of water, cooled in an ice water bath, was added sodium nitrite solution (4.57 g, 66.3 mmol). The resulting mixture was then added to a solution of malononitrile (4.79 g, 72.6 mmol) in a mixture of methanol (MeOH) (12 mL) and water (25 mL). A large quantity of yellow solid quickly precipitated. The mixture was stirred for about 30 minutes at ambient temperature. The solid was collected and purified by recrystallization in hot ethanol. The product (6.17 g, 70%) was obtained as a yellow solid.

B. To a suspension of the yellow solid (2.00 g) prepared above in 10 mL of ethanol was added hydrazine hydrate (2.0 mL). This mixture was refluxed for about 3 hours. The yellow solid was collected and purified by recrystallization in hot ethanol (EtOH). The product, 4-[(4-methoxyphenyl)hydrazono]-4H-pyrazole-3,5-diamine, was isolated as yellow cotton-like solid (1.50 g, 65%); m.p. 263-265° C.; $^1$H NMR (ppm, in DMSO-$d_6$): 10.73 (s, br, 1H), 7.69 (m, 2H), 6.99 (m, 2H), 6.00 (s, br, 4H), 3.81 (s, 3H); $^{13}$C NMR (ppm, in DMSO-$d_6$): 158.4, 147.6, 121.7, 114.0, 113.4, 99.9, 55.3; FTIR (cm$^{-1}$, KBr pellet): 3401, 3301, 3187, 1603, 562, 1498, 1248, 1033, 828; Mass spectrometry (m/e, EI): 232 (M$^+$, 100%); Elemental analysis for $C_{10}H_{12}N_6O$ (obtained/calcd.): C, 52.28/51.72, H, 5.18/5.21, N, 35.88/36.19; Molecular Weight (MW): 232.24.

C. In a similar manner as described above in Paragraph A and B, the following compounds were synthesized:
4-(phenylhydrazono)-4H-pyrazole-3,5-diamine, MW 202.21
4-(p-tolylhydrazono)-4H-pyrazole-3,5-diamine, MW 216.24;
5-[N'-(3,5-diaminopyrazol-4-ylidene)hydrazino]-2-methoxyphenol, MW 248.24;
4-[N'-(3,5-diaminopyrazol-4-ylidene)hydrazino]benzenesulfonic acid, MW 282.27;
4-(morpholin-4-ylhydrazono)-4H-pyrazole-3,5-diamine, MW 211.22;
4-[(2-(morpholin-4-yl)ethyl)hydrazono]-4H-pyrazole-3,5-diamine, MW 239.28;
4-[(1H-imidazol-2-yl)hydrazono]-4H-pyrazole-3,5-diamine, MW 192.18;
4-[(1H-pyrazol-3-yl)-hydrazono]-4H-pyrazole-3,5-diamine, MW 192.18;
4-(thiazol-2-ylhydrazono)-4H-pyrazole-3,5-diamine, MW 209.22;
4-(naphthalen-1-ylhydrazono)-4H-pyrazole-3,5-diamine, MW 252.27;
4-[N'-(3,5-diaminopyrazol-4-ylidene)hydrazino]naphthalene-1-sulfonic acid, MW 332.33;
4-(piperidin-4-ylmethylhydrazono)-4H-pyrazole-3,5-diamine, MW 223.28;
4-(1,2,4-triazin-3-ylhydrazono)-4H-pyrazole-3,5-diamine, MW 205.18;
4-[N'-(3,5-diaminopyrazol-4-ylidene)hydrazino]benzoic acid, MW 246.22;
4-[N'-(3,5-diaminopyrazol-4-ylidene)hydrazino]phenol, MW 218.21;
4-[(4-chlorophenyl)hydrazono]-4H-pyrazole-3,5-diamine, MW 236.66;
4-[(4-butylphenyl)hydrazono]-4H-pyrazole-3,5-diamine, MW 258.32;
N-{4-[N'-(3,5-diaminopyrazol-4-ylidene)hydrazino]phenyl}acetamide, MW 274.3;
1-[N'-(3,5-diaminopyrazol-4-ylidene)hydrazino]naphthalen-2-ol, MW 268.27.

Example 2

Preparation of Compounds of Formula (I), formula (Ia) and formula (Ib)

A. 4-Fluoroaniline (95 µL, 1.0 mmol) was weighed into a 25 mL test tube. Deionized water (1-2 mL) was added to the test tube and the suspension was cooled to below 5° C. in an ice bath. Concentrated HCl (250 µL, 3.0 mmol) was added dropwise to the mixture. If the solution remained inhomogeneous, dimethylformamide (DMF) was added until all the solids had dissolved (0-2 mL). An aqueous sodium nitrite solution (290 µL of a 5.25 M solution, 1.5 mmol) was added dropwise to this mixture and allowed to stir for approximately 5 minutes. The resulting clear pale yellow solution was then added dropwise to a second 25 mL test tube containing 1.4 mL of an ice cold aqueous solution which was 1.82 M (2.3 mmol) in sodium acetate trihydrate and 1.09 M (1.5 mmol) in malononitrile. A precipitate formed immediately. The reaction solution was stirred for 1-2 hrs while warming to ambient temperature. The solution was then filtered and the precipitate was washed twice with 5 mL of deionized water. The product was dried overnight under vacuum to yield 169 mg (90%) of the desired malononitrile derivative as a yellow solid. A portion of this solid (94 mg, 0.5 mmol) was weighed into a 25 mL test tube. Anhydrous ethanol (1.5 mL) was added and the slurry was heated to 75° C. Once the solid had dissolved, hydrazine hydrate (1 mmol) was added dropwise via micropipette. A precipitate usually formed within 10 minutes. The reaction was monitored for the disappearance of the starting material by thin layer chromatography (TLC). Once the reaction was complete, the solution was allowed to cool to ambient temperature. The solid was isolated by filtration, washed with ethanol, and dried to yield 17 mg (15%) of 4-[(4-fluorophenyl)hydrazono]-4H-pyrazole-3,5-diamine as a mustard coloured solid.

B. In a similar manner, the following compounds were prepared:

1. 3-[N'-(3,5-diaminopyrazol-4-ylidene)hydrazino]phenol was prepared using 93 mg (0.5 mmol) of 2-[(3-hydroxyphenyl)-hydrazono]malononitrile, which was derived from 3-aminophenol (109 mg, 1.0 mmol) and malononitrile (1.5 mmol), and hydrazine hydrate. After heating for 4 hrs, a small amount of solid had formed. The solid was filtered off and the filtrate was concentrated to a gummy black solid. This material was dissolved in ethyl acetate and a small amount of gummy solid was precipitated from the solution by the addition of hexanes. The solid was removed by filtration and the filtrate was again concentrated. The resulting solid was purified by flash chromatography eluting with methylene chloride/methanol (7:1) to yield 45 mg (33%) of the compound as a black solid.

2. 4-[(3-ethylphenyl)hydrazono]-4H-pyrazole-3,5-diamine was prepared using 99 mg (0.5 mmol) of 2-[(3-ethylphenyl)hydrazono]malononitrile, which was derived from 3-ethylaniline (124 µL, 1.0 mmol) and malononitrile (1.5 mmol), and hydrazine hydrate. Precipitate formed in the reaction tube approximately 10 minutes after the addition of hydrazine hydrate. The resulting solid was isolated by filtration, precipitated from an ethyl acetate solution by the addition of hexanes, and dried to yield 12 mg (10%) of the compound as a yellow solid.

3. 4-[(3-methoxyphenyl)hydrazono]-4H-pyrazole-3,5-diamine was prepared using 100 mg (0.5 mmol) of 2-[(3-methoxyphenyl)hydrazono]malononitrile, which was derived from m-anisidine (112 µL, 1.0 mmol) and malononitrile (1.5 mmol), and hydrazine hydrate. Precipitate formed in the reaction tube approximately 10 minutes after the addition of hydrazine hydrate. The resulting solid was isolated by filtration, recrystallized from ethanol, and dried to yield 25 mg (22%) of the compound as a brownish orange solid.

4. 4-[(3-chlorophenyl)hydrazono]-4H-pyrazole-3,5-diamine was prepared using 102 mg (0.5 mmol) of 2-[(3-chlorophenyl)hydrazono]malononitrile, which was derived from 3-chloroaniline (106 µL, 1.0 mmol) and malononitrile (1.5 mmol) as described in Example 2, and hydrazine hydrate. Precipitate formed in the reaction tube approximately 5 min after the addition of hydrazine hydrate. The resulting solid was isolated by filtration, precipitated from an ethyl acetate solution by the addition of hexanes, and dried to yield 17 mg (14%) of the compound as a yellow solid; $^1$H NMR (ppm, DMSO-$d_6$): 5.98 (br, s, 2H), 6.38 (br, s, 2H), 7.18 (d, 1H), 7.40 (t, 1H), 7.60 (d, 1H), 7.69 (s, 1H), 10.78 (s, 1H).

5. 4-[(3-fluorophenyl)hydrazono]-4H-pyrazole-3,5-diamine was prepared using 94 mg (0.5 mmol) of 2-[(3-fluorophenyl)hydrazono]malononitrile, which was derived from 3-fluoroaniline (96 µL, 1.0 mmol) and malononitrile (1.5 mmol) and hydrazine hydrate. Precipitate formed in the reaction tube approximately 5 minutes after the addition of hydrazine hydrate. The resulting solid was isolated by filtration, washed with ethanol, and dried to yield 41 mg (37%) of the compound as a yellow solid. $^1$H NMR (ppm, DMSO-$d_6$): 6.2 (br s, 4H), 7.0 (t, 1H), 7.35-7.62 (m, 3H), 10.80 (s, 1H).

6. 4-[(3-fluoro-4-methoxyphenyl)hydrazono]-4H-pyrazole-3,5-diamine was prepared using 109 mg (0.5 mmol) of 2-[(3-fluoro-4-methoxyphenyl)hydrazono]malononitrile, which was derived from 3-fluoro-p-anisidine (141 mg, 1.0 mmol) and malononitrile (1.5 mmol), and hydrazine hydrate. Precipitate formed in the reaction tube immediately after the addition of hydrazine hydrate. The resulting solid was isolated by filtration, washed with ethanol, and dried to yield 85 mg (68%) of the compound as a mustard coloured solid.

7. 4-(naphthalen-2-ylhydrazono)-4H-pyrazole-3,5-diamine was prepared using 110 mg (0.5 mmol) of 2-[(naphthalen-2-yl)hydrazono]malononitrile, which was derived from 2-aminonaphthalene (143 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 86 mg (67%) of the compound as a tan coloured solid.

8. 4-[(4-trifluoromethylphenyl)hydrazono]-4H-pyrazole-3,5-diamine was prepared using 119 mg (0.5 mmol) of 2-[(4-trifluoromethylphenyl)hydrazono]malononitrile, which was derived from 4-(trifluoromethyl)aniline (126 µL, 1.0 mmol) and malononitrile (1.5 mmol), and hydrazine hydrate. No precipitate had formed after heating at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 67 mg (50%) of the compound as a greenish brown solid; $^1$H NMR (ppm, DMSO-$d_6$): 6.03 (br s, 2H), 6.48 (br s, 2H), 7.63 (d, 2H), 7.80 (d, 2H), 10.80 (br s, 1H).

9. -[(3-phenoxyphenyl)hydrazono]-4H-pyrazole-3,5-diamine was prepared using 131 mg (0.5 mmol) of 2-[(3-phenoxyphenyl)hydrazono]malononitrile, which was derived from 3-phenoxyaniline (185 mg, 1.0 mmol) and malononitrile (1.5 mmol), and hydrazine hydrate. Precipitate formed in the reaction tube approximately 5 minutes after the addition of hydrazine hydrate. The resulting solid was isolated by filtration, recrystallized from ethanol, and dried to yield 87 mg (59%) of the compound as a mustard coloured solid.

10. 4-[N'-(3,5-diaminopyrazol-4-ylidene)hydrazino]benzoic acid ethyl ester was prepared using 121 mg (0.5 mmol) of 4-(N'-dicyanomethylenehydrazino)benzoic acid ethyl ester, which was derived from ethyl 4-aminobenzoate (165 mg, 1.0 mmol) and malononitrile (1.5 mmol), and hydrazine hydrate. The hydrazine hydrate was added to the solution at a temperature of 75° C. The solution cleared briefly and then a precipitate formed. The resulting solid was isolated by filtration, washed with ethanol, and dried to yield 45 mg (33%) of the compound as a yellow solid.

11. 4-(3-phenylphenylhydrazono)-4H-pyrazole-3,5-diamine was prepared using 123 mg (0.5 mmol) of 2-[(biphenyl-2-yl)hydrazono]malononitrile, which was derived from 2-aminobiphenyl (169 mg, 1.0 mmol) and malononitrile (1.5 mmol), and hydrazine hydrate. Precipitate formed in the reaction tube immediately after the addition of the hydrazine hydrate then the solution cleared. Very little solid remained after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 85 mg (61%) of the compound as an orange solid.

12. 4-[(2-bromophenyl)hydrazono]-4H-pyrazole-3,5-diamine was prepared using 125 mg (0.5 mmol) of 2-[(2-bromophenyl)hydrazono]malononitrile, which was derived from 2-bromoaniline (172 mg, 1.0 mmol) and malononitrile (1.5 mmol), and hydrazine hydrate. Very little solid had formed after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 102 mg (73%) of the compound as an orange solid.

13. 4-[(3-bromophenyl)hydrazono]-4H-pyrazole-3,5-diamine was prepared using 125 mg (0.5 mmol) of 2-[(3-bromophenyl)hydrazono]malononitrile, which was derived from 3-bromoaniline (172 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 93 mg (66%) of the compound as an orange solid; $^1$H NMR (ppm, DMSO-$d_6$): 6.2 (br s, 4H), 7.21-7.32 (m, 2H), 7.50-7.62 (m, 1H), 7.90 (s, 1H), 10.71 (s, 1H).

14. 4-[(4-bromophenyl)hydrazono]-4H-pyrazole-3,5-diamine was prepared using 125 mg (0.5 mmol) of 2-[(4-bromophenyl)hydrazono]malononitrile, which was derived from 4-bromoaniline (172 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 109 mg (78%) of the compound as a yellow solid; $^1$HNMR (ppm, DMSO-$d_6$): 6.15 (brs, 4H), 7.52 (d, 2H), 7.61 (d, 2H), 10.71 (s, 1H).

15. 4-[(4-phenoxyphenyl)hydrazono]-4H-pyrazole-3,5-diamine was prepared using 131 mg (0.5 mmol) of 2-[(4-phenoxyphenyl)hydrazono]malononitrile, which was derived from 4-phenoxyaniline (185 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 90 mg (61%) of the compound as an orange solid.

16. 4-[(4-iodophenyl)hydrazono]-4H-pyrazole-3,5-diamine was prepared using 148 mg (0.5 mmol) of 2-[(4-iodophenyl)hydrazono]malononitrile, which was derived from 4-iodoaniline (219 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 114 mg (70%) of the compound as a yellow solid.

17. 4-[(4-bromonaphthalen-1-yl)hydrazono]-4H-pyrazole-3,5-diamine was prepared using 149 mg (0.5 mmol) of 2-[(4-bomonaphthalen-1-yl)hydrazono]malononitrile, which was derived from 1-amino-4-bromonaphthalene (222 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared. Very little solid had formed after heating the reaction at 75° C. for 1 hr, however, analysis of the reaction solution by TLC indicated that no starting material remained. The solution was allowed to cool to ambient temperature and the solvent was evaporated. The residue was dissolved in methanol and then precipitated by the addition of water. The resulting solid was isolated by filtration and dried to yield 42 mg (26%) of the compound as a brown solid.

18. 4-(o-tolylhydrazono)-4H-pyrazole-3,5-diamine was prepared using 92 mg (0.5 mmol) of 2-(o-tolylhydrazono)-malononitrile, which was derived from 4-toluidine (107 µL, 1.0 mmol) and malononitrile (1.5 mmol), and hydrazine hydrate. Very little solid had formed after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 43 mg (40%) of the compound as a yellow solid.

19. 4-[(2,6-difluorophenyl)hydrazono]-4H-pyrazole-3,5-diamine was prepared using 103 mg (0.5 mmol) of 2-[(2,6-difluorophenyl)hydrazono]malononitrile, which was derived from 2,6-difluoroaniline (108 µL, 1.0 mmol) and malononitrile (1.5 mmol), and hydrazine hydrate. Precipitate formed in the reaction tube approximately 10 minutes after the addition of hydrazine hydrate. The resulting solid was isolated by filtration, washed with ethanol, and dried to yield 44 mg (37%) of the compound as an orange solid.

20. 4-[(3,4-difluorophenyl)hydrazono]-4H-pyrazole-3,5-diamine was prepared using 103 mg (0.5 mmol) of 2-[(3,4-difluorophenyl)hydrazono]malononitrile, which was derived from 3,4-difluoroaniline (99 µL, 1.0 mmol) and malononitrile (1.5 mmol), and hydrazine hydrate. Precipitate formed in the reaction tube approximately 5 minutes after the addition of hydrazine hydrate. The resulting solid was isolated by filtration, washed with ethanol, and dried to yield 45 mg (38%) of the compound as a yellow solid; $^1$H NMR (ppm, DMSO-$d_6$): 6.18 (br s, 4H), 7.28-7.55 (m, 2H), 7.70-7.82 (m, 1H), 10.80 (br s, 1H).

21. 4-(benzo[1,3]dioxol-5-ylhydrazono)-4H-pyrazole-3,5-diamine was prepared using 107 mg (0.5 mmol) of 2-(benzo[1,3]dioxol-5-yl-hydrazono)malononitrile, which was derived from 3,4-methylenedioxyaniline (137 mg, 1.0 mmol) and malononitrile (1.5 mmol), and hydrazine hydrate. Precipitate formed in the reaction tube approximately 10 minutes after the addition of hydrazine hydrate. The resulting black solid was isolated by filtration, dissolved in acetone, and hexanes was added to precipitate a small amount of black solid. The solid was removed by filtration and the filtrate was concentrated to yield 1.0 mg (1% yield) of the compound as a black solid; $^1$H NMR (200 MHz, DMSO-$d_6$) δ: 6.0 (br s, 6H), 6.92 (d, 1H), 7.18 (d, 1H), 7.38 (s, 1H), 10.60 (br s, 1H).

22. 4-[(4-methylsulfanylphenyl)hydrazono]-4H-pyrazole-3,5-diamine was prepared using 108 mg (0.5 mmol) of 2-[(4-methylsulfanylphenyl)hydrazono]malononitrile, which was derived from 4-methylthioaniline (117 mg, 1.0 mmol) and malononitrile (1.5 mmol), and hydrazine hydrate. Precipitate formed in the reaction tube immediately after the addition of hydrazine hydrate. The resulting solid was isolated by filtration, washed with ethanol, and dried to yield 95 mg (77%) of the compound as an orange solid.

23. 4-[(2,3-dihydrobenzo[1,4]dioxin-6-yl)hydrazono]-4H-pyrazole-3,5-diamine was prepared using 114 mg (0.5 mmol) of 2-[(2,3-dihydro-benzo[1,4]dioxin-6-yl)hydrazono]malononitrile, which was derived from 1,4-benzodioxan-6-amine (151 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared. Very little solid had formed after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 35 mg (27%) of the compound as a tan coloured solid.

24. 4-[(3-chloro-4-methoxyphenyl)hydrazono]-4H-pyrazole-3,5-diamine was prepared using 117 mg (0.5 mmol) of 2-[(3-chloro-4-methoxyphenyl)hydrazono]malononitrile, which was derived from 3-chloro-4-anisidine (157 mg, 1.0 mmol) and malononitrile (1.5 mmol), and hydrazine hydrate. Precipitate formed in the reaction tube immediately after the addition of hydrazine hydrate. The resulting solid was isolated by filtration, washed with ethanol, and dried to yield 93 mg (70%) of the compound as a yellow solid.

25. 4-[(3,4-dichlorophenyl)hydrazono]-4H-pyrazole-3,5-diamine was prepared using 120 mg (0.5 mmol) of 2-[(3,4-dichlorophenyl)hydrazono]malononitrile, which was derived from 3,4-dichloroaniline (162 mg, 1.0 mmol) and malononitrile (1.5 mmol), and hydrazine hydrate. Precipitate formed in the reaction tube immediately after the addition of hydrazine hydrate. The resulting solid was isolated by filtration, precipitated from an ethyl acetate solution by the addition of hexanes, and dried to yield 53 mg (39%) of the compound as a yellow solid; $^1$H NMR (ppm, DMSO-$d_6$): 6.30 (br, s, 4H), 7.55-7.79 (m, 2H), 7.95 (s, 1H), 10.80 (s, 1H).

26. 4-[(3,5-dichlorophenyl)hydrazono]-4H-pyrazole-3,5-diamine was prepared using 120 mg (0.5 mmol) of 2-[(3,5-dichlorophenyl)hydrazono]malononitrile, which was derived from 3,5-dichloroaniline (162 mg, 1.0 mmol) and malononitrile (1.5 mmol), and hydrazine hydrate. Precipitate formed in the reaction tube approximately 5 minutes after the addition of hydrazine hydrate. The resulting solid was isolated by filtration, precipitated from an ethyl acetate solution by the addition of hexanes, and dried to yield 25 mg (18%) of the compound as a yellow solid.

27. 4-[(2-isopropylphenyl)hydrazono]-4H-pyrazole-3,5-diamine was prepared using 106 mg (0.5 mmol) of 2-[(2-isopropylphenyl)hydrazono]malononitrile, which was derived from 2-isopropylaniline (142 μL, 1.0 mmol) and malononitrile (1.5 mmol), and hydrazine hydrate. Precipitate formed in the reaction tube approximately 5 minutes after the addition of hydrazine hydrate. The resulting solid was isolated by filtration, washed with ethanol, and dried to yield 90 mg (73%) of the compound as a greenish yellow solid.

28. 4-[(3,4-dimethoxyphenyl)hydrazono]-4H-pyrazole-3,5-diamine was prepared using 115 mg (0.5 mmol) of 2-[(3,4-dimethoxyphenyl)hydrazono]malononitrile, which was derived from 4-aminoveratrole (153 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared. Very little solid had formed after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 46 mg (35%) of the compound as a mustard coloured solid.

29. 4-[(3-trifluoromethylphenyl)hydrazono]-4H-pyrazole-3,5-diamine was prepared using 119 mg (0.5 mmol) of 2-[(3-trifluoromethylphenyl)hydrazono]malononitrile, which was derived from 3-(trifluoromethyl)aniline (125 μL, 1.0 mmol) and malononitrile (1.5 mmol), and hydrazine hydrate. Precipitate formed in the reaction tube approximately 10 minutes after the addition of hydrazine hydrate. The resulting solid was isolated by filtration, washed with ethanol, and dried to yield 43 mg (31%) of the compound as a yellow solid.

30. 3-[N'-(3,5-diaminopyrazol-4-ylidene)hydrazino]benzoic acid ethyl ester was prepared using 121 mg (0.5 mmol) of 3-(N'-dicyanomethylenehydrazino)benzoic acid ethyl ester, which was derived from 3-aminobenzoate (149 μL, 1.0 mmol) and malononitrile (1.5 mmol), and hydrazine hydrate. Precipitate formed in the reaction tube approximately 10 minutes after the addition of hydrazine hydrate. The resulting solid was isolated by filtration, washed with ethanol, and dried to yield 58 mg (42%) of the compound as a light brown solid.

31. 4-[(3-methoxy-5-trifluoromethylphenyl)hydrazono]-4H-pyrazole-3,5-diamine was prepared using 134 mg (0.5 mmol) of 2-[(3-methoxy-5-trifluoromethylphenyl)hydrazono]malononitrile, which was derived from 3-methoxy-5-trifluoromethylaniline (191 mg, 1.0 mmol) and malononitrile (1.5 mmol), and hydrazine hydrate. Very little solid had formed after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 10 mg (7%) of the compound as a yellow solid.

32. 4-[(2-chlorophenyl)hydrazono]-4H-pyrazole-3,5-diamine was prepared using 102 mg (0.5 mmol) of 2-[(2-chlorophenyl)hydrazono]malononitrile, which was derived from 2-chloroaniline (105 μL, 1.0 mmol) and malononitrile (1.5 mmol), and hydrazine hydrate. Precipitate formed in the reaction tube approximately 10 minutes after the addition of hydrazine hydrate. The resulting solid was isolated by filtration, washed with ethanol, and dried to yield 34 mg (29%) of the compound as a yellow solid.

33. 4-[(3-iodophenyl)hydrazono]-4H-pyrazole-3,5-diamine was prepared using 148 mg (0.5 mmol) of 2-[(3-iodophenyl)hydrazono]malononitrile, which was derived from 3-iodoaniline (219 mg, 1.0 mmol) and malononitrile (1.5 mmol), and hydrazine hydrate. The hydrazine hydrate was added to the solution at a temperature of 75° C. despite the fact that the starting material had not fully dissolved. The solution cleared briefly and then a precipitate formed. The resulting solid was isolated by filtration, washed with ethanol, and dried to yield 122 mg (74%) of the compound as a mustard coloured solid.

34. 4-[(9-ethyl-9H-carbazol-3-yl)hydrazono]-4H-pyrazole-3,5-diamine was prepared using 143 mg (0.5 mmol) of 2-[(9-ethyl-9H-carbazol-3-yl)hydrazono]malononitrile, which was derived from 3-amino-9-ethylcarbazole (210 mg, 1.0 mmol) and malononitrile (1.5 mmol), and hydrazine hydrate. Solids had not formed after heating the reaction at 75° C. for 1 hr, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 46 mg (29%) of the compound as a black solid.

35. 4-[(2-benzenesulfonylphenyl)hydrazono]-4H-pyrazole-3,5-diamine was prepared using 94 mg (0.5 mmol) of 2-[(2-benzenesulfonylphenyl)hydrazono]malononitrile, which was derived from 2-(phenylsulfonyl)aniline (233 mg, 1.0 mmol) and malononitrile (1.5 mmol), and hydrazine hydrate. Precipitate formed in the reaction tube approximately 20 minutes after the addition of hydrazine hydrate. The resulting solid was isolated by filtration, washed with ethanol, and dried to yield 68 mg (20%) of the compound as an orange coloured solid.

36. 1-phenyl-4-phenylazo-1H-pyrazole-3,5-diamine was prepared using 200 mg (1.2 mmol) of 2-(phenylhydrazono)malononitrile, which was derived from aniline (10 mL, 107 mmol) and malononitrile (161 mmol), and phenylhydrazine (767 mg, 7.1 mmol). Solids had not formed after heating the reaction at 75° C. for 3 hrs, however, analysis of the reaction solution by TLC indicated that no starting material remained. The solution was allowed to cool to ambient temperature and the solvent was evaporated. The residue was dissolved in ethyl acetate and then precipitated by the addition of hexanes. The resulting solid was isolated by filtration and dried to yield 77 mg (23%) of the compound as an orange coloured solid.

37. (3,5-diamino-4-phenylazopyrazol-1-yl)phenylmethanone was prepared using 85 mg (0.5 mmol) of 2-(phenylhydrazono)malononitrile, which was derived from aniline (10 mL, 107 mmol) and malononitrile (161 mmol), and benzoic hydrazide (68 mg, 0.5 mmol). Solids had not formed after heating the reaction at 75° C. for 3 hrs, however, analysis of the reaction solution by TLC indicated that no starting material remained. The solution was allowed to cool to ambient temperature and the solvent was evaporated. The residue was dissolved in methanol and then precipitated by the addition of water. The resulting solid was isolated by filtration and dried to yield 20 mg (13%) of the compound as an orange coloured solid.

38. 1-(4-bromophenyl)-4-phenylazo-1H-pyrazole-3,5-diamine was prepared using 85 mg (0.5 mmol) of 2-(phenylhydrazono)malononitrile, which was derived from aniline (10 mL, 107 mmol) and malononitrile (161 mmol), and 4-bromophenylhydrazine hydrochloride (112 mg, 0.5 mmol) with the addition of 0.5 mL of 5% sodium hydroxide solution. Solids had not formed after heating the reaction at 75° C. for 3 hrs, however, analysis of the reaction solution by TLC indicated that no starting material remained. The solution was allowed to cool to ambient temperature and the solvent was evaporated. The residue was dissolved in methanol and then precipitated by the addition of water. The resulting solid was isolated by filtration and dried to yield 49 mg (27%) of the compound as a brown solid.

39. 4-(3,5-diamino-4-phenylazopyrazol-1-yl)benzoic acid was prepared using 85 mg (0.5 mmol) of 2-(phenylhydrazono)malononitrile, which was derived from aniline (10 mL, 107 mmol) and malononitrile (161 mmol), and 4-hydrazinobenzoic acid (76 mg, 0.5° mmol). After reacting for 4 hrs, the reaction remained as a slurry; however, analysis of the reaction solution by TLC indicated that no starting material remained. The resulting solid was isolated by filtration, washed with ethanol, and dried to yield 22 mg (14%) of the compound as a brown solid.

40. 1-(4-fluorophenyl)-4-phenylazo-1H-pyrazole-3,5-diamine was prepared using 85 mg (0.5 mmol) of 2-(phenylhydrazono)malononitrile, which was derived from aniline (10 mL, 107 mmol) and malononitrile (161 mmol), and 4-fluorophenylhydrazine hydrochloride (81 mg, 0.5 mmol) with the addition of 0.5 mL of 5% sodium hydroxide solution. After reacting for 4 hrs, very little solid had formed; however, analysis of the reaction solution by TLC indicated that no starting material remained. The resulting solid was removed by filtration and the solvent was evaporated from the filtrate to yield 29 mg (20%) of the compound as a brown solid.

41. 4-(pyridin-3-ylhydrazono)-4H-pyrazole-3,5-diamine was prepared using 2-[(pyridin-3-yl)hydrazono]malononitrile (342 mg, 2 mmol), which was derived from 3-aminopyridine (940 mg, 10 mmol)) and malononitrile (858 mg, 13 mmol), and hydrazine hydrate (110 mg, 2.2 mmol) in ethanol. Solids had not formed after heating the reaction at 80° C. for 40 minutes, however, analysis of the reaction solution by TLC indicated that no starting material remained. The solution was allowed to cool to ambient temperature and the solvent was evaporated. The product was obtained after upon re-crystallization from ethanol as a yellow solid (150 mg); $^1$H NMR (ppm, DMSO-d$_6$): 6.18 (br., s, 4H), 7.20 (dd, 1H), 8.00 (dd, 1H), 8.38 (d, 1H), 8.85 (s, 1H), 10.77 (br., s, 1H).

42. 4-[(5-methoxybenzothiazol-2-yl)hydrazono]-4H-pyrazole-3,5-diamine was prepared using 2-[(6-methoxybenzothiazol-2-yl)hydrazono]malononitrile (200 mg), which was derived from 2-amino-6-methoxybensothiazole (1.17 g) and malononitrile (0.82 g), and hydrazine hydrate (0.2 mL) in ethanol. Solids had not formed after heating the reaction at 40° C. for 2 hrs. The solution was allowed to cool to ambient temperature and concentrated. The product was obtained after column chromatography purification (80 mg, 35%).

43. 4-(benzothiazol-2-ylhydrazono)-4H-pyrazole-3,5-diamine was prepared using 2-[(6-benzothiazol-2-yl)hydrazono]malononitrile (80 mg), which was derived from 2-aminobensothiazole (925 mg) and malononitrile (0.65 g), and hydrazine hydrate (0.1 mL) in ethanol. Solids had not formed after heating the reaction at 60° C. for 3 hrs. The solution was allowed to cool to ambient temperature and concentrated. The product was obtained after thin layer chromatography purification (47 mg, 50%).

44. 4-[(1H-pyrazol-3-yl)hydrazono]-4H-pyrazole-3,5-diamine was prepared using 3-aminopyrazole (0.5 g), malononitrile (1.8 g), and hydrazine hydrate (0.3 g). The product was obtained after column chromatography purification (157 mg, 14%).

45. 4-[(4H-[1,2,4]-triazol-3-yl)hydrazono]-4H-pyrazole-3,5-diamine was prepared by using 3-amino-1,2,4-triazole (0.88 g), malononitrile (1.0 g), and hydrazine hydrate (0.5 ml) to yield 34 mg of the compound (6%).

46. 4-[(3,5-difluorophenyl)hydrazono]-4H-pyrazole-3,5-diamine was prepared by using 3,5-difluoroaniline (0.31 g), malononitrile (0.4 g) and hydrazine hydtrate (0.2 g) to yield 0.201 g of the compound (35%).

47. 4-[(2,3,4-trifluorophenyl)hydrazono]-4H-pyrazole-3, 5-diamine was prepared by using 2,3,4-trifluoroaniline (0.36 g), malononitrile (0.4 g) and hydrazine hydrate (0.2 g) to yield 0.337 g of the compound (54%).

48. 1-methyl-4-phenylazo-1H-pyrazole-3,5-diamine was prepared using 2-phenylhydrazonomalononitrile (425 mg) and methylhydrazine sulfate (720 mg). The compound was purified by column chromatography and afforded a yellow solid.

49. 7-[N'-(3,5-diaminopyrazol-4-ylidene)hydrazino]-4-trifluoromethylchroman-2-one was prepared from 7-amino-4-trifluoromethylchromen-2-one (0.25 g), malononitrile (0.15 g) and hydrazine hydrate (0.3 mL). The compound (0.101 g) was isolated after purification by column chromatography.

50. 4-[N'-(3,5-diaminopyrazol-4-ylidene)hydrazino]benzenesulfonamide was prepared from 4-aminobenzenesulfonamide (0.344 g, 2 mmol), malononitrile (0.172 g, 2.6 mmol) and hydrazine hydrate (0.03 g, 0.6 mmol). Filtration and washing with cold ethanol afforded the compound as a yellow powder (0.139 g); MS (m/z, ES+): 282 (M+1, 100%); $^1$H NMR (ppm, 200 MHz, DMSO-$d_6$) δ 10.97 (br. s, 1H), 7.96-7.50 (m, 4H), 7.30 (br. s, 2H), 6.44 (br. s, 2H), 6.02 (br. s, 2H).

51. 4-[N'-(3,5-diaminopyrazol-4-ylidene)hydrazino]-N-(2,6-dimethylpyrimidin-4-yl)benzenesulfonamide was prepared from 4-amino-N-(2,6-dimethylpyrimidin-4-yl)benzenesulfonamide (0.557 g, 2 mmol), malononitrile (0.172 g, 2.6 mmol) and hydrazine hydrate (0.03 g, 0.6 mmol). Filtration and washing with cold ethanol afforded the compound as an orange-red powder (0.195 g); MS (m/z, ES+): 388 (M+1, 100%); $^1$H NMR (ppm, 200 MHz, DMSO-$d_6$) δ 11.75 (br. s, 1H), 7.81 (d, 2H), 7.76 (d, 2H), 6.80 (s, 1H), 6.48 (br. s, 2H), 6.0 (br. s, 2H), 2.38 (s, 3H), 2.24 (s, 3H).

52. 4-[N'-(3,5-diaminopyrazol-4-ylidene)hydrazino]-N-(pyrimidin-2-yl)benzenesulfonamide was prepared from 4-amino-N-pyrimidin-2-ylbenzenesulfonamide (0.500 g, 2 mmol), malononitrile (0.172 g, 2.6 mmol) and hydrazine hydrate (0.03 g, 0.6 mmol). Filtration and washing with cold ethanol afforded the compound as a yellow powder (0.175 g). MS (m/z, ES+): 360 (M+1, 100%).

53. 4-[(4-methoxy-3-nitrophenyl)hydrazono]-4H-pyrazole-3,5-diamine was prepared using methoxy-3-nitroaniline (0.35 g, mmol), malononitrile (0.4 g), and hydrazine hydrate (0.3 mL). The compound was filtered off and recrystallized from EtOH yielding 0.21 g (36%). MS (m/z, ES+): 278.1 (M+1, 100%).

Example 3

Preparation of 4-(pyridin-4-ylhydrazono)-4H-pyrazole-3,5-diamine 4-(pyridin-4-ylhydrazono)-4H-pyrazole-3,5-diamine was prepared by dissolving 4-aminopyridine (0.36 g) in a mixture of 2 ml of $H_3PO_4$ (85%) and 1 ml of $HNO_3$ (68%). The solution was cooled at −5° C. and then $NaNO_2$ (0.28 g) solution was added. After being stirred at 0° C. for 1 hr, the mixture was added dropwise into a solution of malononitrile (0.5 g), acetic acid (2.4 g), KOAc (6.3 g) and $Na_2CO_3$ (5.6 g). The resulting mixture was kept stirring at 0° C. for 1 hr, and 100 mL of water was added. The solid obtained after being filtered and dried was re-dissolved in 5 mL of EtOH and hydrazine hydrate (0.5 g) was added at 40° C. After one hour of reaction, the solid precipitated upon cooling to 0° C. was collected by filtration and the title compound was obtained after re-crystallization from EtOH (278, mg, 36%).

Example 4

Preparation of 4-(2,3,4,5,6-pentafluorophenylhydrazono)-4H-pyrazole-3,5-diamine

Pentafluoroaniline (1.0 g) dissolved in 12 mL of $CH_3COOH$ was added to a solution of $NaNO_2$ (0.41 g) in concentrated $H_2SO_4$ at 5° C. The reaction mixture was kept stirring at 5° C. for 1 hr and then slowly added to a solution of malononitrile (1.0 g) mixed with 37 g of NaOAc in 50 mL of $H_2O$ at 5-10° C. The reaction mixture was extracted with ethyl acetate (EtOAc) (3×150 mL) an hour later. The combined organic phase was washed with brine, dried with anhydrous $MgSO_4$ and then evaporated. The residue was dissolved in 5 ml of anhydrous EtOH and 0.2 g of $N_2H_4$ was added to it at 40° C. After being stirred at 70° C. for 2 hrs, the solvents were removed and the residue was purified by column yielding 87 mg of the title compound (5.4%).

Example 5

Preparation of 4-(benzo[1,2,5]thiadiazol-4-ylhydrazono)-4H-pyrazole-3,5-diamine

To a solution of 4-amino-2,1,3-benzothiadiazole (0.38 g, 2.5 mmol) in a mixture of DMF (4 mL) and water (3.6 mL) at 0° C. was added 0.58 mL of concentrated HCl. This mixture was then added to a solution of sodium acetate trihydrate (1.4 g, 10 mmol) and malononitrile (0.3 g, 4.5 mmol) in water (7 mL) at 5° C. A precipitate formed immediately. After stirring for 2 hours, the solid was isolated by filtration and dried in vacuo. The solid was then dissolved in ethanol (20 mL) at 45° C. To this solution was added hydrazine hydrate (0.3 g, 6.0 mmol) and heating was continued for 1 hour. A solid precipitated from the solution and was isolated by filtration to afford 0.41 g of crude material. The crude material (0.1 g) was purified by preparative TLC eluting with $CHCl_3$:MeOH=4:1 to yield 0.029 g (18%) of the title compound as a yellow solid.

Example 6

Preparation of 4-[(4-fluoro-3-trifluoromethylphenyl)hydrazono]-4H-pyrazole-3,5-diamine A. Sodium acetate trihydrate (28 g, 203 mmol) was dissolved in 140 mL of water. Malononitrile (12 g, 182 mmol) was added and the solution was stirred until all the solids had dissolved. This solution was allowed to cool in an ice bath to approximately 0° C. and put aside. A solution of 4-fluoro-3-trifluoromethylaniline (17.9 g, 100 mmol) in 24 mL of water and 30 mL of DMF was cooled to 0° C. Concentrated HCl (23.2 mL) was added. A cooled solution of sodium nitrite (9.2 g, 133 mmol) in 20 mL of water was then added at a rate such that the temperature did not exceed 5° C. The phenyldiazo salt solution was added slowly to the malononitrile solution at a rate such that the temperature did not exceed 7° C. Yellow precipitate formed upon the addition. The solution was stirred for one hour. The resulting solid was isolated by filtration and dried under high vaccum.

B. A solution of the material prepared above in 200 mL of anhydrous ethanol was warmed to 30° C. until all of the solids had dissolved. Hydrazine hydrate (5 mL, 100 mmol) was added drop wise to the stirring solution. Heating was continued for seven hours. The solvent was evaporated from the reaction solution. The resulting solids were dissolved in ethyl acetate (<20 mL/g) and precipitated by the addition of hexanes (up to 60 mL/g) to provide the title compound as a yellow solid (16.4 g, 57%); IR (cm$^{-1}$, KBr pellet): 531, 585, 642, 670, 742, 775, 832, 901, 923, 942, 1046, 1127, 1157, 1241, 1261, 1290, 1321, 1403, 1433, 1495, 1515, 1564, 1599, 1627, 3309; $^1$H NMR (ppm, 200 MHz, DMSO-d$_6$) δ 10.8 (S, 1H), 8.05 (dd, 1H), 8.0 (m, 1H), 7.5 (t, 1H), 6.2 (brs, 4H); MS (m/z, ES+): 289.1 (M+1, 100%); Anal. Calcd for $C_{10}H_8F_4N_6$: C, 41.67; H, 2.80; N, 29.16. Found: C, 41.13; H, 3.04; N, 28.85.

Example 7

Preparation of 4-[(3-nitrophenyl)hydrazono]-4H-pyrazole-3,5-diamine

4-[(3-Nitrophenyl)hydrazono]-4H-pyrazole-3,5-diamine was prepared using 2-[(3-nitrophenyl)hydrazono]malononitrile (0.107 g, 0.5 mmol) which was derived from 3-nitroaniline (0.133 g, 1.0 mmol) and malononitrile (1.5 mmol) in a manner similar to that described in Example 2, and hydrazine hydrate. The resulting solid (0.088 g) was isolated by filtration, a portion (0.060 g) of which was purified by flash chromatography to yield 0.024 g (28%) of the title compound as an orange solid; MS (m/z, ES+): 248.0 (M+1, 100%).

Example 8

Preparation of {2-[N'-(3,5-diaminopyrazol-4-ylidene)hydrazino]phenyl}methanol

{2-[N'-(3,5-Diaminopyrazol-4-ylidene)hydrazino]phenyl}methanol was prepared using 2-[(2-hydroxymethylphenyl)hydrazono]malononitrile (0.100 g, 0.5 mmol) which was derived from 3-aminobenzyl alcohol (0.123 g, 1.0 mmol) and malononitrile (1.5 mmol) in a manner similar to that described in Example 2, and hydrazine hydrate. The title compound was obtained as a brown solid (32 mg, yield 28%); $^1$H NMR (ppm, 200 MHz, DMSO-d$_6$) δ 4.51 (d, 2H), 5.20 (t, 1H), 6.0 (br s, 4H), 7.15 (d, 1H), 7.30 (t, 1H), 7.45-7.60 (m, 2H), 10.60 (br s, 1H).

Example 9

Preparation of 4-[(1H-indazol-5-yl)hydrazono]4H-pyrazole-3,5-diamine 37091

4-[(1H-Indazol-5-yl)hydrazono]-4H-pyrazole-3,5-diamine was prepared using 2-[(1H-indazol-5-yl)hydrazono]malononitrile (0.105 g, 0.5 mmol) which was derived from 5-aminoindazole (0.133 g, 1.0 mmol) and malononitrile (1.5 mmol) in a manner similar to that described in Example 2, and hydrazine hydrate. The resulting solid was isolated by filtration, washed with ethanol, and dried to yield 0.076 g (63%) of the title compound as a brown solid; $^1$H NMR (ppm, 200 MHz, DMSO-d$_6$) δ 6.0 (br s, 4H), 7.50 (d, 1H), 7.94 (d, 1H), 8.0 (s, 1H), 8.08 (s, 1H), 10.68 (br s, 1H), 13.08 (s, 1H).

Example 10

Preparation of 4-(quinolin-6-ylhydrazono)-4H-pyrazole-3,5-diamine 4-(Quinolin-6-ylhydrazono)-4H-pyrazole-3,5-diamine was prepared using 2-(quinolin-6-ylhydrazono)malononitrile (0.11 g, 0.5 mmol) which was derived from 6-aminoquinoline (0.144 g, 1.0 mmol) and malononitrile (1.5 mmol) in a manner similar to that described in Example 2, and hydrazine hydrate. The resulting solid was isolated by filtration and purified by flash chromatography to yield 0.025 g (20%) of the title compound as an orange solid; $^1$H NMR (ppm, 200 MHz, DMSO-d$_6$) δ 5.95 (br s, 2H), 6.45 (br s, 2H), 7.40-7.55 (m, 1H), 7.98 (d, 1H), 8.10 (s, 1H), 8.20-8.40 (m, 2H), 8.79 (d, 1H), 10.35 (brs, 1H).

Example 11

Preparation of {4-[N-(3,5-diaminopyrazol-4-ylidene)hydrazino]benzyl}phosphonic acid diethyl ester {4-[N'-(3,5-Diaminopyrazol-4-ylidene)hydrazino]benzyl}phosphonic acid diethyl ester was prepared using [4-(N'-dicyanomethylenehydrazino)benzyl]phosphonic acid diethyl ester (0.16 g, 0.5 mmol) which was derived from diethyl 4-aminobenzylphosphonate (0.243 g, 1.0 mmol) and malononitrile (1.5 mmol) in a manner similar to that described in Example 2, and hydrazine hydrate. The title compound was purified by flash chromatography and isolated as a golden solid (0.116 g, 66%); $^1$H NMR (ppm, 200 MHz, DMSO-d$_6$) δ 1.20 (t, 6H), 3.23 (d, 2H), 3.95 (q, 4H), 6.0 (brs, 4H), 7.28 (d, 2H), 7.60 (d, 2H), 10.70.

Example 12

Preparation of 4-(benzo[2,1,3]thiadiazol-5-ylhydrazono)-4H-pyrazole-3,5-diamine

A. To a suspension of MoCl$_5$ (8 g) in 50 ml of THF was added 10 ml of H$_2$O and followed by the addition of Zn dust (3 g) 5 minutes later. 5-Nitrobenzo-2,1,3-thiadiazole (1.0 g) was then added to this mixture and the resulting reaction mixture was kept under reflux for 20 minutes. Benzo[1,2,5]thiadiazol-5-ylamine (0.4 g) was isolated by filtration and purified by column chromatography to be used in the next step.

B. The title compound was prepared by using benzo[1,2,5]thiadiazol-5-ylamine (0.19 g), malononitrile (0.15 g) and hydrazine hydrate (0.3 mL) in a manner similar to that described in Example 2. The title compound was purified by column chromatography to yield 0.047 g (14%).

Example 13

Preparation of 4-[(3-methylsulfanylphenyl)hydrazono]-4H-pyrazole-3,5-diamine

A. To a suspension of 3-methylthioaniline (0.278 g, 2 mmol) in 3 mL of water cooled in an ice bath was added 0.5 mL of conc. HCl (6 mmol). An aqueous solution of NaNO$_2$ (0.179 g, 2.6 mmol) was slowly added to the mixture. A red color solution obtained was kept stirring at −5° C. for 5 minutes, and then added to the mixture of malononitrile (0.172 mg, 2.6 mmol) and NaOAc.3H$_2$O (0.816 g, 6 mmol) in 3 mL of water. The mixture was stirred at ambient temperature for an hour, and the intermediate was collected by filtration and dried in vacuum to yield a brown yellow powder (0.433 g), which was used for the next step.

B. The intermediate obtained above (0.108 g, 0.5 mmol) was suspended in 2 mL of ethanol and 1 mL of ethanol solution of hydrazine (30 mg, 0.6 mmol) was added to the suspension. The mixture was heated to reflux for an hour. Upon cooling to ambient temperature, a yellow precipitation was obtained. Filtration and washing with ethanol afforded 0.128 g of the title compound. MS (m/z, ES+): 249 (M+1, 100%).

Example 14

Preparation of 4-[(3-methylsulfanylphenyl)hydrazono]-4H-pyrazole-3,5-diamine To a 1.5 mL methanol solution of the intermediate obtained in Example 65 (0.065 g, 0.3 mmol) in an ice bath was added 1 mL of aqueous solution of $NaIO_4$ (0.086 g, 0.4 mmol). The reaction process was monitored by TLC. The reaction mixture was filtered after the disappearance of the starting material on TLC. The filtrate was evaporated to dryness and then re-dissolved in ethanol. Hydrazine (30 mg, 0.6 mmol) was added to the ethanol solution. The mixture was heat at 60° C. for 2 hours. The title compound was obtained as an orange-yellow powder after purified by preparative-TLC (0.036 g); MS (m/z, ES+): 265 (M+1, 100%). $^1$H NMR (ppm, 200 MHz, DMSO-$d_6$) δ 10.84 (br. s, 1H), 7.95 (s, 1H), 7.80 (m, 1H), 7.60 (m, 1H), 7.50 (m, 1H), 6.42 (br. s, 2H), 5.99 (br. s, 2H), 2.80 (s, 3H).

Example 15

Preparation of 4-(quinazolin-6-ylhydrazono)-4H-pyrazole-3,5-diamine

A. Quinazoline (2 g) was nitrated with 25 mL of mixture of nitric acid 90%, 10 mL) and sulfuric acid (+20% $SO_3$, 15 mL) at 0° C. for 20 minutes, and then at ambient temperature for 1 hour. The mixture was then poured on ice, neutralized with KOH and the pH was adjusted to 8 with $K_2CO_3$ (pH 8). Filtration and recrystallization from EtOH yielded the crystalline product 6-nitroquinazoline (1.7 g).

B. $SnCl_2$ (8.5 g) dissolved in 8.5 mL of conc. HCl was added to the solution of 6-nitroquinazoline in 42.5 mL of 6 N HCl at 0° C. The reaction mixture was neutralized with KOH 10 minutes later and then extracted with diethyl ether ($Et_2O$) and EtOAc. The product 6-aminoquinazoline was obtained (0.67 g) after the removal of the solvent.

C. In a manner similar to that described in Example 2,4-(quinazolin-6-ylhydrazono)-4H-pyrazole-3,5-diamine was prepared using 6-aminoquinazoline (0.27 g), malononitrile (0.2 g) and hydrazine hydrate (0.4 g) to yield 0.067 g (14%) of the title compound: MS (m/z, ES+): 255.3 (M+1, 100%).

Example 16

Preparation of 4-[(1-methyl-1H-benzotriazol-5-yl)hydrazono]-4H-pyrazole-3,5-diamine A. 1-Methyl-5-nitrobenzotriazole (0.7 g) was reduced by $SnCl_2$ (4.0 g) at 0° C. in 5 mL of conc. HCl. The pH of the reaction mixture was adjusted to basic and the mixture was extracted with EtOAc. The product 5-amino-1-methylbenzotriazole (0.4 g) obtained after removal of the solvent was used for the next reaction without further purification.

B. The title compound was prepared following the similar procedure as described in Example 2. 5-Amino-1-methylbenzotriazole (0.25 g), malononitrile (0.17 g) and hydrazine hydrate (0.3 g) yielded 0.151 g (35%) of the title compound after recrystallization from EtOH; MS (m/z, ES+): 258.1 (M+1, 100%).

Example 17

Preparation of 4-[(3-methyl-3H-benzotriazol-5-yl)hydrazono]-4H-pyrazole-3,5-diamine A. 3-Methyl-5-nitrobenzotriazole (0.8 g) was reduced by $SnCl_2$ (4.5 g) at 0° C. in 5 mL of conc. HCl. The pH of the reaction mixture was adjusted to basic and the mixture was extracted with EtOAc. The product, 5-amino-3-methylbenzotriazole (0.6 g), obtained after removal of the solvent, was used for the next reaction without further purification.

B. 4-[(3-methyl-3H-benzotriazol-5-yl)hydrazono]-4H-pyrazole-3,5-diamine was prepared following the similar procedure as described in Example 2. 5-Amino-3-methylbenzotriazole (0.25 g), malononitrile (0.2 g) and hydrazine hydrate (0.3 g) yielded 0.188 g (44%) of the title compound after recrystallization from EtOH; MS (m/z, ES+): 258.1 (M+1, 100%).

Example 18

Preparation of 1-benzyl-4-phenylazo-1H-pyrazole-3,5-diamine

1-Benzyl-4-phenylazo-1H-pyrazole-3,5-diamine was prepared using 2-(phenyl-hydrazono)malononitrile (0.085 g, 0.5 mmol), which was derived from aniline (10 mL, 107 mmol) and malononitrile (161 mmol), as described in Example 2. The following change was made to the procedure: Benzylhydrazide dihydrochloride (0.097 g, 0.5 mmol) was used in the place of hydrazine hydrate. Additionally, 0.25 mL of 2 M sodium hydroxide solution was added to the reaction tube. Solids had not formed after heating the reaction at 75° C. for 3 hours, however, analysis of the reaction solution by TLC indicated that no starting material remained. The solvent was evaporated and the solids were redissolved in 1 M HCl solution, which was then washed with diethyl ether. The aqueous layer was neutralized with saturated $NaHCO_3$ solution and extracted three times with ethyl acetate. The combined organic layers were dried over $MgSO_4$, filtered and evaporated. This material was then purified by flash chromatography eluting with $CH_2Cl_2$:MeOH (20:1) to yield 0.013 g (9%) of the title compound as an orange solid; $^1$H NMR (ppm, 200 MHz, DMSO-$d_6$) δ 4.95 (s, 2H), 5.9 (br s, 2H), 6.75 (br s, 2H), 7.20-7.45 (m, 8H), 7.68 (d, 2H).

Example 19

Preparation of 1-{2-[3,5-diamino-4-(pyridin-3-ylazo)pyrazol-1-yl]-2-oxoethyl}pyrrolidine-2-carboxylic acid methyl ester A. A mixture of L-proline methyl ester (2.7 g, 16 mmol), $K_2CO_3$ (4.9 g, 35.5 mmol) and benzyl 2-bromoacetate (3.6 g, 16 mmol) in 18 mL of toluene was heated to 86° C. for 5 hours. The milky suspension was then cooled to ambient temperature and treated with aqueous $NaHCO_3$ and ethyl acetate. The collected organic phase was extracted with 10% HCl. The acid phase was neutralized to pH 10 with $K_2CO_3$ and extracted with ethyl acetate. The organic layer was washed with saline, dried and evaporated to dryness. A pale brown liquid was obtained in 2.5 g, yield 59%. MS (m/z, ES+): 278 (M+1, 100%); $^1$H NMR (ppm, 300 MHz, DMSO-$d_6$): 7.36 (m, 5H), 5.10 (s, 2H), 3.60 (d, J=17 Hz, 1H), 3.57 (s, $OCH_3$), 3.52 (dd, 1H), 3.49 (d, J=17 Hz, 1H), 3.00 (m, 1H), 2.67 (dd, 1H), 2.02 (m, 1H), 1.65-1.90 (m, 3H).

B. Ethanol solution (2 mL) of N-benzyloxycarbonylmethylpyrrolidine-2-carboxylic acid methyl ester (0.534 g, 2 mmol) prepared above and Pd/C (10%, 8.9 mg) was stirred under $H_2$ atmosphere for 4 hours. Acetic acid (3 drops) was then added. After the reaction, the solution was filtrated through a celite plug. After solvent evaporation, the residue oil was mixed with N-hydroxysuccinimide (0.276 g, 2.5 mmol) and suspended in 5 mL of ethylene glycol dimethyl ether. To this mixture was added DCC (0.515 g, 2.5 mmol) solution in 3 mL of ethylene glycol ether. After stirred at ambient temperture overnight, the reaction mixture was filtrated to remove DCU powder. The filtrate is directly used in next reaction.

C. The NHS ester solution made above (5 mL) was slowly added to the solution of 5-amino-4-(nicotinylhydrazono)-3-amino-4H-pyrazole (0.226 g, 1 mmol) and triethylamine (0.101 g, 1 mmol) in 8 mL of DMF at 78° C. Saline and ethyl acetate were added to the reaction mixture 1 hour later. The collected organic layer was concentrated and purified by column chromatography eluted with $CH_2Cl_2$:MeOH (15:1). A sticky solid was obtained as the title compound (0.180 g, 50%); MS (m/z, ES+): 373 (M+1, 32%), 204 (100%); $^1$H NMR (ppm, 300 MHz, DMSO-$d_6$) δ 8.98 (d, 1H), 8.46 (dd, 1H), 8.26 (br. s, $NH_2$), 8.14 (ddd, 1H), 7.45 (dd, 1H), 6.33 (br. s, $NH_2$), 4.11 (d, J=18.6 Hz, 1H), 3.99 (d, J=18.6 Hz, 1H), 3.63 (dd, 1H), 3.60 (s, OCH), 3.09 (m, 1H), 2.80 (dd, 1H), 2.09 (m, 1H), 1.69-1.93 (m, 3H).

Example 20

Preparation of 3-[N'-(3,5-diaminopyrazol-4-ylidene) hydrazino]benzenesulfonamide 3-Aminobenzosulfonamide (0.33 g, 1.92 mmol) was dissolved in 3.6 mL of $H_2O$ and 0.56 mL of conc. HCl was added. The mixture was treated with $NaNO_2$ (0.22 g, 3.19 mmol) in 0.5 mL of $H_2O$ at 0° C. This diazonium salt solution was then added into the mixture of malononitrile solution (0.3 g) and NaOAc trihydrate (1.4 g) in 8 mL of $H_2O$ at 10° C. The solid product, collected by filtration and used directly for next reaction, was re-dissolved in 20 mL of EtOH. Hydrazine hydrate (0.3 mL) was added to the solution and the mixture was kept at 55° C. for about an hour. The title compound was obtained in a yield of 20% (0.110 g); MS (m/z, ES+): 282.1 (M+1, 100%).

Example 21

Preparation of 4-(isoquinolin-5-ylhydrazono)-4H-pyrazole-3,5-diamine

5-Aminoisoquinoline (5 g, 34.7 mmol) was dissolved in 150 mL of an aqueous solution containing 58.8 g of sulfuric acid. This mixture was cooled to 0° C. and a solution of sodium nitrite (4 g, 58 mmol) dissolved in 10 mL of water was added drop-wise. This solution was then slowly added to a mixture of malononitrile (4 g, 61 mmol) and sodium acetate trihydrate (165 g, 1.2 mol) dissolved in 300 mL of water at 0° C. A red precipitate formed which was isolated by filtration. The above formed product was suspended in 150 mL of ethanol and hydrazine hydrate (4.0 mL, 122 mmol) was added. The reaction was heated to reflux for 4 hours. The solvent was then evaporated and the crude material was purified by silica gel chromatography eluting with $CHCl_3$: MeOH=5:1 to 3:1 to yield 5.14 g (29%) of the title compound as a yellow solid; IR ($cm^{-1}$, KBr pellet): 3428 (s), 3174 (s), 1639 (s), 1596 (s), 1556 (s), 1510 (s), 1477 (s), 1368 (s), 1329 (m), 1307 (s), 1269 (s), 1232 (m), 1206 (m), 1138 (s), 1090 (w), 1028 (m), 904 (w), 820 (m), 805 (s), 745 (s), 653 (m), 589 (m); $^1$H NMR (ppm, 200 MHz, DMSO-$d_6$) δ 10.95 (s, 1H), 9.25 (s, 1H), 8.5 (d, 1H), 8.35 (d, 1H), 8.05 (d, 1H), 7.95 (d, 1H), 7.85 (t, 1H), 6.3 (br s, 4H); MS (m/z, ES+): 254.2 (M+1, 25%); Anal. Calcd for $C_{12}H_{11}N_7$: C, 56.91; H, 4.38; N, 38.71. Found: C, 56.35; H, 4.35; N, 38.86.

Example 22

Preparation of Compounds of the Invention where R5 is aryl

A. An aqueous solution (1 mL) of $NaNO_2$ (83 mg; 1.2 mmol) was added dropwise to a stirred solution of an appropriately optionally substituted aniline (1.0 mmol) in 10% HCl (4 mL) under ice-cooling. After 15 minutes this solution was added dropwise to a cold solution of malononitrile (79 mg; 1.2 mmol) in aqueous sodium acetate (1.4 g in 7 mL of $H_2O$). A precipitate (yellow to brown) was filtered off, washed with water and dried in vacuum.

B. To a stirred solution of the appropriately optionally substituted (arylhydrazono)malononitrile (0.75 mmol) obtained above in THF (35 mL) was added dropwise a solution of hydrazine hydrate (1 mmol) in THF (10 mL) at 55° C., and the mixture was stirred for 30 minutes. The solvent was evaporated and the residue was re-crystallized from ethanol or ethanol/chloroform mixture.

C. In the manner described above, the following compounds of the invention were prepared:

1. 192 mg of 4-[(4-nitro-3-trifluoromethylphenyl)hydrazono]-4H-pyrazole-3,5-diamine was prepared in two steps starting with 515 mg (2.5 mmol) of 4-nitro-3-(trifluoromethyl)aniline. MS (m/z, ES+): 316 (M+1). Yield=61%.

2. 255 mg of 4-[(4-chloro-3-trifluoromethylphenyl)hydrazono]-4H-pyrazole-3,5-diamine was prepared in two steps starting with 195.5 mg (1.0 mmol) of 5-amino-2-chlorobenzotrifluoride. MS (m/z, ES+): 305 (M+1). Yield 83%.

3. 249 mg of 4-[(2,2-difluorobenzo[1,3]dioxol-5-yl)hydrazono]-4H-pyrazole-3,5-diamine was prepared in two steps starting with 195.0 mg (1.13 mmol) of 2,2-difluorobenzo[1,3]dioxol-5-ylamine. MS (m/z, ES+): 283 (M+1). Yield 78%.

4. 299 mg of 4-[(2,2,3,3-tetrafluoro-2,3-dihydrobenzo[1,4]dioxin-6-yl)hydrazono]-4H-pyrazole-3,5-diamine was prepared in two steps starting with 245.0 mg (1.1 mmol) of 2,2,3,3-tetrafluoro-2,3-dihydrobenzo[1,4]dioxin-6-ylamine. MS (m/z, ES+): 333 (M+1). Yield 82%.

5. 254 mg of 4-[(4-trifluoromethanesulfonylphenyl)hydrazono]-4H-pyrazole-3,5-diamine was prepared in two steps starting with 225.0 mg (1.0 mmol) of 4-trifluoromethanesulfonylphenylamine. MS (m/z, ES+): 335 (M+1). Yield 76%.

6. 78 mg of 4-[(4-phenylaminophenyl)hydrazono]-4H-pyrazole-3,5-diamine was prepared in two steps starting with 184.0 mg (1.0 mmol) of N-phenylbenzene-1,4-diamine. MS (m/z, ES+): 294 (M+1). Yield 27%.

7. 303 mg of N-butyl-3-[N'-(3,5-diaminopyrazol-4-ylidene)hydrazino]benzenesulfonamide was prepared in two steps starting with 228.0 mg (1.0 mmol) of 3-amino-N-butyl-benzenesulfonamide. MS (m/z, ES+): 338 (M+1). Yield 90%.

8. 145 mg of 4-[(3-methanesulfonylphenyl)hydrazono]-4H-pyrazole-3,5-diamine was prepared in two steps starting with 171.0 mg (1.0 mmol) of 3-methanesulfonylphenylamine. MS (m/z, ES+): 281 (M+1). Yield 52%.

9. 234 mg 4-[(4-methanesulfonylphenyl)hydrazono]-4H-pyrazole-3,5-diamine was prepared in two steps starting with 171.0 mg (1.0 mmol) of 4-methanesulfonylphenylamine. MS (m/z, ES+): 281 (M+1). Yield 83%.

10. 202 mg of 4-{[4-(morpholine-4-sulfonyl)phenyl]hydrazono}-4H-pyrazole-3,5-diamine was prepared in two steps starting with 181.0 mg (0.75 mmol) of 4-(morpholinosulfonyl)aniline. MS (m/z, ES+): 352 (M+1). Yield 77%.

11. 205 mg 4-{[4-(pyrrolidine-1-sulfonyl)phenyl]hydrazono}-4H-pyrazole-3,5-diamine was prepared in two steps starting with 170.0 mg (0.75 mmol) of 4-(tetrahydro-1H-pyrrol-1-ylsulfonyl)aniline. MS (m/z, ES+): 336 (M+1). Yield 82%.

12. 238 mg of 4-[(1,1-dioxo-1H-benzo[b]thiophen-6-yl)hydrazono]-4H-pyrazole-3,5-diamine was prepared in two steps starting with 179.0 mg (0.99 mmol) of 1,1-dioxo-1H-1$\lambda^6$-benzo[b]thiophen-6-ylamine. MS (m/z, ES+): 291 (M+1). Yield 83%.

13. 175 mg of 4-[(4-morpholin-4-ylphenyl)hydrazono]4H-pyrazole-3,5-diamine was prepared in two steps starting with 178.0 mg (1.0 mmol) of 4-(morpholin-4-yl)phenylamine. MS (m/z, ES+): 288 (M+1). Yield 61%.

14. 142 mg of 4-[(3-chloro-4-(morpholin-4-yl)phenyl)hydrazono]-4H-pyrazole-3,5-diamine was prepared in two steps starting with 160.0 mg (0.75 mmol) of 3-chloro-4-(morpholin-4-yl)phenylamine. MS (m/z, ES+): 322. Yield 59%.

15. 71 mg of 4-[(4-(piperidin-1-yl)phenyl)hydrazono]-4H-pyrazole-3,5-diamine was prepared in two steps starting with 176 mg (1.0 mmol) of 4-(piperidin-1-yl)phenylamine. Yield=25%. MS (m/z, ES+): 286 (M+1).

16. 42 mg of 4-(phthalazin-5-ylhydrazono)-4H-pyrazole-3,5-diamine was prepared in two steps starting with 75 mg (0.5 mmol) of phthalazin-5-ylamine. Yield 33%. MS (m/z, ES+): 253.1 (M+1).

17. 242 mg of 4-[(4-benzylphenyl)hydrazono]-4H-pyrazole-3,5-diamine was prepared in two steps starting with 183 mg (1.0 mmol) of 4-benzylphenylamine. Yield 82.8%. MS (m/z, ES+): 293 (M+1).

18. 345 mg of 4-[(6-(piperidin-1-yl)pyridin-3-yl)hydrazono]-4H-pyrazole-3,5-diamine was prepared in five steps starting with 317 mg (2.0 mmol) of 2-chloro-5-nitropyridine. Yield 60.0%. MS (m/z, ES+): 287 (M+1).

19. 28 mg of 4-{[6-(4-methylpiperazin-1-yl)pyridin-3-yl]hydrazono}-4H-pyrazole-3,5-diamine (isolated by preparative TLC) was prepared in five steps starting with 158.5 mg (1.0 mmol) of 2-chloro-5-nitropyridine. Yield 9.3%. MS (m/z, ES+): 302.1 (M+1, 30%).

20. 208 mg of 4-[(6-(morpholin-4-yl)pyridin-3-yl)hydrazono]-4H-pyrazole-3,5-diamine was prepared in five steps starting with 158.5 mg (1.0 mmol) of 2-chloro-5-nitropyridine. Yield 72%. MS (m/z, ES+): 289.3 (M+1).

21. 273 mg of 4-[(3-trifluoromethanesulfonylphenyl)hydrazono]-4H-pyrazole-3,5-diamine was prepared in two steps starting with 225 mg (1.0 mmol) of 3-trifluoromethanesulfonylphenylamine. Yield 82%. MS (m/z, ES+): 335 (M+1).

22. 12.5 mg of 4-[N'-(3,5-diaminopyrazol-4-ylidene)hydrazino]-2-diethylaminomethylphenol (isolated by preparative TLC) was prepared in two steps starting with 145.5 mg (0.75 mmol) of 4-amino-2-diethylaminomethylphenol. Yield 5.5%. MS (m/z, ES+): 304.3 (M+1).

23. 277 mg of 2-{3-[N'-(3,5-diaminopyrazol-4-ylidene)hydrazino]benzenesulfonyl}ethanol was prepared in two steps starting with 225 mg (1.0 mmol) of 2-(3-aminobenzenesulfonyl)ethanol. Yield 89.3%. MS (m/z, ES+): 311.2 (M+1).

24. 25 mg of 2-[{5-[N'-(3,5-diaminopyrazol-4-ylidene)hydrazino]pyridin-2-yl}(2-hydroxyethyl)amino]ethanol (isolated by preparative TLC) was prepared in five steps starting with 158.5 mg (1.0 mmol) of 2-chloro-5-nitropyridine. Yield 8.1%. MS (m/z, ES+): 307.1 (M+1, 80%).

25. 191 mg of 4-(4-(phenyl)phenylhydrazono)-4H-pyrazole-3,5-diamine was prepared in two steps starting with 169 mg (1.0 mmol) of biphenyl-4-ylamine. Yield 68.9%. MS (m/z, ES+): 279.3 (M+1).

26. 133 mg of 4-[(2,3-difluoro-4-trifluoromethylphenyl)hydrazono]-4H-pyrazole-3,5-diamine was prepared in two steps starting with 98.5 mg (0.5 mmol) of 4-amino-2,3-difluorobenzotrifluoride. Yield 87%. MS (m/z, ES+): 307.8 (M+1, 100%).

27. 237 mg of 4-[(2,6-dimethoxypyridin-3-yl)hydrazono]-4H-pyrazole-3,5-diamine was prepared in two steps starting with 154 mg (1.0 mmol) of 2,6-dimethoxypyridin-3-ylamine. Yield 90%. MS (m/z, ES+): 264 (M+1).

28. 161 mg of 4-{[4-(4-methylaminobenzyl)phenyl]hydrazono}-4H-pyrazole-3,5-diamine was prepared in two steps starting with 212 mg (2.0 mmol) of 4-(4-methylaminobenzyl)phenylamine. Yield 50%. MS (m/z, ES+): 321 (M+1).

29. 77 mg of 4-[(3-(morpholin-4-ylmethyl)phenyl)hydrazono]-4H-pyrazole-3,5-diamine was prepared in two steps starting with 192 mg (1.0 mmol) of 3-(morpholin-4-yl)methylphenylamine. Yield 26%. MS (m/z, ES+): 302 (M+1).

30. 248 mg of 4-[(3-(piperidin-1-ylmethyl)phenyl)hydrazono]-4H-pyrazole-3,5-diamine was prepared in two steps starting with 190 mg (1.0 mmol) of 3-(piperidin-1-yl)methylphenylamine. Yield 83%. MS (m/z, ES+): 300.9 (M+1).

31. 245 mg of 4-[N'-(3,5-diaminopyrazol-4-ylidene)hydrazino]-N-methylbenzenesulfonamide was prepared in three steps starting with 216 mg (1.0 mmol) of N-methyl-4-nitrobenzenesulfonamide. Yield 83%. MS (m/z, ES+): 296.1 (M+1).

32. 154 mg of 3-[N'-(3,5-diaminopyrazol-4-ylidene)hydrazino]-N-methylbenzenesulfonamide was prepared in three steps starting with 216 mg (1.0 mmol) of N-methyl-3-nitrobenzenesulfonamide. Yield 52%. MS (m/z, ES+): 296.3 (M+1).

33. 105 mg of 4-[N'-(3,5-diaminopyrazol-4-ylidene)hydrazino]-N-ethylbenzenesulfonamide was prepared in two steps starting with 120 mg (0.6 mmol) of 4-amino-N-ethylbenzenesulfonamide. Yield 56%. MS (m/z, ES+): 310.6 (M+1).

34. 330 mg of 3-[N'-(3,5-diaminopyrazol-4-ylidene)hydrazino]-N-ethylbenzenesulfonamide was prepared in two steps starting with 240 mg (1.2 mmol) of 3-amino-N-ethylbenzenesulfonamide. Yield 89%. MS (m/z, ES+): 310.7 (M+1).

35. 164 mg of 4-[(4-methyl-3-(morpholin-4-yl)phenyl)hydrazono]-4H-pyrazole-3,5-diamine was prepared in two steps starting with 310 mg (1.61 mmol) of 4-methyl-3-(morpholin-4-yl)phenylamine. Yield 47%. MS (m/z, ES+): 302 (M+1, 100%). $^1$H NMR (ppm, 200 MHz, DMSO-$d_6$) δ 2.25 (s, 3H), 2.95-3.05 (t, 4H), 3.65-3.75 (t, 4H), 5.3-6.5 (m, 4H), 6.8 (d, 1H), 6.85 (s, 1H), 7.55 (d, 1H), 10.8 (br s, 1H).

36. 286 mg of 4-[(3-fluoro-5-trifluoromethylphenyl)hydrazono]-4H-pyrazole-3,5-diamine was prepared in two steps starting with 185 mg (1.033 mmol) of 3-amino-5-fluorobenzotrifluoride. Yield 96%. MS (m/z, ES+): 289.1 (M+1).

37. 174 mg of 4-[(4-(morpholin-4-ylmethyl)phenyl)hydrazono]-4H-pyrazole-3,5-diamine was prepared in two steps starting with 281 mg (1.46 mmol) of 4-(morpholin-4-yl)methylphenylamine. Yield 39%. MS (m/z, ES+): 302 (M+1).

38. 159 mg of 4-{[4-((4-methylpiperazin-1-yl)methyl)phenyl]hydrazono}-4H-pyrazole-3,5-diamine was prepared in two steps starting with 205 mg (1.00 mmol) of 4-(4-methylpiperazin-1-yl)methylphenylamine. Yield 50.6%. MS (m/z, ES+): 315 (M+1, 20%). $^1$H NMR (ppm, 200 MHz, DMSO-$d_6$) δ 2.1 (s, 3H), 2.2-2.5 (br m, 4H), 3.15-3.25 (br m, 4H), 3.45 (s, 2H), 5.5-6.5 (br m, 4H), 7.25 (d, 2H), 7.55 (d, 2H), 10.75 (s, 1H).

39. 264 mg of 4-[(4-(piperidin-1-ylmethyl)phenyl)hydrazono]-4H-pyrazole-3,5-diamine was prepared in two steps starting with 190 mg (1.00 mmol) of 4-(piperidin-1-yl)methylphenylamine. Yield 88.2%. MS (m/z, ES+): 300 (M+1, 20%). $^1$H NMR (ppm, 200 MHz, DMSO-d$_6$) δ 1.2-1.6 (br m, 6H), 2.2-2.35 (br m, 4H), 3.4 (s, 2H), 5.5-6.5 (br m, 4H), 7.25 (d, 2H), 7.55 (d, 2H), 10.75 (s, 1H).

40. 145 mg of 4-{[4-(2-(morpholin-4-yl)ethyl)phenyl]hydrazono}-4H-pyrazole-3,5-diamine was prepared in two steps starting with 206 mg (1.00 mmol) of 4-(2-(morpholin-4-yl)ethyl)phenylamine. Yield 46.0%. MS (m/z, ES+): 316 (M+1, 100%). $^1$H NMR (ppm, 200 MHz, DMSO-d$_6$) δ 2.2-2.6 (br, m, 6H), 2.6-2.8 (br, m, 2H), 3.4-3.6 (m, 4H), 5.5-6.5 (br, m, 4H), 7.20 (d, 2H), 7.50 (d, 2H), 10.7 (s, 1H).

41. 237 mg of 4-[(3-(morpholin-4-ylmethyl)-5-nitrophenyl)hydrazono]-4H-pyrazole-3,5-diamine was prepared in two steps starting with 302 mg (1.27 mmol) of 3-(morpholin-4-yl)methyl-5-nitrophenylamine. Yield 53.7%. MS (m/z, ES+): 347 (M+1). $^1$H NMR (ppm, 200 MHz, DMSO-d$_6$) δ 2.3-2.5 (br, m, 4H), 3.5-3.7 (br, m, 4H), 3.55 (s, 2H), 5.5-6.5 (br, m, 4H), 7.95 (s, 1H), 8.0 (s, 1H), 8.35 (s, 1H), 10.75 (s, 1H).

42. 181 mg of 4-{[3-((4-methylpiperazin-1-yl)methyl)phenyl]hydrazono}-4H-pyrazole-3,5-diamine was prepared in two steps starting with 335 mg (1.63 mmol) of 3-((4-methylpiperazin-1-yl)methyl)phenylamine. Yield 40.8%. MS (m/z, ES+): 315 (M+1, 60%).

43. 97 mg of 4-[(3-(pyrrolidin-1-ylmethyl)phenyl)hydrazono]-4H-pyrazole-3,5-diamine was prepared in two steps starting with 242 mg (1.37 mmol) of 3-(pyrrolidin-1-yl)methylmethylphenylamine. The final product was isolated by column purification followed by precipitation from ethyl acetate by addition of hexane. Yield 21.0%.

44. 145 mg of 4-({3-[2-(2-methoxyethoxy)ethoxymethyl]phenyl}hydrazono)-4H-pyrazole-3,5-diamine was prepared in two steps starting with 206 mg (1.00 mmol) of 4-(2-morpholin-4-ylethyl)phenylamine. The final product was isolated by column purification followed by precipitation from ethyl acetate by addition of hexane. Yield 46.0%. MS (m/z, ES+): 335 (M+1, 100%).

Example 23

Preparation of 4-[(2-methyl-4-(morpholin-4-yl)phenyl)hydrazono]-4H-pyrazole-3,5-diamine 2-Methyl-4-morpholin-4-ylphenylamine (170 mg, 0.885 mmol) was dissolved in 2N HCl (8 mL). A solution of NaNO$_2$ (69 mg) in water (2.5 mL) was added at 0° C. and the green solution was stirred for 15 minutes and then added dropwise to the cooled (0° C.) solution of malononitrile (69 mg; 1.0 mmol) in water:NaOAc (5 mL) with stirring. The dark brown solid was filtered off, dried on filter in vacuum, and then dissolved in ether:THF mixture 3:1 (25 mL). Hydrazine hydrate (80 µL) was added in one portion at ambient temperature. The solution was then heated at 40° C. for 15 minutes, and the solvents were evaporated. The dark yellow solid was precipitated from ethyl acetate via addition of hexane, filtered and dried to provide 100 mg of the title compound (yield 33%); MS (m/z, ES+): 302.2 (M+1, 100%).

Example 24

Preparation of {2-[N'-(3,5-diaminopyrazol-4-ylidene)hydrazino]phenyl}methanol

A. To a solution of 2-hydroxymethylaniline (2.46 g, 0.02 mol) in 2 N HCl (80 mL) was added a solution of sodium nitrite (1.65 g, 24 mmol) in water (20 mL) at 5° C. The resulting reaction mixture was stirred for 10 minutes before it was added dropwise to a solution of malononitrile (1.58 g, 24 mmol) and sodium acetate (17 g) in water (150 mL) at 5° C. The yellow precipitate was filtered off, washed with water and dried in vacuum (3.95 g, 98%).

B. To a solution of the product obtained above (2.0 g, 10 mmol) in THF (300 mL) was added dropwise a solution of hydrazine hydrate (1.33 g, 26 mmol) in THF (50 mL) at 65° C. and then the mixture was stirred for 30 minutes. The solvent was evaporated in vacuum and the crude product was recrystallized from ethanol to give the title compound as a brownish yellow powder (0.971 g, 88%); MS (m/z, ES+): 233 (M+1, 100%).

Example 25

Preparation of 4-[(2-methyl-5-nitrophenyl)hydrazono]4H-pyrazole-3,5-diamine

A. To a solution of 2-hydroxymethylaniline (3.04 g, 0.02 mol) in 2 N HCl (80 mL) was added a solution of sodium nitrite (1.65 g, 24 mmol) in water (20 mL) at 5° C. The resulting reaction mixture was stirred for 10 minutes before it was added dropwise to a solution of malononitrile (1.58 g, 24 mmol) and sodium acetate (17 g) in water (150 mL) at 5° C. The yellow precipitate was filtered off, washed with water and dried in vacuum (4.51 g, 98%) and used without purification.

B. To a solution of the product obtained above (2.56 g, 11 mmol) in THF (300 mL) was added dropwise a solution of hydrazine hydrate (0.82 g, 16.5 mmol) in THF (50 mL) at 65° C. and then the mixture was stirred for 30 minutes. The solvent was evaporated in vacuum and the crude product was recrystallized from ethanol to give the title compound as a orange powder (2.77 g, 96%); MS (m/z, ES+): 262 (M+1, 100%).

Example 26

Preparation of 4-[(4-fluoro-2-(morpholin-4-ylmethyl)phenyl)hydrazono]-4H-pyrazole-3,5-diamine 4-Fluoro-2-(morpholin-4-yl)methylphenylamine (208 mg, 0.99 mmol) was dissolved in 2 N HCl (10 mL). A solution of NaNO$_2$ (79 mg) in water (2.5 mL) was added at 0° C. and the clear solution was stirred for 15 minutes and added dropwise to the cooled (0° C.) solution of malononitrile (72 mg, 1.04 mmol) in water:NaOAc (2.3 g) (5 mL) with stirring. The bright yellow solid was filtered off, dried in vacuum, and then dissolved in ether:THF mixture 3:1 (25 mL). Hydrazine hydrate (100 µL) was added in one portion at ambient temperature. The solution was then heated at 40° C. for 5 minutes, and the solvents were evaporated. The deep orange oil obtained was dissolved in ethyl acetate:hexane (2:1) and filtered through silica gel pad to remove the unreacted hydrazine. The product was isolated by crystallization from hexane:EtOAc (3:1) (24.5 mg, 8%). The concentrated mother liquor was purified by column chromatography (CH$_2$Cl$_2$:MeOH=20:3) to yield the title compound in amount of 188 mg (59.5%); MS (m/z, ES+): 320.3 (M+1, 100%).

Example 27

Preparation of 4-[(3-fluoro-4-(morpholin-4-ylmethyl)phenyl)hydrazono]-4H-pyrazole-3,5-diamine 3-Fluoro-4-(morpholin-4-yl)methylphenylamine (210 mg, 1.0 mmol) was dissolved in 2 N HCl (10 mL). A solution of NaNO$_2$ (79 mg) in water (2.5 mL) was added at 0° C. and the clear solution was stirred for 15 minutes and added dropwise to the cool (0° C.) solution of malononitrile (72 mg; 1.04 mmol) in water:NaOAc (2.3 g) (5 mL) with stirring. The bright yellow solid was filtered off, dried in vacuum, and then dissolved in ether:THF:EtOH mixture 3:2:1 (40 mL). Hydrazine hydrate (100 µL) was added in one portion at ambient temperature. The solution was then heated at 40° C. for 5 minutes, and the solvents were evaporated. The residue was dissolved in ethyl acetate, washed with NH$_4$Cl solution and separated organic layer was dried over Na$_2$SO$_4$. The title compound (164 mg, 81%) was purified by column chromatography (CH$_2$Cl$_2$:MeOH=20:3); MS (m/z, ES+): 320.1 (M+1, 100%).

Example 28

Preparation of 4-[(3-(morpholin-4-ylmethyl)-5-trifluoromethylphenyl)hydrazono]-4H-pyrazole-3,5-diamine 3-(Morpholin-4-yl)methyl-5-trifluoromethylphenylamine (145 mg, 0.55 mmol) was dissolved in 2N HCl (7 mL). A solution of NaNO$_2$ (69 mg) in water (2.5 mL) was added at 0° C. and the clear solution was stirred for 15 minutes and added dropwise to the cool (0° C.) solution of malononitrile (56 mg) in water:NaOAc (5 mL) with stirring. The product was extracted with ether (40 mL). To this ether extract hydrazine hydrate (70 µL) was added in one portion at ambient temperature. The solution was then heated at 40° C. for 5 minutes, and the solvent was evaporated. The title compound (168 mg, 83%) was purified by column chromatography (CH$_2$Cl$_2$:MeOH=20:3); MS (m/z, ES+): 370.3 (M+1, 70%).

Example 29

Preparation of {3-[N'-(3,5-diaminopyrazol-4-ylidene)hydrazino]-5-nitrophenyl}methanol (3-Amino-5-nitrophenyl)methanol (168 mg, 1.0 mmol) was dissolved in 2 N HCl (7 mL). A solution of NaNO$_2$ (75 mg) in water (2.5 mL) was added at 0° C. and the clear solution was stirred for 15 minutes and added dropwise to the cool (0° C.) solution of malononitrile (56 mg) in water:NaOAc (5 mL) with stirring. The product was extracted with ether (40 mL). To this ether extract hydrazine hydrate (80 µL) was added in one portion at ambient temperature. The solution was then heated at 40° C. for 10 minutes, and the solvent was evaporated. The title compound was isolated by crystallization from ethyl acetate:hexane in amount of 115 mg (41%); MS (m/z, ES+): 278.1 (M+1, 100%).

Example 30

Preparation of 3-[N'-(3,5-diaminopyrazol-4-ylidene)hydrazino]-N-(2-hydroxyethyl)benzenesulfonamide A. 3-Nitrobenzenesulfonyl chloride (2.22 g) dissolved in 20 mL of THF was added to a solution of 2-aminoethanol (2.0 g) and tryethylamine (2.0 g) in 20 mL of THF. The reaction mixture was kept at ambient temperature overnight. The solvent was removed and the residue was dissolved in water (20 mL) and then extracted with EtOAc (2×50 mL). The solvent of the organic layer was removed and the residue was dissolved in 50 mL of EtOH and a catalytic amount of Raney-Nickel was added, followed by the addition of hydrazine hydrate (2 mL). The reaction mixture was kept at ambient temperature under argon overnight, filtered through a celite cake. The solvent of the filtrate was removed yielding 1.1 g of 3-amino-N-(2-hydroxyethyl)benzenesulfonamide which was used in the next step without further purification.

B. The title compound was prepared following a similar procedure as described in Example 2: 3-Amino-N-(2-hydroxyethyl)benzenesulfonamide (0.55 g), malononitrile (0.8 g) and hydrazine hydrate (0.7 mL) yielded 0.251 g of the title compound after purification by column chromatography; MS (m/z, ES+): 326.1 (M+1).

Example 31

Preparation of 4-[(2H-benzotriazol-5-yl)hydrazono]-4H-pyrazole-3,5-diamine

A. 2H-Benzotriazol-5-ylamine was prepared following the similar procedure as described in Example 12. 5-Nitro-2H-benzotriazole (1.6 g) yielded 0.35 g of 2H-benzotriazol-5-ylamine. In a manner similar to that described in Example 2, 2H-benzotriazol-5-ylamine (0.35 g), malononitrile (0.3 g) and hydrazine hydrate (0.5 mL) yielded 0.23 g of the title compound after purification by column chromatography. MS (m/z, ES+): 244.2 (M+1, 100%).

B. In a similar manner, 4-[(2-methyl-2H-benzotriazol-5-yl)hydrazono]-4H-pyrazole-3,5-diamine was prepared from 2-methyl-2H-benzotriazol-5-ylamine (which was prepared from methyl-5-nitro-2H-benzotriazole (2.0 g) in a manner similar to that described above) (0.24 g), malononitrile (0.2 g) and hydrazine hydrate (0.2 g) to yield 0.181 g. MS (m/z, ES+): 258 (M+1, 100%).

Example 32

Preparation of 4-(quinolin-5-ylhydrazono)-4H-pyrazole-3,5-diamine

A. In a manner similar to that described in Example 5,4-(quinolin-5-ylhydrazono)-4H-pyrazole-3,5-diamine was prepared. 5-Aminoquinoline (0.35 g), malononitrile (0.3 g) and hydrazine hydrate (0.3 mL) yielded 0.043 g of the title compound after the purification by preparative TLC (⅓ of the crude product).

B. In a similar manner, the following compounds were prepared:

1. 400 mg of 4-[(3-trifluoromethoxyphenyl)hydrazono]-4H-pyrazole-3,5-diamine was prepared from 3-trifluoromethoxyphenylamine (0.42 g), malononitrile (0.3 g) and hydrazine hydrate (0.3 mL). MS (m/z, ES+): 287.1 (M+1, 100%).

2. 350 mg of 4-(quinolin-8-ylhydrazono)-4H-pyrazole-3,5-diamine was prepared from 8-aminoquinoline (0.35 g), malononitrile (0.3 g) and hydrazine hydrate (0.3 mL). MS (m/z, ES+): 254 (M+1, 100%).

3. 430 mg of 4-(quinolin-3-ylhydrazono)-4H-pyrazole-3,5-diamine was prepared from 3-aminoquinoline (0.35 g), malononitrile (0.3 g) and hydrazine hydrate (0.3 mL). MS (m/z, ES+): 254 (M+1, 40%).

4. 600 mg of 4-[(6-chloropyridin-3-yl)hydrazono]-4H-pyrazole-3,5-diamine was prepared from 2-chloro-5-aminopyridine (0.62 g), malononitrile (0.8 g) and hydrazine hydrate (0.5 mL).

5. 610 mg of 4-[(6-methoxypyridin-3-yl)hydrazono]-4H-pyrazole-3,5-diamine was prepared from 2-methoxy-5-aminopyridine (0.6 g), malononitrile (0.4 g) and hydrazine hydrate (0.5 mL). MS (m/z, ES+): 234.1 (M+1, 100%).

Example 33

Preparation of 4-[(4-methoxy-3-(morpholin-4-yl)methylphenyl)hydrazono]-4H-pyrazole-3,5-diamine A. A solution of 2-bromomethyl-1-methoxy-4-nitrobenzene (1.23 g, 5 mmol), triethylamine (0.3 mL) and morpholine (1.0 mL, 11.5 mmol) in 45 mL of THF was heated at 60° C. for 30 minutes. The solvent was evaporated in vacuo. The residue was mixed with water (20 mL) and extracted with ether. Organic layers was separated, dried over $MgSO_4$ and concentrated in vacuo to yield a yellow solid (1.222 g, 97%), which was used in the next step without further purification.

B. To a solution of 4-(2-methoxy-5-nitrobenzyl)morpholine (252 mg, 1.0 mmol) in THF:ethanol mixture (1:1) (25 mL) was added a catalytical amount of Raney-Nickel and hydrazine hydrate (450 mg; 9.0 mmol) and the mixture was stirred for 1 hour at ambient temperature, filtered through a Celite/silica gel pad. The filtrate was evaporated to yield the pure 4-methoxy-3-morpholin-4-ylmethylphenylamine (149 mg, 67%), which was used in the next step without purification.

C. An aqueous solution (1 mL) of $NaNO_2$ (55 mg; 0.79 mmol) was added dropwise to a stirred solution of 4-methoxy-3-morpholin-4-ylmethylphenylamine (149 mg 0.67 mmol) in 2 M HCl (2 mL) cooled in an ice-bath. After 3 minutes, this solution was added quickly to a cold solution of malononitrile (47 mg; 0.71 mmol) in aqueous sodium acetate (0.4 g in 5 mL of $H_2O$). The precipitate was collected by filtration, washed with water and dried in vacuum (170 mg, 85%).

D. To a stirred solution of 2-[(4-methoxy-3-(morpholin-4-yl)methylphenyl)hydrazono]malononitrile obtained above (0.57 mmol) in THF (25 mL) was added dropwise a solution of hydrazine hydrate (50 mg, 1 mmol) in THF (1 mL) at 55° C., and the mixture was stirred for 30 minutes. The solvent was removed and the title compound (160 mg, 85%) was purified by column chromatography eluted with MeOH:$CH_2Cl_2$, 3:1; MS (m/z, ES+): 332.3 (M+1, 20%).

E. In a similar manner as described above, the following compounds were prepared:

1. 4-[N'-(3,5-diaminopyrazol-4-ylidene)hydrazino]-2-(morpholin-4-yl)methylphenol: 2-Bromomethyl-4-nitrophenol (1.16 g, 5 mmol), triethylamine (0.3 mL) and morpholine (1.0 mL, 11.5 mmol) yielded 1.02 g (86%) of 2-(morpholin-4-yl)methyl-4-nitrophenol. 2-(Morpholin-4-yl)methyl-4-nitrophenol (236.4 mg, 0.984 mmol) and hydrazine hydrate (450 mg, 9.0 mmol) afforded pure 4-amino-2-(morpholin-4-yl)methylphenol (187 mg, 91%). 4-Amino-2-(morpholin-4-yl)methylphenol (187 mg, 0.9 mmol), malononitrile (66 mg; 1.0 mmol) and hydrazine hydrate (40 mg; 0.8 mmol) yielded 106 mg of the product in 52% yield after purification by column chromatography eluted with MeOH:$CH_2Cl_2$, 3:1; MS (m/z, ES+): 318.3 (M+1, 40%).

2. 169 mg of 4-[(2,6-dichloropyridin-3-yl)hydrazono]-4H-pyrazole-3,5-diamine was prepared from 2,6-dichloropyridin-3-ylamine (163 mg, 1.0 mmol), malononitrile (70 mg, 1.06 mmol) and hydrazine hydrate (72 μL, 1.3 mmol), 62% yield; MS (m/z, ES+): 272.04 (100%), 274.04 (70%).

3. 96 mg of 4-[(3-diethylaminomethylphenyl)hydrazono]-4H-pyrazole-3,5-diamine was prepared from 3-diethylaminomethylphenylamine (336 mg, 1.88 mmol), malononitrile (128 mg, 1.94 mmol) and hydrazine hydrate (144 μL, 2.6 mmol) with 17.8% yield; MS (m/z, ES+): 288.15 (M+1, 75%).

4. 170 mg of 4-[(3-dimethylaminomethylphenyl)hydrazono]-4H-pyrazole-3,5-diamine was prepared from 3-dimethylaminomethylphenylamine (243 mg, 1.62 mmol), malononitrile (108 mg, 1.63 mmol) and hydrazine hydrate (144 μL, 2.6 mmol), 40.5% yield; MS (m/z, ES+): 260.14 (M+1, 100%).

5. 102 mg of 4-[(6-fluoropyridin-3-yl)hydrazono]-4H-pyrazole-3,5-diamine was prepared from 5-amino-2-fluoropyridine (224 mg, 2.0 mmol), malononitrile (140 mg, 2.12 mmol) and hydrazine hydrate (160 μL, 3.2 mmol) with 23% yield; MS (m/z, ES+): 222.06 (M+1, 100%).

6. 449 mg of 4-[(4-methylpyridin-3-yl)hydrazono]-4H-pyrazole-3,5-diamine was prepared from 4-methylpyridin-3-ylamine (270 mg, 2.5 mmol), malononitrile (170 mg, 2.57 mmol) and hydrazine hydrate (150 μL, 3.0 mmol) with 82.7% of yield; MS (m/z, ES+): 218.12 (M+1, 100%).

7. 89 mg of 4-(isoquinolin-5-ylazo)-1-methyl-1H-pyrazole-3,5-diamine was prepared from 5-aminoisoquinoline (1.0 g), malononitrile (1.0 g) and $CH_3NHNH_2.H_2SO_4$ (0.5 g, neutralized by 0.3 g of NaOH); MS (m/z, ES+): 268.4 (M+1, 100%).

Alternatively, the compounds of the invention may be prepared by the methods disclosed in the following Reaction Schemes A. Compounds of the invention can be obtained starting from β-cyanoketones as illustrated in the following Reaction Scheme 2:

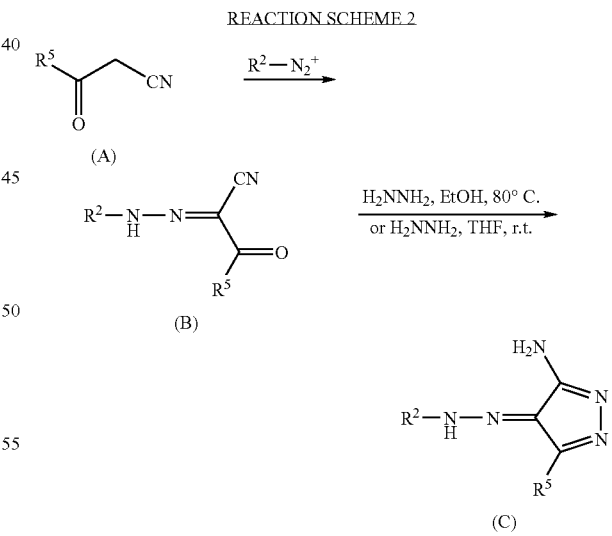

A β-cyanoketone (A) reacts with a diazonium salt in the presence of a base to yield the hydrazono-β-cyanoketone (B) which will react with hydrazine either in EtOH or in THF to afford the aminopyrazole. β-Cyanoketones can either be purchased from a chemical supplier such as Aldrich/Sigma and Lancaster or be prepared according to the methods illustrated below in Reaction Schemes 3 and 4:

REACTION SCHEME 3

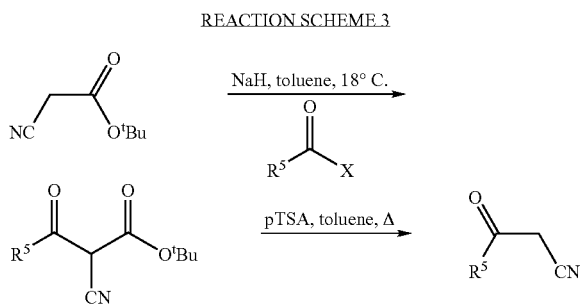

REACTION SCHEME 4

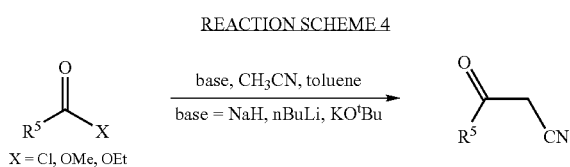

X = Cl, OMe, OEt

B. Compounds of the invention can also be prepared from aminopyrazoles. In this method, the aminopyrazole reacts with the diazonium salt to yield the desired compound of the invention as illustrated in Reaction Scheme 5 below:

REACTION SCHEME 5

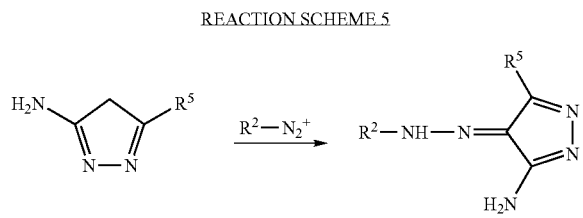

Aminopyrazoles used in this method can be purchased from a chemical supplier such as Aldrich/Sigma and Lancaster. They can also be prepared from β-cyanoketones as illustrated in below in Reaction Scheme 6 or the procedures described in J. Med. Chem., 11, 981 (1968), J. Med. Chem., 11, 984 (1968) and in U.S. Pat. No. 3,341,413. Costanzo, A.; Bruni, F; Auzzi, G.; Selleri, S.; Pecori, L. *J. Heterocycl. Chem.* 1990, 27, 695.

REACTION SCHEME 6

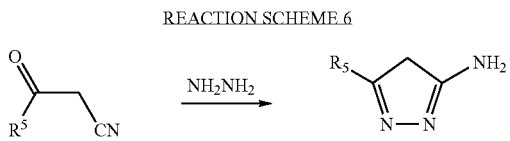

The following Examples illustrate compounds of the invention as prepared by the foregoing Reaction Schemes.

Example 34

Preparation of 4-(isoquinolin-5-ylhydrazono)-5-phenethyl-4H-pyrazol-3-ylamine

To an ice cooled solution of 5-aminoisoquinoline (0.1 g, 0.68 mmol) in 3 mL of 4 M $H_2SO_4$ was added the cooled solution of $NaNO_2$ (0.08 g, 1.16 mmol) in 0.5 mL of water. This diazonium salt was then added into a solution of 3-oxo-5-phenylpentanenitrile (0.1 g, 0.58 mmol) and NaOAc trihydrate (3.3 g, 24.3 mmol) in a mixture of 3 mL of AcOH and 3 mL of water. The solid residue was collected by filtration, dried and then redissolved in 5 mL of ethanol and treated with hydrazine hydrate (0.2 mL). After 2 hours at 45° C., the solvents were removed and the residue was purified by column chromatography ($CHCl_3$:MeOH=6:1) to yield 30 mg of the title compound. MS (m/z, ES+): 343 (M+1).

Example 35

Preparation of 5-but-3-enyl-4-(quinolin-6-ylhydrazono)-4H-pyrazol-3-ylamine

A. A mixture of 6-aminoquinoline (173 mg, 1.2 mmole) in 1.4 mL of water was cooled in an ice bath. The solution was acidified with conc. HCl (0.6 mL, 7.2 mmole). A solution of $NaNO_2$ (99 mg, 1.44 mmole) in 0.5 mL of water was then added. The diazonium mixture was added to a solution of 1-cyano-5-hexen-2-one (123 mg, 1 mmole) and NaOAc trihydrate (979 mg, 7.2 mmole) in a DMF-water mixture. From this reaction, 291 mg of a dark brown solid was obtained, which was then treated with hydrazine (1 mmole) in hot ethanol. After the reaction was complete, the ethanol was evaporated and diethyl ether was added. A brown powder product was isolated by filtration. The crude material was purified by column chromatography ($CH_2Cl_2$:MeOH=25:1) to yield 80 mg (27%) of the title compound as an orange powder. MS (m/z, ES+): 293 (M+1, 100%); $^1$H NMR (ppm, 300 MHz, DMSO-$d_6$-CDCl$_3$) δ 11.60 (br s, 1H), 8.75 (d, 1H), 8.22 (d, 1H), 8.02-8.16 (m, 2H), 7.97 (d, 1H), 7.40 (m, 1H), 6.55 (br s, 2H), 5.85 (m, 1H), 5.03 (dd, 1H), 4.92 (d, 1H), 2.92 (t, 2H), 2.00 (t, 2H).

B. In a similar manner, 5-but-3-enyl-4-(pyridin-3-ylhydrazono)-4H-pyrazol-3-ylamine was prepared from 3-aminopyridine (113 mg, 1.2 mmole) and 1-cyano-5-hexen-2-one (123 mg, 1 mmole). The crude material was pruified by preparative TLC ($CH_2Cl_2$:MeOH=21:1) to yield 131 mg (54%) of the title compound as an orange powder. MS (m/z, ES+): 243 (M+1, 100%); $^1$H NMR (ppm, 300 MHz, DMSO-$d_6$) δ 11.68 (br s, 1H), 8.89 (s, 1H), 8.46 (m, 1H), 7.96 (d, 1H), 7.46 (dd, 1H), 7.19 (brs, 2H), 5.87 (m, 1H), 5.07 (dd, 1H), 4.96 (d, 1H), 2.84 (br m, 2H), 2.46 (t, 2H).

C. In a similar manner, 5-but-3-enyl-4-[(3-nitrophenyl)hydrazono]4H-pyrazol-3-ylamine was prepared from 3-nitroaniline (166 mg, 1.2 mmole) and 1-cyano-5-hexen-2-one (123 mg, 1 mmole) with NaOAc (979 mg, 7.2 mmole) according to a procedure similar to Example 2. The crude material was purified by a prepreparative TLC ($CH_2Cl_2$:MeOH=21:1) to yield 175 mg (61%) of the title compound as an orange powder. MS (m/z, ES+): 287 (M+1, 100%); $^1$H NMR (ppm, 300 MHz, DMSO-$d_6$-CDCl$_3$) δ 11.60 (br s, 1H), 8.38 (s, 1H), 7.99 (m, 1H), 7.57 (t, 1H), 6.64 (br s, 2H), 5.84 (m, 1H), 5.03 (d, 1H), 4.92 (d, 1H), 2.88 (m, 2H), 2.48 (m, 2H).

Example 36

The compounds described in this example were prepared using the following procedure: A solution of 3-fluoroaniline (777 mg, 7 mmole) dissolved in 10.5 mL of water was cooled in an ice bath and acidified by the addition of 1.75 mL of conc. HCl (~18 mmole). The solution of $NaNO_2$ (665 mg, 9.6 mmole) in 2.8 mL of water was slowly added to the mixture. Total volume of the solution reached 15.05 mL. This mixture was stirred in a salt ice bath for 15 minutes. The resulting diazonium solution was then aliquoted (2.15 mL each) into several solutions containing one of the β-cyanoketones (1.3 mmole) indicated below and NaOAc trihydrate (410 mg, 3 mmole) in 3 mL of $H_2O$:DMF (1:2). The mixture was stirred at ambient temperature for 1 hour and the resulting yellow precipitate was isolated by filtration, washed with excess water, and dried in vacuo overnight to provide the desired product. A suspension of the desired product (0.5 mmole) in 2 mL of ethanol was heated to 80° C. A solution of hydrazine hydrate (40 μL, 0.75 mmole) in 1 mL of ethanol was slowly added to the suspension. A clear dark coloured solution was generally observed. The reaction mixture was then refluxed for 1 hour. After the reaction was complete, the solvent was evaporated. The products were isolated as yellow solids either by precipitation with ether-hexanes or by preparative TLC.

1. 4-[(3-Fluorophenyl)hydrazono]-5-m-tolyl-4H-pyrazol-3-ylamine was synthesized from 3-oxo-3-m-tolylpropionitrile to yield 105 mg of the product. MS (m/z, ES+): 297.1 (18%), 296.1 (M+1, 92%).

2. 4-[(3-Fluorophenyl)hydrazono]-5-p-tolyl-4H-pyrazol-3-ylamine was synthesized from 3-oxo-3-p-tolylpropionitrile to yield 66 mg of the product. MS (m/z, ES+): 297.1 (23%), 296.1 (M+1, 100%).

3. 5-(3-Chlorophenyl)-4-[(3-fluorophenyl)hydrazono]-4H-pyrazol-3-ylamine was synthesized from 3-oxo-3-(3-chlorophenyl)propionitrile to yield 25 mg of the product. MS (m/z, ES+): 319.1 (9%), 318.1 (35%), 317.1 (21%), 316.1 (M+1, 95%).

4. 5-(4-Chlorophenyl)-4-[(3-fluorophenyl)hydrazono]-4H-pyrazol-3-ylamine was synthesized from 3-oxo-3-(4-chlorophenyl)propionitrile to yield 43 mg of the product. MS (m/z, ES+): 318.1 (16%), 317.1 (12%), 316.1 (M+1, 46%).

5. 4-[(3-Fluorophenyl)hydrazono]-5-(3-trifluoromethylphenyl)-4H-pyrazol-3-ylamine was synthesized from 3-oxo-3-(3-trifluoromethylphenyl)propionitrile to yield 101 mg of the product. MS (m/z, ES+): 351.1 (20%), 350.1 (M+1, 100%).

6. 4-[(3-Fluorophenyl)hydrazono]-5-(4-trifluoromethoxyphenyl)-4H-pyrazol-3-ylamine was synthesized from 3-oxo-3-(4-trifluoromethoxyphenyl)propionitrile to yield 38 mg of the product. MS (m/z, ES+): 367.1 (23%), 366.1 (M+1, 100%); $^1$H NMR (ppm, 200 MHz, DMSO-$d_6$) δ 12.34 (br. s, 1H), 8.56 (s, 1H), 8.40 (m, 1H), 7.90-7.26 (m, 7H), 7.17 (m, 1H).

7. 4-[(3-Fluorophenyl)hydrazono]-5-(4-methoxyphenyl)-4H-pyrazol-3-ylamine was synthesized from 3-oxo-3-(4-methoxyphenyl)propionitrile to yield 44 mg of the product. MS (m/z, ES+): 313.2 (20%), 312.1 (96%); $^1$H NMR (ppm, 200 MHz, DMSO-$d_6$) δ 12.26 (br s, 1H), 8.05 (d, 2H), 7.77-7.37 (m, 3H), 7.36-6.79 (m, 5H), 3.80 (s, 3H).

8. 4-[(3-Fluorophenyl)hydrazono]-5-furan-2-yl-4H-pyrazol-3-ylamine was synthesized from 3-oxo-3-furan-2-ylpropionitrile to yield 90 mg of the product. $^1$H NMR (ppm, DMSO-$d_6$) δ 12.21 (br s, 1H), 7.82 (s, 1H), 7.72-7.42 (m, 3H), 7.37 (br s, 1H), 7.16 (m, 1H), 7.07 (m, 1H), 6.66 (s, 1H).

9. 4-[(3-Fluorophenyl)hydrazono]-5-(2-methylfuran-3-yl)-4H-pyrazol-3-ylamine was synthesized from 3-oxo-3-(2-methylfuran-3-yl)propionitrile to yield 101 mg of the product. $^1$H NMR (ppm, DMSO-$d_6$) δ 12.05 (br s, 1H), 7.75-7.42 (m, 4H), 7.38 (br s, 2H), 7.12 (m, 1H), 6.95 (s, 1H), 2.52 (s, 3H).

10. 4-[(3-Fluorophenyl)hydrazono]-5-phenyl-4H-pyrazol-3-ylamine was synthesized from 3-oxo-3-phenylpropionitrile to yield 58 mg of the product. MS (m/z, ES+): 282 (M+1, 100%).

11. 4-{5-Amino-4-[(3-fluorophenyl)hydrazono]-4H-pyrazol-3-yl}benzoic acid methyl ester was synthesized from 4-(1-oxo-but-3-ynyl)benzoic acid methyl ester to yield 29 mg of the product. $^1$H NMR (ppm, DMSO-$d_6$) δ 12.45 (br s, 1H), 8.30 (d, 2H), 8.10 (d, 2H), 7.90-7.30 (m, 5H), 7.20 (m, 1H), 3.90 (s, 3H).

Example 37

The compounds described in this example were prepared by the following procedure: Sodium hydride (800 mg, 60% in oil, 20 mmol) was weighed into a 200 mL flask under argon. Freshly distilled anhydrous toluene (55 mL) was introduced into the flask and the slurry was cooled to 15° C. t-Butyl cyanoacetate (5.6 g, 40 mmole) was then slowly added to this suspension. Production of gas was observed and a white cloudy mixture was obtained. A solution of phenylmethyleneacetyl chloride (3.4 g, 20 mmole) in 5 mL of anhydrous toluene was added to the mixture. After the reaction was stirred at ambient temperature for 30 minutes, a yellow orange mixture was observed, which became a clear orange solution after 1 hour. The mixture was stirred at ambient temperature overnight. The cloudy solution was worked up by the addition of a mixture of 100 mL of ether and 20 mL of water. The organic phase was separated and washed once with diluted HCl solution and dried over anhydrous $Na_2SO_4$, filtered and evaporated in vacuo to afford a yellow oil.

The obtained yellow oil was then dissolved in 120 mL of anhydrous toluene and 4-toluenesulfonic acid (380 mg, 2 mmol) was added. After it was refluxed for 4 hours, TLC showed that more than 50% of de-protection occurred. The reaction mixture was then mixed with 100 mL of ether, washed with the acidified water, dried over anhydrous $Na_2SO_4$ and filtered. After the solvent was evaporated, the oil was purified by column chromatography (hexane:$CH_2Cl_2$=1.5:1) to yield 1.1 g of the desired compound as a white solid. MS (m/z, ES–): 173 (M, 13), 172 (M–1, 100).

The solution of substituted aniline (0.5 mmole) in 0.5 mL of water cooled in an ice bath was acidified with conc. HCl (0.14 mL, 1.7 mmole). A solution of $NaNO_2$ (51 mg, 0.74 mmole) in 0.25 mL of water was then added slowly. The mixture was stirred at 0 to –5° C. for 30 min. This diazonium solution was then added to a mixture of the compound obtained above (118 mg, 0.68 mmole) and NaOAc trihydrate (231 mg, 1.7 mmole) in 2 mL of DMF:$H_2O$ (1:1) mixture. The product, as a yellowish solid, precipitated instantly, was collected by filtration and dried in vacuo.

The product obtained above (0.3 mmole) was weighed into a 10 mL flask and dissolved in 2 mL of ethanol. The solution was stirred and heated to 70° C. A solution of hydrazine hydrate (18 mg, 0.36 mmole) in 1 mL of ethanol was added dropwise. A clear orange solution was obtained. The solution was refluxed for 2 hours. The solvent was then evaporated in vacuo and the crude material was purified by preparative TLC.

1. 4-[(3-Fluorophenyl)hydrazono]-5-phenethyl-4H-pyrazol-3-ylamine was synthesized from 3-fluoroaniline to yield 9 mg of the product. MS (m/z, ES+): 310.2 (M+1, 100%).

2. 4-[(3-Chlorophenyl)hydrazono]-5-phenethyl-4H-pyrazol-3-ylamine was synthesized from 3-chloroaniline to yield 13 mg of the product. $^1$H NMR (ppm, DMSO-$d_6$) δ 11.72 (br s, 1H), 7.80-7.59 (m, 2H), 7.46 (m, 1H), 7.40-7.00 (m, 8H), 3.18-2.90 (m, 4H).

3. 4-[(3,5-Difluorophenyl)hydrazono]-5-phenethyl-4H-pyrazol-3-ylamine was synthesized from 3,5-difluoroaniline to yield 67 mg of the product. $^1$H NMR (ppm, DMSO-d$_6$) 11.77 (br. s, 1H), 7.55-7.00 (m, 10H), 3.17-2.92 (m, 4H).

Example 38

Preparation of 5-(4-methoxybenzyl)-4-(phenylhydrazono)-4H-pyrazol-3-ylamine

To a warm suspension of 4-(4-methoxyphenyl)-3-oxo-2-(phenylhydrazono)butyronitrile (1 g, 3.4 mmol) in ethanol was slowly added a solution of hydrazine hydrate (204 mg, 4.08 mmol) in 10 mL of ethanol. The solution was heated to reflux and a brownish clear solution was obtained. After 2 hours of reflux, the solvent was removed in vacuo. The obtained oil was dissolved with minimum amount of isopropanol, and a yellow powder was precipitated by the addition of water. The title compound was isolated by filtration in a yield of 560 mg. The filtrate was further purified by column chromatography (CH$_2$Cl$_2$:MeOH=15:1) and an additional 370 mg of the title compound was obtained. The total yield was 92%. MS (m/z, ES+): 308 (M+1, 100%); $^1$H NMR (ppm, CDCl$_3$) δ 7.77 (m, 2H), 7.43 (m, 2H), 7.38 (m, 1H), 7.21 (d, 2H), 6.86 (d, 2H), 5.41 (br s, 2H), 4.30 (s, 2H), 3.79 (s, 3H).

Example 39

Preparation of 5-phenyl-4-(phenylhydrazono)-4H-pyrazol-3-ylaminez

The title compound was prepared using 124 mg (0.5 mmol) of 3-oxo-3-phenyl-2-(phenylhydrazono)propionitrile. Hydrazine hydrate was added to a solution of 3-(phenylhydrazono)pentane-2,4-dione in ethanol. Precipitate formed in the reaction tube approximately 1.5 hours after the addition of hydrazine hydrate. The resulting solid was isolated by filtration, washed with ethanol, and dried to yield 31 mg of the title compound as a yellow solid (24%). $^1$H NMR (ppm, DMSO-d$_6$) δ 6.3 (br s, 2H), 7.25-7.55 (m, 6H), 7.75 (d, 2H), 8.0-8.20 (m, 2H), 12.10 (s, 1H); IR (cm$^{-1}$, KBr pellet): 3376 (w), 3269 (w), 3170 (m), 3082 (m), 3025 (m), 2956 (m), 2847 (m), 1625 (s), 1590 (m), 1577 (m), 1511 (s), 1492 (m), 1481 (m), 1457 (m), 1447 (m), 1397 (s), 1350 (s), 1303 (w), 1285 (w), 1210 (w), 1171 (w), 1070 (w), 975 (m), 916 (w), 808 (w), 775 (m), 762 (m), 729 (m), 686 (s), 664 (w), 578 (m); MS (m/z, ES+): 265.2 (M+2, 1%), 264.2 (M+1, 5%).

Example 40

Preparation of 5-aminomethyl-4-[(3-fluorophenyl)hydrazono]-4H-pyrazol-3-ylamine

A. A solution of 3-fluoroaniline (1.67 g, 15 mmole) in 17 mL of water, acidified with 3.75 mL of conc. HCl (45 mmole) in an ice bath, was treated with NaNO$_2$ (1.35 g, 19.5 mmole). The diazonium solution was then added to the solution of 4-(1,3-dioxo-1,3-dihydroisoindol-2-yl)-3-oxobutyronitrile (2.28 g, 10 mmole) with NaOAc (6.12 g, 45 mmole) in DMF/water mixture (30:35 mL). From this reaction, 3.4 g of 2-{5-amino-4-[(3-fluorophenyl)hydrazono]-4H-pyrazol-3-ylmethyl}isoindole-1,3-dione, as a yellow powder, was obtained, which was then treated with hydrazine (22 mmole) portionwise in hot ethanol. After the reaction was completed, a few grams of silica gel was mixed and the solvent was evaporated. The powdery residue was purified by column chromatography (CH$_2$Cl$_2$:MeOH:NH$_3$.H$_2$O=600:150:6) to yield 1.5 g (61%) of the title compound as an orange powder. $^1$H NMR (ppm, 200 MHz, DMSO-d$_6$) δ 7.40-7.70 (m, 3H), 7.12 (m, 1H), 7.00 (br s, 2H), 4.01 (s, 2H).

B. In a similar manner, 2-{5-amino-4-[(3,4-difluorophenyl)hydrazono]-4H-pyrazol-3-ylmethyl}isoindole-1,3-dione was prepared.

Example 41

Preparation of 3-({5-amino-4-[(3-fluorophenyl)hydrazono]-4H-pyrazol-3-ylmethyl}carbamoyl)acrylic acid A. 5-Aminomethyl-4-[(3-fluorophenyl)hydrazono]-4H-pyrazol-3-ylamine (60 mg, 0.25 mmole) was dissolved in 3 mL of anhydrous DMF. To this solution was added triethylamine (0.51 mmole, 52 mg) and then a solution of maleic anhydride (30.2 mg, 0.31 mmole) in 1 mL of DMF. The reaction mixture was stirred at ambient temperature for 30 minutes and then worked up by the addition of saline and ethyl acetate. The mixture was acidified with 1 mL of 1.5 M HCl. The aqueous phase was extracted with ethyl acetate. The combined organic layer was washed with saline three times and dried over anhydrous MgSO$_4$. The solution was then filtered, concentrated and purified by preparative TLC (CH$_2$Cl$_2$:MeOH:trace acetic acid=6:1) to yield 58 mg of the title compound as a yellow powder. MS (m/z, ES−): 331 (M−1, 100%); $^1$H NMR (ppm, 300 MHz, DMSO-d$_6$) δ 11.90 (br s, 1H), 7.35-7.70 (m, 3H), 7.30 (br s, 2H), 6.12 (d, 1H), 5.70 (d, 1H), 4.52 (s, 2H).

B. In a similar manner, N-{5-amino-4-[(3-fluorophenyl)hydrazono]4H-pyrazol-3-ylmethyl}nicotinamide was prepared by reacting 5-aminomethyl-4-[(3-fluorophenyl)hydrazono]-4H-pyrazol-3-ylamine (60 mg, 0.25 mmole) with nicotinoyl chloride hydrochloride (46.3 mg, 0.26 mmole). The reaction was worked up by the addition of saline and ethyl acetate. The crude material was purified by preparative TLC (CH$_2$Cl$_2$:MeOH=9:1) to yield 36 mg (41%) of the title compound as a yellow powder. MS (m/z, ES+): 340 (M+1, 100%); $^1$H NMR (ppm, 300 MHz, DMSO-d$_6$) δ 11.80 (br s, 1H), 9.01 (br s, 2H), 8.70 (d, 1H), 8.20 (d, 1H), 7.30-7.70 (m, 4H), 6.85-7.25 (m, 3H), 4.70 (br s, 2H).

C. In a similar manner, N-{5-amino-4-[(3-fluorophenyl)hydrazono]-4H-pyrazol-3-ylmethyl}succinamic acid was prepared by reacting 5-aminomethyl-4-[(3-fluorophenyl)hydrazono]-4H-pyrazol-3-ylamine (60 mg, 0.25 mmole) with succinic anhydide (40 mg, 0.4 mmole). The reaction was worked up by the addition of aqueous ammonium chloride solution and ethyl acetate. The crude material was purified by preparative TLC (CH$_2$Cl$_2$:CH$_3$OH:H$_2$O:HOAc=210:21:1.6: 0.8) to yield 45 mg (51%) of the title compound as a yellow powder. MS (m/z, ES−): 333 (M−1, 42%); $^1$H NMR (ppm, 300 MHz, DMSO-d$_6$) δ 8.23 (br s, 1H), 7.35-7.63 (m, 3H), 6.83-7.20 (m, 3H), 4.42 (s, 2H), 2.33 (m, 4H).

Example 42

Preparation of 1-[3-({5-amino-4-[(3-fluorophenyl)hydrazono]-4H-pyrazol-3-ylmethyl}carbamoyl)acryloyl]pyrrolidine-2-carboxylic acid methyl ester To a suspension of L-proline methyl ester hydrochloride (200 mg, 1.21 mmole) in 8 mL of ethylene glycol dimethyl ether was added triethylamine (244 mg, 2.4 mmole). The white cloudy mixture was stirred at ambient temperature for 20 min, and was then treated with maleic anhydride in 1 mL of diethyl ether. After 1 hour, the reaction mixture was filtered. The filtrate was mixed with a solution of N-hydroxysuccinimide (172 mg, 1.5 mmole) in ethylene glycol dimethyl ether, and then DCC (412 mg, 2 mmole) was added. The reaction mixture was stirred at ambient temperature overnight. After filtration, the solution of the NHS ester was added in 4 mL portions to a solution of 5-(aminomethyl)-4-(3-fluorophenylhydrazono)-3-amino-4H-pyrazole (60 mg, 0.25 mmole) and triethylamine (0.51 mmole, 52 mg) in 4 mL of DMF at 45° C. After stirring at ambient temperature for 45 minutes, the reaction was quenched by the addition of saline and ethyl acetate. The ethyl acetate extracts were concentrated and the resulting crude material was purified by preparative TLC ($CH_2Cl_2$:$CH_3OH$=12:1) to yield 44 mg (38%) of the title compound as a yellow powder. MS (m/z, ES+): 444 (M+1, 56%), 445 (M+2, 13%); $^1$H NMR (ppm, 300 MHz, DMSO-$d_6$) δ 11.92 (br s, 1H), 8.80 (br s, 1H), 7.35-7.62 (m, 3H), 7.10 (d, J=14.8 Hz, 1H), 7.09 (br s, $NH_2$), 6.90 (d, J=14.8 Hz, 1H), 4.56 (dd, J=8.5 Hz, 1H), 4.36 (dd, J=8.5, 4.0 Hz, 1H), 3.66 (m, 1H), 3.60 (s, $OCH_3$), 3.45 (m, 1H), 3.34 (m, 1H), 2.17 (m, 1H), 1.75-2.00 (m, 3H).

Example 43

Preparation of 1-[({5-amino-4-[(3-fluorophenyl) hydrazono]-4H-pyrazol-3-ylmethyl}carbamoyl)methyl]pyrrolidine-2-carboxylic acid methyl ester A. Preparation of N-benzyloxycarbonylmethylpyrrolindine-2-carboxylic acid methyl ester: A mixture of L-proline methyl ester (2.7 g, 16 mmole), $K_2CO_3$ (4.9 g, 35.5 mmole) and benzyl 2-bromoacetate (3.6 g, 16 mmole) in 18 mL of toluene was heated to 86° C. for 5 hours. The milky suspension was then cooled to ambient temperature and treated with aqueous $NaHCO_3$ and ethyl acetate. The collected organic phase was extracted with 10% HCl. The aqueous phase was made basic to pH 10 with $K_2CO_3$ and extracted with ethyl acetate. After washing with saline, the organic solution was dried over $Na_2SO_4$, filtered and evaporated to dryness. A pale brown liquid was obtained in a yield of 2.5 g (59%). MS (m/z, ES+): 278 (M+1, 100%); $^1$H NMR (ppm, 300 MHz, DMSO-$d_6$) δ 7.36 (m, 5H), 5.10 (s, 2H), 3.60 (d, J=17 Hz, 1H), 3.57 (s, $OCH_3$), 3.52 (dd, 1H), 3.49 (d, J=17 Hz, 1H), 3.00 (m, 1H), 2.67 (dd, 1H), 2.02 (m, 1H), 1.65-1.90 (m, 3H).

B. Preparation of NHS ester of N-carboxymethylpyrrolindine-2-carboxylic acid methyl ester: N-Benzyloxycarbonyl-methyl-pyrrolindine-2-carboxylic acid methyl ester (534 mg, 2 mmole) and Pd/C (10%, 8.9 mg) in 2 mL of ethanol was stirred under $H_2$ atmosphere for 4 hours. Acetic acid (3 drops) was then added. After the reaction, the solution was filtered through a celite plug. The solvent was evaporated in vacuo and the residue was mixed with N-hydroxysuccinimide (276 mg, 2.5 mmole) in 5 mL of ethylene glycol dimethyl ether. To this mixture was added DCC (515 mg, 2.5 mmole) in 3 mL of ethylene glycol ether. After being stirred at ambient temperature overnight, the reaction mixture was filtered. The filtrate was used directly in the next reaction.

C. The NHS ester solution, prepared above, was added in 3 mL portions to a solution of 5-(aminomethyl)-4-(3-fluorophenylhydrazono)-3-amino-4H-pyrazole (117 mg, 0.5 mmole) and triethylamine (1 mmole, 101 mg) in 7 mL of DMF at 45° C. After stirring for 45 minutes at ambient temperature, the reaction was worked up by the addition of saline and ethyl acetate. The ethyl acetate extracts were concentrated in vacuo and the crude material was purified by column chromatography ($CH_2Cl_2$:$CH_3OH$=15:1) to yield 120 mg (31%) of the title compound as a yellow powder. MS (m/z, ES+): 404 (M+1, 100%); $^1$H NMR (ppm, 300 MHz, DMSO-$d_6$) δ 11.80 (brs, 1H), 8.10 (brs, 1H), 7.30-7.60 (m, 3H), 7.01 (m, 1H), 6.95 (br s, NH2), 4.44 (dd, J=15.0, 5.6 Hz, 1H), 4.29 (dd, J=15.0, 3.9 Hz, 1H), 3.45 (s, 3H), 3.14-3.38 (m, 2H), 2.95 (d, 1H), 2.78 (m, 1H).

Example 44

Preparation of 1-[({5-amino-4-[(3-fluorophenyl) hydrazono]-4H-pyrazol-3-ylmethyl}carbamoyl)methyl]pyrrolidine-2-carboxylic acid 1-[({5-Amino-4-[(3-fluorophenyl)hydrazono]-4H-pyrazol-3-ylmethyl}carbamoyl)-methyl]pyrrolidine-2-carboxylic acid methyl ester (80 mg, 0.20 mmole) was dissolved in 1.5 mL of 95% ethanol with KOH (19.7 mg (85%), 0.29 mmole). The solution was heated at 76° C. for 1 hour. The reaction was quenched by the addition of 1 mL of water and then acidified to pH 3 with 1.5 M HCl. The solution was evaporated to dryness together with 2-PrOH and silica gel. The resulting powder was then placed onto a silica gel column. The crude material was purified by column chromatography ($CH_2Cl_2$:MeOH:$H_2O$:HOAc=240:60:4.7:2.2) to yield 70 mg of the title compound as a yellow powder. MS (m/z, ES−): 388 (M−1, 100%); $^1$H NMR (ppm, 300 MHz, DMSO-$d_6$) δ 8.77 (br s, 1H), 7.35-7.60 (m, 3H), 7.09 (m, 1H), 6.99 (br s, 2H), 4.50 (m, 2H), 3.31 (m, 1H), 3.01 (m, 2H), 2.29 (m, 1H), 2.05 (m, 1H), 1.93 (m, 1H), 1.72 (m, 1H), 1.50-1.61 (m, 2H).

Example 45

Preparation of N-{5-amino-4-[(3-fluorophenyl)hydrazono]-4H-pyrazol-3-ylmethyl}methanesulfonamide Methanesulfonyl chloride was reacted with 5-(aminomethyl)-4-(3-fluorophenylhydrazono)-3-amino-4H-pyrazole (60 mg, 0.25 mmole) in DMF at ambient temperature to yield 43 mg (52%) of the title compound. $^1$H NMR (ppm, 300 MHz, DMSO-$d_6$) δ 11.49 (br s, 1H), 7.20-7.50 (m, 3H), 6.70-7.10 (m, 2H), 6.45 (br s, NH2), 4.40 (d, 2H), 2.79 (s, 3H, $CH_3$).

Example 46

Preparation of 4-[(3-fluorophenyl)hydrazono]-5-morpholin-4-ylmethyl-4H-pyrazol-3-ylamine To a mixture of 5-(aminomethyl)-4-(3-fluorophenylhydrazono)-3-amino-4H-pyrazole (60 mg, 0.25 mmole) and triethylamine (71 µL, 0.512 mmole) in 3 mL of anhydrous DMF was added solid di(2-tosyloxyethyl)ether (108 mg, 0.25 mmole). The reaction was heated at 87° C. for 5-6 hours, and was then worked up by the addition of saline and ethyl acetate. The crude material was purified by preparative TLC ($CH_2Cl_2$:$CH_3OH$=15:1) to yield 13 mg of the title compound as a yellow powder. MS (m/z, ES+): 305 (M+1, 100%); $^1$H NMR (ppm, 300 MHz, DMSO-$d_6$) δ 7.53 (m, 1H), 7.40 (m, 2H), 7.03 (m, 1H), 6.45 (br s, 2H), 3.97 (s, 2H), 3.74 (m, 4H), 2.65 (m, 4H).

Example 47

Preparation of N{5-amino-4-[(3-fluorophenyl)hydrazono]-4H-pyrazol-3-ylmethyl}malonamic acid benzyl ester A solution of malonic acid monobenzyl ester (1.5 eq, 0.26 mmol) in anhydrous DMF (3 mL) was added to a 10 mL reaction vessel containing PS-carbodiimide (2 eq, 380 mg). The reaction mixture was stirred at ambient temperature under argon for 10 minutes before a solution of 5-aminomethyl-4-[(3-fluorophenyl)hydrazono]-4H-pyrazol-3-ylamine (40 mg, 0.17 mmol) in anhydrous DMF (3 mL) was added. The mixture was further stirred for approximately 16 hours before it was filtered, washed with DMF (3×3 mL) and concentrated under reduced pressure. The title compound was obtained in a yield of 38 mg (55%) as a yellow powder with no further purification. MS (m/z, ES+): 411 (M+1, 100%); $^1$H NMR (ppm, 300 MHz, DMSO-$d_6$) δ 11.40 (brs, 1H, N—H pyrazole), 8.45 (s, 1H, N—H amide), 7.40-7.60 (m, 3H, Ar—H), 7.28-7.35 (m, 5H, Ar—H), 7.05-7.15 (t, 1H, F—Ar—H), 5.15 (s, 2H, benzyl $CH_2$), 4.47 (s, 1H, $CH_aH_b$ amide), 4.43 (s, 1H, $CH_aH_b$ amide), 3.35 (2H, $CH_2$ pyrazole-overlap with $H_2O$).

Example 48

Preparation of butane-1-sulfonic acid {5-amino-4-[(3-fluorophenyl)hydrazono]-4H-pyrazol-3-ylmethyl}amide A. A solution of 5-aminomethyl-4-[(3-fluorophenyl)hydrazono]-4H-pyrazol-3-ylamine (40 mg, 0.17 mmol) in anhydrous DMF (3 mL) was added to a 10 mL reaction vessel containing PS-DIEA (2.5 eq, 150 mg) and butane-1-sulfonyl chloride (1.1 eq, 0.19 mmol) suspended in anhydrous DMF (3 mL). The reaction mixture was stirred at ambient temperature under argon for approximately 16 hours before it was filtered, washed with DMF (3×5 mL) and concentrated under reduced pressure. The resulting yellow residue was recrystallized from ether to yield 13 mg (22%) of the title compound as a yellow powder. MS (m/z, ES+): 355 (M+1, 100%).

B. In a similar manner, N-{5-amino-4-[(3-fluorophenyl)hydrazono]-4H-pyrazol-3-ylmethyl}-4-fluorobenzenesulfonamide was prepared as a yellow residue, which was recrystallized from dichloromethane to yield 4 mg (6%) of the title compound as a yellow powder (4 mg, 0.010 mmol, 6% yield). MS (m/z, ES+): 394.06 (M+1, 100%).

Example 49

Preparation of 5-aminomethyl-4-[(3,4-difluorophenyl)hydrazono]-4H-pyrazol-3-ylamine A. 3,4-Difluoroaniline (2.94 g, 22.8 mmole) was mixed with 25 mL of water and cooled in an ice-bath. To this solution was slowly added conc. HCl (5.7 mL, 68.4 mmole). A white precipitation was observed. To this mixture was slowly added a solution of $NaNO_2$ (2.05 g, 29.6 mmole) in 7 mL of water. A pale-yellow clear solution was obtained. The resulting diazonium solution was then added to a solution of 4-(1,3-dioxo-1,3-dihydroisoindol-2-yl)-3-oxobutyronitrile (4.4 g, 19.2 mmole) and NaOAc trihydrate (68.4 mmole) in 100 mL of DMF and 60 mL of water. The mixture was stirred at ambient temperature for 1 hour. The product was isolated by filtration and dried in vacuo to yield 7.1 g of a yellow powder.

B. The yellow powder obtained above was dissolved in 190 mL of THF and the solution was heated to 63° C. To this solution was added a suspension of hydrazine hydrate (22 mmole) in 30 mL of THF. In approximately 1 hour a precipitate gradually formed. The mixture was then cooled to ambient temperature and the solid was collected by filtration to yield 4.7 g (66%) of a yellow powder. MS (m/z, ES−): 399 (M−1, 100%); $^1$H NMR (ppm, 300 MHz, DMSO-$d_6$) δ 11.77 (br s, 1H), 8.79 (br s, $NH_2$), 7.93 (m, 4H), 7.63 (m, 1H), 7.45 (m, 2H), 5.03 (s, 2H), 4.86 (br s, $NH_2$).

C. The yellow powder obtained in the second step was refluxed in ethanol with a catalytic amount of toluenesulfonic acid (95 mg, 0.5 mmol). In approximately 45 minutes, a clear brownish solution was obtained and a significant amount of yellow precipitate appeared after an additional 35 min. To this mixture was added an additional 16 mmol of hydrazine hydrate. Again the solution became clear brown and then a yellow precipitate formed. The reaction was refluxed for an additional hour. The mixture was then cooled to 65° C. and the title compound as a yellow powder was isolated by hot filtration in a yield of 3.6 g. MS (m/z, ES+): 253 (M+1, 24%), 236 (M−$NH_3$, 22%); $^1$H NMR (ppm, 300 MHz, DMSO-$d_6$) δ 8.09 (m, 2H), 7.56 (m, 1H), 6.82 (br. s, $NH_2$), 3.86 (s, 2H).

Example 50

Preparation of N-{5-amino-4-[(3,4-difluorophenyl)hydrazono]-4H-pyrazol-3-ylmethyl}-2-chloro-6-methylnicotinamide To a 10 mL reaction vessel containing PS-carbodiimide (2 eq, 175 mg) and HOBt (1.7 eq, 20 mg) was added a solution of 2-chloro-6-methylnicotinic acid (1.5 eq, 0.12 mmol) in anhydrous $CH_2Cl_2$ (2 mL) and anhydrous DMF (0.2 mL). The reaction mixture was stirred at ambient temperature under argon for 30 minutes before a solution of 5-aminomethyl-4-[(3,4-difluorophenyl)hydrazono]-4H-pyrazol-3-ylamine (20 mg, 0.079 mmol) in anhydrous DCM (3 mL) and anhydrous DMF (0.7 mL) was added. The reaction mixture was further stirred for approximately 16 hours before it was filtered, washed with DCM (3×3 mL) and concentrated under reduced pressure. The title compound was obtained as a yellow powder (yield 26%). MS (m/z, ES+): 406 ($Cl^{35}$M+1, 20%), 408 ($Cl^{37}$M+1, 10%).

Example 51

Preparation of N-{5-amino-4-[(3,4-difluorophenyl)hydrazono]-4H-pyrazol-3-ylmethyl}nicotinamide To a solution of 5-aminomethyl-4-[(3,4-difluorophenyl)hydrazono]-4H-pyrazol-3-ylamine (245 mg, 0.97 mmole) and triethylamine (202 mg, 2 mmole) in 10 mL of anhydrous DMF was added nicotinoyl chloride (178 mg, 1.0 mmol) in 7 mL of anhydrous DMF. The reaction was stirred at ambient temperature for 1 hour, and then mixed with saline and ethyl acetate. The title compound was purified by column chromatography ($CH_2Cl_2$:$CH_3OH$=13:1) to yield 119 mg of the title compound as a yellow powder. MS (m/z, ES−): 356 (M−1, 20%); $^1$H NMR (ppm, 400 MHz, DMSO-$d_6$) δ 11.86 (br s, 1H), 9.04 (brs, 1H), 9.01 (s, 1H), 8.67 (d, 1H), 8.19 (d, 1H), 7.71 (dd, 1H), 7.57 (m, 1H), 7.47 (m, 2H), 7.11 (br s, 2H), 4.69 (s, 2H).

Example 52

Preparation of 5-[(bis-pyridin-3-ylmethylamino)methyl]-4-[(3,4-difluorophenyl)hydrazono]-4H-pyrazol-3-ylamine A. A 2 mL suspension of 5-aminomethyl-4-[(3,4-difluorophenyl)hydrazono]-4H-pyrazol-3-ylamine (100 mg, 0.397 mmole) and triethylamine (120 µL, 0.86 mmole) was heated to 66° C. To this orange solution was added dropwise a solution of 3-bromomethylpyridine (110 mg, 0.43 mmole) in 1 mL of DMF. The reaction was stirred at 76° C. overnight, and then mixed with saline and ethyl acetate. The crude material was purified by prepreparative TLC ($CH_2Cl_2$: $CH_3OH$=10:1) to yield 20 mg of the title compound as a yellow powder. MS (m/z, ES+): 435 (M+1, 73%), 94 (100%).

B. In a similar manner, 5-[(bis-pyridin-2-ylmethylamino) methyl]-4-[(3,4-difluorophenyl)hydrazono]-4H-pyrazol-3-ylamine and ({5-amino-4-[(3,4-difluorophenyl)hydrazono]-4H-pyrazol-3-ylmethyl}ethoxycarbonylmethylamino)-acetic acid ethyl ester were prepared.

Example 53

Preparation of 4-[(3,4-difluorophenyl)hydrazono]-5-morpholin-4-ylmethyl-4H-pyrazol-3-ylamine The mixture of 5-aminomethyl-4-[(3,4-difluorophenyl) hydrazono]-4H-pyrazol-3-ylamine (125 mg, 0.5 mmole) and triethylamine (152 mg, 1.5 mmole) in 5 mL of dry DMF was heated to 87° C. To this solution was added slowly di(2-tosyloxyethyl)ether (311 mg, 0.75 mmole) in 1 mL of DMF. The reaction mixture was heated at 87° C. for 1.5 hours, and then worked up by the addition of saline and ethyl acetate. The crude material was purified by preparative TLC ($CH_2Cl_2$: $CH_3OH$=16:1) to yield 23 mg of the title compound as a yellow powder. MS (m/z, ES+): 323 (M+1, 100%); $^1$H NMR (ppm, 300 MHz, $CDCl_3$) δ 7.52 (m, 2H), 7.24 (m, 1H), 6.25 (br s, 2H), 3.95 (s, 2H), 3.74 (m, 4H), 2.64 (m, 4H).

Example 54

Preparation of 5-{[bis-(2-morpholin-4-ylethyl) amino]methyl}-4-[(3,4-difluorophenyl)hydrazono]-4H-pyrazol-3-ylamine and 4-[(3,4-difluorophenyl)-hydrazono]-5-[(2-morpholin-4-ylethylamino) methyl]-4H-pyrazol-3-ylamine A. To an ice cooled solution of 4-(2-hydroxyethyl)morpholine (1.22 mL, 10 mmole) and triethylamine (1.39 mL, 10 mmole) in ethylene glycol dimethyl ether (10 mL) was slowly added MsCl (1.1 g, 10 mmole) in 5 mL of ether. A white precipitate formed immediately. After stirring at 0° C. for 10 minutes and then at ambient temperature for 35 minutes, the reaction mixture was cooled again and quenched by the addition of water. The reaction solution was extracted with diethyl ether and the ether solution was washed with $NaHCO_3$ solution and saline, dried over $Na_2SO_4$, filtered and concentrated in vacuo. The resulting solid residue (380 mg) was used in following reaction without further purification.

B. A solution of 5-aminomethyl-4-[(3,4-difluorophenyl) hydrazono]-4H-pyrazol-3-ylamine (252 mg, 1 mmole), NaI (1.1 mg) and triethylamine (101 mg, 1.0 mmole) in 5 mL of DMF was heated to 60° C. To this solution was slowly added the mesylate prepared above in 7 mL DMF. The reaction was stirred overnight and then quenched by the addition of saline and ethyl acetate. The organic phase was isolated, dried over $Na_2SO_4$, filtered and concentrated in vacuo. The crude material was purified by column chromatography ($CH_2Cl_2$: $CH_3OH$=10:1 to $CH_2Cl_2$:$CH_3OH$:$NH_3$—$H_2O$=486:65:6). The fractions containing product were further purified by preparative TLC. The first title compound was isolated in a yield of 126 mg as a yellow powder. MS (m/z, ES+): 478 (M+1, 26%), 114 (100%), 141 (53%); $^1$H NMR (ppm, 400 MHz, DMSO-$d_6$) δ 7.66 (m, 1H), 7.44-7.61 (m, 2H), 7.15 (br s, 2H), 3.82 (s, 2H), 3.49 (t, 8H), 2.61 (t, 4H), 2.41 (t, 4H), 2.33 (t, 8H). The second title compound was isolated in a yield of 33 mg as a yellow powder. MS (m/z, ES+): 366 (M+1, 92%), 236 (100%), 114 (93%); $^1$H NMR (ppm, 400 MHz, DMSO-$d_6$) δ 7.70 (m, 1H), 7.45-7.61 (m, 2H), 6.97 (br s, 2H), 3.79 (t, 2H), 3.49 (t, 2H), 3.38 (t, 4H), 2.58 (m, 1H), 2.33 (t, 2H), 2.22 (t, 4H).

Example 55

Preparation of 5-but-3-enyl-4-[(3,4-difluorophenyl) hydrazono]-4H-pyrazol-3-ylamine A. To a suspension of sodium hydride (800 mg 60% in oil, 20 mmole) in 55 mL of anhydrous toluene at 10° C., t-butyl cyanoacetate (5.6 g, 40 mmole) was added dropwise over 15 min. Hydrogen gas was released and a milky white mixture was obtained. To this mixture was added slowly a solution of 4-pentenoyl chloride (2.4 g, 20 mmole) in 5 mL of toluene. The mixture was stirred at ambient temperature overnight and was then quenched by the addition of 10 mL of water and 200 mL of diethyl ether. The ether solution was washed with 1.5 M of HCl, dried over anhydrous $Na_2SO_4$, filtered and evaporated in vacuo to give a liquid residue. The residue was then redissolved in 100 mL of anhydrous toluene, mixed with toluenesulfonic acid (380 mg, 2 mmole), and heated to reflux for several hours. The reaction solution underwent a color change from clear colorless to brown red. The reaction mixture was stirred at ambient temperature overnight, and was quenched by the addition of 10 mL of water and 100 mL diethyl ether. The solution was filtered to remove a brown solid and the filtrate was washed with 1.5 M HCl. The aqueous phase was extracted with ether and ethyl acetate. The combined organic solutions were dried over anhydrous $Na_2SO_4$, evaporated in vacuo. The crude material was purified by column chromatography ($CH_2Cl_2$) to yield 805 mg (33%) of the desired compound as a pale-yellow oil. MS (m/z, ES+): 124 (M+1, 100%).

B. 3,4-Difluoroaniline (75 mg, 0.58 mmole) was mixed in 0.5 mL water and then acidified with conc. HCl (0.15 mL, 1.8 mmole) in an ice bath. To this mixture was slowly added 0.25 mL of an aqueous solution of $NaNO_2$ (52 mg, 0.75 mmole). The diazonium salt was then added to the mixture of 3-oxo-hept-6-enenitrile (86 mg, 0.69 mmole) obtained above and NaOAc trihydrate (238 mg, 1.8 mmole) in 3 mL of a mixture of water and DMF (1:1). The resulting yellow brown precipitate was filtered and then treated with hydrazine hydrate (30 mg, 0.6 mmole) in 4 mL of ethanol at reflux for 3 hours. The solvent was removed in vacuo. The brownish residue was purified by preparative TLC ($CHCl_3$:MeOH=20:1) to yield 74 mg (46%) of the title compound as a brown yellow powder. MS (m/z, ES+): 278 (M+1, 100%); $^1$H NMR (ppm, 200 MHz, DMSO-$d_6$) δ 11.82 (br s, 1H), 7.72 (m, 1H), 7.56 (m, 2H), 6.79 (br s, 2H), 5.90 (m, 1H), 5.20-4.80 (m, 2H), 2.85 (m, 2H), 2.55 (m, 2H).

Example 56

Preparation of 5-but-3-enyl-4-(isoquinolin-5-ylhydrazono)-4H-pyrazol-3-ylamine

A. 5-Aminoisoquinoline (175 mg, 1.2 mmole) was mixed in 1.5 mL of 4 M sulfuric acid in an ice bath. To this mixture was slowly added 0.3 mL of an aqueous solution of $NaNO_2$ (80 mg, 1.16 mmole). The resulting diazonium solution was then added to a mixture of 3-oxohept-6-enenitrile (108 mg, 0.88 mmole) obtained as described in Example 22 and NaOAc trihydrate (1.7 g, 12.5 mmole) dissolved in 3 mL of acetic acid and 1.5 mL of water. The mixture was extracted with ethyl acetate. The extracts were dried over $Na_2SO_4$, filtered, and evaporated in vacuo to give a sticky residue which was then treated with hydrazine hydrate (36 mg, 0.72 mmole) in 10 mL of ethanol at refluxing temperature for 4 hours. The solvent was removed in vacuo and the brownish oil residue obtained was purified by preparative TLC ($CH_2Cl_2$: MeOH=15:1) to yield 55 mg (22%) of the title compound as an orange yellow powder. MS (m/z, ES+): 293 (M+1, 100%), 294 (M+2, 19%); $^1$H NMR (ppm, 200 MHz, DMSO-$d_6$) δ 9.39 (s, 1H), 8.58 (d, 1H), 8.20 (d, 1H), 8.05 (d, 1H), 7.91 (d, 1H), 7.75 (t, 1H), 6.79 (br s, 2H), 5.90 (m, 1H), 5.20-4.80 (m, 2H), 2.93 (t, 2H), 2.49 (m, 2H).

B. In a similar manner, 5-aminotetrazole (0.1 g, 1.1 mmol) and 3-amino-5-tert-butylpyrazole (0.2 g, 1.43 mmol) yielded 21 mg of 5-tert-butyl-4-[(1H-tetrazol-5-yl)hydrazono]-4H-pyrazol-3-ylamine. MS (m/z, ES+): 236.

Example 57

Preparation of 5-aminomethyl-4-(isoquinolin-5-ylhydrazono)-4H-pyrazol-3-ylamine

5-Aminoisoquinoline (175 mg, 1.2 mmole) was mixed in 1.5 mL 4 M sulfuric acid in an ice bath. To this mixture was added slowly a 0.3 mL of aqueous solution of $NaNO_2$ (80 mg, 1.16 mmole). The red diazonium solution was then added to the mixture of 4-(1,3-dioxo-1,3-dihydroisoindol-2-yl)-3-oxobutyronitrile (200 mg, 0.88 mmole) and NaOAc trihydrate (1.7 g, 12.5 mmole) dissolved in a mixture of 3 mL of acetic acid, 1.5 mL of water and 6 mL of DMF. The resulting brown precipitate was isolated by filtration to give 281 mg of 4-(1, 3-dioxo-1,3-dihydroisoindol-2-yl)-2-(isoquinolin-5-ylhydrazono)-3-oxobutyronitrile, in the form of a salt. The solid was then suspended with NaOAc trihydrate (108 mg, 0.8 mmole) in 24 mL of ethanol and heated to reflux. Excess hydrazine hydrate was added to the mixture in 4 portions (4×36 mg, 2.8 mmole) at intervals of one hour. The suspension became a clear red solution. The solvent was removed in vacuo. The residue was purified by column chromatography ($CH_2Cl_2$:MeOH=10:1) to afford a yellow solid. This material was further purified by preparative TLC ($CH_2Cl_2$:MeOH: $NH_3.H_2O$=200:40:2) to yield 18 mg of the title compound as an orange powder. MS (m/z, ES+): 268 (M+1, 90%).

Example 58

Preparation of N-{5-amino-4-[(3-fluorophenyl)hydrazono]-4H-pyrazol-3-ylmethyl}isonicotinamide To a solution of 5-aminomethyl-4-[(3-fluorophenyl)hydrazono]-4H-pyrazol-3-ylamine (60 mg, 0.256 mmole), DMAP (31.2 mg, 0.256 mmole), and isonicotinic anhydride (70.2 mg, 0.31 mmole) in DMF (4 mL) was added triethylamine (51.7 mg, 0.512 mmole). The reaction mixture was stirred at ambient temperature for 30 minutes, and then saline and ethyl acetate were added. The aqueous phase was extracted with ethyl acetate. The organic extracts were dried over $Na_2SO_4$, filtered and concentrated in vacuo. The crude material was purified by preparative TLC to yield 43 mg (50%) of the title compound as a yellow powder. $^1$H NMR (ppm, 300 MHz, DMSO-$d_6$) δ 11.92 (br s, 1H), 9.15 (br s, 1H), 8.67 (m, 2H), 7.76 (m, 2H), 7.30-7.63 (m, 3H), 6.70-7.25 (m, 3H), 4.70 (s, 2H).

Example 59

Preparation of 4-{5-amino-4-[(3-fluorophenyl)hydrazono]-4H-pyrazol-3-yl}benzoic acid A suspension of 3-fluoroaniline (0.364 g, 3.28 mmol) in water (6.5 mL) cooled in an ice/salt bath was acidified with conc. HCl (1 mL, 12 mmol) to give a clear yellow solution. To this solution was added dropwise the cold solution of $NaNO_2$ (0.277 g in 2 mL of $H_2O$) while maintaining the reaction temperature below 5° C. The diazonium solution was stirred at ice bath temperature for approximately 15 minutes before it was added portion-wise to a cold mixture of methyl 4-(2-cyanoacetyl)benzoate (0.756 g, 3.72 mmol) and NaOAc (1.62 g) in water (3 mL) and DMF (6 mL). The resulting yellow suspension was stirred at ambient temperature for 1 hour. The solid was collected by filtration and washed with excess amount of water and dried in vacuo to yield a yellow solid (0.817 mmol, 25%). This yellow solid was refluxed in ethanol (10 mL) and hydrazine hydrate (47 uL, 0.96 mmol) was added. The solution was refluxed for 2 hours at which point the reaction mixture was concentrated in vacuo. The residue was purified by column chromatography ($CHCl_3$:$CH_3CN$: MeOH=20:5:1) to yield a yellow solid (0.297 mmol, 9% overall yield). $^1$H NMR (ppm, 300 MHz, DMSO-$d_6$) δ 12.26 (br s, 1H), 8.23 (d, 1H), 8.02 (d, 1H), 7.40-7.63 (m, 5H), 7.17 (t, 1H), 3.86 (s, 3H). The solid (0.048 g, 0.142 mmol) was refluxed in ethanol (10 mL) containing ground KOH (0.260 g, 85%) for 4 hours and left to stir at ambient temperature overnight. HCl (1.5 M) solution was then added until a pH of 2-4 was achieved. The reaction mixture was concentrated and purified by column chromatography ($CH_2Cl_2$:MeOH=9:1) to yield the title compound as a yellow-brown powder (0.070 mmol, 50% yield). $^1$H NMR (ppm, 300 MHz, DMSO-$d_6$) δ 12.60 (br, 1H), 8.25 (d, 1H), 8.05 (d, 1H), 7.40-7.65 (m, 3H), 7.33 (s, 2H), 7.15 (t, 1H); MS (m/z, ES-): 324 (100%), 325 (20%).

Example 60

Preparation of 5-methyl-4-[(2H-tetrazol-5-yl)hydrazono]-4H-pyrazol-3-ylamine

A. A solution of aminotetrazole (0.1 g, 1.1 mmol) in 4 M sulfuric acid (3.0 mL, 12.0 mmol) was cooled to −5° C. To this mixture was then added a cooled solution of sodium nitrite (0.08 g, 1.1 mmol) in 0.5 mL of water. The solution was then added to a solution of 3-amino-5-methylpyrazole (0.2 g, 2.1 mmol) and NaOAc trihydrate (1.5 g, 11 mmol) dissolved in a mixture of water (1 mL) and HOAc (3 mL). After stirring for 2 hours, water (50 mL) was added and the crude material was extracted from the aqueous layer three times with ethyl acetate (150 mL). The combined ethyl acetate solutions were washed with brine, dried over anhydrous $MgSO_4$, filtered and evaporated. The crude material was purified by column chromatography ($CHCl_3$:MeOH:$NH_4OH$=3:1:0.005). The isolated material was then further purified by preparative TLC ($CHCl_3$:MeOH:$NH_4OH$=3:1:0.005) to yield 7 mg (3%) of the title compound as a red solid.

B. In a similar manner, 5-[N'-(3-amino-5-methylpyrazol-4-ylidene)hydrazino]-2H-[1,2,3]triazole-4-carboxylic acid was prepared.

Example 61

Preparation of 4-(phenylhydrazono)-5-pyridin-2-yl-4H-pyrazol-3-ylamine

A. Ethyl picolinate (10 g, 66.2 mmol) and acetonitrile (4 mL) were premixed and added into a suspension of potassium tert-butoxide (10.6 g, 94.5 mmol) in 200 mL of dry toluene at 80° C. The mixture was stirred at this temperature overnight. The solid precipitate was collected by filtration and dried in vacuo. The product was isolated as its potassium salt (12 g).

B. To a suspension of aniline (2.0 g, 21.5 mmole) in 30 mL of water was added conc. HCl (4.5 mL, 54 mmol) in an ice bath. NaNO$_2$ (0.8 g, 12.6 mmole) dissolved in 2.5 mL of water was added to this mixture slowly. The diazonium solution was then added to the mixture of the potassium salt of 3-oxo-3-pyridin-2-yl-propionitrile (2.0 g, 11.0 mmole) obtained above and NaOAc trihydrate (10.0 g, 73.5 mmole) dissolved in 50 mL of water at 10° C. The precipitate was collected by filtration and then resuspended in 40 mL of ethanol. Hydrazine hydrate (1.0 g) was added slowly to this suspension at 80° C. and the mixture was stirred at this temperature for 2 hours. The title compound was obtained after recrystallization from ethanol (1.0 g). MS (m/z, ES+): 265.3 (M+1, 100%).

Example 62

Preparation of 4-(pyridin-3-ylhydrazono)-5-thiophen-2-yl-4H-pyrazol-3-ylamine

To a suspension of 3-aminopyridine (0.28 g, 2.98 mmole) in water was added conc. HCl (1.0 mL, 12 mmol) in an ice bath. NaNO$_2$ (0.2 g, 3.15 mmole) in water was added to this mixture slowly. The diazonium solution was then added to the mixture of 3-oxo-3-thiophen-2-ylpropionitrile (0.25 g, 1.65 mmol) and NaOAc trihydrate (5.0 g, 36.7 mmole) dissolved in 5 mL of water and 2 mL of DMF at 10° C. The precipitate was collected by filtration and then resuspended in 20 mL of ethanol. Hydrazine hydrate (0.5 g) was added slowly to this suspension at 80° C. and the mixture was stirred at this temperature for 3 hours. The solvent was removed in vacuo. The title compound was obtained after recrystallization from EtOAc/ethanol twice (0.115 g). MS (m/z, ES+): 271.2 (M+1, 100%).

Example 63

Preparation of 5-(1-methyl-1H-pyrrol-2-yl)-4-(phenylhydrazono)-4H-pyrazol-3-ylamine A. 1-Methyl-1H-pyrrole-2-carboxylic acid methyl ester (5 g, 35.9 mmol) and CH$_3$CN (2.5 mL) were premixed and added into a suspension of potassium tert-butoxide (5.3 g, 47.2 mmol) in 150 mL of dry toluene at 90° C. The mixture was stirred at this temperature overnight. The solid precipitate was collected by filtration, washed with EtOAc and redissolved in 20 mL of water. The resulting solution was acidified with 1 N HCl to approximately pH 1 and was then extracted with EtOAc. The product 3-(1-methyl-1H-pyrrol-2-yl)-3-oxopropionitrile was obtained after removal of the solvent (1.9 g).

B. To a suspension of aniline (1.5 g, 16.1 mmol) in 10 mL of water was added conc. HCl (4 mL, 48 mmol) in an ice bath. NaNO$_2$ (1.3 g, 20.5 mmol) dissolved in 5 mL of water was added to this mixture slowly. A portion of this diazonium solution (⅔) was then added to the mixture of 3-(1-methyl-1H-pyrrol-2-yl)-3-oxopropionitrile (1.0 g, 6.75 mmol) obtained above and NaOAc trihydrate (10.0 g, 73.5 mmole) dissolved in a mixture of 15 mL of water, 10 mL of DMF and 5 mL of acetic acid at 10° C. The precipitate was collected by filtration and dried. It was resuspended in 50 mL of ethanol. Hydrazine hydrate (1.0 g) was added slowly to this suspension at 80° C. and the mixture was stirred at this temperature for 1.5 hours. The solvent was removed and the residue was purified by column chromatography (CH$_2$Cl$_2$:MeOH=20:1). The title compound was obtained after recrystallization from Et$_2$O:hexane (0.5 g). $^1$H NMR (ppm, 300 MHz, CDCl$_3$) δ 12.00 (br s, 1H), 7.69 (d, 2H), 7.40 (t, 2H), 7.30 (t, 1H), 6.86 (t, 1H), 6.63 (dd, 1H), 6.29 (dd, 1H), 5.53 (s, 2H), 3.79 (s, 3H); FTIR (KBr disk, cm$^{-1}$): 3367 (s), 1615 (s), 1508 (s), 1475 (s), 1451 (s), 1394 (s), 1342 (s), 1312 (s), 1291 (s), 1220 (m), 1197 (m), 1164 (m), 1087 (m), 1072 (m), 1017 (m), 956 (m), 802 (w), 773 (m), 729 (s), 690 (m), 608 (w), 574 (w); MS (m/z, ES+): 267.2 (M+1, 70); Anal. Calcd for C$_{14}$H$_{14}$N$_6$: C, 63.14; H, 5.30; N, 31.56. Found C, 63.12; H, 5.31; N, 31.42.

C. In a similar manner, 5-(1-methyl-1H-pyrrol-2-yl)-4-(pyridin-3-ylhydrazono)-4H-pyrazol-3-ylamine was prepared from 3-aminopyridine (0.25 g, 2.66 mmol) to yield 0.21 g of the product. MS (m/z, ES+): 268.2 (M+1, 100%).

D. In a similar manner, 5-(1-methyl-1H-pyrrol-2-yl)-4-(quinolin-6-ylhydrazono)-4H-pyrazol-3-ylamine was prepared from 6-aminoquinoline (0.25 g, 1.73 mmol) to yield 85 mg of the product. MS (m/z, ES+): 318.3 (M+1, 100%).

Example 64

Preparation of 5-(2-morpholin-4-ylethyl)-4-(phenylhydrazono)-4H-pyrazol-3-ylamine A. A mixture of ethyl 5-bromovalerate (8 g, 38.3 mmole), morpholine (3.67 g, 42 mmole) and triethylamine (4.2 g, 42 mmole) in ethanol (100 mL) was heated to reflux overnight. The solution was concentrated to afford a gummy white solid which was mixed with diethyl ether and filtered to remove the solid. The filtrate was washed with saline (3×50 mL), dried over Na2SO4, filtered and concentrated in vacuo to afford 7.1 g (87%) of ethyl 5-morpholin-4-ylpentanoate as a pale brown liquid. MS (m/z, ES+): 217 (M+2, 100%), 216 (M+1, 57%).

B. To a suspension of sodium hydride (2 g 60% in oil, 49.7 mmole) in dry toluene (58 mL) at 76° C. was added dropwise neat acetonitrile (2.6 mL, 49.7 mmole). Subsequently, a solution of ethyl 5-morpholin-4-ylpentanoate (7.13 g, 33.2 mmole) in dry toluene (24 mL) was added dropwise over 30 minutes. The reaction mixture was stirred at 76° C. overnight. The solution was then cooled to ambient temperature, the resulting solid was isolated by filtration and washed with toluene and diethyl ether to afford 5.8 g (75%) of the product, 5-morpholin-4-yl-3-oxo-2-(phenylhydrazono)pentanenitrile, as a pale-brown powder. MS (m/z, ES+): 211 (M+1, 100%).

C. To a suspension of 5-morpholin-4-yl-3-oxo-2-(phenylhydrazono)pentanenitrile (1.2 mmole) in 15 mL of diethyl ether was slowly added a solution of hydrazine hydrate (2.4 mmol) in 2 of THF which resulted in a clear red solution. After 2 hours, another portion of hydrazine (2.4 mmol) was added at which point some yellow precipitate was observed. The reaction was stirred at ambient temperature overnight. The solid was collected by filtration, purified by recrystalization from ethanol and dried in vacuo to yield 150 mg (41%) of the title compound. MS (m/z, ES+): 301 (M+1, 100%). $^1$H NMR (ppm, 300 MHz, DMSO-d$_6$) δ 11.63 (br s, 1H), 7.67 (m, 2H), 7.44 (m, 2H), 7.29 (m, 1H), 6.97 (br s, 2H), 3.55 (m, 4H), 2.93 (m, 2H), 2.66 (m, 2H), 2.43 (m, 4H).

Example 65

Preparation of 5-(3-Aminopropyl)-4-[(3-fluorophenyl)hydrazono]-4H-pyrazol-3-ylamine A. To a mixture of phthalic anhydride (14.8 g, 100 mmole) and 4-aminobutyric acid (10.3 g, 100 mmole) in 150 mL of dry toluene was added triethylamine (1.3 mL, 9.3 mmole). The reaction mixture was heated to reflux in a flask equipped with a Dean Stark trap and condensor. After refluxing for 2.5 hours, the reaction solution was cooled in an ice bath which resulted in the formation of a white precipitate. The solid was isolated by filtration and washed with 5% HCl (3×80 mL) followed by cold water (2×70 mL). 4-Phthalimidobutyric acid was obtained as a white powder (16.8 g, 72%). m.p.: 118-118.6° C.

B. To a suspension of 4-phthalimidobutyric acid (16.5 g, 71 mmole) and oxalyl chloride (9.3 g, 73.4 mmole) in 118 mL of dry toluene was slowly added a solution of DMF (0.23 mL) in 29 mL of toluene. The evolution of gas was observed. The mixture was stirred at ambient temperature for 2 to 3 hours which resulted in a clear pale yellow solution. The solution of 4-phthalimidobutyric chloride was used in the following reaction without further purification.

C. To a suspension of sodium hydride (3.0 g, 60% in oil, 75 mmole) in dry toluene (126 mL) at 15° C. was slowly added t-butyl cyanoacetate (14.1 g, 100 mmole). The generation of hydrogen gas was observed. The reaction was stirred for 1 hour at which point the solution of 4-phthalimidobutyric chloride was introduced over a period of 15 min. The reaction mixture was then stirred at ambient temperature overnight. The reaction was worked up by the addition of water and 1.5 M HCl. The aqueous layer was extracted with diethyl ether (2×200 mL) and the organic extracts were washed with saline and dried over anhydrous Na$_2$SO$_4$, filtered and concentrated in vacuo to afford an oil. The oil was then dissolved in dry toluene (200 mL) and toluenesulfonic acid (500 mg, 2.6 mmole) was added. The solution was then heated to reflux. A brown residue was noted to have oiled out of solution. After approximately 2 hours, the hot solution was decanted from the reaction flask to separate it from the dark oil by-product. The solution was allowed to cool to ambient temperature, at which point more by-product had oiled out of solution. The decantation step was repeated. The resulting clear solution was concentrated in vacuo to afford an oil. This oil was subjected to column chromatography (CH$_2$Cl$_2$:MeOH=100:1) to provide a material enriched in the desired product, i.e., 6-phthalimido-3-oxo-hexanenitrile. This material was then mixed with hexanes to yield 5.73 g (31%) of a white powder. MS (m/z, ES+): 257 (M+1, 10%), 216 (M+1-CH$_3$CN, 20%).

D. To an orange red solution of 6-phthalimido-3-oxohexanenitrile (512 mg, 2 mmole) and NaOAc trihydrate (1.2 g, 9 mmole) in 16 mL of water:DMF (1:2) was added the pale brown solution of 3-fluoroaniline diazonium salt, made from a reaction of 3-fluoroaniline (3 mmole, 333 mg) with 0.75 mL of conc. HCl and NaNO$_2$ (3.6 mmole, 248 mg) in water at −5° C. A yellow orange powder was instantly formed. The solid was isolated by filtration and dryed to give 702 mg (93%) of a yellow powder. MS (m/z, ES+): 379 (M+1, 100%). The resulting yellow powder was then treated with hydrazine hydrate (3.4 mmole) in ethanol (15 mL). The suspension was heated to 82° C. for 1 hour. The mixture became a clear orange solution and then a yellow precipitate was observed. The title compound was isolated by filtration in a yield of (449 mg, 85%) as a yellow powder. MS (m/z, ES+): 263 (M+1, 50%), 123 (100%).

E. In a similar manner, 5-(3-aminopropyl)-4-(phenylhydrazono)-4H-pyrazol-3-ylamine was prepared using aniline. The crude material was purified by column chromatography to yield 140 mg (29%) of the title compound. MS (m/z, ES+): 245 (M+1, 33%), 105 (100%); $^1$H NMR (ppm, 300 MHz, DMSO-d$_6$) δ 7.66 (m, 2H), 7.44 (m, 2H), 7.29 (m, 1H), 6.54 (br s, NH2), 2.81 (t, 2H), 2.59 (t, 2H), 1.76 (m, 2H).

Example 66

Preparation of 4-[(3-fluorophenyl)hydrazono]-5-(3-morpholin-4-yl-propyl)-4H-pyrazol-3-ylamine A suspension of 5-(3-aminopropyl)-4-[(3-fluorophenyl)hydrazono]-4H-pyrazol-3-ylamine, obtained in Example 32, (400 mg, 1.53 mmole) and triethylamine (6 mmole) in 10 mL of DMF was heated to 96° C. To this solution was slowly added a solution of ethylene glycol ditosylate (3 mmole) in 10 mL DMF. The reaction was worked up by the addition of saline and ethyl acetate. The organic phase was separated, dried over anhydrous Na$_2$SO$_4$, filtered and concentrated in vacuo. The crude material was purified by column chromatography and further by preparative TLC. The resulting 34 mg of oil was dissolved in a minimum amount of diethyl ether and then mixed with hexanes to yield 22 mg of the title compound as a yellow powder. MS (m/z, ES+): 333 (M+1, 100%).

Example 67

Preparation of 5-(4-methoxybenzyl)-4-(pyridin-3-ylhydrazono)-4H-pyrazol-3-ylamine A. 3-Aminopyridine (18 g, 0.195 mol) in 221 mL of water was cooled in an ice bath with and acidified with conc. HCl (98 mL, 1.2 mol). The solution was then treated with NaNO$_2$ (16.2 g, 0.234 mole) dissolved in 60 mL of water at −5° C. The resulting diazonium solution was then added to a solution of sodium acetate (1.17 mole) and 4-(4-methoxyphenyl)-3-oxobutyronitrile (~0.19 mole) dissolved in 800 mL of water. The yellow precipitate was isolated by filtration and dried in vacuo to afford a pale brown powder (24 g, 52%).

B. The powder prepared above was suspended in 350 mL of ethanol and heated to 82° C. Hydrazine hydrate (0.12 mole) was then added slowly. After 2 hours, the reaction solution was concentrated in vacuo and the resulting oil was subjected to column chromatography (CH$_2$Cl$_2$:MeOH=20 to 15:1). The resulting oil was dissolved in ~30 mL of i-PrOH and mixed with 90 mL of water. After cooled in ice, a yellow powder precipitated from solution. The solution was filtered and the resulting solid was dried to yield 22 g (80%) of the title compound. MS (m/z, ES+): 243 (M+1, 100%). $^1$H NMR (ppm, 300 MHz, DMSO-d$_6$) δ 11.68 (br s, 1H), 8.89 (s, 1H), 8.45 (m, 1H), 7.95 (m, 1H), 7.44 (m, 1H), 7.16 (brs, 2H), 5.87 (m, 1H), 5.06 (dd, 1H), 4.95 (d, 1H), 2.82 (m, 2H), 2.45 (m, 2H, overlapped with DMSO).

Example 68

Preparation of 5-(4-morpholin-4-ylbutyl)-4-(phenylhydrazono)-4H-pyrazol-3-ylamine A. The mixture of ethyl 5-bromovalerate (8 g, 38 mmole), morpholine (3.7 g, 42 mmole) and triethylamine (4.2 g, 42 mmole) in 100 mL of ethanol was refluxed overnight. The reaction solution was concentrated, mixed with diethyl ether, and then filtrated to remove the salt, $Et_3NHBr$. The filtrate was washed with saline, dried over anhydrous $Na_2SO_4$, filtered and concentrated in vacuo to afford 7.1 g (86%) of a colourless oil.

B. To a solution of sodium hydride (2 g, 60% in oil, 49.7 mmol) in dry toluene (60 mL) at 76° C. was added acetonitrile (2 g, 49.7 mmol). A solution of ethyl 5-(N-morpholino)valerate in 20 mL of toluene was then added dropwise. The mixture was stirred at 76° C. overnight. The solution was filtered to afford 5.8 g (75%) of the product, 7-morpholin-4-yl-3-oxoheptanenitrile, as a white powder.

C. Aniline (419 mg, 4.5 mmole) in 5 mL of water was cooled in an ice bath and acidified with conc. HCl (1.1 mL, 13.2 mmol). This mixture was then treated with a solution of $NaNO_2$ (373 mg, 5.4 mmole) in 1.3 mL water at −5° C. The diazonium salt solution was added a solution of NaOAc trihydrate (1.8 g, 13.5 mmole) and 7-morpholin-4-yl-3-oxoheptanenitrile (3 mmole) dissolved in 15 mL of water. The resulting yellow precipitate was isolated by filtration and dried in vacuo to yield 548 mg (58%) of the product, 7-morpholin-4-yl-3-oxo-2-(phenylhydrazono)-heptanenitrile, as a pale yellow powder.

D. The powder of 7-morpholin-4-yl-3-oxo-2-(phenylhydrazono)-heptanenitrile (510 mg, 1.6 mmole) and hydrazine hydrate (3.2 mmole) were suspended in 20 mL of ether:THF (1:1) and stirred at ambient temperature overnight. Water was added to the reaction and the mixture was extracted with ethyl acetate. The organic extracts were washed with saline. The volume of the organic solution was reduced which resulted in the precipitation of a yellow solid. The solution was filtered to yield 270 mg (51%) of the title compound as a yellow powder. MS (m/z, ES+): 329 (M+1, 100%); $^1$H NMR (ppm, 300 MHz, DMSO-$d_6$) δ 11.58 (br s, 1H), 7.66 (m, 2H), 7.44 (m, 2H), 7.30 (m, 1H), 6.98 (br s, 2H), 3.51 (m, 4H), 2.79 (m, 2H), 2.20-2.33 (m, 5H), 1.72 (m, 2H), 1.47 (m, 2H).

Example 69

The compounds in this Example were prepared according to the following procedure: Sodium hydride (320 mg, 60% in mineral oil, 8 mmol) was suspended in DMF (8 mL). The mixture was cooled to 0° C. and t-butyl cyanoacetate (572 mL, 4 mmol) in DMF (1 mL) was added dropwise by syringe. The reaction mixture was stirred at 0° C. for 30 min. and was then cooled to −10° C. with an acetone-ice bath. The acid chloride (4 mmol) in DMF (2 mL) was added dropwise by syringe. After the addition was complete (~1 hour), the mixture was added into cold water (10 mL) and acidified with dilute HCl (2 N) to pH 2. The precipitate was collected by filtration and washed with water (2×4 mL) followed by hexane (2×4 mL). The product was either air-dried or dissolved in dichloromethane, dried over anhydrous $MgSO_4$, filtered, and concentrated in vacuo to give the product as a moisture free solid.

The cyanoketone precursor obtained above was dissolved in toluene (10 mL) followed by the addition of p-toluenesulfonic acid (10%, 76 mg). The reaction mixture was stirred at reflux temperature and the progress of the reaction was monitored by TLC. After the reaction was complete (~4 hours), the solution was allowed to cool and the solvent was evaporated. The solid obtained in this step was used for the next reaction.

A solution of aniline (91 μL, 1 mmol) in 1 mL of water was cooled in an ice bath to 0° C. and was acidified with conc. HCl (300 μL, 3.6 mmol). To the reaction mixture was added a solution of $NaNO_2$ (90 mg, 1.3 mmol) in 0.5 mL of water. This mixture was then added to a cooled solution of the above prepared cyanoketone (1 mmol) and NaOAc trihydrate (340 mg, 2.5 mmol) dissolved in 4 mL of a water DMF mixture (3:1). After stirring for 2 hours, the resulting solid was collected by filtration, washed with water, and air dried. This material was used in the following step without further purification.

The solid prepared above (~1 mmol) was dissolved in ethanol (5 mL) and the solution was heated to 65° C. A solution of hydrazine hydrate (50 mg, 1 mmol) in ethanol (2 mL) was then added slowly. The reaction was refluxed for 2 hours at which point most of the starting material had been converted to a polar yellow spot as indicated by TLC analysis. The solvent was evaporated in vacuo and the resulting crude material was purified by column chromatography ($CH_2Cl_2$: $CH_3OH$=20:1) to yield the desired product as a yellow powder.

1. 5-(2-fluorophenyl)-4-(phenylhydrazono)-4H-pyrazol-3-ylamine was prepared from 2-fluorobenzoyl chloride (4 mmol). The product was purified by precipitation from isopropanol by the addition of water to yield 17 mg (5%) of the compound. $^1$H NMR (ppm, 500 MHz, $CDCl_3$) δ 8.52 (t, 1H), 7.77 (d, 2H), 7.48 (t, 2H), 7.40-7.46 (m, 1H), 7.39 (q, 1H), 7.33 (t, 1H), 7.23 (dd, 1H), 5.6 (br s, 2H); MS (m/z, ES+): 282.2 (M+1, 100%).

2. 5-ethyl-4-(phenylhydrazono)-4H-pyrazol-3-ylamine was prepared from propionyl chloride with the exception that the decarboxylation step was achieved by treatment with TFA (500 μL) at ambient temperature for 2 hours. The product was purified by precipitation from isopropanol by the addition of water to yield 47 mg (18%) of the compound. $^1$H NMR (ppm, 500 MHz, $CDCl_3$) δ 9.5 (br s, 1H), 7.73 (d, 2H), 7.44 (t, 2H), 7.34 (t, 1H), 5.47 (br s, 2H), 3.02 (q, 2H), 1.40 (t, 3H); MS (m/z, ES+): 216.2 (M+1, 100%).

3. 5-(3,4-dimethoxyphenyl)-4-(phenylhydrazono)-4H-pyrazol-3-ylamine was prepared from 3,4-dimethoxybenzoyl chloride. The product was isolated without further purification to yield 32 mg (6%) of the compound. $^1$H NMR (ppm, 500 MHz, $CDCl_3$) δ 7.75 (d, 2H), 7.68 (d, 1H), 7.51 (dd, 1H), 7.45 (t, 2H), 7.36 (t, 1H), 6.97 (d, 1H), 5.6 (br s, 2H), 3.95 (s, 3H), 3.95 (s, 3H); MS (m/z, ES−): 322.3 (M−1, 100%).

4. 5-(2-chloro-6-methylpyridin-4-yl)-4-(phenylhydrazono)-4H-pyrazol-3-ylamine was prepared from 2-chloro-6-methylisonicotinoyl chloride with the exception that the decarboxylation step was achieved by treatment with p-toluenesulfonic acid and TFA (20 μL) at 80° C. for 2 hours. The product was isolated without further purification to yield 49 mg (15%) of the compound. $^1$H NMR (ppm, 500 MHz, $CDCl_3$) δ 7.94 (s, 1H), 7.84 (s, 1H), 7.75 (d, 2H), 7.51 (t, 2H), 7.40 (t, 1H), 6.01 (br s, 2H), 2.62 (s, 3H); MS (m/z, ES+): 313.3 ($Cl^{35}$M+1, 100%), 315 ($Cl^{37}$M+1, 60%).

5. 5-(3,5-dimethylisoxazol-4-yl)-4-(phenylhydrazono)-4H-pyrazol-3-ylamine was prepared from 3,5-dimethylisoxazole-4-carbonyl chloride. The product was isolated without further purification to yield 44 mg (23%) of the compound. $^1$H NMR (ppm, 500 MHz, $CDCl_3$) δ 7.69 (d, 2H), 7.44 (t, 2H), 7.36 (t, 1H), 5.76 (br s, 2H), 2.52 (s, 3H), 2.37 (s, 3H); MS (m/z, ES+): 283.4 (M+1, 100%).

6. 5-(4-chlorophenoxymethyl)-4-(phenylhydrazono)-4H-pyrazol-3-ylamine was prepared from (4-chlorophenoxy)acetyl chloride. The crude material was purified by column chromatography ($CH_2Cl_2$:$CH_3OH$=20:1) to yield 23 mg (2%) of the compound. MS (m/z, ES+): 328.2 (Cl$^{35}$M+1, 100%), 330.2 (Cl$^{37}$M+1, 60%), 200.2 (M–117, 80%).

7. 5-(4-chloro-3-nitrophenyl)-4-(phenylhydrazono)-4H-pyrazol-3-ylamine was prepared from 4-chloro-3-nitrobenzoyl chloride. The crude material was purified by column chromatography (CH2Cl2:CH3OH=20:1) to yield 73 mg (5%) of the compound. MS (m/z, ES+): 343.1 (M+1, 100%).

8. 5-(4-chlorobenzyl)-4-(phenylhydrazono)-4H-pyrazol-3-ylamine was prepared from (4-chlorophenyl)acetyl chloride. The crude material was purified by column chromatography (CH$_2$Cl$_2$:CH$_3$OH=20:1) to yield 48 mg (4%) of the compound. MS (m/z, ES+): 312.2 (Cl$^{35}$M+1, 100%), 314.2 (Cl$^{37}$M+1, 70%).

9. 5-benzhydryl-4-(phenylhydrazono)-4H-pyrazol-3-ylamine was prepared from diphenylacetyl chloride. The crude material was purified by column chromatography (CH$_2$Cl$_2$:CH$_3$OH=20:1) to yield 79 mg (6%) of the compound. MS (m/z, ES+): 354.3 (M+1, 100%).

10. 5-(5-bromopyridin-3-yl)-4-(phenylhydrazono)-4H-pyrazol-3-ylamine was prepared from 5-bromonicotinoyl chloride. The crude material was purified by column chromatography (CH$_2$Cl$_2$:CH$_3$OH=20:1) to yield 10 mg (1%) of the compound. MS (m/z, ES+): 342.9 (Br$^{79}$M+1, 100%), 344.9 (Br$^{81}$M+1, 100%).

11. 5-cyclopropyl-4-(phenylhydrazono)-4H-pyrazol-3-ylamine was prepared from cyclopropanecarbonyl chloride. The crude material was purified by column chromatography (CH$_2$Cl$_2$:CH$_3$OH=20:1) to yield 26 mg (3%) of the compound. MS (m/z, ES+): 228.3 (M+1, 100%).

12. 5-benzo[1,2,5]oxadiazol-5-yl-4-(phenylhydrazono)-4H-pyrazol-3-ylamine was prepared from benzo[1,2,5]oxadiazole-5-carbonyl chloride. The crude material was purified by column chromatography (CH$_2$Cl$_2$:CH$_3$OH=20:1) to yield 29 mg (3%) of the compound. MS (m/z, ES+): 306.4 (M+1, 100%).

13. 5-(4-nitrophenyl)-4-(phenylhydrazono)-4H-pyrazol-3-ylamine was prepared from 4-nitrobenzoyl chloride. The crude material was purified by column chromatography (CH$_2$Cl$_2$:CH$_3$OH=20:1) to yield 8 mg (1%) of the compound. MS (m/z, ES+): 309.3 (M+1, 100%).

14. 5-(2-chloropyridin-4-yl)-4-(phenylhydrazono)-4H-pyrazol-3-ylamine was prepared from 2-chloroisonicotinoyl chloride. The crude material was purified by column chromatography (CH$_2$Cl$_2$:CH$_3$OH=20:1) to yield 36 mg (3%) of the compound. MS (m/z, ES+): 299.3 (Cl$^{35}$M+1, 100%), 301.3 (Cl$^{37}$M+1, 50%).

15. 5-(3-nitrophenyl)-4-(phenylhydrazono)-4H-pyrazol-3-ylamine was prepared from 3-nitrobenzoyl chloride. The crude material was purified by column chromatography (CH$_2$Cl$_2$:CH$_3$OH=20:1) to yield 27 mg (2%) of the compound. MS (m/z, ES+): 309.3 (M+1, 100%).

16. 5-benzo[1,3]dioxol-5-yl-4-(phenylhydrazono)-4H-pyrazol-3-ylamine was prepared from benzo[1,3]dioxole-5-carbonyl chloride. The crude material was purified by column chromatography (CH$_2$Cl$_2$:CH$_3$OH=20:1) to yield 158 mg (13%) of the compound. MS (m/z, ES+): 308.3 (M+1, 100%).

17. 5-(3-bromophenyl)-4-(phenylhydrazono)-4H-pyrazol-3-ylamine was prepared from 3-bromobenzoyl chloride. The crude material was purified by column chromatography (CH$_2$Cl$_2$:CH$_3$OH=20:1) to yield 28 mg (2%) of the compound. MS (m/z, ES+): 342.1 (Br$^{79}$M+1, 100%), 344.1 (Br81M+1, 60%).

18. 5-(3-fluorophenyl)-4-(phenylhydrazono)-4H-pyrazol-3-ylamine was prepared from 3-fluorobenzoyl chloride. The crude material was purified by column chromatography (CH$_2$Cl$_2$:CH$_3$OH=20:1) to yield 32 mg (3%) of the compound. MS (m/z, ES+): 282.2 (M+1, 100%).

19. 5-(4-fluoro-3-methylphenyl)-4-(phenylhydrazono)-4H-pyrazol-3-ylamine was prepared from 4-fluoro-3-methylbenzoyl chloride. The crude material was purified by column chromatography (CH$_2$Cl$_2$:CH$_3$OH=20:1) to yield 23 mg (2%) of the compound. MS (m/z, ES+): 296.3 (M+1, 100%).

20. 5-(4-fluorophenyl)-4-(phenylhydrazono)-4H-pyrazol-3-ylamine was prepared from 4-fluorobenzoyl chloride. The crude material was purified by column chromatography (CH$_2$Cl$_2$:CH$_3$OH=20:1) to yield 27 mg (3%) of the compound. MS (m/z, ES+): 282.3 (M+1, 100%).

21. 5-(2,5-dimethoxybenzyl)-4-(phenylhydrazono)-4H-pyrazol-3-ylamine was prepared from (2,5-dimethoxyphenyl)acetyl chloride. The crude material was purified by column chromatography (CH$_2$Cl$_2$:CH$_3$OH=20:1) to yield 34 mg (3%) of the compound. MS (m/z, ES+): 338.4 (M+1, 100%).

22. 5-(1-ethylpropyl)-4-(phenylhydrazono)-4H-pyrazol-3-ylamine was prepared from 2-ethylbutyryl chloride. The crude material was purified by column chromatography (CH$_2$Cl$_2$:CH$_3$OH=20:1) to yield 32 mg (3%) of the compound. MS (m/z, ES+): 258.5 (M+1, 100%).

23. 5-isobutyl-4-(phenylhydrazono)-4H-pyrazol-3-ylamine was prepared from 3-methylbutyryl chloride. The crude material was purified by column chromatography (CH$_2$Cl$_2$:CH$_3$OH=20:1) to yield 66 mg (7%) of the compound. MS (m/z, ES+): 244.4 (M+1, 100%).

24. 5-(3,4-difluorophenyl)-4-(phenylhydrazono)-4H-pyrazol-3-ylamine was prepared from 3,4-difluorobenzoyl chloride. The crude material was purified by column chromatography (CH$_2$Cl$_2$:CH$_3$OH=20:1) to yield 18 mg (2%) of the compound. MS (m/z, ES+): 300.3 (M+1, 100%).

25. 2',5'-dimethyl-4-(phenylhydrazono)-4H,2'H-[3,3']bipyrazolyl-5-ylamine was prepared from 2,5-dimethyl-2H-pyrazole-3-carbonyl chloride. The crude material was purified by column chromatography (CH$_2$Cl$_2$:CH$_3$OH=20:1) to yield 17 mg (2%) of the compound. MS (m/z, ES+): 282.3 (M+1, 100%).

26. 5-(4-methyl-3-nitrophenyl)-4-(phenylhydrazono)-4H-pyrazol-3-ylamine was prepared from 4-methyl-3-nitrobenzoyl chloride. The crude material was purified by column chromatography (CH$_2$Cl$_2$:CH$_3$OH=20:1) to yield 38 mg (3%) of the compound. MS (m/z, ES+): 323.2 (M+1, 100%).

27. 4-(phenylhydrazono)-5-quinoxalin-2-yl-4H-pyrazol-3-ylamine was prepared from quinoxaline-2-carbonyl chloride. The crude material was purified by column chromatography (CH$_2$Cl$_2$:CH$_3$OH=20:1) to yield 7 mg (1%) of the compound. MS (m/z, ES+): 316.2 (M+1, 100%).

28. 5-(2-methylsulfanylpyridin-3-yl)-4-(phenylhydrazono)-4H-pyrazol-3-ylamine was prepared from 2-methylsulfanyinicotinoyl chloride. The crude material was purified by column chromatography (CH$_2$Cl$_2$:CH$_3$OH=20:1) to yield 14 mg (1%) of the compound. MS (m/z, ES+): 311.4 (M+1, 100%), 264.2 (M-46, 60%).

29. 5-(4-methyl-[1,2,3]thiadiazol-5-yl)-4-(phenylhydrazono)-4H-pyrazol-3-ylamine was prepared from 4-methyl-[1,2,3]thiadiazole-5-carbonyl chloride. The crude material was purified by column chromatography (CH$_2$Cl$_2$:CH$_3$OH=20:1) to yield 9 mg (1%) of the compound. MS (m/z, ES+): 286.2 (M+1, 100%).

30. 4-(phenylhydrazono)-5-(3,4,5-trimethoxyphenyl)-4H-pyrazol-3-ylamine was prepared from 3,4,5-trimethoxybenzoyl chloride. The crude material was purified by column chromatography (CH$_2$Cl$_2$:CH$_3$OH=20:1) to yield 12 mg (1%) of the compound. MS (m/z, ES+): 354.3 (M+1, 100%).

31. 4-(phenylhydrazono)-5-(4-trifluoromethylsulfanylphenyl)-4H-pyrazol-3-ylamine was prepared from 4-trifluoromethylsulfanylbenzoyl chloride. The crude material was purified by column chromatography (CH$_2$Cl$_2$:

CH$_3$OH=20:1) to yield 29 mg (2%) of the compound. MS (m/z, ES+): 364.3 (M+1, 100%).

32. 5-(3,5-difluorophenyl)-4-(phenylhydrazono)-4H-pyrazol-3-ylamine was prepared from 3,5-difluorobenzoyl chloride. The crude material was purified by column chromatography (CH$_2$Cl$_2$:CH$_3$OH=20:1) to yield 36 mg (3%) of the compound. MS (m/z, ES+): 300.4 (M+1, 100%).

33. 5-(6-chloropyridin-3-yl)-4-(phenylhydrazono)-4H-pyrazol-3-ylamine was prepared from 6-chloronicotinoyl chloride. The crude material was purified by column chromatography (CH$_2$Cl$_2$:CH$_3$OH=20:1) to yield 23 mg (2%) of the compound. MS (m/z, ES+): 299.4 (Cl$^{35}$M+1, 100%), 301.0 (Cl$^{37}$M+1, 70%).

34. 5-(3-phenoxypropyl)-4-(phenylhydrazono)-4H-pyrazol-3-ylamine was prepared from 4-phenoxybutyryl chloride. The crude material was purified by column chromatography (CH$_2$Cl$_2$:CH$_3$OH=20:1) to yield 38 mg (3%) of the compound. MS (m/z, ES+): 322.3 (M+1, 100%).

35. 5-(2,2-dimethylpropyl)-4-(phenylhydrazono)-4H-pyrazol-3-ylamine was prepared from 3,3-dimethylbutyryl chloride. The crude material was purified by column chromatography (CH$_2$Cl$_2$:CH$_3$OH=20:1) to yield 4 mg (0.5%) of the compound. MS (m/z, ES+): 258.2 (M+1, 100%).

36. 5-(2-phenylcyclopropyl)-4-(phenylhydrazono)-4H-pyrazol-3-ylamine was prepared from trans-2-phenylcyclopropanecarbonyl chloride. The crude material was purified by column chromatography (CH$_2$Cl$_2$:CH$_3$OH=20:1) to yield 8 mg (0.5%) of the compound. MS (Mm/z): 304.6 (M+1, 100%).

37. 5-(2-methylsulfanylethyl)-4-(phenylhydrazono)-4H-pyrazol-3-ylamine was prepared from 3-methylsulfanylpropionyl chloride. The crude material was purified by column chromatography (CH$_2$Cl$_2$:CH$_3$OH=20:1) to yield 35 mg (3%) of the compound. MS (m/z, ES+): 262.2 (M+1, 100%).

38. 5-(3,4-dimethoxybenzyl)-4-(phenylhydrazono)-4H-pyrazol-3-ylamine was prepared from (3,4-dimethoxyphenyl)acetyl chloride. The crude material was purified by column chromatography (CH$_2$Cl$_2$:CH$_3$OH=20:1) to yield 19 mg (1%) of the compound. MS (m/z, ES+): 338.4 (M+1, 100%).

39. 5-benzo[b]thiophen-2-yl-4-(phenylhydrazono)-4H-pyrazol-3-ylamine was prepared from benzo[b]thiophene-2-carbonyl chloride. The crude material was purified by column chromatography (CH$_2$Cl$_2$:CH$_3$OH=20:1) to yield 14 mg (1%) of the compound. MS (m/z, ES+): 320.2 (M+1, 100%).

40. 5-(3-fluoro-4-methylphenyl)-4-(phenylhydrazono)-4H-pyrazol-3-ylamine was prepared from 3-fluoro-4-methylbenzoyl chloride. The crude material was purified by column chromatography (CH$_2$Cl$_2$:CH$_3$OH=20:1) to yield 24 mg (2%) of the compound. MS (m/z, ES+): 296.3 (M+1, 100%).

41. 5-(2-nitrophenoxymethyl)-4-(phenylhydrazono)-4H-pyrazol-3-ylamine was prepared from (2-nitrophenoxy)acetyl chloride. The crude material was purified by column chromatography (CH$_2$Cl$_2$:CH$_3$OH=20:1) to yield 20 mg (1%) of the compound. MS (m/z, ES+): 339.3 (M+1, 80%), 200.2 (M−138, 100%).

42. 5-(5-methyl-3-phenylisoxazol-4-yl)-4-(phenylhydrazono)-4H-pyrazol-3-ylamine was prepared from 5-methyl-3-phenylisoxazole-4-carbonyl chloride. The crude material was purified by column chromatography (CH$_2$Cl$_2$:CH$_3$OH=20:1) to yield 16 mg (1%) of the compound. MS (m/z, ES+): 345.2 (M+1, 100%).

43. 4-(phenylhydrazono)-5-(2-trifluoromethoxyphenyl)-4H-pyrazol-3-ylamine was prepared from 2-trifluoromethoxybenzoyl chloride. The crude material was purified by column chromatography (CH$_2$Cl$_2$:CH$_3$OH=20:1) to yield 41 mg (3%) of the compound. MS (m/z, ES+): 348.3 (M+1, 90%), 349.3 (M+2, 100%).

44. 4-(phenylhydrazono)-5-(4-trifluoromethylphenyl)-4H-pyrazol-3-ylamine was prepared from 4-trifluoromethylbenzoyl chloride. The crude material was purified by column chromatography (CH$_2$Cl$_2$:CH$_3$OH=20:1) to yield 23 mg (2%) of the compound. MS (m/z, ES+): 332.4 (M+1, 100%).

45. 5-(3,4-dimethylphenyl)-4-(phenylhydrazono)-4H-pyrazol-3-ylamine was prepared from 3,4-dimethylbenzoyl chloride. The crude material was purified by column chromatography (CH$_2$Cl$_2$:CH$_3$OH=20:1) to yield 23 mg (2%) of the compound. MS (m/z, ES+): 292.3 (M+1, 100%), 293.4 (M+2, 100%).

46. 5-phenethyl-4-(phenylhydrazono)-4H-pyrazol-3-ylamine was prepared from 3-phenylpropionyl chloride. The crude material was purified by column chromatography (CH$_2$Cl$_2$:CH$_3$OH=20:1) to yield 23 mg (2%) of the compound. MS (m/z, ES+): 292.2 (M+1, 100%).

47. 1'-phenyl-4-(phenylhydrazono)-5'-propyl-4H, 1'H-[3,4']bipyrazolyl-5-ylamine was prepared from 1-phenyl-5-propyl-1H-pyrazole-4-carbonyl chloride. The crude material was purified by column chromatography (CH$_2$Cl$_2$:CH$_3$OH=20:1) to yield 28 mg (2%) of the compound. MS (m/z, ES+): 372.3 (M+1, 100%).

48. 5-isopropyl-4-(phenylhydrazono)-4H-pyrazol-3-ylamine was prepared from isobutyryl chloride. The crude material was purified by column chromatography (CH$_2$Cl$_2$:CH$_3$OH=20:1) to yield 22 mg (2%) of the compound. MS (m/z, ES+): 230.3 (M+1, 100%).

49. N-{4-[5-amino-4-(phenylhydrazono)-4H-pyrazol-3-yl]phenyl}acetamide was prepared from 4-acetylaminobenzoyl chloride. The crude material was purified by column chromatography (CH$_2$Cl$_2$:CH$_3$OH=20:1) to yield 66 mg (5%) of the compound. MS (m/z, ES+): 321.4 (M+1, 100%), 322.4 (M+2, 100%).

50. 5-(3-chlorothiophen-2-yl)-4-(phenylhydrazono)-4H-pyrazol-3-ylamine was prepared from 3-chlorothiophene-2-carbonyl chloride. The crude material was purified by column chromatography (CH$_2$Cl$_2$:CH$_3$OH=20:1) to yield 48 mg (4%) of the compound. MS (m/z, ES+): 304.2 (Cl$^{35}$M+1, 100%), 306.4 (Cl$^{37}$M+1, 90%).

51. 5-(3-Methoxybenzyl)-4-(phenylhydrazono)-4H-pyrazol-3-ylamine was prepared from (3-methoxyphenyl)acetyl chloride. The crude material was purified by column chromatography (CH$_2$Cl$_2$:CH$_3$OH=20:1) to yield 15 mg (1%) of the compound. MS (m/z, ES+): 308.3 (M+1, 100%).

52. 5-(2,5-dimethylfuran-3-yl)-4-(phenylhydrazono)-4H-pyrazol-3-ylamine was prepared from 3-(2,5-dimethylfuran-3-yl)-3-oxopropionitrile (0.6 mmol). The product was purified by precipitation from isopropanol by the addition of water to yield 26 mg (42%) of the compound. $^1$H NMR (ppm, 500 MHz, CDCl$_3$) δ 7.30 (d, 1H), 7.45 (t, 1H), 7.34 (t, 1H), 6.29 (s, 1H), 5.65 (br s, 2H), 2.50 (s, 3H), 2.33 (s, 3H); MS (m/z, ES+): 282.3 (M+1, 100%).

53. 5-[N'-(3-amino-5-methylpyrazol-4-ylidene)hydrazino]-2H-[1,2,3]triazole-4-carboxylic acid was prepared from 3-[3-(4-chlorophenylsulfanylmethyl)phenyl]-3-oxopropionamide (0.05 mmol). The crude material was purified by column chromatography (CH$_2$Cl$_2$:CH$_3$OH=20:1) to yield 13 mg of the compound. MS (m/z, ES+): 420.3 (Cl$^{35}$M+1, 100%), 422.3 (Cl$^{37}$M+1, 80%).

54. 4-(phenylhydrazono)-5-thiophen-3-yl-4H-pyrazol-3-ylamine was prepared from 3-oxo-3-thiophen-3-yl-propionitrile (1.0 mmol). The crude material was purified by recrystallization to yield 33 mg (12%) of the compound. MS (m/z, ES+): 270.3 (M+1, 100%).

55. 5-(2-nitrophenyl)-4-(phenylhydrazono)-4H-pyrazol-3-ylamine was prepared from 3-(2-nitro-phenyl)-3-oxopropionitrile (1.0 mmol). The crude material was purified by recrystallization to yield 17 mg (6%) of the compound. MS (m/z, ES+): 309.3 (M+1, 100%).

56. 5-(1-methyl-1-[1,2,4]triazol-1-ylethyl)-4-(phenylhydrazono)-4H-pyrazol-3-ylamine was prepared from 4-methyl-3-oxo-4-[1,2,4]triazol-1-ylpentanenitrile (1.0 mmol). The crude material was purified by recrystallization to yield 29 mg (10%) of the compound. MS (m/z, ES+): 297.4 (M+1, 80%), 228.3 (M−68, 100%).

57. 5-(5-methyl-2-trifluoromethylfuran-3-yl)-4-(phenylhydrazono)-4H-pyrazol-3-ylamine was prepared from 3-(5-methyl-2-trifluoromethylfuran-3-yl)-3-oxopropionitrile (1.0 mmol). The crude material was purified by column chromatography to yield 14 mg (4%) of the compound. MS (m/z, ES+): 336.3 (M+1, 100%).

58. 5-(2-tert-butyl-5-methylfuran-3-yl)-4-(phenylhydrazono)-4H-pyrazol-3-ylamine was prepared from 3-(2-tert-butyl-5-methylfuran-3-yl)-3-oxopropionitrile (1.0 mmol). The crude material was purified by column chromatography to yield 30 mg (10%) of the compound. MS (m/z, ES+): 324.4 (M+1, 100%).

59. 5-(2-methylfuran-3-yl)-4-(phenylhydrazono)-4H-pyrazol-3-ylamine was prepared from 3-(2-methylfuran-3-yl)-3-oxopropionitrile (1.0 mmol). The crude material was purified by column chromatography and was then recrystallized to yield 28 mg (10%) of the compound. MS (m/z, ES+): 268.3 (M+1, 100%).

60. 5-furan-2-yl-4-(phenylhydrazono)-4H-pyrazol-3-ylamine was prepared from 3-furan-2-yl-3-oxopropionitrile (1.0 mmol). The crude material was purified by recrystallization to yield 71 mg (28%) of the compound. MS (m/z, ES+): 254.3 (M+1, 100%).

61. 4-(phenylhydrazono)-5-quinolin-6-yl-4H-pyrazol-3-ylamine was prepared from 3-oxo-3-quinolin-6-ylpropionitrile (0.5 mmol). The product was isolated without further purification to yield 11 mg (7%) of the compound. MS (m/z, ES+): 315.2 (M+1, 100%).

62. 5-[5-(4-chlorophenyl)-2-methylfuran-3-yl]-4-(phenylhydrazono)-4H-pyrazol-3-ylamine was prepared from 3-[5-(4-chlorophenyl)-2-methylfuran-3-yl]-3-oxopropionitrile (0.2 mmol). The product was isolated without further purification to yield 15 mg (21%) of the compound. MS (m/z, ES+): 378.4 (Cl$^{35}$M+1, 100%), 380.4 (Cl$^{37}$M+1, 50%).

63. 5-benzo[b]thiophen-3-yl-4-(phenylhydrazono)-4H-pyrazol-3-ylamine was prepared from 3-benzo[b]thiophen-3-yl-3-oxopropionitrile (0.5 mmol). The product was isolated without further purification to yield 17 mg (11%) of the compound. MS (m/z, ES+): 320.2 (M+1, 100%).

64. 5-(4-Chlorophenyl-sulfanylmethyl)-4-(phenylhydrazono)-4H-pyrazol-3-ylamine was prepared from 4-(4-chlorophenylsulfanyl)-3-oxobutyronitrile (0.5 mmol) The crude material was purified by column chromatography (CH$_2$Cl$_2$:CH$_3$OH=20:1) to yield 13 mg of the compound. MS (m/z, ES+): 420.3 (Cl$^{35}$M+1, 100%), 422.3 (Cl$^{37}$M+1, 80%).

Example 70

Preparation of 5-cyclopropyl-4-(pyridin-3-ylhydrazono)-4H-pyrazol-3-ylamine

A. Ethyl cyclopropylcarboxylate (5.6 g, 49.1 mmol) and acetonitrile (7 mL) were premixed and added into a suspension of potassium tert-butoxide (15 g, 133.7 mmol) in 250 mL of dry toluene at 70° C. This mixture was stirred at 80° C. overnight. The solid precipitate was collected by filtration, washed with ethyl acetate and diethyl ether, and dried in vacuo. The product was isolated as its potassium salt (6.78 g).

B. To an ice cold suspension of 3-aminopyridine (0.56 g, 5.95 mmole) in 9.2 mL of water was added conc. HCl (1.46 mL, 18 mmol). NaNO$_2$ (0.54 g, 8.51 mmole) dissolved in 2.5 mL of water was added to this mixture slowly. Half of this diazonium solution was then added to the mixture of the potassium salt of 3-cyclopropyl-3-oxopropionitrile (0.6 g, 5.49 mmole) obtained above and NaOAc trihydrate (2 g, 14.7 mmole) dissolved in 15 mL of water at 10° C. The precipitate was collected by filtration and then resuspended in 30 mL of ethanol. Hydrazine hydrate (0.5 mL) was added slowly to this suspension at 80° C. and the mixture was stirred at this temperature for 2 hours. The solvents were removed in vacuo. The title compound was obtained after recrystallization from ethanol in a yield of 0.28 g. MS (m/z, ES+): 229 (M+1, 100%).

C. In a similar manner, 3-[N'-(3-amino-5-cyclopropylpyrazol-4-ylidene)hydrazino]-N-methylbenzenesulfonamide was prepared from 3-amino-N-methylbenzenesulfonamide (0.385 g, 2.06 mmol) to yield 0.21 g of the product. MS (m/z, ES+): 321 (M+1, 100%).

D. In a similar manner, 3-[N'-(3-amino-5-cyclopropylpyrazol-4-ylidene)hydrazino]-N-(2-hydroxyethyl)benzenesulfonamide was prepared from 3-amino-N-(2-hydroxyethyl)benzenesulfonamide (0.55 g, 2.54 mmol) to yield 0.3 g of the product. MS (m/z, ES+): 351 (M+1, 100%).

E. In a similar manner, 3-[N'-(3-amino-5-cyclopropylpyrazol-4-ylidene)hydrazino]benzenesulfonamide was prepared from 3-aminobenzenesulfonamide (0.51 g, 2.96 mmol) to yield 0.1 g of the product. MS (m/z, ES+): 307 (M+1, 100%).

Example 71

The compounds in this example were prepared by the following procedure: Concentrated hydrochloric acid (1.46 mL, 17.5 mmol) was added drop-wise to a solution of the substituted aniline (6.0 mmol) dissolved in 9.2 mL of water at 0° C. To this mixture was then added a cooled solution of NaNO$_2$ (0.54 g, 7.8 mmol) dissolved in 4 mL of water. The solution was stirred for 30 minutes and was then added to a solution of the substituted pyrazole (6.2 mmol) and NaOAc trihydrate (3.3 g, 24 mmol) dissolved in a mixture of water (6 mL) and AcOH (6 mL). The resulting solid was isolated by filtration and dried. The crude material was purified by recrystallization or column chromatography.

1. 5-methyl-4-(phenylhydrazono)-4H-pyrazol-3-ylamine was prepared from aniline (0.56 g, 6.0 mmol) and 3-amino-5-methylpyrazole (0.6 g, 6.2 mmol). The resulting solid was isolated by filtration and dried. The crude material was purified by recrystallization from ethyl acetate/hexanes to yield 0.21 g (18%) of the compound as a yellow solid. $^1$H NMR (ppm, 200 MHz, DMSO-d$_6$) δ 11.8 (br s, 1H), 7.65 (m, 2H), 7.4 (m, 2H), 7.3 (m, 1H), 6.6 (br s, 2H), 2.2 (s, 3H); MS (m/z, ES+): 202.1 (M+1, 100%).

2. 4-(3-fluorophenylhydrazono)-5-methyl-2H-pyrazol-3-ylamine was prepared from 3-fluoroaniline (0.66 g, 6.0 mmol) and 3-amino-5-methylpyrazole (0.54 g, 5.6 mmol). The crude material was purified by column chromatography eluting with CH$_2$Cl$_2$:CH$_3$OH (9:1) to yield 0.227 g (19%) of the compound as an orange solid.

3. 4-[(3-chlorophenyl)hydrazono]-5-methyl-4H-pyrazol-3-ylamine was prepared from 3-chloroaniline (0.77 g, 6.0 mmol) and 3-amino-5-methylpyrazole (0.58 g, 6.0 mmol). The crude material was purified by chromatography (CH$_2$Cl$_2$:CH$_3$OH=10:1) to yield 0.41 g (22%) of the compound as an orange solid.

4. 5-methyl-4-[(4H-[1,2,4]triazol-3-yl)hydrazono]-4H-pyrazol-3-ylamine was prepared from 3-amino-1,2,4-triazole (0.88 g, 10.5 mmol) and 3-amino-5-methylpyrazole (1.0 g, 10.3 mmol). The crude material was extracted from the aqueous layer three times with ethyl acetate (100 mL). The combined ethyl acetate solutions were washed with brine, dried over magnesium sulphate, filtered and evaporated. A portion of the crude material was purified by column chromatography ($CHCl_3$:$CH_3OH$=7:1). The isolated material was then further purified by preparative TLC ($CHCl_3I$:$CH_3OH$=7:1) to yield 0.047 g (8%) of the compound as a red solid. $^1H$ NMR (ppm, 200 MHz, DMSO-$d_6$) δ 12.0 (br s, 1H), 8.2 (br s, 1H), 6.8 (br s, 2H), 2.2 (s, 3H).

5. 3-[N'-(3-amino-5-methylpyrazol-4-ylidene)hydrazino]-1H-pyrazole-4-carboxylic acid ethyl ester was prepared from 3-amino-4-carbethoxypyrazole (0.46 g, 3.0 mmol) and 3-amino-5-methylpyrazole (0.50 g, 5.1 mmol). The water was removed by evaporation and the crude material was purified by recrystallization from ethanol to yield 0.43 g (58%) of the compound as an orange solid.

6. 3-[N'-(3-amino-5-methylpyrazol-4-ylidene)hydrazino]-1H-pyrazole-4-carboxylic acid was prepared by dissolving 3-[N'-(3-amino-5-methylpyrazol-4-ylidene)hydrazino]-1H-pyrazole-4-carboxylic acid ethyl ester (0.2 g, 0.8 mmol) in ethanol containing sodium hydroxide (0.2 g, 5 mmol) and the solution was stirred overnight. The mixture was then acidified to pH 1 with 1N hydrochloric acid and the resulting solid was isolated by filtration. The crude material was purified by preparative TLC eluting with ($CHCl_3$:MeOH:$H_2O$=4:1: 0.005) to yield 39 mg (22%) of the compound as a red solid.

7. 4-[(3,4-difluorophenyl)hydrazono]-5-methyl-4H-pyrazol-3-ylamine was prepared from 3,4-difluoroaniline (0.62 g, 4.8 mmol) and 3-amino-5-methylpyrazole (0.6 g, 6.2 mmol) according to procedure described above except that the substituted aniline was initially dissolved in a mixture of water (7.2 mL) and DMF (2.0 mL) prior to being acidified. The crude material was initially purified by column chromatography ($CH_2Cl_2$:MeOH=20:1). The isolated material was further purified by recrystallization from ethyl acetate/hexanes to yield 0.2 g (18%) of the compound as a yellow solid. MS (m/z, ES+): 238.1 (M+1, 100%).

8. 5-methyl-4-[(4-trifluoromethylphenyl)hydrazono]-4H-pyrazol-3-ylamine was prepared from 4-trifluoromethylaniline (0.36 g, 2.2 mmol) and 3-amino-5-methylpyrazole (0.3 g, 3.1 mmol) according to procedure described above except that the substituted aniline was initially dissolved in a mixture of water (3.6 mL) and DMF (2.0 mL) prior to being acidified. The crude material was purified by column chromatography ($CHCl_3$:MeOH=10:1) to yield 0.041 g (7%) of the compound as an orange solid. MS (m/z, ES+): 270.2 (M+1, 100%).

9. 5-methyl-4-[(3-nitrophenyl)hydrazono]-4H-pyrazol-3-ylamine was prepared from 3-nitroaniline (0.35 g, 2.5 mmol) and 3-amino-5-methylpyrazole (0.3 g, 3.1 mmol) according to the procedure described above except that the substituted aniline was initially dissolved in a mixture of water (3.6 mL) and DMF (2.0 mL) prior to being acidified. The product was isolated in a yield of 176 mg (29%) of the compound as a red solid and was not further purified. MS (m/z, ES+): 247.2 (M+1, 100%).

10. 4-(isoquinolin-5-ylhydrazono)-5-methyl-4H-pyrazol-3-ylamine was prepared from 5-aminoisoquinoline (0.7 g, 4.9 mmol) and 3-amino-5-methylpyrazole (0.6 g, 6.2 mmol) according to the procedure described above except that the substituted aniline was initially dissolved in a mixture of water (6.0 mL) and DMF (6.0 mL) prior to being acidified. The crude material was purified by chromatography eluting with ($CH_2Cl_2$:MeOH=6:1) to yield 0.089 g (7%) of the compound as a red solid. MS (m/z, ES+): 253.2 (M+1, 50%), 129 (M−123, 100%).

11. 5-methyl-4-(pyridin-3-ylhydrazono)-4H-pyrazol-3-ylamine was prepared from 3-aminopyridine (0.6 g, 6.3 mmol) and 3-amino-5-methylpyrazole (0.6 g, 6.2 mmol). The crude material was purified by recrystallization from ethanol to yield 0.35 g (27%) of the compound as a yellow/orange solid.

12. 5-methyl-4-(phthalazin-5-ylhydrazono)-4H-pyrazol-3-ylamine was prepared from 5-aminophthalazine (0.25 g, 1.7 mmol) and 3-amino-5-methylpyrazole (0.5 g, 5.2 mmol). The crude material was purified by column chromatography eluting with dichloromethane/methanol (4:1) to yield 0.031 g (7%) of the compound as a red solid. MS (m/z, ES+): 254 (M+1, 100%).

13. 4-[(4-methoxyphenyl)hydrazono]-5-methyl-4H-pyrazol-3-ylamine was prepared from anisole (0.25 g, 2 mmol) and 3-amino-5-methylpyrazole (0.2 g, 2 mmol) according to the procedure described above except that the 3-amino-5-methylpyrazole was dissolved in 2 mL of water containing NaOAc trihydrate (1.1 g, 8 mmol). The resulting crude material was purified by flash silica gel chromatography eluting with ($CH_2Cl_2$:EtOH=10:2) to yield 0.054 g (12%) of the compound as a yellow solid. $^1H$ NMR (ppm, 500 MHz, DMSO-$d_6$) δ 7.67 (d, 2H), 7.01 (d, 2H), 3.8 (s, 3H), 2.4 (s, 3H); MS (m/z, ES−): 230.2 (M−1, 100%).

14. 4-[(3-fluorophenyl)hydrazono]-4H-pyrazol-3-ylamine was prepared from 3-fluoroaniline (0.33 g, 3.0 mmol) and 3-aminopyrazole (0.25 g, 3.0 mmol). The crude material was extracted from the aqueous layer three times with ethyl acetate (15 mL). The combined ethyl acetate solutions were washed with brine, dried over magnesium sulphate, filtered and evaporated. The crude material was purified by flash silica gel chromatography eluting with ($CHCl_3$:MeOH=9:1) to yield 0.063 g (10%) of the compound as a yellow solid. $^1H$ NMR (ppm, 200 MHz, DMSO-$d_6$) δ 12.0 (br s, 1H), 7.8 (br s, 1H), 7.4-7.8 (m, 4H), 6.8-7.2 (m, 3H).

15. 4-(phenylhydrazono)-4H-pyrazol-3-ylamine was prepared from aniline (0.56 g, 6.0 mmol) and 3-aminopyrazole (0.51 g, 6.1 mmol). The water was removed under reduced pressure and the resulting crude material was purified by column chromatography ($CHCl_3$:MeOH=9:1) to yield 0.071 g (6%) of the compound as a yellow solid. $^1H$ NMR (ppm, 200 MHz, DMSO-$d_6$) δ 12.0 (br s, 1H), 7.8 (br s, 1H), 7.6-7.8 (m, 2H), 7.2-7.6 (m, 3H), 6.8 (br s, 1H), 6.2 (br s, 1H).

16. 4-[(3,4-difluorophenyl)hydrazono]-4H-pyrazol-3-ylamine was prepared from 3,4-difluoroaniline (0.62 g, 4.8 mmol) and 3-aminopyrazole (0.4 g, 4.8 mmol) according to the procedure described above except that the aniline was initially dissolved in a mixture of water (7.2 mL) and DMF (1.16 mL) prior to being acidified. The solvents were removed under reduced pressure and the resulting crude material was purified by column chromatography eluting with ($CHCl_3$: MeOH=10:1) to yield 0.41 g (38%) of the compound as a yellow solid. $^1H$ NMR (ppm, 200 MHz, DMSO-$d_6$) δ 12.0 (br s, 1H), 7.2-8.0 (m, 4H), 6.9 (m, 2H).

17. 4-[N'-(3-aminopyrazol-4-ylidene)hydrazino]benzenesulfonamide was prepared from 4-aminobenzenesulfonamide (1.0 g, 5.8 mmol) and 3-aminopyrazole (0.8 g, 9.6 mmol) according to the procedure described above except that the 3-aminopyrazole was dissolved in 30 mL of water containing NaOAc trihydrate (5.5 g, 40 mmol). The resulting crude material was purified by column chromatography ($CH_2Cl_2$:MeOH=10:1) to yield 0.121 g (8%) of the compound as a yellow solid. MS (m/z, ES+): 267.0 (M+1, 100%).

18. 4-[(3-fluoro-4-methoxyphenyl)hydrazono]-4H-pyrazol-3-ylamine was prepared from 3-fluoro-p-anisidine (0.47 g, 3.3 mmol) and 3-aminopyrazole (0.6 g, 7.2 mmol) according to the procedure described above except that the 3-aminopyrazole was dissolved in 30 mL of water containing NaOAc trihydrate (5.5 g, 40 mmol). The resulting crude material was recrystallized from ethyl acetate/hexanes and the further purified by column chromatography ($CH_2Cl_2$:MeOH=5:1) to yield 0.081 g (10%) of the compound as a yellow solid. MS (m/z, ES+): 236.1 (M+1, 100%).

19. 5-tert-butyl-4-[(3-fluorophenyl)hydrazono]-4H-pyrazol-3-ylamine was prepared from 3-fluoroaniline (0.33 g, 3.0 mmol) and 3-amino-5-tert-butylpyrazole (0.4 g, 3.0 mmol). The solvent was removed under reduced pressure and the resulting crude material was purified by column chromatography ($CH_2Cl_2$:MeOH=9:1) to yield 0.099 g (13%) of the title compound as an orange solid. $^1$H NMR (ppm, 200 MHz, DMSO-$d_6$) δ 11.6 (br s, 1H), 7.4-7.7 (m, 4H), 7.1 (br s, 2H), 1.4 (s, 9H).

Example 72

A. The compounds described in this example were prepared according to the following procedure: Concentrated HCl (1.46 mL, 17.5 mmol) was added drop wise to a solution of the substituted aniline (6.0 mmol) dissolved in 9.2 mL of water at 0° C. To this mixture was then added a cooled solution of $NaNO_2$ (0.54 g, 7.8 mmol) in 4 mL of water. The solution was stirred for 30 minutes and was then added to a solution of the substituted pyrazole (6.2 mmol) and NaOAc trihydrate (3.3 g, 24 mmol) dissolved in a mixture of water (6 mL) and AcOH (6 mL). The resulting solid was isolated by filtration and dried. The crude material was purified by recrystallization or column chromatography.

1. {4-[(3,4-Difluorophenyl)hydrazono]-4H-pyrazol-3-yl}ethylamine was prepared from 3,4-difluoroaniline (0.31 g, 2.4 mmol) and ethyl-(1H-pyrazol-3-yl)amine (0.27 g, 2.4 mmol) according to the procedure described above except that the substituted aniline was dissolved in water (3 mL) and DMF (1 mL). The resulting solid was purified by preparative TLC (EtOAc:hexane=1:1) to yield 0.047 g (8%) of the compound as an orange solid. MS (m/z, ES+): 252.1 (M+1, 100%).

2. Ethyl-{4-[(3-methyl-3H-benzotriazol-5-yl)hydrazono]-4H-pyrazol-3-yl}amine was prepared from 3-methyl-5-aminobenzotriazole (0.25 g, 1.7 mmol) and ethyl-(1H-pyrazol-3-yl)amine (0.18 g, 1.6 mmol). The resulting solid was purified by preparative TLC (EtOAc:hexane=1:1) to yield 0.063 g (12%) of the compound as a yellow solid. MS (m/z, ES+): 271.2 (M+1, 100%).

3. 4-[N'-(3-Ethylaminopyrazol-4-ylidene)-hydrazino]benzenesulfonamide was prepared from 4-aminobenzenesulfonamide (0.41 g, 2.4 mmol) and ethyl-(1H-pyrazol-3-yl)-amine (0.27 g, 2.4 mmol). The crude material was purified by preparative TLC ($CHCl_3$:MeOH=6:1) to yield 0.081 g (12%) of the title compound as a yellow solid. MS (m/z, ES+): 295.1 (M+1, 65%).

4. Ethyl-[4-(pyridin-3-ylhydrazono)-4H-pyrazol-3-yl]amine was prepared from 3-aminopyridine (0.41 g, 4.4 mmol) and ethyl-(1H-pyrazol-3-yl)-amine (0.27 g, 2.4 mmol). The crude material was purified by preparative TLC ($CH_2Cl_2$:MeOH=9:1) to yield 0.081 g (12%) of the compound as an orange solid. MS (m/z, ES+): 217.2 (M+1, 100%).

5. Ethyl-[4-(isoquinolin-5-ylhydrazono)-4H-pyrazol-3-yl]amine was prepared from 5-aminoisoquinoline (0.5 g, 3.5 mmol) and ethyl-(1H-pyrazol-3-yl)amine (0.3 g, 2.7 mmol). The crude material was purified by preparative TLC ($CHCl_3$:MeOH=5:1) to yield 0.039 g (4%) of the compound as an orange solid.

B. A solution of 3-aminopyrazole (1.0 g, 12.0 mmol) in 10 mL of formic acid was heated to 108° C. for 12 hours in a round bottom flask equipped with a condenser and a magnetic stirring bar. The formic acid was then removed by vacuum distillation and the white product was washed with water. The resulting solid was then dried under high vacuum overnight to yield 1.34 g (96%) of N-(2H-pyrazol-3-yl)formamide. To this solid (0.31 g, 2.8 mmol) in 10 mL of anhydrous THF at –10° C. was added excess lithium aluminum hydride. The reaction was stirred under argon overnight and then quenched with a saturated sodium bicarbonate solution. The resulting white solid was removed by filtration and the mother liquor was then dried over anhydrous $MgSO_4$, filtered, and concentrated under reduced pressure. Methyl-(2H-pyrazol-3-yl)amine was isolated in a yield of 0.317 g (120%) as a pale brown oil and was used in subsequent reactions without further purification.

1. {4-[(3,4-Difluorophenyl)hydrazono]-4H-pyrazol-3-yl}methylamine was prepared from 3,4-difluoroaniline (0.44 g, 3.41 mmol) and 3-(N-methylamino)pyrazole (0.30 g, 3.1 mmol) according to the procedure described above in Paragraph A with the following exceptions. The substituted aniline was dissolved in water (3 mL) and DMF (1 mL). The substituted pyrazole and NaOAc trihydrate (1.9 g, 13.95 mmol) were dissolved in 5 mL of water. The resulting solid was purified by preparative TLC (EtOAc:hexane=4:1) to yield 30 mg (3%) of the title compound as an orange solid. MS (m/z, ES+): 238 (M+1, 100%).

C. A solution of 3-amino-5-methylpyrazole (2.3 g, 23.7 mmol) dissolved in glacial acetic acid (15 mL) was refluxed at 120° C. for 16 hours to afford a transparent yellow solution. This solution was cooled to ambient temperature which resulted in the formation of white needles. The crystals were isolated via filtration, washed with water until the pH of the water became neutral and dried under high vacuum to yield 0.73 g (22%) of N-(5-methyl-2H-pyrazol-3-yl)acetamide. This solid (0.43 g, 3.1 mmol) was then suspended in 10 mL of anhydrous THF at 0° C. under argon. Excess lithium aluminum hydride in anhydrous THF (10 mL) was added over 24 hours and was stirred for an additional 48 hours. The reaction mixture was quenched by the careful addition of a saturated sodium bicarbonate solution. The solids were washed with THF and the organics were combined, dried over anhydrous $MgSO_4$ and evaporated to yield 0.29 g (81%) of ethyl-(5-methyl-2H-pyrazol-3-yl)amine as a yellow oil.

1. {4-[(3,4-difluorophenyl)hydrazono]-5-methyl-4H-pyrazol-3-yl}ethylamine was prepared from 3,4-difluoroaniline (0.33 g, 3.5 mmol) and ethyl-(5-methyl-2H-pyrazol-3-yl)amine (0.29 g, 2.34 mmol) according to the procedure described above in Paragraph A with the following exceptions. The substituted aniline was initially dissolved in a mixture of water (4 mL) and DMF (1 mL) prior to being acidified. The substituted pyrazole was mixed with NaOAc trihydrate (0.73 g, 8.87 mmol) in 6 mL of water. The resulting yellow precipitate was isolated by filtration and dried under high vacuum to afford 600 mg of crude material. A portion of the solid (300 mg) was dissolved in 17 mL of ethyl acetate and extracted with 80 mL (8×10 mL) of 1.56 N HCl. The aqueous phase was then neutralized with a saturated sodium bicarbonate solution yielding a yellow precipitate which was isolated by filtration (170 mg). The solid was purified by preparative TLC ($CH_2Cl_2$:MeOH=98:2) to yield 0.052 g (17%) of the compound as a yellow solid. $^1$H NMR (ppm, 200 MHz, DMSO-$d_6$) δ 12.1 (br s, 1H), 7.3-7.8 (m, 3H), 3.3 (merged with $H_2O$), 2.5 (s, 1H), 1.1 (t, 3H).

2. Ethyl-[5-methyl-4-(pyridin-3-yl-hydrazono)-4H-pyrazol-3-yl]amine was prepared from 3-aminopyridine (0.31 g, 3.5 mmol) and ethyl-(5-methyl-2H-pyrazol-3-yl)amine (0.5 g, 3.2 mmol) with the exception that the substituted pyrazole was mixed with NaOAc trihydrate (0.73 g, 5.48 mmol) in 6 mL of water. The resulting crude material was purified by preparative TLC ($CH_2Cl_2$:MeOH=9:1) to yield 0.040 g (5%) of the compound as a yellow solid. MS (m/z, ES+): 231 (M+1, 100%).

3. Ethyl-{4-[(3-fluorophenyl)hydrazono]-5-methyl-4H-pyrazol-3-yl}amine was prepared from 3-fluoroaniline (0.33 g, 3.5 mmol) and ethyl-(5-methyl-2H-pyrazol-3-yl)amine (0.5 g, 3.2 mmol) according to procedure described in Paragraph A above with the exception that the substituted pyrazole was mixed with NaOAc trihydrate (0.73 g, 5.48 mmol) in 6 mL of water. The resulting crude material was purified by preparative TLC eluting with ($CH_2Cl_2$:MeOH=9:1) to yield 0.036 g (4%) of the title compound as a yellow solid. MS (m/z, ES+): 248 (M+1, 100%).

D. A solution of 3-amino-5-methylpyrazole (5.33 g, 54.8 mmol) in 20 mL formic acid was heated to 108° C. in a round bottom flask equipped with a condenser and a magnetic stirring bar. The reaction was stirred overnight, at which point the formic acid was removed by vacuum distillation. The product was then washed with water, which was also removed by vacuum distillation. The white product, N-(5-methyl-2H-pyrazol-3-yl)-formamide, was then dried in vacuo. This solid was then partially dissolved in 50 mL of anhydrous THF under argon. The reaction solution was cooled to −10° C. and an excess of lithium aluminum hydride was added slowly while stirring. The solution was allowed to warm to room temperature over 24 hours. The reaction mixture was then cooled to −10° C. and was quenched by the addition of a saturated sodium bicarbonate solution. The resulting solution was filtered and the solids were washed with THF. The filtrate was dried over anhydrous $MgSO_4$, filtered, and concentrated to yield 6.8 g (100%) of methyl-(5-methyl-2H-pyrazol-3-yl)amine. $^1$H NMR (ppm, 300 MHz, DMSO-$d_6$) δ☐11.0 (br s☐☐1H), 5.17 (s, 1H), 4.80 (br s, 1H), 2.5 (d, 3H), 2.1 (s, 3H).

1. {4-[(3,4-difluorophenyl)hydrazono]-5-methyl-4H-pyrazol-3-yl}methylamine was prepared from 3,4-difluoroaniline (750 mg, 7.92 mmol) and 3-(N-methylamino)-5-methylpyrazole (0.80 g, 7.2 mmol) according to the procedure described in Paragraph A above with the following exceptions. The substituted aniline was dissolved in a mixture of water (8 mL) and DMF (2 mL). The substituted pyrazole was mixed with NaOAc trihydrate (3.64 g, 27.3 mmol) in 10 mL of water. The resulting solid was purified by column chromatography (EtOAc:hexane=1:1) to yield 0.70 g (39%) of a by-product and 0.145 g (8%) of the compound as a yellow solid. MS (m/z, ES+): 252 (M+1, 100%); $^1$H NMR (ppm, 400 MHz, DMSO-$d_6$) δ 2.3 (s, 3H), 2.5 (s, 3H) {2.5/2.3=1.5}3.2 (d, 3H) 3.3 (d, 3H) {3.3/3.2=1.5}6.6 (bs, 1H), 7.6-8.0 (m, 4H) 12.0 (bs, 1H) 12.3 (bs, 1H) {12.0/12.3=1.5}[*Ratios indicate tautamers]; $^1$H NMR (ppm, DMSO-$d_6$+$D_2O$, 400 MHz) δ 2.5 (s, 3H), 3.2 (s, 3H), 7.1-7.6 (m, 3H); FTIR ($cm^{-1}$, KBr pellet) 490 (w), 516 (w), 550 (w), 724 (m), 770 (m), 819 (m), 868 (m), 983 (m), 1016 (m), 1087 (m), 1141 (m), 1192 (m), 1257 (m), 1301 (m), 1335 (m), 1384 (m), 1429 (s), 1506 (s), 1541 (m), 1626 (m), 2769 (m), 2808 (m), 2924 (m), 3045 (m).

2. {4-[(3-Fluorophenyl)hydrazono]-5-methyl-4H-pyrazol-3-yl}methylamine was prepared from 3-fluoroaniline (0.34 g, 3.06 mmol) and 3-(N-methylamino)-5-methylpyrazole (0.32 g, 2.85 mmol) according to the procedure describee above in Paragraph A with the exception that the substituted pyrazole was mixed with sodium acetate trihydrate (0.43 g, 3.14 mmol) in 5 mL of water. The crude material isolated in an amount of 0.46 g. An amount of this (0.25 g) was purified by column chromatography (EtOAc:hexane=1:1) to yield 0.050 g (13%) of the compound as a yellow solid. MS (m/z, ES+): 234 (M+1, 100%).

E. Methyl isonicotinate (9 g, 60 mmol) and of acetonitrile (4 mL) were premixed and added to a suspension of potassium tert-butoxide (10.6 g, 94.5 mmol) in 200 mL of dry toluene at 80° C. This mixture was stirred at this temperature overnight. The solid precipitate was collected by filtration and dried in vacuo. The product was isolated as the potassium salt in a yield of 10 g (92%). This salt (9 g, 49 mmol) was mixed with hydrazine hydrate (5 mL, 100 mmol) and concentrated HCl (4.5 mL, 54 mmol) in ethanol (150 mL). The solution was refluxed for 8 hours at which point an additional 4 mL of hydrazine hydrate was added. Refluxing was continued overnight. The solvent was removed by distillation and the resulting crude material was purified by column chromatography, eluting with $CH_2Cl_2$:$CH_3OH$ (5:1) to yield 4.1 g (52%) of 5-pyridin-4-yl-2H-pyrazol-3-ylamine. This material (4.1 g, 26 mmol) was dissolved in formic acid (50 mL) and heated to 70° C. for 2 hours. The formic acid was removed by distillation to afford 4.5 g (92%) of (N-(5-pyridin-4-yl-2H-pyrazol-3-yl)formamide. The solid was dissolved in anhydrous THF (200 mL). Lithium aluminum hydride (3 g, 79 mmol) suspended in 200 mL of THF was added slowly and, once the addition was complete, the reaction was heated to reflux for 2 hours. The reaction was quenched by the addition of saturated sodium sulphate solution and the solution was passed through a celite cake. The residue was washed with THF and methanol and the combined organic solutions were concentrated under reduced pressure. The resulting crude material was purified by column chromatography ($CH_2Cl_2$:MeOH=5:1) to yield 1.8 g (43%) of methyl-(5-pyridin-4-yl-2H-pyrazol-3-yl) amine.

1. {4-[(3-fluorophenyl)hydrazono]-5-pyridin-4-yl-4H-pyrazol-3-yl}methylamine was prepared from 3-fluoroaniline (70 mg, 0.69 mmol) and methyl-(5-pyridin-4-yl-2H-pyrazol-3-yl)amine (0.1 g, 0.57 mmol) according to the procedure described in Paragraph A above with the exception that the substituted pyrazole was mixed with NaOAc trihydrate (0.31 g, 2.28 mmol) in water (2 mL) and DMF (1 mL). The resulting solid was purified by column chromatography (EtOAc:hexane=4:1) to yield 0.15 g (88%) of the compound as a yellow solide. $^1$H NMR (ppm, 400 MHz, DMSO-$d_6$) δ 13.0 (br s, 1H), 8.6 (dd, 2H), 8.2 (br s, 1H), 8.1 (dd, 2H), 7.45-7.7 (m, 3H), 7.15 (dt, 1H), 3.0 (d, 3H); MS (m/z, ES+): 297 (M+1, 100%).

2. Mmethyl-[4-(phthalazin-5-ylhydrazono)-5-pyridin-4-yl-4H-pyrazol-3-yl]amine was prepared from 4-aminoquinazoline (0.15 g, 1.04 mmol) and methyl-(5-pyridin-4-yl-2H-pyrazol-3-yl)amine (0.2 g, 1.15 mmol) according to the procedure described above in Paragraph A with the following exceptions. The substituted aniline was dissolved in water (5 mL) and DMF (2 mL) prior to acidification. The substituted pyrazole was mixed with NaOAc trihydrate (0.62 g, 4.59 mmol) in water (5 mL) and DMF (1 mL). The resulting solid was purified by column chromatography (EtOAc:hexane=4:1) to yield 0.080 g (23%) of the compound as an orange solid. MS (m/z, ES+): 331 (M+1, 100%).

3. {4-[(3,4-difluorophenyl)hydrazono]-5-pyridin-4-yl-4H-pyrazol-3-yl}methylamine was prepared from 3,4-difluoroaniline (75 mg, 0.57 mmol) and methyl-(5-pyridin-4-yl-2H-pyrazol-3-yl)amine (0.1 g, 0.57 mmol) according to the procedure described above in Paragraph A with the following exceptions. The substituted aniline was dissolved in water (1 mL) and DMF (0.5 mL). The substituted pyrazole was mixed with NaOAc trihydrate (0.32 g, 2.32 mmol) in water (3 mL) and DMF (1 mL). The resulting solid was purified by column chromatography (EtOAc:hexane=4:1) to yield 0.02 g (11%) of the compound as an orange solid. MS (m/z, ES+): 315 (M+1, 100%).

Example 73

Preparation of tert-butyl-[5-methyl-4-(phenylhydrazono)-4H-pyrazol-3-yl]amine

The title compound was prepared using 100 mg (0.4 mmol) of N-tert-butyl-3-oxo-2-(phenylhydrazono)butyramide which was synthesized using aniline (1.7 mmol) and N-tert-butyl acetoacetamide (393 mg, 2.5 mmol). Hydrazine hydrate (2.3 mmol) was added to a solution of N-tert-butyl-3-oxo-2-(phenylhydrazono)butyramide in ethanol. Very little solid had formed after heating the reaction at 75° C. for 1 hour, however, analysis of the reaction solution by TLC indicated that no starting material remained. The solution was allowed to cool to ambient temperature and the solvent was evaporated. The residue was recrystallized from ethanol/water. The resulting solid was isolated by filtration and dried to yield 38 mg (43%) of the title compound as a yellow solid. $^1$H NMR (ppm, 200 MHz, CDCl$_3$) δ 1.42 (s, 9H), 2.20 (s, 3H), 5.35 (br s, 1H), 6.95 (t, 1H), 7.15-7.35 (m, 4H), 9.95 (br s, 1H); IR (cm$^{-1}$, KBr pellet): 3368 (w), 3197 (w), 3038 (w), 2973 (w), 2928 (w), 1631 (m), 1602 (m), 1565 (m), 1516 (s), 1498 (s), 1391 (w), 1366 (m), 1225 (m), 1187 (w), 1166 (w), 1119 (w), 1074 (w), 1059 (w), 949 (w), 895 (w), 775 (w), 748 (w), 691 (m), 561 (w); MS (m/z, ES+): 276.2 (M+18, 5%), 259.2 (M+1, 1%), 203.1 (M-55, 5%).

Example 74

Preparation of (2-morpholin-4-ylethyl)[5-phenyl-4-(phenylhydrazono)-4H-pyrazol-3-yl]amine 5-Phenyl-4-(phenylhydrazono)-4H-pyrazol-3-ylamine (65 mg, 0.25 mmol) was dissolved in 5 mL of acetonitrile. Potassium carbonate (70 mg, 0.5 mmol) and a catalytic amount of sodium iodide were added and the solution was heated to reflux. 4-(2-chloroethyl)morpholine hyrdochloride (50 mg, 0.25 mmol) was added in small portions over 30 min. After heating at reflux for 6 hours, the reaction was allowed to cool to ambient temperature and was stirred overnight. Some of the residual 4-(2-chloroethyl)morpholine was removed by stirring the solution over 50 mg of polystyrene bound thiophenol with 1 drop of diethylisopropylamine. The solution was filtered through celite and evaporated to a tan solid. The solid was then dissolved in ethyl acetate and precipitated with hexanes. The solid was isolated by filtration and air dried. The material was purified by column chromatography (CH$_2$Cl$_2$:MeOH=10:1) to yield two fractions in amounts of 28 mg and 35 mg (total 67%). $^1$H NMR (ppm, 200 MHz, CDCl$_3$) δ 2.60 (t, 4H), 2.80 (t, 2H), 3.70 (t, 4H), 4.18 (t, 2H), 7.25-7.50 (m, 8H), 7.78 (d, 2H), 8.15 (d, 2H).

Example 75

Preparation of N-[5-phenyl-4-(phenylhydrazono)-4H-pyrazol-3-yl]nicotinamide

5-Phenyl-4-(phenylhydrazono)-4H-pyrazol-3-ylamine (66 mg, 0.25 mmol) was dissolved in 5 mL of anhydrous methylene chloride. Nicotinoylchloride hydrochloride (50 mg, 0.28 mmol) and triethylamine (78 μL, 0.56 mmol) were added to the solution. Slight fuming of the reaction was noted and the solution became red. The reaction was stirred at ambient temperature for 48 hours. The reaction was filtered to remove a small amount of white solid. To the filtrate was added 30 mL of methylene chloride. The solution was washed with 20 mL of a 5% HCl solution. The aqueous layer was washed with methylene chloride and the combined methylene chloride fractions were washed with water and saturated NaHCO$_3$ solution. The methylene chloride solution was dried over MgSO$_4$, filtered, and evaporated to afford a solid. The material was purified by flash chromatography (CH$_2$Cl$_2$:MeOH=15:1) to yield 34 mg (36%) of the title compound as a yellow solid. $^1$H NMR (ppm, 200 MHz, CDCl$_3$) δ 7.30-7.55 (m, 8H), 7.75 (d, 2H), 8.20-8.30 (m, 2H), 8.55 (d, 1H), 8.81 (d, 1H), 9.45 (s, 1H).

Example 76

Preparation of 4-(phenylhydrazono)-5-pyridin-4-yl-4H-pyrazol-3-ylamine

A. Ethyl isonicotinate (7.6 g, 50 mmol) and of acetonitrile (70 mmol) were premixed and added to a suspension of potassium tert-butoxide (5.6 g, 50 mmol) in 200 mL of dry toluene at 90° C. This mixture was stirred at this temperature overnight. The solid precipitate was collected by filtration and dried in vacuo. The product was isolated as the potassium salt in a yield of 7.5 g (81%).

B. To a suspension of aniline (0.56 g, 6.0 mmole) in 9.2 mL of water was added conc. HCl (1.46 mL, 19 mmol) in an ice bath. NaNO$_2$ (0.54 g, 8.5 mmole) dissolved in water was added to this mixture slowly. The diazonium solution was then added to the mixture of the potassium salt of 3-oxo-3-pyridin-4-ylpropionitrile (1.5 g, 8.3 mmole) obtained above and NaOAc trihydrate (3.5 g, 25.7 mmole) dissolved in 50 mL of water. The precipitate was collected by filtration and dried in vacuo. The obtained solid was then resuspended in 30 mL of ethanol. Hydrazine hydrate (0.5 mL) was added slowly to this suspension at reflux temperature and the mixture was refluxed for 3 hours. The title compound was obtained after recrystallization from EtOH/hexane (0.49 g, 31%). MS (m/z, ES+): 265 (M+1, 100%).

C. In a similar manner, 4-(isoquinolin-5-ylhydrazono)-5-pyridin-4-yl-4H-pyrazol-3-ylamine was prepared. 5-Aminoisoquinoline (0.5 g, 3.5 mmol) and potassium salt of 3-oxo-3-pyridin-4-ylpropionitrile (1.5 g, 8.3 mmole) yielded 0.089 g of the product (8%). $^1$H NMR (ppm, 300 MHz, DMSO-d$_6$) 612.5 (brs, 1H), 9.39 (s, 1H), 8.65 (d, 2H), 8.60 (d, 1H), 8.4 (d, 1H), 8.12 (d, 3H), 7.95 (d, 1H), 7.79 (t, 1H), 7.45 (br s, 2H); MS (m/z, ES+): 316 (M+1, 30), 158 (M-157, 50), 79 (M-236, 100%).

D. In a similar manner, 2-{3-[N-(3-amino-5-pyridin-4-ylpyrazol-4-ylidene)hydrazino]benzenesulfonyl}ethanol was prepared. 2-(3-Aminobenzenesulfonyl)ethanol (0.5 g, 2.5 mmol) and potassium salt of 3-oxo-3-pyridin-4-ylpropionitrile (1.5 g, 8.3 mmole) yielded 0.101 g of the product (13%). MS (m/z, ES+): 373.2 (M+1, 100%).

E. In a similar manner, 3-[N'-(3-amino-5-pyridin-4-ylpyrazol-4-ylidene)hydrazino]benzenesulfonamide was prepared. 3-Aminobenzene-sulfonamide (1.0 g, 5.8 mmol) and potassium salt of 3-oxo-3-pyridin-4-ylpropionitrile (1.7 g, 9.4 mmole) yielded 0.11 g of the product (6%). MS (m/z, ES+): 344.0 (M+1, 100%).

F. In a similar manner, 4-(phthalazin-5-ylhydrazono)-5-pyridin-4-yl-4H-pyrazol-3-ylamine was prepared. 5-Aminophthalazine (0.25 g, 1.7 mmol) and potassium salt of 3-oxo-3-pyridin-4-ylpropionitrile (0.5 g, 2.8 mmole) yielded 0.031 g of the product (6%). MS (m/z, ES+): 317.2 (M+1, 25%), 159.0 (M-157, 100%).

G. In a similar manner, 4-[(3-morpholin-4-ylmethylphenyl)hydrazono]-5-pyridin-4-yl-4H-pyrazol-3-ylamine was prepared according the procedure described above in Paragraphs A and B with the following modifications: THF was used as the solvent to replace EtOH and the temperature was 55° C. for the hydrazine reaction. 3-Morpholin-4-ylmethylphenylamine (0.192 g, 1.0 mmol) and potassium salt of 3-oxo-3-pyridin-4-ylpropionitrile (0.276 g, 1.5 mmol) yielded 0.117 g of the product (32%). MS (m/z, ES+): 364.4 (M+1. 100%).

H. In a similar manner, 5-pyridin-4-yl-4-(pyridin-3-ylhydrazono)-4H-pyrazol-3-ylamine was prepared. 3-Aminopyridine (0.57 g, 6.0 mmol) and potassium salt of 3-oxo-3-pyridin-4-ylpropionitrile (1.5 g, 8.3 mmole) yielded 0.117 g of the product (7%). MS (m/z, ES+): 266 (M+1, 65%).

I. In a similar manner, 4-[(3-fluorophenyl)hydrazono]-5-pyridin-4-yl-4H-pyrazol-3-ylamine was prepared. 3-Fluoroaniline (0.6 g, 5.4 mmol) and potassium salt of 3-oxo-3-pyridin-4-ylpropionitrile (1.5 g, 8.3 mmole) yielded 0.09 g of the product (6%). MS (m/z, ES+): 283 (M+1, 100%).

J. In a similar manner, 4-[(3-fluoro-4-methoxyphenyl)hydrazono]-5-pyridin-4-yl-4H-pyrazol-3-ylamine was prepared. 3-Fluoro-4-methoxyaniline (0.47 g, 3.3 mmol) and potassium salt of 3-oxo-3-pyridin-4-ylpropionitrile (1.0 g, 5.5 mmole) yielded 0.049 g of the product (5%). MS (m/z, ES+): 313 (M+1, 100%).

K. In a similar manner, 4-[(3,4-difluorophenyl)hydrazono]-5-pyridin-4-yl-4H-pyrazol-3-ylamine was prepared. 3,4-Difluoroaniline (0.31 g, 2.4 mmol) and potassium salt of 3-oxo-3-pyridin-4-ylpropionitrile (1.0 g, 5.5 mmole) yielded 0.071 g of the product (10%). MS (m/z, ES+): 301.4 (M+1, 100%), 287.3 (M−13, 40%).

L. In a similar manner, 4-[(3,4-difluoro-phenyl)hydrazono]-5-pyridin-3-yl-4H-pyrazol-3-ylamine was prepared. 3,4-Difluoroaniline (0.31 g, 2.4 mmol) and potassium salt of 3-oxo-3-pyridin-3-ylpropionitrile (1.5 g, 8.3 mmole) yielded 0.044 g of the product (6%). MS (m/z, ES+): 301.4 (M+1, 100%).

M. In a similar manner, 4-(phenylhydrazono)-5-pyridin-3-yl-4H-pyrazol-3-ylamine was prepared. Aniline (0.5 g, 5.4 mmol) and potassium salt of 3-oxo-3-pyridin-3-ylpropionitrile (1.5 g, 8.3 mmole) yielded 0.21 g of the product (15%). MS (m/z, ES+): 265 (M+1, 100%).

N. In a similar manner, 5-(2-fluorophenyl)-4-(phthalazin-5-ylhydrazono)-4H-pyrazol-3-ylamine was prepared. The potassium salt of 3-(2-fluorophenyl)-3-oxo-propionitrile was prepared from 2-fluorobenzoic acid methyl ester and acetonitrile in the presence of potassium tert-butoxide. 5-Aminophthalazine (0.25 g, 1.7 mmol) and potassium salt of 3-(2-fluorophenyl)-3-oxo-propionitrile (1.5 g, 7.5 mmol) yielded 0.022 g of the product (4%). MS (m/z, ES+): 334 (M+1, 45%).

O. In a similar manner, 4-(phenylhydrazono)-5-thiophen-2-yl-4H-pyrazol-3-ylamine was prepared. Aniline (0.5 g, 5.4 mmol) and 2-theonylacetonitrie (0.5 g, 3.3 mmole) yielded 0.08 g of the product (9%) after recrystallized from EtOH twice. MS (m/z, ES+): 270.8 (M+1, 100%).

P. In a similar manner, 5-(3-methoxythiophen-2-yl)-4-(phenylhydrazono)-4H-pyrazol-3-ylamine was prepared. The potassium salt of 3-(3-methoxythiophen-2-yl)-3-oxo-propionitrile was prepared from 3-methoxythiophene-2-carboxylic acid methyl ester and acetonitril in the presence of potassium tert-butoxide. Aniline (0.5 g, 3.4 mmol) and the potassium salt of 3-(3-methoxythiophen-2-yl)-3-oxopropionitrile (0.6 g, 7.5 mmol) yielded 0.17 g of the product (17%). MS (m/z, ES+): 300 (M+1, 100%).

Example 77

Preparation of 3-morpholin-4-ylmethylphenylamine

A. A solution of 1-bromomethyl-3-nitrobenzene (2.16 g, 10 mmol), morpholine (1.76 g, 20.2 mmol) and triethylamine (1.0 mL) in THF (60 mL) was heated for two hours at 60° C. The solvent was evaporated, water was added and the product was isolated by extraction with ether. The ether extract was dried over Mg$_2$SO$_4$ and the solvent was evaporated. The crystalline residue was used in the next step without further purification. The product, 4-(3-nitrobenzyl)morpholine, was obtained in 94% yield (2.09 g).

B. To a solution of 4-(3-nitrobenzyl)morpholine (2.0 g; 9.0 mmol) in THF/ethanol mixture (1:1, 50 mL) was added a catalytical amount of Raney-Ni and hydrazine hydrate (36.0 mmol) and the mixture was stirred for 15 min at ambient temperature, filtered through a celite pad and the filtrate was evaporated to provide pure 3-morpholin-4-ylmethylphenylamine (2.03 g, 98%).

In addition to the foregoing Preparations and Examples, the following compounds of the invention were prepared as set forth in the following Examples.

Example 78

Preparation of 3-Aminopyrazoles

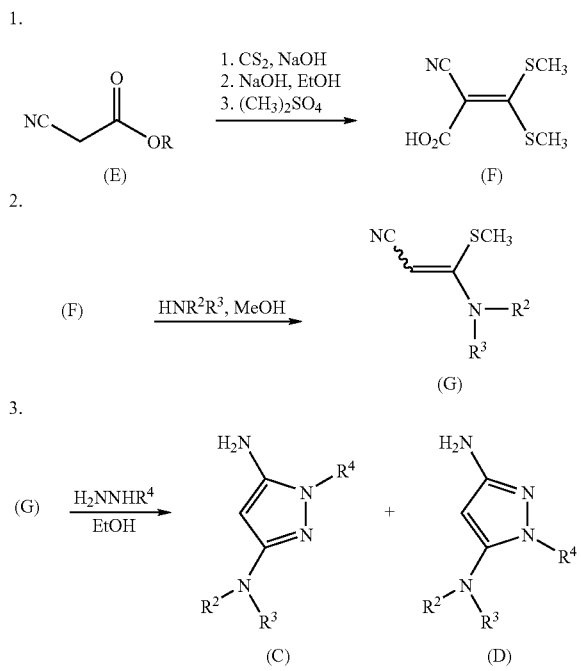

Substituted 3-aminopyrazoles of formulae (C) and/or (D) having a tertiary amine in the 5-position (formulae C or D), utilized in Reaction Scheme 1, were prepared from substituted 3-methylsulfanylacrylonitriles according to the preparation scheme herein, as known to those of ordinary skill in the art (see, e.g., Hendriksen, Lars *Acta Chem. Scand.* 1996, 50, 432). In this preparation, a cyanoacetate ester of formula (E) and carbon disulfide were reacted together in the presence of a suitable base such as NaOH. The ester of the resulting intermediate was hydrolyzed by reaction in a base such as NaOH, while thio groups were alkylated with a suitable alkylating agent such as dimethyl sulfate. The intermediate was then purified by recrystallization, affording a compound of formula (F).

The compound of formula (F) was then reacted with a suitable nucleophile, such as a secondary amine, in a solvent such as methanol, forming the substituted 3-methylsulfanylacrylonitrile of formula (G). The compound of formula (G) was then treated with hydrazine, as its hydrate or acid salt, or with a substituted hydrazine in a solvent such as ethanol, THF, or dioxane to produce the desired substituted aminopyrazoles of formulae (C) and/or (D). The crude material was purified by flash chromatography and was then precipitated from an organic solvent by the addition of an acid such as HCl to afford the products of formulae (C) and/or (D) as hydrochloride salts.

Example 79

Preparation of 3-Aminopyrazoles

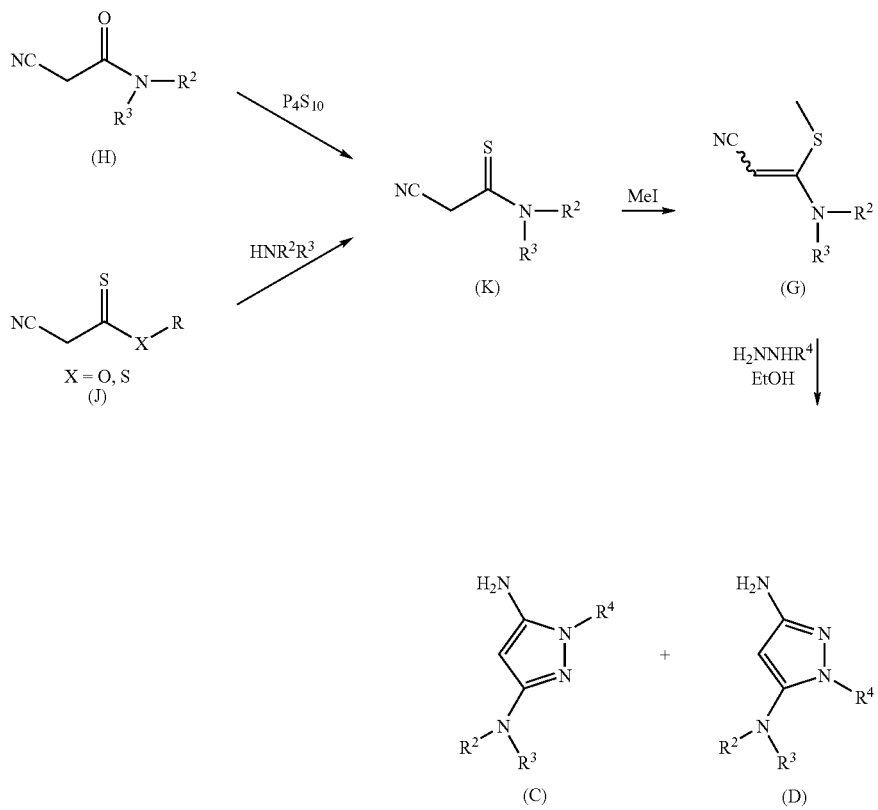

Substituted 3-aminopyrazoles of formulae (C) and/or (D) having a tertiary amine in the 5-position, utilized in Reaction Scheme 1, were also prepared according to the preparation scheme herein. A substituted methylthiopropionitrile of formula (G) was prepared by treating an appropriately substituted cyanoacetamide of formula (H) with a suitable sulfinating reagent such as $P_4S_{10}$ as reported in the literature (Heyde, C.; Zug, I.; Hartmann, H. *Eur. J. Org. Chem.* 2000, 19, 3273), to produce the intermediate compound of formula (K). Alternately, the compound of formula (K) can be prepared by reacting the appropriate secondary amine with a cyanothioacetate of formula (J) (Mueller, H.-G.; Hartke, K. *Arch. Pharm.* 1988, 321, 879) or a cyanodithioacetate (Wilken, J. et al, *Liebigs Ann. Org. Bioorg. Chem.*, 1996, 6, 927). The compound of formula (K) was then reacted with a suitable methylating reagent in the presence of a base to afford the substituted methylthiopropionitrile of formula (G) as described in the literature (Vishwakarma, J. N.; Thomas, A.; Apparao, S.; Ila, H.; Junjappa, H. *J. Chem. Soc. Perkin Trans* 1, 1988, 169). The compound of formula (G) was then further reacted to form 3-aminopyrazoles of formulae (C) and/or (D) as described hereinbefore.

Example 80

Preparation of 3-Aminopyrazoles

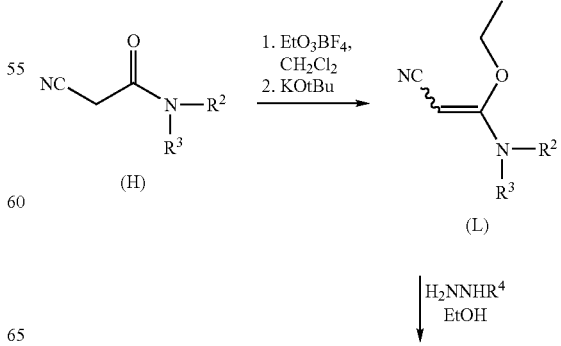

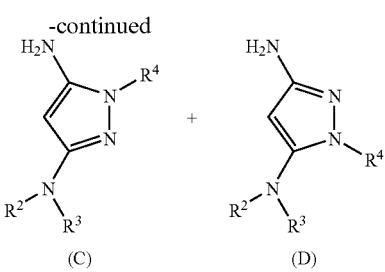

Substituted 3-aminopyrazoles of formulae (C) and/or (D) having a tertiary amine in the 5-position were also prepared according to the preparation scheme herein. A suitably substituted cyanoacetamide of formula (H) was reacted with triethyloxonium tetrafluoroborate in a suitable solvent such as $CH_2Cl_2$ followed by the reaction with a suitable base, such as potassium tert-butoxide, to form the vinyl ether intermediate of formula (L) as described in the literature (Bredereck, H.; et al. *Chem. Ber.* 1971, 104, 3475). The compound of formula (L) was then reacted with hydrazine, as its hydrate or acid salt, or with a substituted hydrazine in a solvent such as ethanol, THF, or dioxane, to produce the desired 3-aminopyrazole(s) of formulae (C) and/or (D). The crude material was purified by flash chromatography and then precipitated from an organic solvent by the addition of an acid such as HCl to afford the product(s) of formulae (C) and/or (D) as a hydrochloride salt.

Example 81

Preparation of
2-Cyano-3,3-bis-methylsulfanyl-acrylic acid

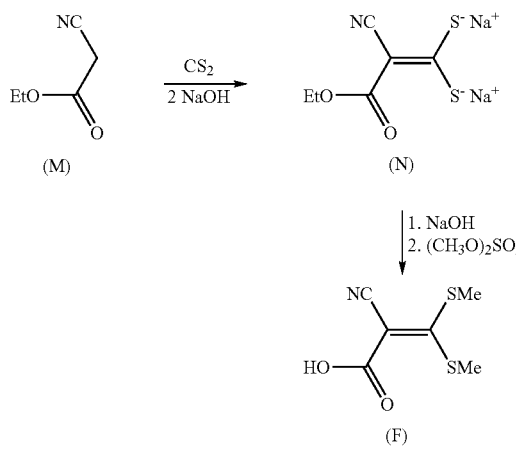

The 2-cyano-3,3-bis-methylsulfanyl-acrylic acid of compound (F) was prepared as described herein, according to the procedure found in the literature (Hendriksen, Lars *Acta Chem. Scand.* 1996, 50, 432). A reaction mixture containing the ethyl cyanoacetate of formula (M) (54 mL, 0.5 mol) and carbon disulfide (30 mL, 0.5 mol) in 600 mL of absolute ethanol was cooled to 0° C. A solution of NaOH (40 g, 1 mol) in 40 mL of water was added at a rate such that the temperature did not exceed 10° C. Once the addition was complete, the reaction was allowed to warm to ambient temperature for 10 minutes and was cooled to 5° C. again. The resulting precipitate was isolated by filtration, was washed with 100 mL of absolute ethanol and 500 mL of diethyl ether and dried under high vacuum. The synthesis was repeated on the same scale to afford a total of 259 g (wet weight) of solid compound of formula (N).

The compound of formula (N) (259 g, ~1 mol) was then introduced to a solution of NaOH (64.4 g, 1.41 mol) dissolved in 455 mL of water. The mixture was heated to 40° C. for 5 hours and was then allowed to cool to ambient temperature. The solution was diluted with 820 mL of absolute ethanol. The layers were separated. The lower layer was diluted with water to a total volume of 1550 mL. This solution was cooled to 5° C. and dimethyl sulfate was added (148 mL, 1.56 mol) at a rate such that the temperature could be maintained between 5° C. and 15° C. Once the addition was complete, the temperature was held at 15° C. for 20 minutes and then between 28-30° C. for 20 minutes. The solution was cooled to 15° C. and filtered. The filtrate was acidified with 4N HCl to pH 1.5-2. The resulting solid was isolated by filtration and washed with water. The solid was purified by recrystallization from water. The resulting solid was isolated by filtration and dried under vacuum to afford 35.0 g (19% yield) of 2-cyano-3,3-bis-methylsulfanyl-acrylic acid, the compound of formula (F).

Example 82

Preparation of
5-Morpholin-4-yl-2H-pyrazol-3-ylamine

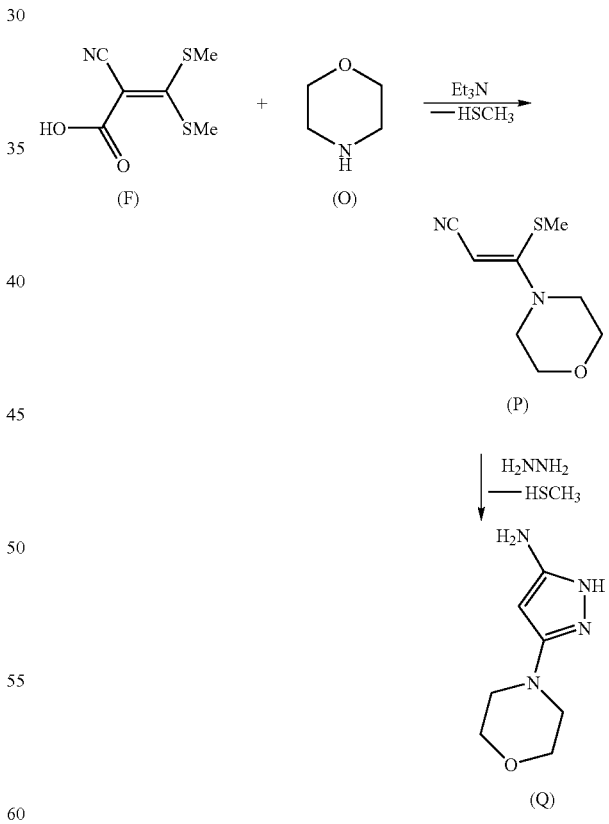

2-Cyano-3,3-bis-methylsulfanyl-acrylic acid (the compound of formula (F), 35 g, 0.18 mol) was dissolved in 250 mL of methanol. Morpholine (the compound of formula (O), 28 mL, 0.32 mol) and triethylamine (25 mL, 0.18 mol) were added to the solution while the temperature was maintained at approximately 20° C. The reaction was warmed slightly to a temperature of between 25-27° C. and this temperature was maintained overnight. The solvents were then removed under reduced pressure taking care not to heat the reaction mixture. The resulting crude material was filtered through a short silica gel column eluting with MeOH:CH$_2$Cl$_2$=1:5 to afford the 3-methylsulfanyl-3-morpholin-4-yl-acrylonitrile of formula (P).

The compound of formula (P) was then dissolved in 100 mL of absolute ethanol and was refluxed with hydrazine hydrate (25 mL, 0.50 mol) overnight. The solvents were removed under reduced pressure and the resulting crude material was purified on a short silica gel column eluting with MeOH:CH$_2$Cl$_2$=1:10 to 1:8 to afford a solid. This material was further purified by recrystallization from EtOAc/hexanes. The solid was dissolved in ethanol and concentrated HCl was added to form a precipitate. The solid was isolated by filtration to yield 9.5 g (26%) of the 5-morpholin-4-yl-2H-pyrazol-3-ylamine of formula (O), as its hydrochloride salt.

The following compounds were also prepared according to the preparation scheme described herein, with the noted exceptions:

5-Pyrrolidin-1-yl-2H-pyrazol-3-ylamine hydrochloride (2.2 g), prepared from the compound of formula (F) (10 g) and pyrrolidine instead of the compound of formula (O) (8 mL);

N$^3$,N$^3$-Dimethyl-1H-pyrazole-3,5-diamine hydrochloride (2.3 g), prepared from the compound of formula (F) (7 g) and dimethylamine instead of the compound of formula (O) (50 mL of a 2 M solution in THF);

5-(4-Methyl-piperazin-1-yl)-2H-pyrazol-3-ylamine (0.4 g), prepared from the compound of formula (F) (2.8 g) and 4-methylpiperazine instead of the compound of formula (O) (4.0 mL, with no addition of triethylamine).

Example 83

Preparation of 3-Pyrrolidin-1-ylmethylphenylamine

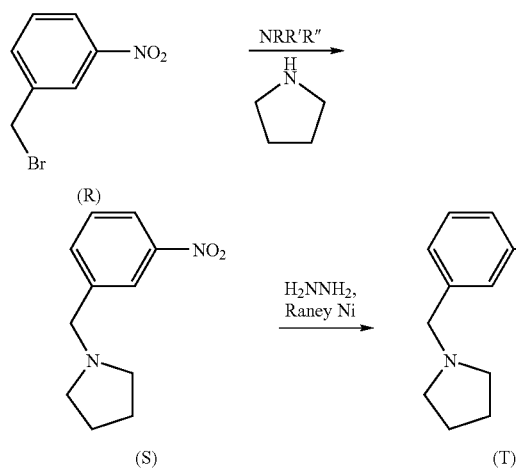

A solution of 1-bromomethyl-3-nitrobenzene (the compound of formula (R), 5 mmol, 1.08 g), pyrrolidine (11 mmol, 0.79 g), and 1.0 mL triethylamine (the compound of formula NRR'R" wherein R=R'=R"=ethyl) in THF (35 mL) was heated at 60° C. for 1 hour. The reaction mixture was allowed to cool to ambient temperature overnight with stirring. Water was then added to the reaction mixture and the product was extracted into diethyl ether. The ether layer was dried over sodium sulfate, filtered, and evaporated to yield 1.03 g (94%) of 1-(3-nitro-benzyl)-pyrrolidine (the compound of formula (S)) which was used in the following reaction without further purification.

The compound of formula (S) (1.03 g, 5.0 mmol) was then dissolved in 40 mL of a mixture of ethanol:THF (1:1) in a reaction vessel. Hydrazine hydrate (0.5 g, 10 mmol) and a catalytic amount of Raney nickel as a slurry in water were then charged to the reaction vessel. The reaction mixture was stirred at ambient temperature, and the reaction was allowed to proceed to completion as determined by TLC analysis. The reaction mixture was filtered through a pad of silica gel/celite. The pad was rinsed with ethanol and the ethanol fractions were combined and evaporated to yield 0.76 g (87%) of the title compound of formula (T).

The following compounds were also prepared according to the preparation scheme described herein, with the noted exceptions:

3-Dimethylaminomethylphenylamine (0.25 g), prepared from the compound of formula (R) (0.43 g), and dimethylamine instead of triethylamine (5 mL of a 2M solution in THF), in the absence of pyrrolidine;

3-Morpholin-4-ylmethyl-phenylamine (2.7 g), prepared from the compound of formula (R) (0.4.3 g), triethylamine (2.0 mL), and morpholine instead of pyrrolidine (3.5 g).

Example 84

Preparation of 3-Amino-N-methyl-benzenesulfonamide

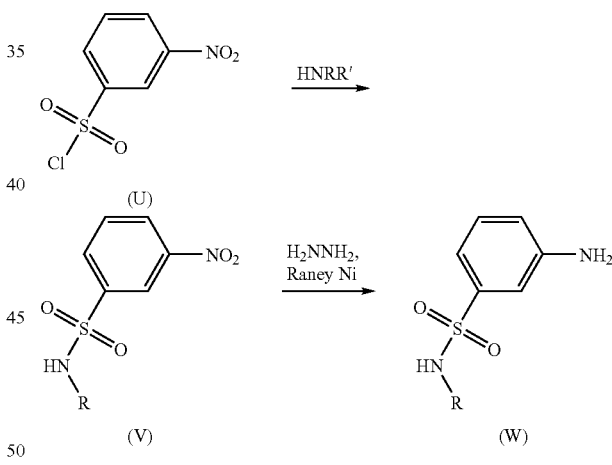

A reaction vessel charged with 3-nitro-benzenesulfonyl chloride (the compound of formula (U), 4.42 g, 20.0 mmol) in 150 mL of dry THF at 0° C. was further charged with methylamine (25.0 mL of a 2M solution in THF, 50 mmol, represented by the formula HNRR' wherein R=H and R'=methyl). The resulting cloudy solution was stirred overnight at ambient temperature. The reaction mixture was then diluted with 150 mL of saturated sodium chloride solution and 50 mL of ethyl acetate. The layers were separated and the aqueous phase was extracted twice with 50 mL of ethyl acetate. The combined organic layers were dried over sodium sulfate, filtered, concentrated under reduced pressure. The resulting crude material was purified by recrystallization from ethanol to yield 4.20 g (19.5 mmol) of N-methyl-3-nitrobenzenesulfonamide, the compound of formula (V) wherein R is methyl.

A reaction vessel charged with the prepared N-methyl-3-nitro-benzenesulfonamide (4.2 g, 19.42 mmol) in 150 ml of ethyl acetate was further charged with 450 mg of 10% palladium on carbon. The reaction mixture was stirred under hydrogen atmosphere for 48 h, then was filtered through a pad of silica gel washing with EtOAc, and the filtrate was concentrated under reduced pressure. The free base was acidified to give 2.1 g, (~11 mmol, 58% yield) of the title compound (a compound of formula (W) wherein R is methyl) as its HCl-salt.

The following compound was also prepared according to the preparation scheme described herein, with the noted exceptions:

3-Amino-N-(2-hydroxyethyl)-benzenesulfonamide (1.1 g), prepared from the compound of formula (U) (2.0 g), and ethanolamine instead of methylamine (2.0 g).

Example 85

Synthesis of Phthalazine-5-ylamine

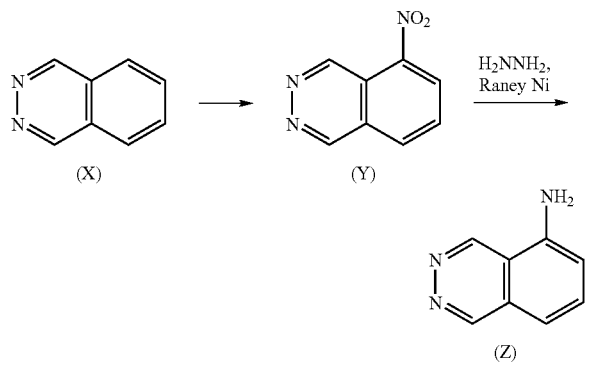

The 5-nitrophthalazine of formula (Y) was prepared according to prior art literature (Patrick, J.; Ragunathan, R., *J. Chem. Soc. Perkin Trans. I,* 1993, 211). A reaction vessel charged with phthalazine (the compound of formula (X), 4.0 g, 30 mmol) in conc. 96% sulfuric acid (30 mL) was further charged with potassium nitrate (14.6 g, 144 mmol) in small portions. Once the addition was complete, the solution was heated to 110° C. overnight. The mixture was then poured over ice and neutralized with sodium hydroxide solution resulting in the formation of a precipitate. The solid was isolated by filtration to yield 2.5 g (47%) of 5-nitrophthalazine of formula (Y) which was used in the following reaction without further purification.

A reaction vessel was charged with the 5-nitrophthalazine (1.9 g, 10.9 mmol) prepared above, dissolved in a mixture of 60 mL of ethanol:THF (5:1). Hydrazine hydrate (2.5 g, 25 mmol) was added to the reaction mixture followed by a catalytic amount of Raney nickel as a slurry in water. The reaction mixture was stirred at ambient temperature for 4 hours. The reaction mixture was then passed through a pad of silica gel/celite which was washed with ethanol. The ethanol fractions were combined and evaporated to yield 1.2 g (79%) of the title compound of formula (Z).

Example 86

Preparation of 6-Methylpyridin-3-ylamine

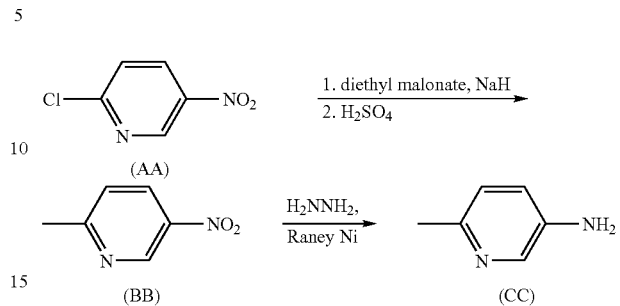

The 2-methyl-5-nitropyridine of formula (BB) was prepared according to prior art literature (Odashima, T.; Sakakura, K.; Kohata, K.; Ishii, H., *Bull. Chem. Soc. Jpn.,* 1993, 66, 797 and references therein). A reaction vessel charged with diethyl malonate (12.5 g, 78.0 mmol) in diethyl ether (450 mL) was further charged with sodium hydride (3.2 g of a 60% slurry in mineral oil, 79 mmol). When the evolution of hydrogen gas subsided, the 2-chloro-5-nitropyridine of formula (AA) (12.5 g, 79.0 mmol) was charged to the vessel with stirring. The solvent was then removed by evaporation and the red, tarry residue was heated to 110° C. for 1 hour. At this point, 6 M $H_2SO_4$ (90 mL) was charged to the vessel and the mixture was heated to reflux overnight. The solution was cooled in an ice bath and was neutralized with potassium hydroxide solution. The solids were removed by filtration and washed with chloroform. The filtrate was extracted with chloroform and the combined chloroform fractions were evaporated. The resulting crude material was purified by flash chromatography to yield 6.1 g (56%) of the 2-methyl-5-nitropyridine of formula (BB) as a pale orange solid.

A reaction vessel charged with the 2-methyl-5-nitropyridine prepared above (0.63 g, 4.5 mmol), dissolved in ethanol (30 mL), was further charged with hydrazine hydrate (0.3 g, 6.0 mmol) and a catalytic amount of Raney nickel as a slurry in water. The mixture was stirred at ambient temperature for 2 hours. The solution was then passed through a pad of silica gel/celite. The pad was then washed with ethanol and the combined ethanol fractions were evaporated to yield 0.46 g, 94%) of the title compound of formula (CC).

Example 87

A. General procedure: The appropriate arylamine or heteroarylamine (1.5 mmol) in 3 mL of water was acidified with concentrated HCl (0.5 mL, 6 mmol). The resulting solution was cooled to 0° C. and a solution of sodium nitrite (0.12 g, 1.7 mmol) in approximately 0.5 mL of water was added. This mixture was then added to a solution of the appropriate 5-substituted 2H-pyrazol-3-ylamine as its free base or its hydrochloride salt (1.4 mmol) and sodium acetate trihydrate (3.5 g, 25 mmol) in 10 mL of water at 10° C. After 30 minutes, the resulting solid was isolated by filtration. The crude material was purified by recrystallization or by flash chromatography.

B. The following compounds were prepared similarly to the procedure described above in Paragraph A.

4-[(3-Fluoro-phenyl)-hydrazono]-5-morpholin-4-yl-4H-pyrazol-3-ylamine (0.1 g) was prepared from 0.18 g (1.6 mmol) 3-fluoroaniline and 0.23 g (1.4 mmol) 5-morpholin-4-yl-2H-pyrazol-3-ylamine. MS (m/z, ES+): 291.7 (M+1, 100%). Yield=25%;

5-Morpholin-4-yl-4-(phenyl-hydrazono)-4H-pyrazol-3-ylamine (0.050 g) was prepared from 0.2 g (2.1 mmol) aniline and 0.25 g (1.5 mmol) 5-morpholin-4-yl-2H-pyrazol-3-ylamine. MS (m/z, ES+): 273.2 (M+1, 100%); $^1$H NMR (200 MHz, ppm, DMSO-$d_6$): δ 11.15 (br s, 1H), 7.6 (d, 2H), 7.45 (t, 2H), 7.25 (t, 1H), 7.15 (br s, 2H), 3.75 (br t, 4H), 3.5 (br s, 4H). Yield=12%;

4-[(6-Chloropyridin-3-yl)-hydrazono]-5-morpholin-4-yl-4H-pyrazol-3-ylamine (0.012 g) was prepared from 0.05 g (0.4 mmol) 4-amino-2-chloropiridine and 0.03 g (0.18 mmol) 5-morpholin-4-yl-2H-pyrazol-3-ylamine. MS (m/z, ES+): 308.1 (M+1, 100%). Yield=23%;

5-Morpholin-4-yl-4-(pyridin-3-yl-hydrazono)-4H-pyrazol-3-ylamine (0.033 g) was prepared from 0.11 g (1.2 mmol) 3-aminopyridine and 0.13 g (0.77 mmol) 5-morpholin-4-yl-2H-pyrazol-3-ylamine. MS (m/z, ES+): 274.2 (M+1, 100%). Yield=16%;

5-Morpholin-4-yl-4-(phthalazin-5-yl-hydrazono)-4H-pyrazol-3-ylamine (0.020 g) was prepared from 0.2 g (1.4 mmol) 5-aminophthalazine and 0.3 g (1.46 mmol) 5-morpholin-4-yl-2H-pyrazol-3-ylamine hydrochloride. MS (m/z, ES+): 325.1 (M+1, 100%). Yield=4%;

4-[(3-Fluoro-4-methoxyphenyl)-hydrazono]-5-morpholin-4-yl-4H-pyrazol-3-ylamine (0.38 g) was prepared from 0.30 g (2.1 mmol) 3-fluoro-4-methoxyphenylamine and 0.50 g (2.4 mmol) 5-morpholin-4-yl-2H-pyrazol-3-ylamine hydrochloride. MS (m/z, ES+): 321.1 (M+1, 100%). Yield=57%;

3-[N'-(3-Amino-5-morpholin-4-yl-pyrazol-4-ylidene)-hydrazino]-benzenesulfonamide (0.27 g) was prepared from 0.40 g (2.3 mmol) 3-amino-benzenesulfonamide and 0.50 g (2.4 mmol) 5-morpholin-4-yl-2H-pyrazol-3-ylamine hydrochloride. MS (m/z, ES+): 352.1 (M+1, 100%). Yield=30%;

3-[N'-(3-Amino-5-morpholin-4-yl-pyrazol-4-ylidene)-hydrazino]-N-methyl-benzenesulfonamide (0.11 g) was prepared from 0.45 g (2.4 mmol) 3-amino-N-methyl-benzenesulfonamide and 0.50 g (2.4 mmol) 5-morpholin-4-yl-2H-pyrazol-3-ylamine hydrochloride. MS (m/z, ES+): 366.1 (M+1, 100%). Yield=13%;

3-[N'-(3-Amino-5-morpholin-4-yl-pyrazol-4-ylidene)-hydrazino]-N-(2-hydroxyethyl)-benzenesulfonamide (0.18 g) was prepared from 0.50 g (2.3 mmol) 3-amino-N-(2-hydroxyethyl)-benzenesulfonamide and 0.40 g (2.4 mmol) 5-morpholin-4-yl-2H-pyrazol-3-ylamine hydrochloride. MS (m/z, ES+): 396.1 (M+1, 100%). Yield=20%;

4-[(6-Methyl-pyridin-3-yl)-hydrazono]-5-morpholin-4-yl-4H-pyrazol-3-ylamine (0.52 g) was prepared from 0.43 g (3.0 mmol) 6-methylpyridin-3-ylamine hydrochloride and 0.50 g (2.5 mmol) 5-morpholin-4-yl-2H-pyrazol-3-ylamine hydrochloride. MS (m/z, ES+): 288.1 (M+1, 100%). Yield=60%;

4-[N'-(3-Amino-5-pyrrolidin-1-yl-pyrazol-4-ylidene)-hydrazino]-benzenesulfonamide (0.021 g) was prepared from 0.28 g (1.6 mmol) 4-aminosulfonamide and 0.19 g (1.0 mmol) 5-morpholin-4-yl-2H-pyrazol-3-ylamine hydrochloride. MS (m/z, ES+): 336 (M+1, 100%). Yield=6%;

5-Pyrrolidin-1-yl-4-[(3-trifluoromethyl-phenyl)-hydrazono]-4H-pyrazol-3-ylamine (0.093 g) was prepared from 0.21 g (1.3 mmol) 3-trifluoromethylphenylamine and 0.20 g (1.1 mmol) 5-pyrrolidin-1-yl-2H-pyrazol-3-ylamine hydrochloride. MS (m/z, ES+): 325.1 (M+1, 100%). Yield=22%;

3-[N'-(3-Amino-5-pyrrolidin-1-yl-pyrazol-4-ylidene)-hydrazino]-N-methyl-benzenesulfonamide (0.13 g) was prepared from 0.29 g (1.3 mmol) 3-amino-N-methyl-benzenesulfonamide and 0.20 g (1.1 mmol) 5-pyrrolidin-1-yl-2H-pyrazol-3-ylamine hydrochloride. MS (m/z, ES+): 350.1 (M+1, 100%). Yield=28%;

5-Pyrrolidin-1-yl-4-(quinolin-6-yl-hydrazono)-4H-pyrazol-3-ylamine (0.074 g) was prepared from 0.19 g (1.3 mmol) 6-aminoquinoline and 0.20 g (1.1 mmol) 5-pyrrolidin-1-yl-2H-pyrazol-3-ylamine hydrochloride. MS (m/z, ES+): 308.3 (M+1, 100%). Yield=19%;

3-[N'-(3-Amino-5-pyrrolidin-1-yl-pyrazol-4-ylidene)-hydrazino]-benzenesulfonamide (0.21 g) was prepared from 0.23 g (1.3 mmol) 3-aminobenzenesulfonamide and 0.20 g (1.1 mmol) 5-pyrrolidin-1-yl-2H-pyrazol-3-ylamine hydrochloride. MS (m/z, ES+): 336.1 (M+1, 100%). Yield=49%;

4-[(6-Chloro-pyridin-3-yl)-hydrazono]-5-pyrrolidin-1-yl-4H-pyrazol-3-ylamine (0.024 g) was prepared from 0.17 g (1.3 mmol) 6-chloropyridin-3-ylamine and 0.2 g (1.1 mmol) 5-pyrrolidin-1-yl-2H-pyrazol-3-ylamine hydrochloride. MS (m/z, ES+): 292.5 (M+1, 100%). Yield=6%;

4-[(3-Fluoro-phenyl)-hydrazono]-5-pyrrolidin-1-yl-4H-pyrazol-3-ylamine (0.070 g) was prepared from 0.15 g (1.3 mmol) 3-fluoroaniline and 0.20 g (1.1 mmol) 5-pyrrolidin-1-yl-2H-pyrazol-3-ylamine hydrochloride. MS (m/z, ES+): 275.1 (M+1, 100%). Yield=20%;

5-Pyrrolidin-1-yl-4-[(3-pyrrolidin-1-ylmethyl-phenyl)-hydrazono]-4H-pyrazol-3-ylamine (0.12 g) was prepared from 0.15 g (0.85 mmol) 3-pyrrolidin-1-ylmethylphenylamine and 0.20 g (1.1 mmol) 5-pyrrolidin-1-yl-2H-pyrazol-3-ylamine hydrochloride. MS (m/z, ES+): 340.2 (M+1, 100%). Yield=42%;

4-[(3-Morpholin-4-ylmethyl-phenyl)-hydrazono]-5-pyrrolidin-1-yl-4H-pyrazol-3-ylamine (0.15 g) was prepared from 0.25 g (1.3 mmol) 3-morpholin-4-ylmethylphenylamine and 0.20 g (1.1 mmol) 5-pyrrolidin-1-yl-2H-pyrazol-3-ylamine hydrochloride. MS (m/z, ES+): 356.2 (M+1, 100%). Yield=33%;

4-[(6-Fluoro-pyridin-3-yl)-hydrazono]-5-pyrrolidin-1-yl-4H-pyrazol-3-ylamine (0.030 g) was prepared from 0.16 g (1.0 mmol) 6-fluoro-pyridin-3-ylamine and 0.2 g (1.1 mmol) 5-pyrrolidin-1-yl-2H-pyrazol-3-ylamine hydrochloride. MS (m/z, ES+): 276.1 (M+1, 100%). Yield=11%;

3-[N'-(3-Amino-5-dimethylamino-pyrazol-4-ylidene)-hydrazino]-benzenesulfonamide (0.12 g) was prepared from 0.23 g (1.3 mmol) 3-aminosulfonamide and 0.20 g (1.2 mmol) $N^3,N^3$-dimethyl-1H-pyrazole-3,5-diamine hydrochloride. MS (m/z, ES+): 310.1 (M+1, 100%). Yield=30%;

N,N-Dimethyl-4-(quinolin-6-yl-hydrazono)-4H-pyrazole-3,5-diamine (0.025 g) was prepared from 0.19 g (1.3 mmol) 6-aminoquinoline and 0.20 g (1.2 mmol) $N^3,N^3$-dimethyl-1H-pyrazole-3,5-diamine hydrochloride. MS (m/z, ES+): 282.1 (M+1, 100%). Yield=7%;

4-[(6-Chloro-pyridin-3-yl)-hydrazono]-N,N-dimethyl-4H-pyrazole-3,5-diamine (0.066 g) was prepared from 0.17 g (1.3 mmol) 6-chloropyridin-3-ylamine and 0.2 g (1.2 mmol) $N^3,N^3$-dimethyl-1H-pyrazole-3,5-diamine hydrochloride. MS (m/z, ES+): 266.1 (M+1, 100%). Yield=19%;

4-[(3-Fluoro-phenyl)-hydrazono]-N,N-dimethyl-4H-pyrazole-3,5-diamine (0.15 g) was prepared from 0.15 g (1.3 mmol) 3-fluoroaniline and 0.20 g (1.2 mmol) $N^3,N^3$-dimethyl-1H-pyrazole-3,5-diamine hydrochloride. MS (m/z, ES+): 249.1 (M+1, 100%). Yield=45%;

{3-[N'-(3-Amino-5-dimethylaminopyrazol-4-ylidene)-hydrazino]-5-trifluoromethylphenyl}-methanol (0.25 g) was prepared from 0.25 g (1.3 mmol) (3-amino-5-trifluoromethylphenyl)-methanol and 0.20 g (1.2 mmol) $N^3,N^3$-dimethyl-1H-pyrazole-3,5-diamine hydrochloride. MS (m/z, ES+): 329.1 (M+1, 100%). Yield=59%;

N,N-Dimethyl-4-[(3-morpholin-4-ylmethylphenyl)-hydrazono]-4H-pyrazole-3,5-diamine (0.14 g) was prepared from 0.25 g (1.3 mmol) 3-morpholin-4-ylmethylphenylamine and 0.20 g (1.2 mmol) $N^3,N^3$-dimethyl-1H-pyrazole-3,5-diamine hydrochloride. MS (m/z, ES+): 330.2 (M+1, 100%). Yield=33%;

4-[(6-Fluoro-pyridin-3-yl)-hydrazono]-N,N-dimethyl-4H-pyrazole-3,5-diamine (0.030 g) was prepared from 0.16 g (1.0 mmol) 6-fluoropyridin-3-ylamine and 0.20 g (1.2 mmol) $N^3,N^3$-dimethyl-1H-pyrazole-3,5-diamine hydrochloride. MS (m/z, ES+): 250 (M+1, 100%); Yield=12%;

4-[(3-Dimethylaminomethylphenyl)-hydrazono]-5-morpholin-4-yl-4H-pyrazol-3-ylamine (0.030 g) was prepared from 0.16 g (1.0 mmol) 3-dimethylaminomethylphenylamine and 0.20 g (1.2 mmol) $N^3,N^3$-dimethyl-1H-pyrazole-3,5-diamine hydrochloride. MS (m/z, ES+): 330.1 (M+1, 100%). Yield=7%;

3-[N'-(3-Amino-5-dimethylaminopyrazol-4-ylidene)-hydrazino]-N-methyl-benzenesulfonamide (0.26 g) was prepared from 0.23 g (1.3 mmol) 3-amino-N-methyl-benzenesulfonamide and 0.35 g (2.15 mmol) $N^3,N^3$-dimethyl-1H-pyrazole-3,5-diamine hydrochloride. MS (m/z, ES+): 324.1 (M+1, 100%). Yield=65%;

N,N-Dimethyl-4-(pyridin-3-yl-hydrazono)-4H-pyrazole-3,5-diamine (0.17 g) was prepared from 0.56 g (6.0 mmol) 3-amino-N-methyl-benzenesulfonamide and 0.5 g (3.1 mmol) $N^3,N^3$-dimethyl-1H-pyrazole-3,5-diamine hydrochloride. MS (m/z, ES+): 232.5 (M+1, 100%). Yield=24%;

N,N-Dimethyl-4-(phthalazin-5-yl-hydrazono)-4H-pyrazole-3,5-diamine (0.050 g) was prepared from 0.40 g (2.8 mmol) 5-aminophthalazine and 0.40 g (2.4 mmol) $N^3,N^3$-dimethyl-1H-pyrazole-3,5-diamine hydrochloride. MS (m/z, ES+): 283.1 (M+1, 100%). Yield=7%;

4-{N'-[3-Amino-5-(4-methylpiperazin-1-yl)-pyrazol-4-ylidene]-hydrazino}-benzenesulfonamide (0.030 g) was prepared from 0.55 g (3.2 mmol) 4-aminosulfonamide and 0.40 g (2.2 mmol) 5-(4-methylpiperazin-1-yl)-2H-pyrazol-3-ylamine. MS (m/z, ES+): 365.1 (M+1, 100%). Yield=4%;

5-(4-Methylpiperazin-1-yl)-4-(phenylhydrazono)-4H-pyrazol-3-ylamine dihydrochloride (0.050 g) was prepared from 0.33 g (3.5 mmol) aniline and 0.2 g (1.1 mmol) 5-(4-methylpiperazin-1-yl)-2H-pyrazol-3-ylamine. MS (m/z, ES+): 286.1 (M+1, 100%). Yield=16%.

Example 88

This example illustrates the preparation of representative pharmaceutical compositions for oral administration containing a compound of the invention, or a pharmaceutically acceptable salt thereof:

| A. Ingredients | % wt./wt. |
|---|---|
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
|---|---|
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
|---|---|
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. Ingredients | % wt./wt. |
|---|---|
| Compound of the invention | 20.0% |
| Peanut Oil | 78.0% |
| Span 60 | 2.0% |

The above ingredients are melted, mixed and filled into soft elastic capsules.

| E. Ingredients | % wt./wt. |
|---|---|
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

Example 89

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

Example 90

This example illustrates the preparation of a representative pharmaceutical composition in suppository form containing a compound of the invention, or a pharmaceutically acceptable salt thereof:

| Ingredients | % wt./wt. |
| --- | --- |
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

Example 91

This example illustrates the preparation of a representative pharmaceutical formulation for insufflation containing a compound of the invention, or a pharmaceutically acceptable salt thereof:

| Ingredients | % wt./wt. |
| --- | --- |
| Micronized compound of the invention | 1.0% |
| Micronized lactose | 99.0% |

The ingredients are milled, mixed, and packaged in an insufflator equipped with a dosing pump.

Example 92

This example illustrates the preparation of a representative pharmaceutical formulation in nebulized form containing a compound of the invention, or a pharmaceutically acceptable salt thereof:

| Ingredients | % wt./wt. |
| --- | --- |
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

Example 93

This example illustrates the preparation of a representative pharmaceutical formulation in aerosol form containing a compound of the invention, or a pharmaceutically acceptable salt thereof:

| Ingredients | % wt./wt. |
| --- | --- |
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

The following Examples are directed to various in vitro and in vivo assays which can be utilized by one of ordinary skill in the art to determine the desired pharmaceutical activity of the compounds of the invention.

Example 94

In Vitro Screen

Compounds of the invention were screened using a series of disease related kinase targets, such as integrin linked kinase-1. Synthesized libraries of compounds are tested against each of the targets to find compounds that inhibit one of the targets preferentially. The desired in vitro potency of the inhibitor is such that the compound is useful as a therapeutic agent, i.e. in the nanomolar or micromolar range.

Inhibition of the targets is measured by scintillation counting; the incorporation of radioactive phosphate onto a specific substrate which is immobilized onto a filter paper at the end of the assay. To provide meaningful measurements of inhibition, the assays are performed both in the absence and presence of specific and known inhibitors, and the amount of incorporated radioactivity is compared to provide a baseline measurement.

The baseline activity is the amount of radioactivity incorporated in the absence of inhibitor. The amount of radioactivity incorporated in the presence of an inhibitor is called the 'sample activity', and the % inhibition is expressed by the following formula:

% inhibition=100−(sample activity/baseline activity× 100)

and is usually expressed in conjunction with the compound concentration. By using a range of inhibitor concentrations, the $IC_{50}$ of an inhibitor is estimated (i.e., the concentration at which enzymatic activity is reduced by 50%). The $IC_{50}$ of various compounds against a particular target can be compared, where a lower $IC_{50}$ indicates a more potent compound.

Materials and Methods:

Inhibition Assay: Compounds of the invention were lyophilized and stored at −20° C. Stock solutions were made by weighing out the compounds and dissolving them in dimethyl sulfoxide (DMSO) to a standard concentration, usually 20 mM, and stored at −20° C. The compounds were diluted to a starting intermediate concentration of 250 μM in 1% DMSO, then serially diluted across a row of a 96 well plate using serial 2 fold dilution steps. Diluted 100% DMSO was used as a negative control.

5 μl of each compound dilution were robotically pipetted to Costar serocluster plates maintaining the same plate format. All assays consisted of the following volumes:

5 μl diluted compound
10 μl enzyme preparation
5 μl substrate
5 μl assay ATP and were then incubated 15 minutes at ambient temperature.

From each reaction, 10 µl of reaction mix was spotted onto Millipore Multiscreen-PH opaque plates and washed 2×10 minutes in 1% phosphoric acid. The plates were dried for at 40° C. for 30 min, then the substrate phosphate complexes were quantitated by scintillation counting. These Millipore plates are in a 96 well format with immobilized P81 phosphocellulose membranes. Both the phosphorylated and non-phosphorylated form of the substrate bind to the membrane while ATP (unincorporated phosphate) is removed in the subsequent wash steps. Results are shown in Table 1 below.

Integrin Linked Kinase: The target integrin linked kinase is a full-length recombinant protein expressed in sF9 insect cells by baculovirus infection. The ILK1 substrate is CKRRRLASLR-amide.

Recombinant ILK protein was expressed using cultured insect cells and a baculovirus expression system. Standard techniques for DNA manipulation were used to produce recombinant DNA molecules and baculoviruses (Sambrook. J., Fritsch, E. F. and Maniatis, T. 1989, *Molecular cloning, a laboratory manual*. Second edition. Cold Spring Harbor Laboratory Press. NY; Crossen, R. and Gruenwald, S. 1998. Baculovirus expression Vector System Manual. $5^{th}$ Edition. Pharmingen, San Diego, Calif.) but the isolation of active ILK required some ingenuity.

The ILK open reading frame (Hannigan et al., supra.), excluding the 5' and 3' untranslated regions, was inserted into the baculovirus transfer vector pAcG2T (Pharmingen) to produce a GST fusion protein under the control of the strong AcNPV polyhedrin promoter. A large scale plasmid preparation of the resulting transfer construct was made using a Qiagen Plasmid Midi Kit. This ILK transfer construct was then co-transfected with BaculoGold DNA (Pharmingen) into Sf9 insect cells (Invitrogen) and a high titre preparation of GST-ILK recombinant baculovirus was produced by amplification in Sf9 cells. Liter scale expression of GST-ILK recombinant protein was done in 1000 mL spinner flasks (Bellco) by infection of Hi5 insect cells (Invitrogen) grown in Ex-Cell 400 Serum Free Media (JRH Biosciences) at a multiplicity of infection of approximately 5. The cells were harvested three days after infection and lysed in Hypotonic Lysis Buffer (HLB; 10 mM imidazole, 5 mM EDTA, 0.1% β-mercaptoethanol, 10 µg/mL PMSF, 1 mM benzamidine) by sonication. The lysate was centrifuged at 10,000 g for 20 minutes and the supernatant was discarded. The pellet was washed twice in HLB and then washed twice in High Salt Buffer ("HSB"; 500 mM NaCl, 10 mM imidazole, 5 mM EDTA, 0.1% β-mercaptoethanol, 10 µg/ml PMSF, 1 mM benzamidine). The pellet was then resuspended in DNAse-ATP Buffer ("DAB"; 10 mM $MgCl_2$, 1 mM $MnCl_2$, β-methyl aspartic acid, 2 mM NaF, 0.55 mg/mL ATP, 1 µg/mL DNAse I, 1% NP40, 10 mM imidazole, 5 mM EDTA, 0.1% β-mercaptoethanol, 10 µg/mL PMSF, 1 mM benzamidine) and stirred for 30 minutes at ambient temperature, and then centrifuged at 10,000×g for 20 min. The pellet was resuspended in High Salt Detergent buffer ("HDB"; 1% NP40, 1% Triton X-100, 500 mM NaCl, 10 mM imidazole, 5 mM EDTA, 0.1% β-mercaptoethanol, 10 µg/mL PMSF, 1 mM benzamidine), stirred for 30 minutes at ambient temperature, and then centrufuged at 10,000 g for 20 min. The pellet was then washed once in each of HDB, HSB, and HLB, centrifuging at 10,000 g each time. Finally, the pellet was resuspended in HLB.

The recombinant ILK expressed in insect cells with a baculovirus system was solubilized by treating the insoluble ILK protein with DNAse I and detergents. This produced an ILK protein preparation in the form of a microparticle suspension. This preparation had a high specific activity and was amenable to automated kinase assays.

The compounds of the invention, when tested in the above assay, demonstrated the ability to inhibit ILK.

Example 95

Western Blot Analysis of Phospho-PKB/Akt

The phospho-PKB/Akt Ser473 status of tumor cells was determined by Western blotting of cell lysates. PC3 tumor cells were grown to 60-80% confluency in complete media (DMEM with 10% fetal bovine serum). On day one, the cells were trypsinized, washed and resuspended in complete media at a concentration of $4 \times 10^4$ cells/mL. Then, 2 mL/well of this suspension was seeded into a six-well plate and incubated overnight at 37° C. and 5% $CO_2$. The objective was to obtain cells at about 40% confluency in 24 hours and 60-80% confluency after 48 hours of growth. On day two, the cells were checked for complete adherence. Then the media was aspirated from each well and replaced with serum free media (DMEM only). The plates were incubated at 37° C. and 5% $CO_2$ overnight again. On day 3, media was aspirated from each well again, replaced with serum free media, and test compound treatments were added. Test compounds (i.e., compounds of the invention) were made up as 20 mM 100% DMSO stocks and these are diluted to 2 mM working solutions in serum free media. Then, the 2 mM working solutions were diluted to a final treatment concentration of 12.5 µM by adding 12.5 µL to 2 mL of media in the 6-well plates. The treated plates were incubated at 37° C. and 5% $CO_2$ for 3 hours.

Treated cells in 6-well plates were put on a sloped bed of ice and the media was aspirated off. The cells were rinsed with 500 µL of ice cold phosphate buffered saline, and this was aspirated again. Then, 200 µL of SDS PAGE sample buffer (2% sodium docecyl sulfate, 62.5 µM Tris pH 6.8, 10% glycerol, 5% β-mercaptoethanol, 0.0025% bromophenol blue) was added and cells were scraped with a rubber-tipped cell scraper. The lysates were transferred into a 1.7 mL microfuge tube and stored frozen at –20° C. The SDS PAGE procedure was carried out on a Hoefer SE600 electrophoresis system. The frozen cell lysates were denatured for 5 minutes in a boiling water bath and pulse centrifuged for 10 seconds. Approximately 80 µL or 20 µg of total protein was loaded into a 15-well 11×15 cm 10% acrylamide separating gel. Equal sample loading was accomplished by pilot experiments to verify amount and consistency of protein loading by Western blotting with the nonphospho protein antibody. The gel was run overnight at ambient temperature in 1× running buffer (15% glycine, 1% SDS, 25 mM Tris base) with 9 mA applied. Then the gel was transferred to nitrocellulose in a Transphor apparatus with 1× transfer buffer (9% glycine, 20 mM Tris base) at a current of 400 mA for 3 hours at 4° C.

The membrane was blocked for 1 hour at ambient temperature in blocking solution (5% nonfat dry skim milk powder in 20 µM Tris, 250 µM NaCl, 0.05% Tween). The blot was then washed 3 times for 5 minutes each in TTBS (20 µM Tris, 250 µM NaCl, 0.05% Tween), then incubated overnight at 4° C. with primary antibody polyclonal phospho-PKB/Akt Ser473 diluted 1:750 in TTBS. The membrane was then washed 3 times for 5 minutes each at ambient temperature with TTBS. The blot was then incubated with secondary antibody goat anti-rabbit HRP conjugated IgG diluted 1:5000 in TTBS for 45 minutes at ambient temperature, followed by one quick TTBS rinse, another 2 washes for 15 minutes each in TTBS, and a final 20 minutes wash in TBS. To image the membrane, it was placed into freshly prepared ECL solution, sandwiched in clear plastic wrap, and exposed to film for 30 secends to 10 minutes, depending upon the strength of the luminescence signal. The film was then developed. The image was recorded and quantitated using BioRad's Gel Doc 1000 camera system and Multi-analyst Version 1.1 software. The calculation of % Inhibition=100−[(density of test treatment/density of DMSO treatment)×100].

See Dryer R. L. and Latta G. F. (1989) "Experiental Biochemistry" New York: Oxford University Press; and Laemmli U.K. (1970) "Cleavage of structural proteins during the assembly of the head of bacteriophage T4" *Nature* 227(259): 680-5 for additional discussion of the use of Western Blot analysis.

Example 96

Inhibition of Nitric Oxide and Cytokine Release

Macrophages isolated from the murine peritoneal cavity are a suitable sample for studying the activation properties of this immunologically important cell type. Macrophages are important in natural resistance to infection and are among the first cells to be exposed to infectious agents and become activated. Lipopolysaccharide (LPS) and interferon gamma (IFN-γ) are potent activators of macrophages, priming them for a variety of biological effects. These biological effects are mediated in part by the release of nitric oxide (NO) and the increased production of pro-inflammatory cytokines. Peritoneal exudate macrophages were isolated by peritoneal lavage with ice-cold sterile physiological saline 24 hours after intraperitoneal injection of BALB/c and CB57BL/6 mice with 0.3 ml of sterile Zymosan A (1 mg/0.5 mL 0.9% saline). Cells were washed, resuspended in RPMI 1640 supplemented with 2 mM L-glutamine, 100 units/mL penicillin, 100 μg/mL streptomycin, and 5% FBS. $1.5 \times 10^5$ cells/well were seeded in 96-well plates and followed by 3 hour incubation at 37° C. with 5% $CO_2$ (macrophages were allowed to attach) cells were stimulated with LPS (0.5 mg/mL) and IFN-γ (100 U/mL) in the absence or presence of the test compounds. All treatments were replicated six times. Cells were incubated for an additional 24 hours, and cell free culture supernatants from each well were collected for NO and cytokine determination. The remaining cells were stained with crystal violet to determine effect of the compound on cell survival.

For a discussion of the stimulation of primary mouse peritoneal macrophages for NO and cytokine determination see, e.g., Calandra T., Spiegel L. A., Metz C. N., and Bucala R. "Macrophage migration inhibitory factor is a critical mediator of the activation of immune cells by exotoxins of Gram-positive bacteria" *Proc Natl Acad Sci USA* (1998) 95(19): 11383-8; Lu L., Bonham C. A., Chambers F. G., Watkins S. C., Hoffman R. A., Simmons R. L., and Thomson A. W. "Induction of nitric oxide synthase in mouse dendritic cells by IFN-gamma, endotoxin, and interaction with allogeneic T cells: nitric oxide production is associated with dendritic cell apoptosis" *J. Immunol.* (1996) 157(8): 3577-86; Keil D. E., Luebke R. W., and Pruett S. B. "Differences in the effects of dexamethasone on macrophage nitrite production: dependence on exposure regimen (in vivo or in vitro) and activation stimuli" *Int J. Immunopharmaco*" (1995) 17(3): 157-66; and Skeen M. J., Miller M. A., Shinnick T. M., and Ziegler H. K. "Regulation of murine macrophage IL-12 production. Activation of macrophages in vivo, restimulation in vitro, and modulation by other cytokines" *J. Immunol.* (1996) 156(3): 1196-206.

Inhibition of NO Release Determination:

The production of NO was determined by assaying culture supernatants for $NO_2^-$, a stable reaction product of NO with molecular oxygen. Briefly, 100 μL of culture supernatant was reacted with an equal volume of Griess reagent at ambient temperature for 10 minutes. The absorbance at 550 nm was determined. All measurements were performed six times. The concentration of NO2- was calculated by comparison with a standard curve prepared using NaNO2.

For discussion of measuring nitric oxide in tissue culture supernatants, see, e.g., Amano F., and Noda T. "Improved detection of nitric oxide radical (NO) production in an activated macrophage culture with a radical scavenger, carboxy PTIO and Griess reagent" *FEBS Lett*. (1995) 368(3): 425-8; Archer S. "Measurement of Nitric oxide in biological models" (1993) *FASEB J.* 7:349-360; Arima H., Nishimoto Y., Motoyama K., Hirayama F., and Uekama K. "Inhibitory effects of novel hydrophilic cyclodextrin derivatives on nitric oxide production in macrophages stimulated with lipopolysaccharide" *Pharm Res*. (2001) 18(8):1167-73; Kim Y. M., and Son K. "A nitric oxide production bioassay for interferon-gamma" *J. Immunol Methods*. (1996) 198(2):203-9; and Patel R., Attur M. G., Dave M. N., Kumar S., Lee J. C., Abramson S. B., and Amin A. R. "Regulation of nitric oxide and prostaglandin E2 production by CSAIDS (SB203580) in murine macrophages and bovine chondrocytes stimulated with LPS" *Inflamm Res*. (1999) 48(6):337-43.

Inhibition of IL-12 Release Determination:

Murine primary macrophage will get activated following incubation with LPS in the presence of sub-optimal doses of IFN-γ. Upon activation, macrophages participate actively in the onset of inflammation by releasing bioactive molecules that amplify the initial inflammatory response. Stimulated macrophages demonstrate up-regulated expression of MHC-II receptors, increased release of NO and produce a number of pro-inflammatory cytokines including IL-12, IL-6, TNF-α, MIP-1α and MIP-1β.

Briefly, IL-12 levels in the supernatants from stimulated macrophages were determined with PharMingen's OptEIA ELISA set developed using an anti-mouse IL-12 Ab pair and mouse rIL-12 standard (PharMingen). Maxisorp F16 multiwell strips (Nunc, Roskilde, Denmark) were coated with anti-mouse IL-12 capture Ab (at recommended concentration) in 0.1 M $NaHCO_3$, pH 9.5, 100 μL/well, overnight at 4° C. Plates were washed three times with 0.05% Tween 20 in PBS (PBST) and blocked for 1 hour at ambient temperature with 200 mL/well of 10% FCS in PBS (blocking and dilution buffer). Plates were washed three times with PBST and duplicate samples (100 μL/well) or standards (100 μL/well) in diluent buffer were incubated for 2 hours at ambient temperature. Plates were washed five times with PBST and incubated with biotinylated anti-mouse IL-12 and avidin-horseradish peroxidase conjugate (at concentrations recommended by the manufacturer) for 1 hour at ambient temperature. Plates were washed seven times with PBST and 100 μL of 3,3',5,5'-tetramethylbenzidine substrate solution was added to each well. After 15-30 minute incubation at ambient temperature, color development was terminated by adding 50 μL of 2 N $H_2SO_4$. Absorbance was read at 450 nm with an EL 312e microplate reader. The detection limit for IL-12 was 15.6 pg/ml.

For discussion of measuring Interleukin-12 (IL-12) in tissue culture supernatants, see, e.g., Skeen M. J., Miller M. A., Shinnick T. M., and Ziegler H. K. "Regulation of murine macrophage IL-12 production, Activation of macrophages in vivo, restimulation in vitro, and modulation by other cytokines" *J. Immunol.* (1996) 156(3):1196-206.

Example 97

In Vitro Angiogenesis Assay

Angiogenesis, the formation of new blood vessels from pre-existing endothelium, is a critical process involved in numerous physiological and pathological conditions. Disruption of this tightly regulated process has been implicated in both chronic inflammation and solid tumour growth. The matrigel morphogenesis assay is an in vitro model used to mimic the process by which endothelial cells form capillaries in vivo. Human umbilical vein endothelial cells (HUVECs) were plated over matrigel, a complex mixture of solubilized basement membrane components, and cultured in serum poor medium with specific growth factors and in the presence of the test compound. HUVEC cells cultured for 24 hours in M199 with 0.5% FCS were plated at $6\times10^5$ cells/well in 12-well plates pre-coated with 300 µL of Matrigel (10.7 mg/mL) in M199 with 0.5% FCS in the presence of VEGF (1 ng/mL), and in the absence or presence of the test compounds. After 5 hours of incubation in a 5% $CO_2$-humidified atmosphere at 37° C., the three-dimensional organization of the cells (the capillary-like structures) was examined using an inverted photomicroscope. The cells were fixed with crystal violet (0.05% in 20% ethanol) and photographed using a digital camera. Qualitative analysis was accomplished by comparing the pattern, size and integrity of the vessels formed in the test wells with those of the VEGF control wells. Quantitative analysis was performed on the images collected using the Image-Pro Plus software program.

For further discussion regarding in vitro angiogenesis assay, see, e.g., Grant D. S., Lelkes P. I., Fukuda K., and Kleinman H. K. "Intracellular mechanisms involved in basement membrane induced blood vessel differentiation in vitro" In Vitro Cell Dev Biol. (1991) 27A(4):327-36; Kubota Y., Kleinman H. K., Martin G. R., and Lawley T. J. "Role of laminin and basement membrane in the morphological differentiation of human endothelial cells into capillary-like structures" *J. Cell Biol.* (1988) 107(4):1589-98; Passaniti A., Taylor R. M., Pili R., Guo Y., Long P. V., Haney A., Pauly R. R., Grant D. S., and Martin G. R. "A simple, quantitative method for assessing angiogenesis and antiangiogenic agents using reconstituted basement membrane, heparin, and fibroblast growth factor" (1992) *Lab. Invest.* 67:519-528; and Salani, D., Taraboletti, G., Rosano, L., Di Castro, V., Borsotti, P., Giavazzi, R., and Bagnato, A., "Endothelin-1 induces an angiogenic phenotype in culture cells and stimulates neovascularization" *In Vivo. Am. J. of Pathol.* (2000) 157(5):1703-1711.

Example 98

Tumor Cell Invasion Assay

Tumor cell invasion was assayed using a modified Boyden chamber 24-well cell culture plate. The chambers were constructed with a porous membrane dividing a top and bottom chamber. An additional thin Matrigel (extracellular matrix extract) layer on top of the membrane was used so that the tumor cells must move through the Matrigel and the membrane before entering the bottom chamber. Tumor cells were plated into the top chamber in serum free media, and allowed to move to the bottom chamber which contained fibroblast conditioned media as an attractant.

The invasion assays were carried out using BD BioCoat FluoroBlok Invasion plates. The plates were first warmed to ambient temperature from −20° C. storage and the matrigel layer was rehydrated with 0.5 mL of 37° C. phosphate buffered saline added to the top chambers. The plates were incubated at 37° C. in normal atmosphere for 2 hours. Then the PBS rehydrant was carefully removed from the top chamber just before use. Before the assay was carried out, fibroblast conditioned media was produced by seeding $3\times10^6$ cells of NIH 3T3 into 30 mL of media in a T150 cell culture flask and grown at 37° C. and 5% $CO_2$ for 72 hours. The media was harvested by centrifuging at 1800×g for 10 minutes (Eppendorf 5810), aliquoted into 10 mL portions, and stored at −20° C.

The test compound solution was prepared by diluting the 20 mM stock solution in 100% DMSO with serum free media to a final concentration of 500 µM or 250 µM. Tumor cells DU-145 were grown to 50-70% confluency in complete media (DMEM with 10% fetal bovine serum). On the day of the assay the cells were trypsinized, washed and resuspended in serum free media (DMEM) at a concentration of $1\times10^6$ cells/mL. Then 450 µL of this cell suspension was added to the top chamber plus 50 µL of the test compound solution to yield the final concentration of 50 or 25 µM. The solution containing the equivalent amount of DMSO as in the test compound treatment was used as the negative control. Each treatment was done in duplicate. Into the bottom chambers were added 750 µL of 50% complete media and 50% fibroblast conditioned media. These plates were incubated at 37° C. and 5% $CO_2$ for 24 hours.

The degree of tumor cell invasion was measured by first staining the cells with the fluorescent dye, calcein AM, and then measuring the fluorescence in a plate reading fluorometer as follows: After the 24 hour incubation, the invasion top plate was transferred to a new bottom plate containing 0.5 mL of Hanks buffered salt solution with 5 µg/mL of calcein AM and then incubated for 1 hour at 37° C. and 5% $CO_2$. Fluoresence in each well was determined on a Fluoroskan Ascent FL (Labsystems) on bottom read with excitation/emission wavelengths of 485/538 nm and was expressed as relative fluorescence units (RFU). The percent inhibition of invasion was calculated from these RFU's using the formula: % Inhibition=100−(RFU of test treatment/RFU of DMSO treatment)×100.

See, e.g., Crouch M. F. (2000) "An automated fluorescence based assay of neurite formation" *J. Neurosci Methods* 104 (1):87-91; and Repesh L. A. (1989) "A new in vitro assay for quantitating tumor cell invasion" *Invasion Metastasis* 9(3):192-208 for additional discussion about invasion and migration assays.

Example 99

Tumor Cell Migration Assay

Tumor cell migration assay was conducted in the similar way as described in Example 96 except that the plates used were constructed with only a porous membrane dividing a top and bottom chamber without the additional thin matrigel (extracellular matrix extract) layer on top of the membrane (BD Fluoroblock plates). The percent inhibition of migration was determined in the same way as illustrated in Example 96.

See, e.g., Crouch M. F. (2000) "An automated fluorescence based assay of neurite formation" *J. Neurosci Methods* 104 (1):87-91; and Repesh L. A. (1989) "A new in vitro assay for quantitating tumor cell invasion" *Invasion Metastasis* 9(3): 192-208 for additional discussion about invasion and migration assays.

Example 100

Irritant Contact Dermatitis Model (ICD)

Female Balb/c (H2-$^d$) mice were used in this experiment (n=8). ICD was induced with phorbol 12-myristate 13-acetate (PMA), 4 µg/ear (in 20 µL acetone). Dexamethasone was used as a positive control (0.5 mg/kg) and was administered s.c. in 50 mL volume prior to irritation. The irritant was painted onto the dorsal side of the right ear pinna. The test compounds were delivered via oral gavage at a dose between 50-300 mg/kg (10 mL/kg). Ear thickness was measured with a spring-loaded dial micrometer before irritation and at 3, 6 and 24 hours after painting the irritant. The efficacy of the anti-inflammatory effect of the test compounds was determined by comparison of the thickness of the inflamed ear and the control ear.

Example 101

PMN Model (Chemotaxis)

In each experiment Balb/c mice (females, n=30) were used. All mice were injected intraperitoneally with Zymosan (1 mg/0.5 mL saline). The test compound was delivered via oral gavage at a dose of 200 mg/kg (10 mL/kg) one hour prior and one hour post Zymosan injection. Mice were euthanized (asphyxiation with $CO_2$) 4 hours after Zymosan administration, and the abdomen was swabbed with 70% ethanol. The peritoneal skin was retracted back to expose the underlying muscle layer. Peritoneal polymorphonuclear leukocytes (PMN) were collected by flushing the peritoneal cavity with 10 mL of ice-cold PBS containing 1% FBS. After gentle agitation of the abdomen, the peritoneal lavage samples will be withdrawn and transferred to pre-labelled tubes (the tubes were kept on ice). The efficacy of the anti-inflammatory effect of the test compounds was evaluated by determining the change in number of recruited polimorphonuclear cells. A decreased number of recruited PMN indicated reduced in vivo migration of neutrophils and correlated with the anti-inflammatory effect of the test compounds.

For additional discussion regarding Zymosan induced peritonitis, see, e.g., Ajuebor M. N., Flower R. J., Hannon R., Christie M., Bowers K., Verity A., and Perretti M. "Endogenous monocyte chemoattractant protein-1 recruits monocytes in the zymosan peritonitis model" *J. Leukoc Biol.* (1998) 63(1):108-16; Getting S. J., Flower R. J., and Perretti M. "Inhibition of neutrophil and monocyte recruitment by endogenous and exogenous lipocortin 1" *Br. J. Pharmacol.* (1997) 120(6):1075-82; Nakamura S., Yoshinaga M., and Hayashi H. "Interaction between lymphocytes and inflammatory exudate cells. II. A proteolytic enzyme released by PMN as a possible mediator for enhancement of thymocyte response" *J. Immunol.* (197.6) 117(1):1-6; and Whelan J., Broughton K. S., Lokesh B., and Kinsella J. E. "In vivo formation of leukotriene E5 by murine peritoneal cells" *Prostaglandins* (1991) 41(1):29-42.

Example 102

Orthotopic Lung Model

Materials and Methods:
Cell Implantation for donor tumors: NCI-H460 human lung large cell carcinoma cells were harvested by trypsinization and adjusted to a final concentration of $1 \times 10^6$ cells/80 mL. Male nude rats (CR:NIH-RNU) were endobronchially implanted with $1 \times 10^6$ tumor cells using a 20 gauge, 2 inch Teflon catheter passed into the right caudal lobe via a small tracheotomy incision.

Implantation of tumor fragments: These tumor-bearing rats were sacrificed at three weeks following implantation and their tumors harvested in cold RPMI 1640. Viable tumor was cut into 1-2 mm diameter pieces by "crossed scalpels" technique. A 50 mg portion was placed into a 16 gauge, 2 inch Teflon catheter and implanted into 6-week-old male nude rats using a similar technique. Animals were treated with Augmentin at 0.35 mg/mL in water for 2 weeks.

Preparation of agents: The test compound was prepared fresh each day by dissolving it in an acceptable recipient at 10 mg/mL under sterile conditions. Cisplatin injection, 1 mg/mL, was obtained from the hospital pharmacy.

Study Design: There were four arms in the study: control; test compound alone; cisplatin alone; test compound and cisplatin combination. Also, there were two groups in the study: in group I, all animals were followed until death to assess maximum length of survival and in group II, all animals were simultaneously sacrificed from each treatment arm as control animals became severely cachectic or died. This allows us to directly compare, at the same point in time, the therapeutic effects of each study arm on tumor related endpoints, such as primary tumor weight, tumor/body weight ratio, mediastinal lymph node weight and metastatic pattern. Renal and liver functions of each animal were also examined by serum biochemistry to assess possible toxicities.

Both test compound (5 mg daily) and cisplatin (5 mg/kg weekly for 3 weeks) were administered by intraperitoneal injection. Treatment commenced 7 days and 14 days post implantation for the test compound and cisplatin, respectively. Animals were sacrificed when they showed signs of significant morbidity or impending death. At necropsy the heart-lung blocks, kidney, brain, and chest wall were removed, serially sectioned, stained with H & E, and examined in a blinded fashion by a pathologist.

Statistical Analysis: Statistical analysis for length of survival, primary tumor, body, and mediastinal lymph node weight were evaluated using ANOVA or unpaired Student's t-test. Incidence of metastasis was evaluated by using a contingency table with Fisher's exact test. Differences of $P<0.05$ were considered to be significant. Immunocytochemistry. The H-460 cell line was seeded into 8-chamber slides ($10^4$ cells/well) and treated with 25 uM of the test compound after reaching a confluency of 60 to 80%. Cells were harvested at 2, 4, 8 and 24 hours after treatment and incubated overnight at 4° C. with the primary antibodies. For phosphorylated Akt/PKB expression anti-phospho-Akt/PKB (Ser-473), was used at a concentration of 2 µg/mL, followed by incubation with the secondary antibody, biotinylated rabbit-IgG at a concentration of 7 µg/mL. For phosphorylated GSK-3β expression anti-phospho-GSK-3β (Ser-9), a concentration of 6 µg/mL was used, followed by incubation with the same secondary antibody. Streptavidin-peroxidase was used as a detection system. DAB was used as chromogen and counterstaining was performed with hematoxylin. Slides were assessed as either positive or negative according to the amount and intensity of staining. Phospho-Akt/PKB and phospho-GSK-3β reactivity was quantitated by computerized image analysis using an Image-Pro system and conventional light microscopy.

Example 103

ILK Expression is High in Human Psoriatic Skin as Compared to Normal Skin

Psoriasis is a complex inflammatory autoimmune condition characterized by an abnormal activation of skin T lymphocytes, dermal and epidermal infiltration by various types of leukocytes, hyper-proliferation of keratinocytes and pronounced angiogenic activity within the dermal vasculature. The thickness of the epidermal layer within psoriatic plaques is dramatically greater than that of normal skin of healthy individuals or the uninvolved skin of the psoriasis patient.

To test for ILK expression, skin samples were obtained from a human subject with healthy skin and from patients suffering from the immune-mediated condition psoriasis. Skin preparations were processed using routine formalin-fixation and paraffin embedding techniques. Sections were cut and treated with antigen retrieval methodology and stained with a rabbit anti-ILK polyclonal antibody (catalogue #06-592, Upstate Biotechnology, Lake Placid N.Y.). Sections were then incubated with peroxidase-conjugated goat anti-rabbit polyconal antibody. Slides were then developed using standard techniques.

In normal skin, a low level of ILK expression was evident in the supra-basal layers of skin keratinocytes. These supra-basal layers of skin keratinocytes were almost certainly undergoing the process of terminal differentiation. The staining intensity for ILK was more intense for keratinocytes near the outer keratin layer. Little or no ILK staining was observed for the dermal vascular endothelium. In contrast, staining for ILK was highly intense for the hyper-proliferative keratinocytes within the plaques of patients with psoriasis patients. Within the dermal region of psoriatic patient plaques, cells comprising the vasculature stained strongly for ILK. Further, some of the inflammatory cells present within the dermal region stained positively for ILK. Overall, in contrast to normal skin, ILK was expressed at much higher levels within the epidermal and dermal regions within skin plaques of patients with psoriasis.

Example 104

Expression of ILK in Psoriatic Tissue Correlates with Severity of Disease

The expression of ILK within psoriatic skin was evaluated for a series of plaque biopsy samples obtained from a patient over a 3-month period. The presence and expression pattern of ILK was evaluated by immunohistological analyses. All sections were stained at the same time. For psoriasis, the disease-state can be gauged by the relative thickness of the epidermis. For the series of biopsy samples evaluated, expression levels of ILK closely paralleled the psoriasis disease-state at the tissue level.

The first sample (panel A), was obtained at screening while the patient was experiencing active disease. Staining for ILK was intense for the keratinocytes within the target plaque. Within the dermal region of the plaque, cells within the vasculature as well as cells that had infiltrated the region also stained strongly for ILK. The second sample (panel B) was obtained one month later, a time when disease activity had further intensified. ILK staining intensity with this sample was much stronger than for the first sample. The third sample was taken approximately 4 weeks after sample B, a time during which this subject was exhibiting an improvement in their disease and a reduction in epidermal thickness. For this sample (panel C) there was a correspondent reduction in ILK staining intensity, both for the epidermal keratinocytes and within cells of the dermal vasculature. Sample 4 was obtained 3 months after sample 1, at a time when the subject was experiencing a flare in disease activity. Epidermal thickness for sample 4 was greater than that of sample 3. At this time, an increase in ILK staining intensity was evident within the dermal vasculature and cellular infiltrate as well as for the epidermal keratinocytes (panel D). Thus, expression levels of ILK within the psoriatic plaque varied with disease activity with high ILK expression correlating with symptoms of active disease.

Example 105

Anti-inflammatory Effect of ILK-inhibition

The anti-inflammatory activity of a compound of the invention was demonstrated in an acute mouse ear-swelling edema model. To induce this inflammatory experimental condition, mice are treated topically on the surface of an ear with tetra phorbol ester (TPA). Application of TPA in such a manner produces a rapid increase in ear thickness caused by fluid buildup and the infiltration of the tissue by inflammatory cells.

Different doses of a compound of the invention were given orally at the same time as an active amount of TPA. Ear measurements performed 6 hours after these treatments showed that a dose of a compound of the invention of 200 mg/kg almost completely prevented the increase in ear swelling stimulated by TPA. The effect of this dose of a compound of the invention on this response was comparable to that produced by dexamethasone, a well-characterized and potent anti-inflammatory agent. Thus, a compound that is known to inhibit the activity of ILK in vitro can also affect the development of symptoms of an experimental inflammatory skin condition in vivo.

Example 106

Demonstration of ILK Inhibition as Therapeutic Intervention in Renal Disorders Methods:

Mice transgenic for the bovine growth hormone (GH) under a methallothionein I promoter are used (Wanke, R., et al. *Pediatric Nephrol* (1991) 5:513-521). Genotype can be confirmed by genomic PCR with bovine GH specific primers (Wanke, R., et al. Pediatric Nephrol (1991) 5:513-521). Glomeruli can be isolated after pooling kidneys from two or more animals. For the animal model, accelerated nephrotoxic serum nephritis (NTX) is induced in 4 to 6 week old females as previously reported (Schadde, E., et al. *Nephrol Dial Transplant* (2000) 15:1046-1053; Neugarten, J., et al. *J. Am Soc Nephrol* (1995) 5:1903-1909). Five days after preimmunization with rabbit IgG, 400 µg of a protein A purified IgG fraction of a nephrotoxic rabbit anti-murine GBM antiserum is intravenously injected, while controls receive carrier only. Mice in each group are sacrificed after 0, 2, and 7 days and a pooled glomerular fraction is obtained from each group for expression analysis. Albuminuria is determined using a commercially available mouse albumin specific ELISA system (Exocell, Philadelphia, PE).

Measuring Levels of ILK from Podocytes

To assess the efficacy of a candidate aminopyrazole ILK inhibiting agent in vivo, the following podocyte extraction method may be used. Single cell RT-PCR is performed as described in Schroppel, B., et al. *Kidney Int* (1998) 53:119-124. Freshly dissected glomeruli from CD-1 mice are transferred to a patch clamp apparatus. Single podocytes are selectively harvested by aspiration of the cells into a micropipette. Reverse transcribed and RT-PCR is performed essentially as described above, but using 50 instead of 30 cycles. Perfusion medium aspirated next to a glomerulus is processed in parallel and serves as negative control. Single cell ILK RT-PCR product identity is verified by restriction digest. Single podocyte RNA is quantified using published real-time RT-PCR technology (Heid, C. A., et al. *Genome Res* (1996) 6:986-994). For determination of ILK copy number per single podocyte cDNA, a standard curve of serial dilutions of ILK plasmid cDNA with known copy numbers is employed. ILK copies per podocyte cDNA are calculated using the Ct value minus the dilution factor and the standard curve (y=-1,6227 Ln (x)+39 with R2=0,9935) generated from duplicate amplification reactions of log fold dilutions between 100,000 and 10 ILK plasmid copies.

In Vitro Podocytes Model:

As an in vitro model system, conditionally immortalized podocytes are used (Mundel, P., et al. *Exp Cell Res* (1997) 236:248-258). Cells are propagated under permissive conditions at 33° C. with RPMI 1640 medium (Life Technologies) supplemented with 10% FCS (Bio Whittaker, Verviers, Belgium), 100 U/ml penicillin, 100 mg/ml streptomycin and 10 U/ml mouse recombinant interferon-g (Sigma). To induce differentiation, podocytes are maintained on type I-collagen (Biochrom, Berlin, FRG) coated surface at 37° C. without interferon-g (non-permissive conditions) for at least 8 days. Cells at passage 12-24 were used. Mouse mesangial cells were employed in control experiments. 90-Day-old mice with severe albuminuria are employed. Wildtype littermates serve as controls. Six to eight animals in each group are analyzed.

| GROUP | ANIMAL TYPE | TREATMENT |
|---|---|---|
| Negative control group: | Wildtype litter mates, week 6-12 of disease progression | Carrier only |
| Positive control group | GH-transgenic mice, week 6-12 of disease progression | Carrier only |
| Test animals | GH-TX mice | Various doses of ILK inhibitor weeks 6-12 |
| Test animals | GH-TX mice | Various doses of ILK inhibitor for full 12 weeks. |

Compounds of the invention are administered orally, intraperitoneally or by subcutaneous infusion pump, in daily doses ranging from 0.01-200 mg/kg. Vehicle (carrier) controls are administered in equivalent volumes by the same routes.

Experimental readouts included albuminuria, serum urea, histology and gene expression profiles.

Negative control mice demonstrate no significant changes in experimental readouts. The positive control group demonstrate significant changes associated with progressive renal glomerulosclerosis in histology and biochemical readouts. In the experimental GH-TX groups treated with various doses of aminopyrazole ILK inhibitor, decreases in measured parameters of progressive renal glomerulosclerosis are demonstrated compared to the positive control group, indicating that administration of aminopyrazole ILK inhibitors results in therapeutic benefit in this model of progressive renal disease.

Example 107

Adriamycin-Induced Proteinuria

This model, which results in focal glomerular sclerosis (FGS), is well described in Wang, Y., et al. *Kidney Int* (2000) 58:1797-1804. Groups of BALB/c mice are injected intravenously on day 0 with a single dose of Adriamycin (ADR, doxorubicin hydrochloride, Pharmacia & Upjohn) at 10-11 mg/kg, or vehicle control. Six to eight animals in each group are analyzed.

| GROUP | TREATMENT |
|---|---|
| Negative control group | Intravenous carrier on day 0, vehicle daily from day 0 |
| Positive control group | intravenous ADR on day 0, vehicle daily from day 0 |
| Test group | Intravenous ADR on day 0, various doses of ILK inhibitor from day 0 |

Compounds of the invention are administered orally, intraperitoneally or by subcutaneous infusion pump, in daily doses ranging from 0.01-200 mg/kg, beginning on day 0. Vehicle (carrier) controls are administered in equivalent volumes by the same routes.

Experimental readouts include weekly body weight, urine volume, urinary protein, serum creatinine and albumin, and terminal histopathology. Negative control mice demonstrate no significant changes in experimental readouts. The positive control group demonstrate significant changes associated with rapid progressive renal disease (FGS) using experimental readouts, namely proteinuria, hypoalbuminemia, hypercreatininemia, and progressive renal injury by histology. In the experimental groups treated with various doses of aminopyrazole ILK inhibitor, decreases in measured parameters of progressive renal disease are demonstrated compared to the positive control group, indicating that administration of aminopyrazole ILK inhibitors results in therapeutic benefit in this model of acute progressive focal glomerular sclerosis.

Example 108

Murine Unilateral Ureteral Obstruction

This model results in epithelial-mesenchymal transdifferentiation in renal fibrosis and is described in Vielhauer V., et al. *J. Am Sox Nephrol* (2001) 12: 1173-1187. Briefly, female inbred C57BL/6 mice weighing ca. 20-26 g are obtained and kept under a ca. 12-h light/dark cycle. Food and water are available ad libitum. Under general anesthesia, unilateral ureteral ligation resulting in UUO is performed by ligating the left distal ureter with a 2/0 Mersilene suture thorugh a low midline abdominal incision. Unobstructed contralateral kidneys serve as controls.

| GROUP (8-10 mice) | PRE-TREATMENT | TREATMENT |
|---|---|---|
| Negative control group | Sham operated mice | Receive carrier only for ten days |
| Positive control group | Mice with one obstructed kidney | Receive carrier only for ten days |
| Test group | Mice with one obstructed kidney | Receive various doses of ILK inhibitor for ten days |

Compounds of the invention are administered orally, intraperitoneally or by subcutaneous infusion pump, in daily doses ranging from 0.01-200 mg/kg. Vehicle (carrier) controls are administered in equivalent volumes by the same routes.

Experimental readouts included histological fibrosis scores, serum urea, collagen levels and ILK mRNA expression. Analysis of ILK mRNA levels are also performed in infiltrating cells (macrophages and T-cells) after cell sorting in renal fibrosis in the UUO model. Negative control (sham operated) mice demonstrate no significant changes in experimental readouts. The UUO control group demonstrate significant changes associated with renal fibrosis in the ligated kidney using experimental readouts. Also observed in these animals is an increase in ILK mRNA induction. In the experimental groups treated with various doses of aminopyrazole ILK inhibitor, the non-ligated kidneys are used as internal controls, and the non-ligated kidneys demonstrate no significant changes associated with renal tubulo-interstitial fibrosis using experimental readouts, however the damaged kidneys demonstrate decreases in measured parameters of renal fibrosis compared to the UUO control group. This result indicates that administration of compounds of the invention results in therapeutic benefit in this model of renal tubulo-interstitial fibrosis.

Example 109

Treatment of AMD using an ILK Inhibitor as an Adjunct to Visudyne™ Therapy

Therapeutic effect of a compound of the invention in AMD is evaluated using visual acuity as the primary clinical outcome. Patients with subforveal CNV lesions caused by AMD are examined for the presence of lesions that meet the inclusion criteria. The inclusion criteria are defined as the presence of lesions measuring 5400 μm or less in greatest linear dimension with evidence of classic CNV and best-corrected visual acuity of approximately 20/40 to 20/200 based on fluorescein angiographic and visual acuity examination. Those determined as qualified for the treatment of AMD are randomly assigned to 4 groups. Group A, B, and C are treated with standard Visudyne™ therapy with an adjunct therapy using an ILK inhibitor. Patients of Group D are treated with standard Visudyne™ therapy in combination with a placebo of the ILK inhibitor.

For standard Visudyne™ therapy, patients are administered with 30 ml of Visudyne™ (0.15 mg per kilogram of body weight). The administration is by intravenous infusion over a period of 10 minutes. Fifteen minutes after the end of the infusion, the laser light is applied for 83 seconds to the CNV lesion through a fundus contact lens of known magnification to result in a light exposure of 50 J/cm$^2$. A circular spot of approximately 6000 microns encompassing the area of the lesion is exposed to the laser light.

For the adjunct therapy, patients of groups A, B, and C receive a daily oral administration of a compound of the invention at the dose of 5, 10, 20 mg per kilogram body weight, respectively. The adjunct treatment commences three days after the patient receiving the standard Visudyne™ therapy and continues for a period of one month.

As follow-up, patients are examined every three months. At each regularly scheduled follow-up visit, best-corrected visual acuity measurement, contrast threshold measurement, ophthalmoscopic examination, stereoscopic fundus photography, and fluorescein angiography are performed.

Example 110

Treatment of Diabetic Retinopathy using an ILK Inhibitor

Therapeutic effect of a compound of the invention in proliferative diabetic retinopathy is evaluated using visual acuity as the primary clinical outcome. Patients with proliferative diabetic retinopathy and visual acuity of 20/100 or better in each eye are included in the clinical evaluation. Patients are randomly assigned to 3 treatment groups and 1 placebo group. Group A, B, and C are treated with daily oral administration of a compound of the invention at the dose of 5, 10, 20 mg per kilogram body weight. Patients of Group D receive placebo. The treatment expands a period of 24 months.

As follow-up, patents are examined every 4 months. At each regularly scheduled follow-up visit, best-corrected visual acuity measurement, contrast threshold measurement, indirect ophthalmoscopic examination, stereoscopic fundus photography, fluorescein angiography, and slit-lamp examination using 78- or 90-diopter lens are performed.

Example 111

Evaluation of ILK Expression in Ocular Vascular Tissue

This example indicates the relevance of ILK as a therapeutic target for diseases with underling pathology of ocular neovascularization.

Post mortem baboon eye samples were subjected to immunohistological analysis for the expression of ILK in ocular vasculature. Freshly obtained tissues were snap-frozen by immersing into a Dewar of liquid nitrogen. Cross sections of 5-10 microns were prepared and fixed in cold acetone (−20 C). Immunohistology was performed using a rabbit anti-ILK antibody (Upstate Biotechnology Institute, NY. Cat.# 06-550) and Zymed Histostatin™ Plus kit (Zymed, Cat.#85-9743).

Abundant expression of ILK was detected in choroidal and retinal endothelium in post mortem baboon eye samples. Under similar condition, no significant level of ILK expression was detected in retinal pigmented epithelial cells. In addition, no significant expression of ILK in neurons and photoreceptors was observed.

Example 112

Treatment of Corneal Neovascularization with an ILK Inhibitor using a Mouse Model The following model provides a quantifiable in vivo assay that can be used to evaluate anti-angiogenic activity of a compound of the invention. Corneal neovascularization is induced by a procedure known as silver nitrate cauterization. The procedure involves topical applications of silver nitrate onto the cornea by gently touching conjunctiva/limbus for one second followed by touching the central cornea of an anesthetized mouse for 8 seconds with a silver nitrate applicator (Graham-Field, NY, Item # 1590, 75% silver nitrate, 25% potassium nitrate). Immediately after, the eye is rinsed with 10 ml of saline followed by topical application of Gentak Ophthalmic Ointment (0.3%, Gentamicin sulfate) on the eye to prevent bacterial infections.

Corneal neovascularization is recorded and evaluated by examining and photographing the cornea daily using a stereo dissecting microscope connected to a color video camera and a computer. Angiogenesis is evaluated based on new blood vessel growth within previous avascular cornea using a scoring system (score of 0-4) that rates from no neovascularization to very severe neovascularization in cornea. In addition, upon completion of the experiment (day 5-7), corneal neovascularization is quantified using computer-assisted image analysis (Image Pro Plus, Media Cybernetics, ML) of dye-stained blood vessels in post mortem whole corneal mounts. Corneal vasculature is stained by IV injection of high molecular weight FITC-dextran into anesthetized mice before euthanasia.

Animals receive daily intra-peritoneal administration of a compound of the invention at the dose of 5, 25 or 50 mg/kg commencing on day-2 after the silver nitrate cauterization procedure until 24 h before the ending of the experiment. Corneal neovascularization of ILK inhibitor-treated animals is compared with that of vehicle-treated animals.

Example 113

Treatment of Choroidal Neovascularization with an ILK Inhibitor Using a Monkey Model of CNV The following model provides an in vivo assay that can be used to evaluate therapeutic potential of a compound of the invention for the treatment of CNV. CNV is induced by argon green laser burns that are placed in the maculae of cynomolgus monkeys using a modification of Ryan's model. The laser burn with size of 50 □m in diameter is induced by exposure to 350-450 mW laser light at 514 nm for 0.1 second using an argon laser (Coherent Argon Dye Laser #920, Coherent Medical Laser, Polo Alto, Calif.).

CNV is monitored by weekly examination with fundus photography and fluorescein angiography. At the termination of the experiment (2-3 months after the induction of CNV), eyes are enucleated under deep anesthesia and fixed in modified Kanovsky fixative. Bisection is performed 20 minutes after fixation. Tissues are then embedded and sections are generated for histological and immunohistological analysis using antibodies against vasculature-specific markers including CD-31 and VE-Cadherin. The extent of neovascularization is quantified using a computer-assisted image analysis system with Image Pro Plus (Media Cybernetics, ML).

Animals receive daily oral administration of a compound of the invention at the dose of 10, 50 or 100 mg/kg for commencing after the onset of CNV (2-3 weeks after the laser treatment). As control, a group of monkeys receive daily oral treatment with vehicle only. CNV in ILK inhibitor-treated animals is compared with that of vehicle-treated animals for angiographic and immunohistological evidence of CNV.

Example 114

Treatment of Retinal Neovascularization with an ILK Inhibitor Using a Mouse Model of Ischmia-lnduced Retinopathy The following model provides an in vivo assay that can be used to evaluate therapeutic potential of a compound of the invention for the treatment of retinopathy. This is a mouse model of retinopathy of prematurity. Retinopathy in mice is induced by using dams and neonatal mice. Mice are exposed with their nursing dams to 75% oxygen/25% nitrogen from postnatal day 7 to day 12, then put back to room air. At day 17, all pups are weighed, euthanised, and perfused with 1 ml fixative (4% paraformaldhyde/8% sucrose/sodium phosphate buffer, pH 7.2) through the left ventricle of heart. Eyes are enucleated and placed in fixative. The fixed tissues are paraffin-embedded and 4-µm sections are cut. Immunohistology procedure is performed to evaluate extent of retinal neovascularization using antibodies against endothelium-specific markers including CD-31 and VE-cadherin. The vascular specific staining is quantified using the computer-assisted image analysis method (Image Pro Plus, Media Cybernetics, ML).

The compound of the invention at the dose of 5, 25 or 50 mg/kg is administered daily through intra-peritoneal injection from day 12 through day 16. The control group receives daily injection of vehicle. The inhibitory effect of the ILK inhibitor on retinal neovascularization is determined by comparing the extent of vascular staining in mice treated with the compound of the invention and those treated with vehicle only.

Example 115

B16 Murine Lung Metastasis Model

This model involves the injection of 200,000 tumour cells into the tail vein of mice. The tumour cells will seed into the lungs and form small tumours there. Intraperitoneal or intravenous injection, or oral gavage treatments will be commence either the day before after injection of the cells and will be performed daily. There will be 10 animals for each treatment group. The treatments will be administered at well tolerated doses and no deleterious side effects are expected. Due to the variation of cell viability, n=4 control mice will be euthanized to monitor the cell number and growth in the lungs progressively throughout the study. Pilot studies have shown that monitoring should begin at 7 days and continue approximately on day 10, day 14 and until day 17 if necessary. When the tumour nodules in these control mice average 100 nodules per animal, mice will be anesthetized by a Ketamine/Xylazine injection given intraperitoneally and the entire study group of animals will be sacrificed and necropsy performed. The lungs containing the metastatic tumours will be excised, weighed and fixed in formalin. The tumours are visibly distinct from normal lung tissue (change in pigment) and the number of metastasis or tumours that have formed in the lungs can be counted using a dissecting microscope. Cells are classified by size being identified as small <0.2 mm, medium 0.2-0.5 mm or large >0.5 mm. Survival without treatment in this model has been established to be 28 days after the initial injection of the tumour cells. Overall health of the mice is observed and weights are taken twice per week.

Progression of the cell burden within the lungs will be monitored by sacrificing non-treated animals at various time points. When the tumour nodule count averages 100 nodules per animal the study will be concluded and all animals sacrificed. This is expected to be around day 14 to day 17.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A pharmaceutical composition comprising a pharmaceutically acceptable excipient and a compound of formula (Ic):

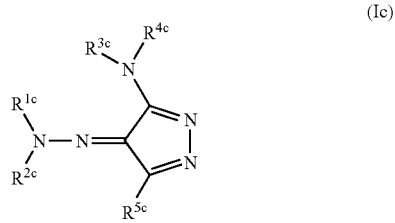

as a single tautomer, a mixture of tautomers, a single stereoisomer, a mixture of stereoisomers, or a racemic mixture; or a pharmaceutically acceptable salt thereof;
wherein:
$R^{1c}$ is hydrogen, alkyl, aryl or aralkyl;
$R^{2c}$ is aryl optionally substituted with one or more substituents selected from the group consisting of fluoro, —$R^{6c}$—N($R^{8c}$)$_2$, —S(O)$_2$—$R^{6c}$—OH, —S(O)$_2$—N($R^{7c}$)$R^{8c}$ and heterocyclylalkyl;
$R^{4c}$ is hydrogen or alkyl;
$R^{3c}$ is hydrogen, alkyl, heterocyclylalkyl, or heterocyclylcarbonyl;
$R^{5c}$ is alkyl, alkenyl, cycloalkyl (optionally substituted by one or more substituents selected from the group consisting of alkyl and aryl);
each $R^{6c}$ is independently a straight or branched alkylene chain;
each $R^{7c}$ is independently hydrogen, alkyl, aryl, aralkyl or heterocyclylalkyl;
$R^{8c}$ is hydrogen, alkyl, aryl aralkyl or hydroxyalkyl,
provided that when $R^{1c}$, $R^{3c}$ and $R^{4c}$ are all hydrogen and $R^{5c}$ is methyl, $R^{2c}$ can not be phenyl optionally substituted with one or more substituents selected from the group consisting of chloro, bromo or alkyl.

2. The pharmaceutical composition of claim 1 wherein the compound is a compound of formula (Ic) wherein:
$R^{2c}$ is phenyl optionally substituted with one or more substituents selected from the group consisting of fluoro, —$R^{6c}$—N($R^{8c}$)$_2$, —S(O)$_2$—$R^{6c}$—OH, —S(O)$_2$—N($R^{7c}$)$R^{8c}$ and heterocyclylalkyl; and
$R^{5c}$ is alkyl, alkenyl, cycloalkyl (optionally substituted by one or more substituents selected from the group consisting of alkyl and phenyl).

3. The pharmaceutical composition of claim 2 wherein the compound is a compound of formula (Ic) selected from the group consisting of the following:
tert-butyl-[5-methyl-4-(phenylhydrazono)-4H-pyrazol-3-yl]amine;
4-(3-fluorophenylhydrazono)-5-methyl-2H-pyrazol-3-ylamine
5-tert-butyl-4-[(3-fluorophenyl)hydrazono]-4H-pyrazol-3-ylamine;
5-but-3-enyl-4-[(3,4-difluorophenyl)hydrazono]-4H-pyrazol-3-ylamine;
4-[(3,4-difluorophenyl)hydrazono]-5-methyl-4H-pyrazol-3-ylamine;
{4-[(3,4-difluorophenyl)hydrazono]-5-methyl-4H-pyrazol-3-yl}ethylamine;
5-ethyl-4-(phenylhydrazono)-4H-pyrazol-3-ylamine;
ethyl-{4-[(3-fluoro-phenyl)hydrazono]-5-methyl-4H-pyrazol-3-yl}amine;
{4-[(3,4-difluorophenyl)hydrazono]-5-methyl-4H-pyrazol-3-yl}methylamine;
5-cyclopropyl-4-(phenylhydrazono)-4H-pyrazol-3-ylamine;
5-isopropyl-4-(phenylhydrazono)-4H-pyrazol-3-ylamine;
5-(2,2-dimethylpropyl)-4-(phenylhydrazono)-4H-pyrazol-3-ylamine;
5-(2-phenylcyclopropyl)-4-(phenylhydrazono)-4H-pyrazol-3-ylamine;
5-(1-ethylpropyl)-4-(phenylhydrazono)-4H-pyrazol-3-ylamine;
5-isobutyl-4-(phenylhydrazono)-4H-pyrazol-3-ylamine;
{4-[(3-fluorophenyl)-hydrazono]-5-methyl-4H-pyrazol-3-yl}methylamine;
3-[N'-(3-amino-5-cyclopropylpyrazol-4-ylidene)hydrazino]-n-(2-hydroxyethyl)-benzenesulfonamide;
3-[N'-(3-amino-5-cyclopropylpyrazol-4-ylidene)hydrazino]benzenesulfonamide;
and 3-[N'-(3-Amino-5-cyclopropylpyrazol-4-ylidene)hydrazino]-N-methylbenzenesulfonamide.

4. A compound of formula (Ic):

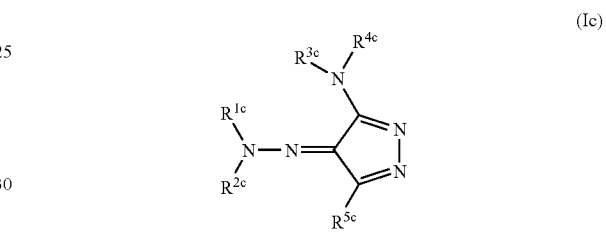

as a single tautomer, a mixture of tautomers, a single stereoisomer, a mixture of stereoisomers, or a racemic mixture; or a pharmaceutically acceptable salt thereof;
wherein:
$R^{1c}$ is hydrogen, alkyl, aryl or aralkyl;
$R^{2c}$ is aryl optionally substituted with one or more substituents selected from the group consisting of fluoro, —$R^{6c}$—N($R^{8c}$)$_2$, —S(O)$_2$—$R^{6c}$—OH, —S(O)$_2$—N($R^{7c}$)$R^{8c}$ and heterocyclylalkyl;
$R^{3c}$ is hydrogen, alkyl, heterocyclylalkyl, or heterocyclylcarbonyl;
$R^{4c}$ is hydrogen or alkyl;
$R^{5c}$ is alkyl, alkenyl, or cycloalkyl (optionally substituted by one or more substituents selected from the group consisting of alkyl and phenyl);
$R^{6c}$ is a straight or branched alkylene chain;
$R^{7c}$ is hydrogen, alkyl, aryl, aralkyl or heterocyclylalkyl; and
$R^{8c}$ is hydrogen, alkyl, aryl, aralkyl or hydroxyalkyl,
provided that when $R^{1c}$, $R^{3c}$ and $R^{4c}$ are all hydrogen and $R^{5c}$ is methyl, $R^{2c}$ can not be phenyl optionally substituted with one or more substituents selected from the group consisting of chloro, bromo or alkyl.

5. The compound of claim 4 selected from the group consisting of the following:
tert-butyl-[5-methyl-4-(phenylhydrazono)-4H-pyrazol-3-yl]amine;
4-(3-fluorophenylazo)-5-methyl-2H-pyrazol-3-ylamine;
5-tert-butyl-4-[(3-fluorophenyl)hydrazono]-4H-pyrazol-3-ylamine;
5-but-3-enyl-4-[(3,4-difluorophenyl)hydrazono]-4H-pyrazol-3-ylamine;
4-[(3,4-difluorophenyl)hydrazono]-5-methyl-4H-pyrazol-3-ylamine;

{4-[(3,4-difluorophenyl)hydrazono]-5-methyl-4H-pyrazol-3-yl}ethylamine;
5-ethyl-4-(phenylhydrazono)-4H-pyrazol-3-ylamine;
ethyl-{4-[(3-fluoro-phenyl)hydrazono]-5-methyl-4H-pyrazol-3-yl}amine;
{4-[(3,4-difluorophenyl)hydrazono]-5-methyl-4H-pyrazol-3-yl}methylamine;
5-cyclopropyl-4-(phenylhydrazono)-4H-pyrazol-3-ylamine;
5-isopropyl-4-(phenylhydrazono)-4H-pyrazol-3-ylamine;
5-(2,2-dimethylpropyl)-4-(phenylhydrazono)-4H-pyrazol-3-ylamine;
5-(2-phenylcyclopropyl)-4-(phenylhydrazono)-4H-pyrazol-3-ylamine;
5-(1-ethylpropyl)-4-(phenylhydrazono)-4H-pyrazol-3-ylamine;
5-isobutyl-4-(phenylhydrazono)-4H-pyrazol-3-ylamine;
{4-[(3-fluorophenyl)-hydrazono]-5-methyl-4H-pyrazol-3-yl}methylamine;
3-[N'-(3-Amino-5-cyclopropylpyrazol-4-ylidene)hydrazino]-N-methylbenzenesulfonamide;
3-[N'-(3-amino-5-cyclopropylpyrazol-4-ylidene)hydrazino]-N-(2-hydroxyethyl)benzene-sulfonamide; and
3-[N'-(3-amino-5-cyclopropylpyrazol-4-ylidene)hydrazino]benzenesulfonamide.

\* \* \* \* \*